United States Patent
Doherty et al.

(10) Patent No.: US 7,332,511 B2
(45) Date of Patent: Feb. 19, 2008

(54) VANILLOID RECEPTOR LIGANDS AND THEIR USE IN TREATMENTS

(75) Inventors: Elizabeth M. Doherty, Newbury Park, CA (US); Jiawang Zhu, Simi Valley, CA (US); Markian Stec, Fillmore, CA (US); Mark H. Norman, Thousand Oaks, CA (US); Hui-Ling Wang, Thousand Oaks, CA (US); Christopher H. Fotsch, Thousand Oaks, CA (US); Ning Chen, Thousand Oaks, CA (US); Partha P. Chakrabarti, Simi Valley, CA (US); Celia Dominguez, Thousand Oaks, CA (US); James Richard Falsey, Westlake Village, CA (US); Christopher Hulme, Simi Valley, CA (US); Jodie Katon, Ventura, CA (US); Thomas Nixey, Newbury Park, CA (US); Vassil I. Ognyanov, Thousand Oaks, CA (US); Liping H. Pettus, Thousand Oaks, CA (US); Robert Michael Rzasa, Ventura, CA (US)

(73) Assignee: Amgen Inc., Thousand Oaks, CA (US)

( * ) Notice: Subject to any disclaimer, the term of this patent is extended or adjusted under 35 U.S.C. 154(b) by 7 days.

(21) Appl. No.: 11/195,159

(22) Filed: Aug. 1, 2005

(65) Prior Publication Data

US 2005/0272777 A1 Dec. 8, 2005

Related U.S. Application Data

(62) Division of application No. 10/638,009, filed on Aug. 8, 2003, now Pat. No. 7,144,888.

(60) Provisional application No. 60/402,422, filed on Aug. 8, 2002.

(51) Int. Cl.
C07D 213/30 (2006.01)
C07D 213/32 (2006.01)
C07D 401/12 (2006.01)
C07D 401/14 (2006.01)
C07D 403/12 (2006.01)
C07D 403/14 (2006.01)
A61K 31/4427 (2006.01)
A61P 19/02 (2006.01)
A61P 35/00 (2006.01)

(52) U.S. Cl. ............... 514/345; 546/268.1; 544/8; 544/53; 544/56; 544/59; 544/63; 544/67; 544/88; 544/106; 544/238; 544/242; 544/338; 540/450; 540/484

(58) Field of Classification Search ........ 546/256, 546/268.1; 514/345, 275

See application file for complete search history.

(56) References Cited

U.S. PATENT DOCUMENTS

| 5,272,167 A | 12/1993 | Girijavallabhan et al. |
|---|---|---|
| 5,459,144 A | 10/1995 | Girijavallabhan et al. |
| 5,750,532 A | 5/1998 | Girijavallabhan et al. |
| 5,916,887 A | 6/1999 | Singh et al. |
| 5,932,590 A | 8/1999 | Ciccarone et al. |
| 5,936,084 A | 8/1999 | Jirousek et al. |
| 5,959,123 A | 9/1999 | Singh et al. |
| 5,965,569 A | 10/1999 | Camps Garcia et al. |
| 5,969,140 A | 10/1999 | Ukita et al. |
| 6,093,737 A | 7/2000 | Anthony et al. |
| 6,153,619 A | 11/2000 | Wood et al. |
| 6,255,489 B1 | 7/2001 | Klintz et al. |

(Continued)

FOREIGN PATENT DOCUMENTS

EP 0 168 262 1/1986

(Continued)

OTHER PUBLICATIONS

Valenzano et al. Curr. Med. Chem. 3185-3202, 2004.*

(Continued)

*Primary Examiner*—Venkataraman Balasubramanian
(74) *Attorney, Agent, or Firm*—Richard V. Person

(57) ABSTRACT

Compounds having the general structure

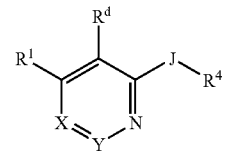

and compositions containing them, for the treatment of acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders.

19 Claims, No Drawings

U.S. PATENT DOCUMENTS

| | | |
|---|---|---|
| 6,306,866 B1 | 10/2001 | Wood et al. |
| 6,407,111 B1 | 6/2002 | Bös et al. |
| 6,562,847 B1 | 5/2003 | Lee |
| 6,569,847 B1 | 5/2003 | Singh et al. |
| 6,593,330 B2 | 7/2003 | Nilsson |
| 6,596,773 B2 | 7/2003 | Bös et al. |
| 6,610,677 B2 | 8/2003 | Davies et al. |
| 6,613,776 B2 | 9/2003 | Knegtel et al. |
| 2002/0151712 A1 | 10/2002 | Lin et al. |
| 2004/0204386 A1 | 10/2004 | Bhatt et al. |

FOREIGN PATENT DOCUMENTS

| | | |
|---|---|---|
| EP | 0 937 459 | 1/1999 |
| EP | 1 300 399 | 4/2003 |
| WO | WO 92/04333 | 3/1992 |
| WO | WO 97/00612 | 1/1997 |
| WO | WO 97/13754 | 4/1997 |
| WO | WO 97/41127 | 11/1997 |
| WO | WO 98/12176 | 3/1998 |
| WO | WO 98/12210 | 3/1998 |
| WO | WO 98/23155 | 6/1998 |
| WO | WO 98/23156 | 6/1998 |
| WO | WO 98/28980 | 7/1998 |
| WO | WO 99/12911 | 3/1999 |
| WO | WO 99/28314 | 6/1999 |
| WO | WO 99/41248 | 8/1999 |
| WO | WO 99/51241 | 10/1999 |
| WO | WO 00/59881 | 10/2000 |
| WO | WO 01/05768 | 1/2001 |
| WO | WO 01/07032 | 2/2001 |
| WO | WO 01/07401 | 2/2001 |
| WO | WO 01/14331 | 3/2001 |
| WO | WO 01/19817 | 3/2001 |
| WO | WO 01/42241 | 6/2001 |
| WO | WO 01/53263 | 7/2001 |
| WO | WO 01/54503 | 8/2001 |
| WO | WO 01/74331 | 10/2001 |
| WO | WO 01/76582 | 10/2001 |
| WO | WO 02/00651 | 1/2002 |
| WO | WO 02/16324 | 2/2002 |
| WO | WO 02/18339 | 3/2002 |
| WO | WO 02/26712 | 4/2002 |
| WO | WO 02/32872 | 4/2002 |
| WO | WO 02/36586 | 5/2002 |
| WO | WO 02/50052 | 6/2002 |
| WO | WO 02/079197 | 10/2002 |
| WO | WO 02/080853 | 10/2002 |
| WO | WO 02/088111 | 11/2002 |
| WO | WO 03/006471 | 1/2003 |
| WO | WO 03/028729 | 4/2003 |
| WO | WO 03/029210 | 4/2003 |
| WO | WO 03/041649 | 5/2003 |
| WO | WO 03/049702 | 6/2003 |
| WO | WO 03/093242 | 11/2003 |
| WO | WO 2004/005283 | 1/2004 |
| WO | WO 2004/046133 | 6/2004 |
| WO | WO 2004/065378 | 8/2004 |
| WO | WO 2004/089286 | 10/2004 |

OTHER PUBLICATIONS

Szallasi et al, Journal of Medicinal Chemistry 47(20): 2717-2723, 2004.*
Sakurai et al., JP 10029979, CA 128: 192655, 1998.*
Hemmi et al., WO 96/01825, CA 124;264958, 1996.*
Kitajima et al., JP 03279382, CA 116: 194340, 1992.*
Prachayasittikul et al., Journal of Heterocyclic Chemistry 28(4), 1051-1060, 1991, CA 115: 207817, 1991.*
Kuzuya et al., Chemical & Pharmaceutical Bulletin 33(6), 2313-2322, 1985, CA 104: 68742, 1986.*
Wagner et al., Arch. Pharm., 299(6), 536-544, 1966, CA 65; 90904, 1966.*
Matsuda, et al.; Bioorganic & Medicinal Chemistry Letters, "*Synthesis and Bioactivities of Novel Pyridazine Derivatives: Inhibitors of Interleukin-1 Beta (IL-1B) Production*" 11, 2369-2372 (2001).
Lee, et al., N-(3-Acloxy-2-benzylpropyl)-N-[4-{methylsufonylamino)benzyl]thiourea Analogues: Novel Potent and High Affinity Antagonists and Partial Antagonists of the Vanilloid Receptor, J Med. Chem., 46: 3116-3126 (2003).

* cited by examiner

VANILLOID RECEPTOR LIGANDS AND THEIR USE IN TREATMENTS

This application is a division of application Ser. No. 10/638,009, filed Aug. 8, 2003, now U.S. Pat. No. 7,144,888, which claims benefit of US Provisional Application No. 60/402,422, filed Aug. 8, 2002, which are hereby incorporated by reference.

BACKGROUND

The vanilloid receptor 1 (VR1) is the molecular target of capsaicin, the active ingredient in hot peppers. Julius et al. reported the molecular cloning of VR1 (Caterina et al., 1997). VR1 is a non-selective cation channel which is activated or sensitized by a series of different stimuli including capsaicin and resiniferatoxin (exogenous activators), heat & acid stimulation and products of lipid bilayer metabolism, anandamide (Premkumar et al., 2000, Szabo 75 et al., 2000, Gauldie et al., 2001, Olah et al., 2001) and lipoxygenase metabolites (Hwang et al., 2000). VR1 is highly expressed in primary sensory neurons (Caterina et al., 1997) in rats, mice and humans (Onozawa et al., 2000, Mezey et al., 2000, Helliwell et al., 1998, Cortright et al., 2001). These sensory neurons innervate many visceral organs including the dermis, bones, bladder, gastrointestinal tract and lungs; VR1 is also expressed in other neuronal and non-neuronal tissues including but not limited to, CNS nuclei, kidney, stomach and T-cells (Nozawa et al., 2001, Yiangou et al., 2001, Birder et al., 2001). Presumably expression in these various cells and organs may contribute to their basic properties such as cellular signaling and cell division.

Prior to the molecular cloning of VR1, experimentation with capsaicin indicated the presence of a capsaicin sensitive receptor, which could increase the activity of sensory neurons in humans, rats and mice (Holzer, 1991; Dray, 1992, Szallasi and Blumberg 1996, 1999). The results of acute activation by capsaicin in humans was pain at injection site and in other species increased behavioral sensitivity to sensory stimuli (Szallasi and Blumberg, 1999). Capsaicin application to the skin in humans causes a painful reaction characterized not only by the perception of heat and pain at the site of administration but also by a wider area of hyperalgesia and allodynia, two characteristic symptoms of the human condition of neuropathic pain (Holzer, 1991). Taken together, it seems likely that increased activity of VR1 plays a significant role in the establishment and maintenance of pain conditions. Topical or intradermal injection of capsaicin has also been shown to produce localized vasodilation and edema production (Szallasi and Blumberg 1999, —Singh et al., 2001). This evidence indicates that capsaicin through it's activation of VR1 can regulate afferent and efferent function of sensory nerves. Sensory nerve involvement in diseases could therefore be modified by molecules which effect the function of the vanilloid receptor to increase or decrease the activity of sensory nerves.

VR1 gene knockout mice have been shown to have reduced sensory sensitivity to thermal and acid stimuli (Caterina et al., 2000)). This supports the concept that VR1 contributes not only to generation of pain responses (i.e. via thermal, acid or capsaicin stimuli) but also to the maintenance of basal activity of sensory nerves. This evidence agrees with studies demonstrating capsaicin sensitive nerve involvement in disease. Primary sensory nerves in humans and other species can be made inactive by continued capsaicin stimulation. This paradigm causes receptor activation induced desensitization of the primary sensory nerve—such reduction in sensory nerve activity in vivo makes subjects less sensitive to subsequent painful stimuli. In this regard both capsaicin and resiniferatoxin (exogenous activators of VR1), produce desensitization and they have been used for many proof of concept studies in in vivo models of disease (Holzer, 1991, Dray 1992, Szallasi and Blumberg 1999).

Bibliography

Birder-L A. Kanai-A J. de-Groat-W C. Kiss-S. Nealen-M L. Burke-N E. Dineley-K E. Watkins-S. Reynolds-I J. Caterina-M J. (2001) Vanilloid receptor expression suggests a sensory role for urinary bladder epithelial cells. PNAS 98: 23: 13396-13401.

Caterina, M. J, Schumacher, M. A., Tominaga, M., Rosen, T. A., Levine, J. D., and Julius, D, (1997). The capsaicin receptor: a heat-activated ion channel in the pain pathway. Nature 389: 816-824.

Caterina-M J. Leffler-A. Malmberg-A B. Martin-W J. Trafton-J. Petersen-Zeitz K R. Koltzenburg-M. Basbaum-A I. Julius-D (2000) Impaired nociception and pain sensation in mice lacking the capsaicin receptor. Science-(WASH-DC). 288: 5464: 306-313.

Cortright-D N. Crandall-M. Sanchez-J F. Zou-T. Krause-J E. White-G (2001) The tissue distribution and functional characterization of human VR1. Biochemical and Biophysical Research Communications 281: 5: 1183-1189

Dray, A., (1992). Therapeutic potential of capsaicin-like molecules. Life Sciences 51: 1759-1765.

Gauldie-S D. McQueen-D S. Pertwee-R. Chessell-I P. (2001) Anandamide activates peripheral nociceptors in normal and arthritic rat knee joints. British Journal of Pharmacology 132: 3: 617-621.

Helliwell-R J A. McLatchie-L M. Clarke-M. Winter-J. Bevan-S.

McIntyre-P (1998) Capsaicin sensitivity is associated with expression of the vanilloid (capsaicin) receptor (VR1) mRNA in adult rat sensory ganglia. Neuroscience Lett. 250: 3: 177-180.

Holzer, P. (1991) Capsaicin: Cellular targets, Mechanisms of Action and selectivity for thin sensory neurons. Pharmacological reviews 43: 2: 143-201

Hwang-S W. Cho-H. Kwak-J. Lee-S Y. Kang-C J. Jung-J. Cho-S. Min-K H. Suh-Y G. Kim-D. Oh-U. (2000) Direct activation of capsaicin receptors by products of lipoxygenases: Endogenous capsaicin-like substances. PNAS 97: 11: 6155-6160.

Mezey-E. Toth-Z E. Cortright-D N. Arzubi-M K. Krause-J E. Elde-R.

Guo-A. Blumberg-P M. Szallasi-A (2000) Distribution of mRNA for vanilloid receptor subtype 1 (VR1), and VR1-like immunoreactivity, in the central nervous system of the rat and human. PNAS 97: 7: 3655-3660.

Nozawa-Y. Nishihara-K. Yamamoto-A. Nakano-M. Ajioka-H.

Matsuura-N. (2001) Distribution and characterization of vanilloid receptors in the rat stomach. Neuroscience Letters 309: 1: 33-36.

Olah-Z. Karai-L. Iadarola-M J. (2001) Anandamide activates vanilloid receptor 1 (VR1) at acidic pH in dorsal root ganglia neurons and cells ectopically expressing VR1. Journal of Biological Chemistry 276: 33, 31163-31170.

Onozawa-K. Nakamura-A. Tsutsumi-S. Yao-J. Ishikawa-R. Kohama-K. (2000) Tissue distribution of capsaicin receptor in the various organs of rats. Proc. Jpn. Acad. Ser. B, Phys.-Biol. Sci. 76: 5: 68-72.

Premkumar-L S. Ahern-G P. (2000) Induction of vanilloid receptor channel activity by protein kinase C. Nature (London) 408: 6815: 985-990.

Singh-L K. Pang-X. Alexacos-N. Letourneau-R. Theoharides-T C. (1999) Acute immobilization stress triggers skin mast cell degranulation via corticotropin releasing hormone, neurotensin, and substance P: A link to neurogenic skin disorders. Brain Behav. Immun. 13: 3: 225-239.

Szallasi, A. Blumberg-P M (1996) Vanilloid receptors: New insights enhance potential as a therapeutic target. Pain 68: 195-208

Szallasi-A. Blumberg-P M. (1999) Vanilloid (capsaicin) receptors and mechanisms. Pharmacol. Rev. 51: 2: 159-211.

Szabo-T. Wang-J. Gonzalez-A. Kedei-N. Lile-J. Treanor-J. Blumberg-P M. (2000) Pharmacological characterization of the human vanilloid receptor type-1 (hVR1). Society for Neuroscience Abstracts. 26:1-2: 634.18.

Tominaga, M., Caterina, M. J., Malmberg, A. B., Rosen, T. A., Gilbert, H., Skinner, K., Raumann, B. E., Basbaum, A. I., and Julius, D., (1998). The cloned capsaicin receptor integrates multiple pain-producing stimuli. Neuron 21: 531-543.

Yiangou-Y. Facer-P. Dyer-N H C. Chan-C L H. Knowles-C. Williams-N S. Anand-P. (2001) Vanilloid receptor 1 immunoreactivity in inflamed human bowel. Lancet (North American Edition) 357: 9265: 1338-1339.

Yiangou-Y. Facer-P. Ford-A. Brady-C. Wiseman-O. Fowler-CJ.

Anand-P. (2001) Capsaicin receptor VR1 and ATP-gated ion channel P2X3 in human urinary bladder. BJU International 87: 9: 774-779.

Wang-H. Bian-D. Zhu-D. Zajic-G. Loeloff-R. Lile-J. Wild-K. Treanor-J.

Curran-E. (2000) Inflammation-induced upregulation of VR1 in rat spinal cord and DRG correlates with enhanced nociceptive processing. Society for Neuroscience Abstracts 26:1-2: 632.15.

SUMMARY

The present invention comprises a new class of compounds useful in the treatment of diseases, such as vanilloid-receptor-mediated diseases and other maladies, such as inflammatory or neuropathic pain and diseases involving sensory nerve function such as asthma, rheumatoid arthritis, osteoarthritis, inflammatory bowel disorders, urinary incontinence, migraine and psoriasis. In particular, the compounds of the invention are useful for the treatment of acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders. Accordingly, the invention also comprises pharmaceutical compositions comprising the compounds, methods for the treatment of vanilloid-receptor-mediated diseases, such as inflammatory or neuropathic pain, asthma, rheumatoid arthritis, osteoarthritis, inflammatory bowel disorders, urinary incontinence, migraine and psoriasis diseases, using the compounds and compositions of the invention, and intermediates and processes useful for the preparation of the compounds of the invention.

The compounds of the invention are represented by the following general structure:

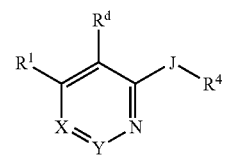

or a pharmaceutically acceptable salt thereof, wherein J, $R^1$, $R^4$, $R^d$, X and Y are defined below.

The foregoing merely summarizes certain aspects of the invention and is not intended, nor should it be construed, as limiting the invention in any way. All patents, patent applications and other publications recited herein are hereby incorporated by reference in their entirety.

DETAILED DESCRIPTION

One aspect of the current invention relates to compounds having the general structure:

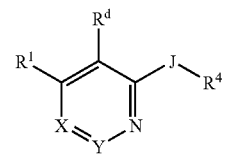

or any pharmaceutically-acceptable salt thereof, wherein:

J is O or S;

X is N or $=C(R^2)$;

Y is N or $=C(R^3)$, wherein at least one of X and Y is not N;

n is independently, at each instance, 0, 1 or 2.

$R^1$ is

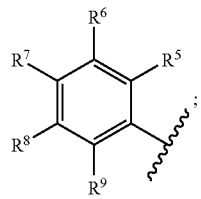

or $R^1$ is $R^b$ substituted by 1, 2 or 3 substituents independently selected from $R^f$, $R^g$, halo, nitro, cyano, —$OR^e$, —$OR^g$, —$OC_{2-6}$alkyl$NR^aR^f$, —$OC_{2-6}$alkyl$OR^f$, —$NR^aR^f$, —$NR^aR^g$, —$NR^fC_{2-6}$alkyl$NR^aR^f$, —$NR^fC_{2-6}$alkyl$OR^f$, naphthyl, —$CO_2R^e$, —$C(=O)R^e$, —$C(=O)NR^aR^f$, —$C(=O)NR^aR^g$, —$NR^fC(=O)R^e$, —$NR^fC(=O)R^g$, —$NR^fC(=O)NR^aR^f$, —$NR^fCO_2R^e$, —$C_{1-8}$alkyl$OR^f$, —$C_{1-6}$alkyl$NR^aR^f$, —$S(=O)_nR^e$, —$S(=O)_2NR^aR^f$, —$NR^aS(=O)_2R^e$ and —$OC(=O)NR^aR^f$, and $R^b$ is additionally substituted by 0, 1 or 2 groups independently selected from $R^c$; or $R^1$ is phenyl that is vicinally fused with a saturated or unsaturated 3-, 4- or 5-atom bridge containing 0, 1, 2 or 3 atoms selected from O, N and S with the remaining atoms being carbon, so long as the combination of O and S atoms is not greater than 2, wherein the heterocycle and bridge are substituted by 0, 1, 2 or 3 substituents independently selected from $R^5$;

$R^2$ is, independently, in each instance, $R^{14}$, halo, $C_{1-8}$alkyl substituted by 0, 1 or 2 substituents selected from $R^{14}$, halo, —$(CH_2)_n$phenyl substituted by 0, 1, 2 or 3 substituents independently selected from $R^{14}$ and halo, or a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the heterocycle or fused phenyl ring is substituted by 0, 1, 2 or 3 substituents independently selected from $R^{14}$ and halo; or $R^2$ is —$OR^4$ or —$N(R^a)R^4$;

$R^3$ is, independently, in each instance, H, halo, —$NH_2$, —$NHC_{1-3}$alkyl, —$N(C_{1-3}$alkyl$)C_{1-3}$alkyl, or $C_{1-3}$alkyl; wherein, when X is $C(R^2)$ and Y is $C(R^3)$ then at least one of $R^2$ and $R^3$ is other than H;

$R^4$ is independently at each instance

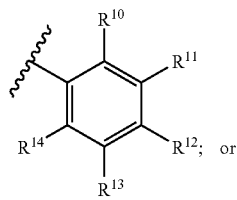

$R^4$ is independently at each instance a saturated or unsaturated 5- or 6-membered ring heterocycle containing 1, 2 or 3 atoms selected from O, N and S that is optionally vicinally fused with a saturated or unsaturated 3-, 4- or 5-atom bridge containing 0, 1, 2 or 3 atoms selected from O, N and S with the remaining atoms being carbon, so long as the combination of O and S atoms is not greater than 2, wherein the heterocycle and bridge are substituted by 0, 1, 2 or 3 substituents independently selected from $R^e$, $C_{1-4}$haloalkyl, halo, cyano, oxo, thioxo, —$OR^f$, —$S(=O)_nR^e$, —$OC_{1-4}$haloalkyl, —$OC_{2-6}$alkyl$NR^aR^f$, —$OC_{2-6}$alkyl$OR^f$, —$OC_{1-6}$alkyl$C(=O)OR^e$, —$NR^aR^f$, —$NR^aC_{1-4}$haloalkyl, —$NR^aC_{2-6}$alkyl$NR^aR^f$, —$NR^aC_{2-6}$alkyl$OR^f$, —$C(=O)R^e$, —$C(=O)OR^f$, —$OC(=O)R^e$, —$C(=O)NR^aR^f$ and —$NR^aC(=O)R^e$; or $R^4$ is independently at each instance naphthyl substituted by 1, 2 or 3 substituents independently selected from $C_{1-4}$haloalkyl, halo, nitro, cyano, —$S(=O)_nR^e$, —$OC_{1-4}$haloalkyl, —$OC_{2-6}$alkyl$NR^aR^f$, —$OC_{2-6}$alkyl$OR^f$, —$OC_{1-6}$alkyl$C(=O)OR^e$, —$NR^aC_{1-4}$haloalkyl, —$NR^aC_{2-6}$alkyl$NR^aR^f$, —$NR^aC_{2-6}$alkyl$OR^f$, —$C(=O)R^e$, —$C(=O)OR^f$, —$OC(=O)R^e$ and —$C(=O)NR^aR^f$; but in no instance is $R^4$-phenyl-$(C_{1-8}$alkyl), -phenyl-O-$(C_{1-8}$alkyl), -phenyl-$NR^aR^a$ or -phenyl-$N(R^a)C(=O)(C_{1-8}$alkyl);

$R^5$ is independently, at each instance, $R^f$, $R^h$, halo, nitro, cyano, —$OR^f$, —$OR^h$, —$OC_{2-6}$alkyl$NR^aR^f$, —$OC_{2-6}$alkyl$OR^f$, —$NR^aR^f$, —$NR^aR^h$, —$NR^fC_{2-6}$alkyl$NR^aR^f$, —$NR^fC_{2-6}$alkyl$OR^f$, naphthyl, —$CO_2R^e$, —$C(=O)R^e$, —$OC(=O)R^e$, —$C(=O)NR^aR^f$, —$C(=O)NR^aR^h$, —$NR^fC(=O)R^e$, —$NR^fC(=O)R^h$, —$NR^fC(=O)NR^aR^f$, —$NR^fCO_2R^e$, —$C_{1-8}$alkyl$OR^f$, —$C_{1-6}$alkyl$NR^aR^f$, —$S(=O)_nR^e$, —$S(=O)_2NR^aR^f$, —$NR^aS(=O)_2R^e$, —$OS(=O)_2R^e$, —$OC(=O)NR^aR^f$, —$OR^h$, —$OC_{2-6}$alkyl$NR^aR^h$, —$OC_{2-6}$alkyl$OR^h$, —$NR^aR^h$, —$NR^fC_{2-6}$alkyl$NR^aR^h$, —$NR^hC_{2-6}$alkyl$NR^aR^f$, —$NR^hC_{2-6}$alkyl$OR^f$, —$NR^fC_{2-6}$alkyl$OR^h$, —$CO_2R^h$, —$OC(=O)R^h$, —$C(=O)R^h$, —$C(=O)NR^aR^h$, —$NR^fC(=O)R^h$, —$NR^hC(=O)R^f$, —$NR^hC(=O)NR^aR^f$, —$NR^fC(=O)NR^aR^h$, —$NR^hCO_2R^e$, —$NR^fCO_2R^h$, —$C_{1-8}$alkyl$OR^h$, —$C_{1-6}$alkyl$NR^aR^h$, —$S(=O)_nR^h$, —$S(=O)_2NR^aR^h$, —$NR^aS(=O)_2R^h$, —$NR^hS(=O)_2R^e$, —$OS(=O)_2R^h$ or —$OC(=O)NR^aR^h$;

$R^6$ is independently, at each instance, H, $C_{1-5}$alkyl, $C_{1-4}$haloalkyl, halo, nitro —$OR^e$, —$OC_{2-6}$alkyl$NR^aR^a$, —$OC_{2-6}$alkyl$OR^a$, —$NR^aR^a$, —$NR^aC_{1-4}$haloalkyl, —$NR^aC_{2-6}$alkyl$NR^aR^a$ or —$NR^aC_{2-6}$alkyl$OR^a$, —$C_{1-8}$alkyl$OR^a$, —$C_{1-6}$alkyl$NR^aR^a$, —$S(C_{1-6}$alkyl), a phenyl ring substituted with 1, 2, or 3 substituents independently selected from $R^{14}$ and halo; or $R^6$ is a saturated or unsaturated 5- or 6-membered ring heterocycle containing 1, 2 or 3 atoms selected from O, N and S substituted with 0, 1, 2, or 3 substituents independently selected from $R^{14}$ and halo;

$R^7$ is independently, at each instance, H, $C_{1-8}$alkyl, $C_{1-4}$haloalkyl, halo, cyano, —$OC_{1-6}$alkyl, —$OC_{1-4}$haloalkyl, —$OC_{2-6}$alkyl$NR^aR^a$, —$OC_{2-6}$a $OR^a$, —$NR^aR^a$, —$NR^aC_{1-4}$haloalkyl, —$NR^aC_{2-6}$alkyl$NR^aR^a$, —$NR^aC_{2-6}$alkyl$OR^a$, —$C_{1-8}$alkyl$OR^a$, —$C_{1-6}$alkyl$NR^aR^a$ or —$S(C_{1-6}$alkyl); or $R^7$ is a saturated or unsaturated 4- or 5-membered ring heterocycle containing a single nitrogen atom, wherein the ring is substituted with 0, 1 or 2 substituents independently selected from halo, $C_{1-2}$haloalkyl and $C_{1-3}$alkyl;

$R^8$ is independently, at each instance, H, $C_{1-5}$alkyl, $C_{1-4}$haloalkyl, halo, nitro, —$OC_{1-6}$alkyl, —$OC_{1-4}$haloalkyl, —$OC_{2-6}$alkyl$NR^aR^a$, —$OC_{2-6}$alkyl$OR^a$, —$NR^aR^a$, —$NR^aC_{1-4}$haloalkyl, —$NR^aC_{2-6}$alkyl$NR^aR^a$, —$NR^aC_{1-8}$akyl$OR^a$, —$C_{1-6}$alkyl$NR^aR^a$, —$S(C_{1-6}$alkyl), a phenyl ring substituted with 1, 2, or 3 substituents independently selected from $R^{14}$ and halo, or $R^8$ is a saturated or unsaturated 5- or 6-membered ring heterocycle containing 1, 2 or 3 atoms selected from O, N and S substituted with 0, 1, 2, or 3 substituents independently selected from $R^{14}$ and halo;

$R^9$ is independently, at each instance, $R^f$, $R^h$, halo, nitro, cyano, —$OR^f$, —$OR^h$, —$OC_{2-6}$alkyl$NR^aR^f$, —$OC_{2-6}$alkyl$OR^f$, —$NR^aR^f$, —$NR^aR^h$, —$NR^fC_{2-6}$alkyl$NR^aR^f$, —$NR^fC_{2-6}$alkyl$OR^f$, naphthyl, —$CO_2R^e$, —$OC(=O)R^e$, —$C(=O)R^e$, —$C(=O)NR^aR^f$, —$C(=O)NR^aR^h$, —$NR^fC(=O)R^e$, —$NR^fC(=O)R^h$, —$NR^fC(=O)NR^aR^f$, —$NR^fCO_2R^e$, —$C_{1-8}$alkyl$OR^f$, —$C_{1-6}$alkyl$NR^aR^f$, —S(=O)$_n$R$^e$, —S(=O)$_2$NR$^a$R$^f$, —NR$^a$S(=O)$_2$R$^e$, —OS(=O)$_2$R$^e$, —OC(=O)NR$^a$R$^f$, —OR$^h$, —OC$_{2-6}$alkylNR$^a$R$^h$, —OC$_{2-6}$alkylOR$^h$, —NR$^a$R$^h$, —NR$^f$C$_{2-6}$alkylNR$^a$R$^h$, —NR$^h$C$_{2-6}$alkylNR$^a$R$^f$, —NR$^h$C$_{2-6}$alkylOR$^f$, —NR$^f$C$_{2-6}$alkylOR$^h$, —CO$_2$R$^h$, —OC(=O)R$^h$, —C(=O)R$^h$, C(=O)NR$^a$R$^h$, —NR$^f$C(=O)R$^h$, —NR$^h$C(=O)R$^f$, —NR$^h$C(=O)NR$^a$R$^f$, —NR$^f$C(=O)NR$^a$R$^h$, —NR$^h$CO$_2$R$^e$, —NR$^f$CO$_2$R$^h$, —C$_{1-8}$alkylOR$^h$, —C$_{1-6}$alkylNR$^a$R$^h$, —S(=O)$_n$R$^h$, —S(=O)$_2$NR$^a$R$^h$, —NR$^a$S(=O)$_2$R$^h$, —NR$^h$S(=O)$_2$R$^e$, —OS(=O)$_2$R$^h$ or —OC(=O)NR$^a$R$^h$; or R$^9$ is a saturated or unsaturated 4- or 5-membered ring heterocycle containing a single nitrogen atom, wherein the ring is substituted with 0, 1 or 2 substituents independently selected from halo, C$_{1-2}$haloalkyl and C$_{1-3}$alkyl;

wherein at least one of R$^5$, R$^6$, R$^7$, R$^8$ and R$^9$ is R$^e$, R$^h$, halo, nitro, cyano, —OR$^h$, —NR$^a$R$^f$, —NR$^a$R$^h$, —NR$^f$C$_{2-6}$alkylNR$^a$R$^f$, —NR$^f$C$_{2-6}$alkylOR$^f$, naphthyl, —CO$_2$R$^e$, —C(=O)R$^e$, —OC(=O)R$^e$, —C(=O)NR$^a$R$^f$, —C(=O)NR$^a$R$^f$, —NR$^f$C(=O)R$^e$, —NR$^f$C(=O)R$^h$, —NR$^f$C(=O)NR$^a$R$^f$, —NR$^f$CO$_2$R$^e$, —C$_{1-8}$alkylOR$^f$, —C$_{1-6}$alkylNR$^a$R$^f$, —S(=O)$_n$R$^e$, —S(=O)$_2$NR$^a$R$^f$, —NR$^a$S(=O)$_2$R$^e$, —OS(=O)$_2$R$^e$, —OC(=O)NR$^a$R$^f$, —OR$^h$, —OC$_{2-6}$alkylNR$^a$R$^h$, —OC$_{2-6}$alkylOR$^h$, —NR$^a$R$^h$, —NR$^f$C$_{2-6}$alkylNR$^a$R$^h$, —NR$^h$C$_{2-6}$alkylNR$^a$R$^f$, —NR$^h$C$_{2-6}$alkylOR$^f$, —NR$^f$C$_{2-6}$alkylOR$^h$, —CO$_2$R$^h$, —OC(=O)R$^h$, —C(=O)R$^h$, —C(=O)NR$^a$R$^h$, —NR$^f$C(=O)R$^h$, —NR$^h$C(=O)R$^f$, —NR$^h$C(=O)NR$^a$R$^f$, —NR$^f$C(=O)NR$^a$R$^h$, —NR$^h$CO$_2$R$^e$, —NR$^f$CO$_2$R$^h$, —C$_{1-8}$alkylOR$^h$, —C$_{1-6}$alkylNR$^a$R$^h$, —S(=O)$_n$R$^h$, —S(=O)$_2$NR$^a$R$^h$, —NR$^a$S(=O)$_2$R$^h$, —NR$^h$S(=O)$_2$R$^e$, —OS(=O)$_2$R$^h$, —OC(=O)NR$^a$R$^h$, or —OC$_{1-8}$alkyl substituted by 1, 2 or 3 substituents independently selected from R$^f$, R$^h$, halo, nitro, cyano, —OR$^f$, —OR$^h$, —OC$_{2-6}$alkylNR$^a$R$^f$, —OC$_{2-6}$alkylOR$^f$, —NR$^a$R$^f$, —NR$^a$R$^h$, —NR$^f$C$_{2-6}$alkylNR$^a$R$^f$, —NR$^f$C$_{2-6}$alkylOR$^f$, naphthyl, —CO$_2$R$^e$, —OC(=O)R$^e$, —C(=O)R$^e$, —C(=O)NR$^a$R$^f$, —C(=O)NR$^a$R$^h$, —NR$^f$C(=O)R$^e$, —NR$^f$C(=O)R$^h$, —NR$^f$C(=O)NR$^a$R$^f$, —NR$^f$CO$_2$R$^e$, —C$_{1-8}$alkylOR$^f$, —C$_{1-6}$alkylNR$^a$R$^f$, —S(=O)$_n$R$^e$, —S(=O)$_2$NR$^a$R$^f$, —NR$^a$S(=O)$_2$R$^e$, —OS(=O)$_2$R$^e$, —OC(=O)NR$^a$R$^f$, —OR$^h$, —OC$_{2-6}$alkylNR$^a$R$^h$, —OC$_{2-6}$alkylOR$^h$, —NR$^a$R$^h$, —NR$^f$C$_{2-6}$alkylNR$^a$R$^h$, —NR$^h$C$_{2-6}$NR$^a$R$^f$, —NR$^h$C$_{2-6}$alkylOR$^f$, —NR$^f$C$_{2-6}$alkylOR$^h$, —CO$_2$R$^h$, —OC(=O)R$^h$, —C(=O)R$^h$, —C(=O)NR$^a$R$^h$, —NR$^f$C(=O)R$^h$, —NR$^h$C(=O)R$^f$, —NR$^h$C(=O)NR$^a$R$^f$, —NR$^f$C(=O)NR$^a$R$^h$, —NR$^h$CO$_2$R$^e$, —NR$^f$CO$_2$R$^h$, —C$_{1-8}$alkylOR$^h$, —C$_{1-6}$alkylNR$^a$R$^h$, —S(=O)$_n$R$^h$, —S(=O)$_2$NR$^a$R$^h$, —NR$^a$S(=O)$_2$R$^h$, —NR$^h$S(=O)$_2$R$^e$, —OS(=O)$_2$R$^h$ and —OC(=O)NR$^a$R$^h$;

R$^{10}$ is independently, at each instance, selected from H, C$_{1-5}$alkyl, C$_{1-4}$haloalkyl, cyano, nitro, —C(=O)R$^e$, —C(=O)OR$^f$, —C(=O)NR$^a$R$^f$, —C(=NR$^a$)R$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^{af}$, —N(R$^a$)C(=NR$^a$)NR$^a$R, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^e$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; or R$^{10}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein there are no more than 2 N atoms, wherein the ring is substituted by 0, 1 or 2 oxo or thioxo groups, wherein the ring is substituted by 0, 1, 2 or 3 groups selected from R$^e$, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$—S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$F$^f$, —NR$^a$C$_{2-6}$alkylNR$^a$R$^h$, —NR$^h$C$_{2-6}$alkylOR$^f$ and —NR$^a$C$_{2-6}$alkylOR$^h$; or R$^{10}$ is C$_{1-4}$alkyl substituted by 0, 1, 2 or 3 groups selected from C$_{1-4}$haloalkyl, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$akylNR$^a$R$^h$, —NR$^h$C$_{2-6}$alkylOR$^f$ and —NR$^a$C$_{2-6}$alkylOR$^h$;

R$^{11}$ is independently, at each instance, selected from H, C$_{1-8}$alkyl, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; or R$^{11}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is substituted by 0, 1 or 2 oxo or thioxo groups, wherein the ring is substituted by 0, 1, 2 or 3 groups selected from R$^e$, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$-OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; or R$^{11}$ is C$_{1-4}$alkyl substituted by 0, 1, 2 or 3 groups selected from C$_{1-4}$haloalkyl, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$) C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$) C(=NR$^a$)NR$^a$R$^h$, —N(R$^h$)S(=O)$_2$R$^e$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; or R$^{10}$ and R$^{11}$ together are a saturated or unsaturated 3-, 4- or 5-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from oxo, thioxo, R$^c$, R$^e$, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^l$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylO$^f$ and —NR$^a$C$_{2-6}$alylOR$^h$; and when R$^{10}$ and R$^{11}$ together form a bridge, R$^{12}$ may additionally be halo or —CF$_3$, R$^{13}$ may additionally be halo or —OR$^a$ or cyano or nitro, and R$^{14}$ may additionally be halo;

R$^{12}$ is independently, at each instance, selected from H, C$_{1-8}$alkyl, cyano, nitro, —C(=O)R$^e$, —C(=O)OR$^f$, —C(=O)NR$^a$R$^f$, —C(=NR$^a$)NR$^a$R$^f$, —OR$^f$, —OC(=O) R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O) R$^e$, —N(R$^a$)C(=O)OR$^f$, —N(R$^a$)C(=O)NR$^a$R$^f$ —N(R$^a$)C (=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)OR$^h$, —C(=O) NR$^a$R$^h$, —C(=NR$^a$)NR$^a$R$^h$, —OR$^h$, —OC(=O)R$^h$, —OC (=O)NR$^a$R$^h$, —OC(=O)N(R$^a$)S(=O)$_2$R$^h$, —OC(=O) (NR$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$^2$N(R$^h$)C(=O)NR$^a$R$^f$, —S(=O)$_2$N(R$^a$)C(=O) NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O) NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S (=O)$_2$R$^h$, —N(R$^h$)S(=O)$_2$NR$^a$R$^f$, —N(R$^a$)S(=O)$_2$ NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; or R$^{12}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is substituted by 0, 1 or 2 oxo or thioxo groups, wherein the ring is substituted by 0, 1, 2 or 3 groups selected from R$^e$, halo, cyano, nitro, —C(=O)R$^e$, —C(=O)OR$^e$, —C(=O) NR$^a$R$^f$, —C(=NR$^a$)NR$^a$R$^f$, —OR$^f$, —OC(=O)R$^e$, —OC (=O)NR$^a$R$^f$, —OC(=O)N(R$^a$)S(=O)$_2$R$^e$, —OC$_{2-6}$alkylN-R$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N (R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O) NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$ alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O) NR$^a$R$^h$, —OC(=O)N(R$^a$)S(=O)$_2$R$^h$, —OC(=O)N(R$^h$)S (=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N (R$^h$)C(=O)R$^e$, —S(=O)$_2$N(R$^a$)C(=O)R$^h$, —S(=O)$_2$N (R$^h$)C(=O)OR$^f$, —S(=O)$_2$N(R$^a$)C(=O)OR$^h$, —S(=O)$_2$N (R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$) C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$) C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$ alkylOR$^f$ and —NR$^a$C$_{2-6}$alkylOR$^h$; or R$^{12}$ is C$_{1-4}$alkyl substituted by 0, 1, 2 or 3 groups selected from C$_{1-4}$haloalkyl, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$ —OC(=O) NR$^a$R$^f$, —OC(=O)N(R$^a$)S(=O)$_2$R$^e$, —OC$_{2-6}$alkYNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N (R$^a$)C(=O)OR$^f$, —S(=O)$_2$N(R$^a$)C(=O)NR$^a$R$^f$, —NR$^a$R$^f$, —N(R$^a$)C(=O)OR$^f$, —N(R$^a$)C(=O)OR$^f$, —N(R$^a$)C(=O) NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$ alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O) NR$^a$R$^h$, —OC(=O)N(R$^a$)S(=O)$_2$R$^h$, —OC(=O)N(R$^h$)S (=O)$_2$R$^e$, —OC$_{2-6}$alkylNR$^a$R$^h$, —OC$_{2-6}$alkylOR$^h$, SR$^h$, —S(=O)R$^h$, —S(=O)$_2$R$^h$, —S(=O)$_2$NR$^a$R$^h$, —S(=O)$_2$N (R$^h$)C(=O)R$^e$, —S(=O)$_2$N(R$^a$)C(=O)R$^h$, —S(=O)$_2$N (R$^h$)C(=O)OR$^f$, —S(=O)$_2$N(R$^a$)C(=O)OR$^h$, —S(=O)$_2$N (R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$) C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$) C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$ —NR$^h$C$_{2-6}$ alkylOR$^f$, —NR$^a$C$_{2-6}$alkylOR$^h$, and additionally substituted by 0, 1 or 2 halo groups; or R$^{11}$ and R$^{12}$ together are a saturated or unsaturated 3-, 4- or 5-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from oxo, thioxo, R$^c$, R$^e$, halo, cyano, nitro, —C(=O)R$^e$, —C(=O)OR$^f$, —C(=O) NR$^a$R$^f$, —C(=NR$^a$)NR$^a$R$^f$, —OR$^f$, —OC(=O)R$^e$, —OC (=O)NR$^a$R$^f$, —OC(=O)N(R$^a$)S(=O)$_2$R$^e$, —OC$_{2-6}$alkylN-R$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N (R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$ —N(R$^a$)C(=O) NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$ alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O) NR$^a$R$^h$, —OC(=O)N(R$^a$)S(=O)$_2$R$^h$, —OC(=O)N(R$^h$)S (=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N (R$^h$)C(=O)R$^e$, —S(=O)$_2$N(R$^a$)C(=O)R$^h$, —S(=O)$_2$N (R$^h$)C(=O)OR$^f$, —S(=O)$_2$N(R$^a$)C(=O)OR$^h$, —S(=O)$_2$N (R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$) C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$) C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$ alkylOR$^f$ and —NR$^a$C$_{2-6}$alkylOR$^h$; wherein when R$^3$ is NH$_2$, then —R$^{11}$—R$^{12}$— is not —C=C—C=N— or any substituted version thereof; or R$^{11}$ and R$^{12}$ together are a saturated or partially unsaturated 3-, 4- or 5-carbon bridge, wherein the bridge is substituted by 0, 1 or 2 substituents selected from oxo, thioxo, R$^c$, R$^e$, halo, cyano, nitro, —C(=O)R$^e$, —C(=O)OR$^f$, —C(=O)NR$^a$R$^f$, —C(=NR$^a$) NR$^a$R$^f$, —OR$^f$, —OC(=O)R$^e$, —OC(=O)NR$^a$R$^f$, —OC (=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O) R$^e$, —N(R$^a$)C(=O)OR$^f$, —N(R$^a$)C(=O)NR$^a$R$^f$, —N(R$^a$)C (=NR$^a$)NR$^a$R$^f$, —N(R$^a$)S(=O)$_2$R$^e$, —N(R$^a$)S(=O)$_2$ NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O) NR$^a$R$^h$, —OC(=O)N(R$^a$)S(=O)$_2$R$^h$, —OC(=O)N(R$^h$)S (=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N (R$^h$)C(=O)R$^e$, —S(=O)$_2$N(R$^a$)C(=O)R$^h$, —S(=O)$_2$N (R$^h$)C(=O)OR$^f$, —S(=O)$_2$N(R$^a$)C(=O)OR$^h$, —S(=O)$_2$N (R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)

C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$,     —N(R$^a$)S(=O)$_2$NR$^a$R$^h$, —NR$^h$C$_{2-6}$ alkylNR$^a$R$^f$, —NR$^a$C$_{2-6}$alkylNR$^a$R$^h$, —NR$^h$C$_{2-6}$ alkylOR$^f$ and —NR$^a$C$_{2-6}$alkylOR$^h$; and when R$^{11}$ and R$^{12}$ together form a bridge, R$^{10}$ may additionally be halo, R$^{13}$ may additionally be halo or —OR$^a$ or cyano or nitro, and R$^{14}$ may additionally be halo;

R$^{13}$ is independently, at each instance, selected from H, C$_{1-8}$alkyl, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$N$^a$R$^f$, —NR$^a$C$_{2-6}$alkylNR$^a$R$^f$, —NR$^a$C$_{2-6}$alkylOR$^f$, —C(=O)$_2$R$^h$, —C(O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$ alkylOR$^f$ and —NR$^a$C$_{2-6}$alkylOR$^h$; or R$^{13}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is substituted by 0, 1 or 2 oxo or thioxo groups, wherein the ring is substituted by 0, 1, 2 or 3 groups selected from R$^e$, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^e$)C(=O)NR$^a$R$^h$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$ alkylOR$^f$ and —NR$^a$C$_{2-6}$alkylOR$^h$; or R$^{13}$ is C$_{1-4}$alkyl substituted by 0, 1, 2 or 3 groups selected from C$_{1-4}$haloalkyl, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O) NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=OR$^f$, —S(=O)$_2$N(R$^a$)C(=O)NR$^a$R$^f$, —NR$^a$R$^f$ —N(R$^a$)C(=O)OR$^f$, —N(R$^a$)C(=O) NR$^a$R$^f$, —NR$^a$C$_{2-6}$alkylNR$^a$R$^f$, —NR$^a$C$_{2-6}$ alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O) NR$^a$R$^h$, —OC(=O)N(R$^a$)S(=O)$_2$R$^h$, —OC(=O)N(R$^h$)S (=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$—S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$,     —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$ alkylOR$^f$ and —NR$^a$C$_{2-6}$alkylOR$^h$;

R$^{14}$ is independently, at each instance, selected from H, C$_{1-5}$alkyl, C$_{1-4}$haloalkyl, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkyNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$—S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$ —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$,     —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$ alkylOR$^f$ and —NR$^a$C$_{2-6}$alkylOR$^h$; or R$^{14}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein there are no more than 2 N atoms, wherein the ring is substituted by 0, 1 or 2 oxo or thioxo groups, wherein the ring is substituted by 0, 1, 2 or 3 groups selected from R$^e$, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O) NR$^a$R$^h$, —OC(=O)N(R$^a$)S(=O)$_2$R$^h$, —OC(=O)N(R$^h$)S (=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N $(R^h)C(=O)R^e$, $-S(=O)_2N(R^a)C(=O)R^h$, $-S(=O)_2N(R^h)C(=O)OR^f$, $-S(=O)_2N(R^a)C(=O)OR^h$, $-S(=O)_2N(R^h)C(=O)NR^aR^f$, $-S(=O)_2N(R^a)C(=O)NR^aR^h$, $-NR^aR^h$, $-N(R^h)C(=O)R^e$, $-N(R^h)C(=O)OR^f$, $-N(R^a)C(=O)OR^h$, $-N(R^h)C(=O)NR^aR^f$, $-N(R^a)C(=O)NR^aR^h$, $-N(R^h)C(=NR^a)NR^aR^f$, $-N(R^a)C(=NR^a)NR^aR^h$, $-N(R^h)S(=O)_2R^e$, $-N(R^a)S(=O)_2R^h$, $-N(R^h)S(=O)_2NR^aR^f$, $-N(R^a)S(=O)_2NR^aR^h$, $-NR^hC_{2-6}alkylNR^aR^f$, $-NR^aC_{2-6}alkylNR^aR^h$, $-NR^hC_{2-6}alkylOR^f$ and $-NR^aC_{2-6}alkylOR^h$; or $R^{14}$ is $C_{1-4}$alkyl substituted by 0, 1, 2 or 3 groups selected from $C_{1-4}$haloalkyl, halo, cyano, nitro, $-C(=O)R^e$, $-C(=O)NR^aR^f$, $-C(=NR^a)NR^aR^f$, $-OR^f$, $-OC(=O)R^e$, $-OC(=O)NR^aR^f$, $-OC(=O)N(R^a)S(=O)_2R^e$, $-OC_{2-6}alkylNR^aR^f$, $-OC_{2-6}alkylOR^f$, $-SR^e$, $-S(=O)R^e$, $-S(=O)_2R^e$, $-S(=O)_2NR^aR^f$, $-S(=O)_2N(R^a)C(=O)R^e$, $-S(=O)_2N(R^a)C(=O)OR^f$, $-S(=O)_2N(R^a)C(=O)NR^aR^f$, $-NR^aR^f$, $-N(R^a)C(=O)R^e$, $-N(R^a)C(=O)OR^f$, $-N(R^a)C(=O)NR^aR^f$, $-N(R^a)C(=NR^a)NR^aR^f$, $-N(R^a)S(=O)_2R^e$, $-N(R^a)S(=O)_2NR^aR^f$, $-NR^aC_{2-6}alkylNR^aR^f$, $-NR^aC_{2-6}alkylOR^f$, $-C(=O)R^h$, $-C(=O)OR^h$, $-C(=O)NR^aR^h$, $-C(=NR^a)NR^aR^h$, $-OR^h$, $-OC(=O)R^h$, $-OC(=O)NR^aR^h$, $-OC(=O)N(R^a)S(=O)_2R^h$, $-OC(=O)N(R^h)S(=O)_2R^e$, $-OC_{2-6}alkylNR^aR^h$, $-OC_{2-6}alkylOR^h$, $-SR^h$, $-S(=O)R^h$, $-S(=O)_2R^h$, $-S(=O)_2NR^aR^h$, $-S(=O)_2N(R^h)C(=O)R^e$, $-S(=O)_2N(R^a)C(=O)R^h$, $-S(=O)_2N(R^h)C(=O)OR^f$, $-S(=O)_2N(R^a)C(=O)OR^h$, $-S(=O)_2N(R^h)C(=O)NR^aR^f$, $-S(=O)_2N(R^a)C(=O)NR^aR^h$, $-NR^aR^h$, $-N(R^h)C(=O)R^e$, $-N(R^a)C(=O)R^h$, $-N(R^h)C(=O)OR^f$, $-N(R^a)C(=O)OR^h$, $-N(R^h)C(=O)NR^aR^f$, $-N(R^a)C(=O)NR^aR^h$, $-N(R^h)C(=NR^a)NR^aR^f$, $-N(R^a)C(=NR^a)NR^aR^h$, $-N(R^h)S(=O)_2R^e$, $-N(R^a)S(=O)_2R^h$, $-N(R^h)S(=O)_2NR^aR^f$, $-N(R^a)S(=O)_2NR^aR^h$, $-NR^hC_{2-6}alkylNR^aR^f$, $-NR^aC_{2-6}alkylNR^aR^h$, $-NR^hC_{2-6}alkylOR^f$ and $-NR^aC_{2-6}alkylOR^h$; wherein at least one of $R^{10}$, $R^{11}$, $R^{12}$, $R^{13}$ and $R^{14}$ is other than H;

$R^a$ is independently, at each instance, H, phenyl, benzyl or $C_{1-6}$alkyl, the phenyl, benzyl and $C_{1-6}$alkyl being substituted by 0, 1, 2 or 3 substituents selected from halo, $C_{1-4}$alkyl, $C_{1-3}$haloalkyl, $-OC_{1-4}$alkyl, $-NH_2$, $-NHC_{1-4}$alkyl, $-N(C_{1-4}$alkyl$)C_{1-4}$alkyl;

$R^b$ is a heterocycle selected from the group of thiophene, pyrrole, 1,3-oxazole, 1,3-thiazol-4-yl, 1,3,4-oxadiazole, 1,3,4-thiadiazole, 1,2,3-oxadiazole, 1,2,3-thiadiazole, 1H-1,2,3-triazole, isothiazole, 1,2,4-oxadiazole, 1,2,4-thiadiazole, 1,2,3,4-oxatriazole, 1,2,3,4-thiatriazole, 1H-1,2,3,4-tetraazole, 1,2,3,5-oxatriazole, 1,2,3,5-thiatriazole, furan, imidazol-2-yl, benzimidazole, 1,2,4-triazole, isoxazole, pyrazol-3-yl, pyrazol-4-yl, pyrazol-5-yl, thiolane, pyrrolidine, tetrahydrofuran, 4,5-dihydrothiophene, 2-pyrroline, 4,5-dihydrofuran, pyridazine, pyrimidine, pyrazine, 1,2,3-triazine, 1,2,4-triazine, 1,3,5-triazine, pyridine, 2H-3,4,5,6-tetrahydropyran, thiane, 1,2-diazaperhydroine, 1,3-diazaperhydroine, piperazine, 1,3-oxazaperhydroine, morpholine, 1,3-thiazaperhydroine, 1,4-thiazaperhydroine, piperidine, 2H-3,4-dihydropyran, 2,3-dihydro-4H-thiin, 1,4,5,6-tetrahydropyridine, 2H-5,6-dihydropyran, 2,3-dihydro-6H-thiin, 1,2,5,6-tetrahydropyridine, 3,4,5,6-tetrahydropyridine, 4H-pyran, 4H-thiin, 1,4-dihydropyridine, 1,4-dithiane, 1,4-dioxane, 1,4-oxathiane, 1,2-oxazolidine, 1,2-thiazolidine, pyrazolidine, 1,3-oxazolidine, 1,3-thiazolidine, imidazolidine, 1,2,4-oxadiazolidine, 1,3,4-oxadiazolidine, 1,2,4-thiadiazolidine, 1,3,4-thiadiazolidine, 1,2,4-triazolidine, 2-imidazolin-1-yl, 2-imidazolin-2-yl, 3-imidazoline, 2-pyrazoline, 4-imidazoline, 2,3-dihydroisothiazole, 4,5-dihydroisoxazole, 4,5-dihydroisothiazole, 2,5-dihydroisoxazole, 2,5-dihydroisothiazole, 2,3-dihydroisoxazole, 4,5-dihydrooxazole, 2,3-dihydrooxazole, 2,5-dihydrooxazole, 4,5-dihydrothiazole, 2,3-dihydrothiazole, 2,5-dihydrothiazole, 1,3,4-oxathiazolidine, 1,4,2-oxathiazolidine, 2,3-dihydro-1H-[1,2,3]triazole, 2,5-dihydro-1H-[1,2,3]triazole, 4,5-dihydro-1H-[1,2,3]triazol-1-yl, 4,5-dihydro-1H-[1,2,3]triazol-3-yl, 4,5-dihydro-1H-[1,2,3]triazol-5-yl, 2,3-dihydro-1H-[1,2,4]triazole, 4,5-dihydro-1H-[1,2,4]triazole, 2,3-dihydro-[1,2,4]oxadiazole, 2,5-dihydro-[1,2,4]oxadiazole, 4,5-dihydro-[1,2,4]thiadiazole, 2,3-dihydro-[1,2,4]thiadiazole, 2,5-dihydro-[1,2,4]thiadiazole, 4,5-dihydro-[1,2,4]thiadiazole, 2,5-dihydro-[1,2,4]oxadiazole, 2,3-dihydro-[1,2,4]oxadiazole, 4,5-dihydro-[1,2,4]oxadiazole, 2,5-dihydro-[1,2,4]thiadiazole, 2,3-dihydro-[1,2,4]thiadiazole, 4,5-dihydro-[1,2,4]thiadiazole, 2,3-dihydro-[1,3,4]oxadiazole, 2,3-dihydro-[1,3,4]thiadiazole, [1,4,2]oxathiazole, [1,3,4]oxathiazole, 1,3,5-triazaperhydroine, 1,2,4-triazaperhydroine, 1,4,2-dithiazaperhydroine, 1,4,2-dioxazaperhydroine, 1,3,5-oxadiazaperhydroine, 1,2,5-oxadiazaperhydroine, 1,3,4-thiadiazaperhydroine, 1,3,5-thiadiazaperhydroine, 1,2,5-thiadiazaperhydroine, 1,3,4-oxadiazaperhydroine, 1,4,3-oxathiazaperhydroine, 1,4,2-oxathiazaperhydroine, 1,4,5,6-tetrahydropyridazine, 1,2,3,4-tetrahydropyridazine, 1,2,3,6-tetrahydropyridazine, 1,2,5,6-tetrahydropyrimidine, 1,2,3,4-tetrahydropyrimidine, 1,4,5,6-tetrahydropyrimidine, 1,2,3,6-tetrahydropyrazine, 1,2,3,4-tetrahydropyrazine, 5,6-dihydro-4H-[1,2]oxazine, 5,6-dihydro-2H-[1,2]oxazine, 3,6-dihydro-2H-[1,2]oxazine, 3,4-dihydro-2H-[1,2]oxazine, 5,6-dihydro-4H-[1,2]thiazine, 5,6-dihydro-2H-[1,2]thiazine, 3,6-dihydro-2H-[1,2]thiazine, 3,4-dihydro-2H-[1,2]thiazine, 5,6-dihydro-2H-[1,3]oxazine, 5,6-dihydro-4H-[1,3]oxazine, 3,6-dihydro-2H-[1,3]oxazine, 3,4-dihydro-2H-[1,3]oxazine, 3,6-dihydro-2H-[1,4]oxazine, 3,4-dihydro-2H-[1,4]oxazine, 5,6-dihydro-2H-[1,3]thiazine, 5,6-dihydro-4H-[1,3]thiazine, 3,6-dihydro-2H-[1,3]thiazine, 3,4-dihydro-2H-[1,3]thiazine, 3,6-dihydro-2H-[1,4]thiazine, 3,4-dihydro-2H-[1,4]thiazine, 1,2,3,6-tetrahydro-[1,2,4]triazine, 1,2,3,4-tetrahydro-[1,2,4]triazine, 1,2,3,4-tetrahydro-[1,3,5]triazine, 2,3,4,5-tetrahydro-[1,2,4]triazine, 1,4,5,6-tetrahydro-[1,2,4]triazine, 5,6-dihydro-[1,4,2]dioxazine, 5,6-dihydro-[1,4,2]dithiazine, 2,3-dihydro-[1,4,2]dioxazine, 3,4-dihydro-2H-[1,3,4]oxadiazine, 3,6-dihydro-2H-[1,3,4]oxadiazine, 3,4-dihydro-2H-[1,3,5]oxadiazine, 3,6-dihydro-2H-[1,3,5]oxadiazine, 5,6-dihydro-2H-[1,2,5]oxadiazine, 5,6-dihydro-4H-[1,2,5]oxadiazine, 3,4-dihydro-2H-[1,3,4]thiadiazine, 3,6-dihydro-2H-[1,3,4]thiadiazine, 3,4-dihydro-2H-[1,3,5]thiadiazine, 3,6-dihydro-2H-[1,3,5]thiadiazine, 5,6-dihydro-2H-[1,2,5]thiadiazine, 5,6-dihydro-4H-[1,2,5]thiadiazine, 5,6-dihydro-2H-[1,2,3]oxadiazine, 3,6-dihydro-2H-[1,2,5]oxadiazine, 5,6-dihydro-4H-[1,3,4]oxadiazine, 3,4-dihydro-2H-[1,2,5]oxadiazine, 5,6-dihydro-2H-[1,2,3]thiadiazine, 3,6-dihydro-2H-[1,2,5]thiadiazine, 5,6-dihydro-4H-[1,3,4]thiadiazine, 3,4-dihydro-2H-[1,2,5]thiadiazine, 5,6-dihydro-[1,4,3]oxathiazine, 5,6-dihydro-[1,4,2]oxathiazine, 2,3-dihydro-[1,4,3]oxathiazine, 2,3-dihydro-[1,4,2]oxathiazine, 3,4-dihydropyridine, 1,2-dihydropyridine, 5,6-dihydropyridine, 2H-pyran, 2H-thiin, 3,6-dihydropyridine, 2,3-dihydropyridazine, 2,5-dihydropyridazine, 4,5-dihydropyridazine, 1,2-dihydropyridazine, 1,4-dihydropyrimidin-1-yl, 1,4-dihydropyrimidin-4-yl, 1,4-dihydropyrimidin-5-yl, 1,4-dihydropyrimidin-6-yl, 2,3-dihydropyrimidine, 2,5-dihydropyrimidine, 5,6-dihydropyrimidine, 3,6-dihydropyrimidine, 5,6-dihydropyrazine, 3,6-dihydropyrazine, 4,5-dihydropyrazine, 1,4-dihydropyrazine, 1,4-dithiin, 1,4-dioxin, 2H-1,2-oxazine, 6H-1,2-oxazine, 4H-1,2-oxazine, 2H-1,3-oxazine, 4H-1,3-oxazine, 6H-1,3- oxazine, 2H-1,4-oxazine, 4H-1,4-oxazine, 2H-1,3-thiazine, 2H-1,4-thiazine, 4H-1,2-thiazine, 6H-1,3-thiazine, 4H-1,4-thiazine, 2H-1,2-thiazine, 6H-1,2-thiazine, 1,4-oxathiin, 2H,5H-1,2,3-triazine, 1H,4H-1,2,3-triazine, 4,5-dihydro-1,2,3-triazine, 1H,6H-1,2,3-triazine, 1,2-dihydro-1,2,3-triazine, 2,3-dihydro-1,2,4-triazine, 3H,6H-1,2,4-triazine, 1H,6H-1,2,4-triazine, 3,4-dihydro-1,2,4-triazine, 1H,4H-1,2,4-triazine, 5,6-dihydro-1,2,4-triazine, 4,5-dihydro-1,2,4-triazine, 2H,5H-1,2,4-triazine, 1,2-dihydro-1,2,4-triazine, 1H,4H-1,3,5-triazine, 1,2-dihydro-1,3,5-triazine, 1,4,2-dithiazine, 1,4,2-dioxazine, 2H-1,3,4-oxadiazine, 1,2-dihydro-1,3,5-oxadiazine, 6H-1,2,5-oxadiazine, 4H-1,3,4-oxadiazine, 4H-1,3,5-oxadiazine, 4H-1,2,5-oxadiazine, 2H-1,3,5-thiadiazine, 6H-1,2,5-thiadiazine, 4H-1,3,4-thiadiazine, 4H-1,3,5-thiadiazine, 4H-1,2,5-thiadiazine, 2H-1,3,4-thiadiazine, 6H-1,3,4-thiadiazine, 6H-1,3,4-oxadiazine, and 1,4,2-oxathiazine, wherein the heterocycle is optionally vicinally fused with a saturated or unsaturated 5-, 6- or 7-membered ring containing 0, 1 or 2 atoms independently selected from N, O and S;

$R^c$ is independently, in each instance, phenyl substituted by 0, 1 or 2 groups selected from halo, $C_{1-4}$alkyl, $C_{1-3}$haloalkyl, —$OR^a$ and —$NR^aR^a$; or $R^c$ is a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the carbon atoms of the heterocycle are substituted by 0, 1 or 2 oxo or thioxo groups, wherein the heterocycle or fused phenyl ring is substituted by 0, 1, 2 or 3 substituents selected from halo, $C_{1-4}$alkyl, $C_{1-3}$haloalkyl, —$OR^a$ and —$NR^aR^a$;

$R^d$ is independently in each instance hydrogen or —$CH_3$;

$R^e$ is, independently, in each instance, $C_{1-9}$alkyl or $C_4$alkyl(phenyl) wherein either is substituted by 0, 1, 2, 3 or 4 substituents selected from halo, $C_{1-4}$haloalkyl, cyano, nitro, —C(=O)$R^e$, —C(=O)O$R^e$, —C(=O)N$R^aR^a$, —C(=N$R^a$)N$R^aR^a$, —$OR^a$, —OC(=O)$R^e$, —OC(=O)N$R^aR^a$, —OC(=O)N($R^a$)S(=O)$_2R^e$, —$OC_{2-6}$alkylN$R^aR^a$ —$OC_{2-6}$alkylO$R^a$, —$SR^a$, —S(=O)$R^e$, —S(=O)$_2R^e$, —S(=O)$_2$N$R^aR^a$, —S(=O)$_2$N($R^a$)C(=O)$R^e$, —S(=O)$_2$N($R^a$)C(=O)O$R^e$, —S(=O)$_2$N($R^a$)C(=O)N$R^aR^a$, —N$R^aR^a$, —N($R^a$)C(=O)$R^e$, —N($R^a$)C(=O)O$R^e$, —N($R^a$)C(=O)N$R^aR^a$, —N($R^a$)C(=N$R^a$)N$R^aR^a$, —N($R^a$)S(=O)$_2R^e$, —N($R^a$)S(=O)$_2$N$R^aR^a$, —$NR^aC_{2-6}$alkylN$R^aR^a$ and —$NR^aC_{2-6}$akylO$R^a$; and wherein the $C_{1-6}$alkyl is additionally substituted by 0 or 1 groups independently selected from $R^h$;

$R^f$ is, independently, in each instance, $R^e$ or H;

$R^g$ is, independently, in each instance, a saturated or unsaturated 5- or 6-membered monocyclic ring containing 1, 2 or 3 atoms selected from N, O and S, so long as the combination of O and S atoms is not greater than 2, wherein the ring is substituted by 0 or 1 oxo or thioxo groups; and $R^h$ is, independently, in each instance, phenyl or a saturated or unsaturated 5- or 6-membered monocyclic ring containing 1, 2 or 3 atoms selected from N, O and S, so long as the combination of O and S atoms is not greater than 2, wherein the ring is substituted by 0 or 1 oxo or thioxo groups, wherein the phenyl or monocycle are substituted by 0, 1, 2 or 3 substituents selected from halo, cyano, nitro, —C(=O)$R^e$, —C(=O)O$R^e$, —C(=O)N$R^aR^f$, —C(=N$R^a$)N$R^aR^f$, —O$R^f$, —OC(=O)$R^e$, —OC(=O)N$R^aR^f$, —OC(=O)N($R^a$)S(=O)$_2R^e$, —$OC_{2-6}$alkylN$R^aR^f$, —$OC_{2-6}$alkylO$R^f$, —$SR^f$, —S(=O)$R^e$, —S(=O)$_2R^e$, —S(=O)$_2$N$R^aR^f$, —S(=O)$_2$N($R^a$)C(=O)$R^e$, —S(=O)$_2$N($R^a$)C(=O)N$R^aR^f$ —N$R^aR^f$, —N($R^a$)C(=O)$R^e$, —N($R^a$)C(=O)O$R^e$, —N($R^a$)C(=O)N$R^aR^f$, —N($R^a$)C(=N$R^a$)N$R^aR^f$, —N($R^a$)S(=O)$_2R^e$, —N($R^a$)S(=O)$_2$N$R^aR^f$, —$NR^aC_{2-6}$alkylN$R^aR^f$ and —$NR^aC_{2-6}$alkylO$R^f$.

In one embodiment, in conjunction with any one of the above and below embodiments, X is N or C($R^2$); Y is N or C($R^3$), wherein at least one of X and Y is not N.

In another embodiment, in conjunction with any one of the above and below embodiments, X is C($R^2$); Y is C($R^3$); and $R^3$ is halo, —$NH_2$, —$NHC_{1-3}$alkyl, —N($C_{1-3}$alkyl)$C_{1-3}$alkyl, or $C_{1-3}$alkyl.

In another embodiment, in conjunction with any one of the above and below embodiments, X is C($R^2$); Y is C($R^3$); and $R^3$ is H;

In another embodiment, in conjunction with any one of the above and below embodiments, X is N; and Y is C($R^3$).

In another embodiment, in conjunction with any one of the above and below embodiments, X is C($R^2$); and Y is N.

Embodiment A: In another embodiment, in conjunction with any one of the above and below embodiments, $R^1$ is

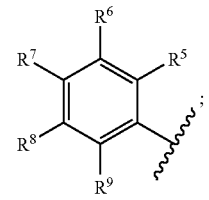

or $R^1$ is $R^b$ substituted by 1, 2 or 3 substituents independently selected from $R^f$, $R^g$, halo, nitro, cyano, —$OR^e$, —$OR^g$, —$OC_{2-6}$alkylN$R^aR^f$, —$OC_{2-6}$alkylO$R^f$, —N$R^aR^f$, —N$R^aR^g$, —N$R^fC_{2-6}$alkylN$R^aR^f$, —N$R^fC_{2-6}$alkylO$R^f$, naphthyl, —$CO_2R^e$, —C(=O)$R^e$, —C(=O)N$R^aR^f$, —C(=O)N$R^aR^g$, —N$R^fC$(=O)$R^e$, —N$R^fC$(=O)$R^g$, —N$R^fC$(=O)N$R^aR^f$, —N$R^fCO_2R^e$, —$C_{1-8}$alkylO$R^f$, —$C_{1-6}$ alkylN$R^aR^f$, —S(=O)$_nR^e$, —S(=O)$_2$N$R^aR^f$, —$NR^fS$(=O)$_2R^e$ and —OC(=O)N$R^aR^f$, and $R^b$ is additionally substituted by 0, 1 or 2 groups independently selected from $R^c$; or $R^1$ is phenyl that is vicinally fused with a saturated or unsaturated 3-, 4- or 5-atom bridge containing 0, 1, 2 or 3 atoms selected from O, N and S with the remaining atoms being carbon, so long as the combination of O and S atoms is not greater than 2, wherein the heterocycle and bridge are substituted by 0, 1, 2 or 3 substituents independently selected from $R^5$.

Embodiment B: In another embodiment, in conjunction with any one of the above and below embodiments, $R^1$ is

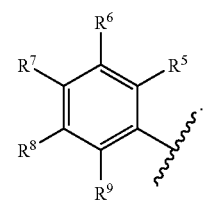

In another embodiment, in conjunction with any one of the above and below embodiments, $R^1$ is phenyl that is vicinally fused with a saturated or unsaturated 3-, 4- or 5-atom bridge containing 0, 1, 2 or 3 atoms selected from O, N and S with the remaining atoms being carbon, so long as the combination of O and S atoms is not greater than 2, wherein the heterocycle and bridge are substituted by 0, 1, 2 or 3 substituents independently selected from $R^5$.

In another embodiment, in conjunction with any one of the above and below embodiments, $R^1$ is phenyl that is vicinally fused with a saturated or unsaturated 3-, 4- or 5-atom bridge containing 1, 2 or 3 atoms selected from O, N and S with the remaining atoms being carbon, so long as the combination of O and S atoms is not greater than 2, wherein the heterocycle and bridge are substituted by 0, 1, 2 or 3 substituents independently selected from $R^5$.

In another embodiment, in conjunction with any one of the above and below embodiments, $R^1$ is phenyl that is vicinally fused with a saturated or unsaturated 3-, 4- or 5-atom bridge containing 1, 2 or 3 atoms selected from O, N and S with the remaining atoms being carbon, so long as the combination of O and S atoms is not greater than 2, wherein the heterocycle and bridge are substituted by 0, 1, 2 or 3 substituents independently selected from $R^5$.

In another embodiment, in conjunction with any one of the above and below embodiments, $R^1$ is naphthyl substituted by 0, 1, 2 or 3 substituents independently selected from $R^5$.

Embodiment C: In another embodiment, in conjunction with any one of the above and below embodiments, $R^1$ is $R^b$ substituted by 1, 2 or 3 substituents independently selected from $R^f$, $R^g$, halo, nitro, cyano, —$OR^e$, —$OR^g$, —$OC_{2-6}$alkyl$NR^aR^f$, —$OC_{2-6}$alkyl$OR^f$, —$NR^aR^f$, —$NR^aR^g$, —$NR^fC_{2-6}$alkyl$NR^aR^f$, —$NR^fC_{2-6}$alkyl$OR^f$, naphthyl, —$CO_2R^e$, —$C(=O)R^e$, —$C(=O)NR^aR^f$, —$C(=O)NR^aR^g$, —$NR^fC(=O)R^e$, —$NR^f(=O)R^g$, —$NR^fC(=O)NR^aR^f$, —$NR^fCO_2R^e$, —$C_{1-8}$alkyl$OR^f$, —$C_{1-6}$alkyl$NR^aR^f$, —$S(=O)_nR^e$, —$S(=O)_2NR^aR^f$, —$NR^aS(=O)_2R^e$ and —$OC(=O)NR^aR^f$, and $R^b$ is additionally substituted by 0, 1 or 2 groups independently selected from $R^c$.

In another embodiment, in conjunction with any one of the above and below embodiments, $R^2$ is, independently, in each instance, $R^{14}$, halo, $C_{1-8}$alkyl substituted by 0, 1 or 2 substituents selected from $R^{14}$ and halo, —$(CH_2)_n$phenyl substituted by 0, 1, 2 or 3 substituents independently selected from $R^{14}$ and halo, or a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the heterocycle or fused phenyl ring is substituted by 0, 1, 2 or 3 substituents independently selected from $R^{14}$ and halo.

In another embodiment, in conjunction with any one of the above and below embodiments, $R^2$ is, independently, in each instance, $R^{14}$ or halo, $C_{1-8}$alkyl substituted by 0, 1 or 2 substituents selected from $R^{14}$ and halo, —$(CH_2)$phenyl substituted by 0, 1, 2 or 3 substituents independently selected from $R^{14}$ and halo, or a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the heterocycle or fused phenyl ring is substituted by 0, 1, 2 or 3 substituents independently selected from $R^{14}$ and halo.

In another embodiment, in conjunction with any one of the above and below embodiments, $R^2$ is $C_{1-8}$alkyl substituted by 0, 1 or 2 substituents selected from $R^{14}$ and halo.

In another embodiment, in conjunction with any one of the above and below embodiments, $R^2$ is —$(CH_2)_{1-2}$phenyl substituted by 0, 1, 2 or 3 substituents independently selected from $R^{14}$ and halo.

In another embodiment, in conjunction with any one of the above and below embodiments, $R^2$ is a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the heterocycle or fused phenyl ring is substituted by 0, 1, 2 or 3 substituents independently selected from $R^{14}$ and halo.

In another embodiment, in conjunction with any one of the above and below embodiments, $R^2$ is H.

In another embodiment, in conjunction with any one of the above and below embodiments, $R^2$ is —$OR^4$ or —$N(R^a)R^4$.

In another embodiment, in conjunction with any one of the above and below embodiments, $R^2$ is —$OR^4$.

In another embodiment, in conjunction with any one of the above and below embodiments, $R^2$ is —$N(R^a)R^4$.

In another embodiment, in conjunction with any one of the above and below embodiments, $R^3$ is, independently, in each instance, H, halo, —$NH_2$, —$NHC_{1-3}$alkyl, —$N(C_{1-3}$alkyl)$C_{1-3}$alkyl, or $C_{1-3}$alkyl; wherein, when X is $C(R^2)$ and Y is $C(R^3)$ then at least one of $R^2$ and $R^3$ is other than H.

In another embodiment, in conjunction with any one of the above and below embodiments, $R^3$ is halo, —$NH_2$, —$NHC_{1-3}$alkyl, —$N(C_{1-3}$alkyl)$C_{1-3}$alkyl, or $C_{1-3}$alkyl.

In another embodiment, in conjunction with any one of the above and below embodiments, $R^3$ is H.

Embodiment D: In another embodiment, in conjunction with any one of the above and below embodiments, $R^4$ is independently at each instance

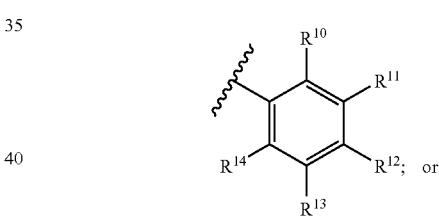

$R^4$ is independently at each instance a saturated or unsaturated 5- or 6-membered ring heterocycle containing 1, 2 or 3 atoms selected from O, N and S that is optionally vicinally fused with a saturated or unsaturated 3-, 4- or 5-atom bridge containing 0, 1, 2 or 3 atoms selected from O, N and S with the remaining atoms being carbon, so long as the combination of O and S atoms is not greater than 2, wherein the heterocycle and bridge are substituted by 0, 1, 2 or 3 substituents independently selected from $R^e$, $C_{1-5}$haloalkyl, halo, cyano, oxo, thioxo, —$OR^f$, —$S(=O)_nR^e$, —$OC_{1-4}$haloalkyl, —$OC_{2-6}$alkyl$NR^aR^f$, —$OC_{2-6}$alkyl$OR^f$, —$OC_{1-6}$alkyl$C(=O)OR^e$, —$NR^aR^f$, —$NR^aC_{1-4}$haloalkyl, —$NR^aC_{2-6}$alkyl$NR^aR^f$, —$NR^aC_{2-6}$alkyl$OR^f$, —$C(=O)R^e$, —$C(=O)OR^f$, —$OC(=O)R^e$, —$C(=O)NR^aR^f$ and —$NR^aC(=O)R^e$; or $R^4$ is independently at each instance naphthyl substituted by 1, 2 or 3 substituents independently selected from $C_{1-4}$haloalkyl, halo, nitro, cyano, —$S(=O)_n$$R^e$, —$OC_{1-4}$haloalkyl, —$OC_{2-6}$alkyl$NR^aR^f$, —$OC_{2-6}$alkyl$OR^f$, —$OC_{1-6}$alkyl$C(=O)OR^e$, —$NR^aC_{1-4}$haloalkyl, —$NR^aC_{2-6}$alkyl$N^aR^f$, —$NR^aC_{2-6}$alylk$OR^f$, —$C(=O)R^e$, —$C(=O)OR^f$, —$OC(=O)R^e$ and —$C(=O)NR^aR^f$; but in no instance is $R^4$-phenyl-($C_{1-8}$alkyl), -phenyl-O-($C_{1-6}$alkyl), -phenyl-$NR^aR^a$ or -phenyl-$N(R^a)C(=O)(C_{1-8}$alkyl).

Embodiment E: In another embodiment, in conjunction with any one of the above and below embodiments, $R^4$ is independently at each instance

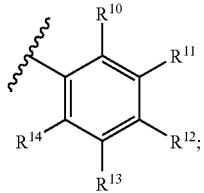

but in no instance is $R^4$-phenyl-O—($C_{1-6}$alkyl), -phenyl-$NR^aR^a$ or -phenyl-N($R^a$)C(=O)($C_{1-6}$alkyl).

Embodiment F: In another embodiment, in conjunction with any one of the above and below embodiments, $R^4$ is independently at each instance a saturated or unsaturated 5- or 6-membered ring heterocycle containing 1, 2 or 3 atoms selected from O, N and S that is optionally vicinally fused with a saturated or unsaturated 3-, 4- or 5-atom bridge containing 0, 1, 2 or 3 atoms selected from O, N and S with the remaining atoms being carbon, so long as the combination of O and S atoms is not greater than 2, wherein the heterocycle and bridge are substituted by 0, 1, 2 or 3 substituents independently selected from $R^e$, $C_{1-4}$haloalkyl, halo, cyano, oxo, thioxo, —$OR^f$, —S(=O)$_nR^e$, —$OC_{1-4}$aloalkyl, —$OC_{2-6}$alkylNR$^a$R$^f$, —$OC_{2-6}$alkylOR$^f$, —$OC_{1-6}$alkylC(=O)OR$^e$, —NR$^a$R$^f$, —NR$^a$C$_{1-4}$haloalkyl, —NR$^a$C$_{2-6}$alkylNR$^a$R$^f$, —NR$^a$C$_{2-6}$alkylOR$^f$, —C(=O)R$^e$, —C(=O)OR$^f$, —OC(=O)R$^e$, —C(=O)NR$^a$R$^f$ and —NR$^a$C(=O)R$^e$.

Embodiment G: In another embodiment, in conjunction with any one of the above and below embodiments, $R^4$ is independently at each instance a saturated or unsaturated 5- or 6-membered ring heterocycle containing 1, 2 or 3 atoms selected from O, N and S that is vicinally fused with a saturated or unsaturated 3-, 4- or 5-atom bridge containing 0, 1, 2 or 3 atoms selected from O, N and S with the remaining atoms being carbon, so long as the combination of O and S atoms is not greater than 2, wherein the heterocycle and bridge are substituted by 0, 1, 2 or 3 substituents independently selected from $R^e$, $C_{1-4}$haloalkyl, halo, cyano, oxo, thioxo, —$OR^f$, —S(=O)$_nR^e$, —$OC_{1-4}$haloalkyl, —$OC_{2-6}$alkylNR$^a$R$^f$, —$OC_{2-6}$alkylOR$^f$, —$OC_{1-6}$alkylC(=O)OR$^e$, —NR$^a$R$^f$, —NR$^a$C$_{1-4}$haloalkyl, —NR$^a$C$_{2-6}$alkylNR$^a$R$^f$, —NR$^a$C$_{2-6}$alkylOR$^f$, —C(=O)R$^e$, —C(=O)OR$^f$, —OC(=O)R$^e$, —C(=O)NR$^a$R$^f$ and —NR$^a$C(=O)R$^e$.

In another embodiment, in conjunction with any one of the above and below embodiments, $R^4$ is independently at each instance naphthyl substituted by 1, 2 or 3 substituents independently selected from $C_{1-4}$haloalkyl, halo, nitro, cyano, —S(=O)$_nR^e$, —$OC_{1-4}$haloalkyl, —$OC_{2-6}$alkylNR$^a$R$^f$, —$OC_{2-6}$alkylOR$^f$, —$OC_{1-6}$alkylC(=O)OR$^e$, —NR$^a$C$_{1-4}$haloalkyl, —NR$^a$C$_{2-6}$alkylNR$^a$R$^f$, —NR$^a$C$_{2-6}$alkylOR$^f$, —C(=O)R$^e$, —C(=O)OR$^f$, —OC(=O)R$^e$ and —C(=O)NR$^a$R$^f$.

In another embodiment, in conjunction with any one of the above and below embodiments, $R^5$ is independently, at each instance, $R^f$, $R^h$, halo, nitro, cyano, —$OR^f$, —$OR^h$, —$OC_{2-6}$alkylNR$^a$R$^f$, —$OC_{2-6}$alkylOR$^f$, —NR$^a$R$^f$, —NR$^a$R$^f$, —NR$^f$C$_{2-6}$alkylNR$^a$R$^f$, —NR$^f$C$_{2-6}$alkylOR$^f$, naphthyl, —CO$_2$R$^e$, —OC(=O)R$^e$, —C(=O)R$^e$, —C(=O)NR$^a$R$^f$, —C(=O)NR$^a$R$^h$, —NR$^f$C(=O)R$^e$, —NR$^f$C(=O) $R^h$, —NR$^f$C(=O)NR$^a$R$^f$, —NR$^f$CO$_2$R$^e$, —$C_{1-8}$alkylOR$^f$, —$C_{1-6}$alkylNR$^a$R$^f$, —S(=O)$_nR^e$, —S(=O)$_2$NR$^a$R$^f$, —NR$^a$S(=O)$_2R^e$, —OS(=O)$_2R^e$, —OC(=O)NR$^a$R$^f$, —OR$^h$, —OC$_{2-6}$alkylNR$^a$R$^h$, —OC$_{2-6}$alkylOR$^h$, —NR$^a$R$^h$, —NR$^f$C$_{2-6}$alkylNR$^a$R$^h$, —NR$^h$C$_{2-6}$alkylNR$^a$R$^f$, —NR$^h$C$_{2-6}$alkylOR$^f$, —NR$^f$C$_{2-6}$alkylOR$^h$, —CO$_2R^h$, —OC(=O)R$^h$, —C(=O)R$^h$, —C(=O)NR$^a$R$^h$, —NR$^f$C(=O)R$^h$, —NR$^h$C(=O)R$^f$, —NR$^h$C(=O)NR$^a$R$^f$, —NR$^f$C(=O)NR$^a$R$^h$, —NR$^h$CO$_2$R$^e$, —NR$^f$CO$_2$R$^h$, —$C_{1-8}$alkylOR$^h$, —$C_{1-6}$alkylNR$^a$R$^h$, —S(=O)$_nR^h$, —S(=O)$_2$NR$^a$R$^h$, —NR$^a$S(=O)$_2R^h$, —NR$^h$S(=O)$_2R^e$, —OS(=O)$_2R^h$ or —OC(=O)NR$^a$R$^h$.

In another embodiment, in conjunction with any one of the above and below embodiments, $R^5$ is H.

In another embodiment, in conjunction with any one of the above and below embodiments, $R^5$ is $R^f$ or $R^h$.

In another embodiment, in conjunction with any one of the above and below embodiments, $R^5$ is independently, at each instance, $R^f$, halo, nitro, cyano, —$OR^f$, —$OR^h$, —$OC_{2-6}$alkylNR$^a$R$^f$, —$OC_{2-6}$alkylOR$^f$, —NR$^a$R$^f$, —NR$^a$R$^h$, —NR$^f$C$_{2-6}$alkylNR$^a$R$^f$, —NR$^f$C$_{2-6}$alkylOR$^f$, —CO$_2R^e$, —OC(=O)R$^e$, —C(=O)R$^e$, —C(=O)NR$^a$R$^f$, —C(=O)NR$^a$R$^h$, —NR$^f$C(=O)R$^e$, —NR$^f$C(=O)R$^h$, —NR$^f$C(=O)NR$^a$R$^f$, —NR$^f$CO$_2R^e$, —$C_{1-8}$alkylOR$^f$, —$C_{2-6}$alkylNR$^a$R$^f$, —S(=O)$_nR^e$, —S(=O)$_2$NR$^a$R$^f$, —NR$^a$S(=O)$_2R^e$, —OS(=O)$_2R^e$, —OC(=O)NR$^a$R$^f$, —OR$^h$, —OC$_{2-6}$alkylNR$^a$R$^h$, —OC$_{2-6}$alkylOR$^h$, —NR$^a$R$^h$, —NR$^f$C$_{2-6}$alkylNR$^a$R$^h$, —NR$^h$C$_{2-6}$alkylNR$^a$R$^h$, —NR$^h$C$_{2-6}$alkylOR$^f$, —NR$^f$C$_{2-6}$alkylOR$^h$, —CO$^2R^h$, —OC(=O)R$^h$, —C(=O)R$^h$, —C(=O)NR$^a$R$^h$, —NR$^f$C(=O)R$^h$, —NR$^h$ C(=O)R$^f$, —NR$^h$C(=O)NR$^a$R$^f$, —NR$^f$C(=O)NR$^a$R$^h$, —NR$^h$CO$_2$R$^e$, —NR$^f$CO$_2$R$^h$, —$C_{1-8}$alkylOR$^h$, —$C_{1-6}$alkylNR$^a$R$^h$, —S(=O)$_nR^h$, —S(=O)$_2$NR$^a$R$^h$, —NR$^a$S(=O)$_2R^h$, —NR$^h$S(=O)$_2R^e$, —OS(=O)$_2R^h$, or —OC(=O)NR$^a$R$^h$.

In another embodiment, in conjunction with any one of the above and below embodiments, $R^5$ is independently, at each instance, H or a phenyl ring substituted with 0, 1, 2, or 3 substituents independently selected from $R^{14}$ and halo; or $R^5$ is a saturated or unsaturated 5- or 6-membered ring heterocycle containing 1, 2 or 3 atoms selected from O, N and S, substituted with 0, 1, 2, or 3 substituents independently selected from $R^{14}$ and halo.

In another embodiment, in conjunction with any one of the above and below embodiments, $R^5$ is independently, at each instance, H or $R^5$ is a saturated or unsaturated 5- or 6-membered ring heterocycle containing 1, 2 or 3 atoms selected from O, N and S, substituted with 0, 1, 2, or 3 substituents independently selected from $R^{14}$ and halo.

In another embodiment, in conjunction with any one of the above and below embodiments, $R^6$ is independently, at each instance, H, $C_{1-5}$alkyl, $C_{1-4}$haloalkyl, halo, nitro —$OR^e$, —$OC_{2-6}$alkylNR$^a$R$^a$, —$OC_{2-6}$alkylOR$^a$, —NR$^a$R$^a$, —NR$^a$C$_{1-4}$haloalkyl, —NR$^a$C$_{2-6}$alkylNR$^a$R$^a$ or —NR$^a$C$_{2-6}$alkylOR$^a$, —$C_{1-8}$alkylOR$^a$, —$C_{1-6}$alkylNR$^a$R$^a$, —S($C_{1-6}$alkyl), a phenyl ring substituted with 1, 2, or 3 substituents independently selected from $R^{14}$ and halo; or $R^6$ is a saturated or unsaturated 5- or 6-membered ring heterocycle containing 1, 2 or 3 atoms selected from O, N and S substituted with 0, 1, 2, or 3 substituents independently selected from $R^{14}$ and halo.

In another embodiment, in conjunction with any one of the above and below embodiments, $R^6$ is independently, at each instance, $C_{1-5}$alkyl, $C_{1-4}$haloalkyl, halo, nitro —$OC_{1-6}$alkyl, —$OC_{1-4}$haloalkyl, —$OC_{2-6}$alkylNR$^a$R$^a$—$OC_{2-6}$alkylOR$^a$, —NR$^a$R$^a$, —NR$^a$C$_{1-4}$haloalkyl, —NR$^a$C$_{2-6}$alkylNR$^a$R$^a$ or —NR$^a$C$_{2-6}$alkylOR$^a$, $C_{1-8}$alkylOR$^a$, —$C_{1-6}$ alkylNR$^a$R$^a$, —S($C^{1-6}$alkyl), a phenyl ring substituted with 1, 2, or 3 substituents independently selected from $R^{14}$ and halo; or $R^6$ is a saturated or unsaturated 5- or 6-membered ring heterocycle containing 1, 2 or 3 atoms selected from O, N and S substituted with 0, 1, 2, or 3 substituents independently selected from $R^{14}$ and halo.

In another embodiment, in conjunction with any one of the above and below embodiments, $R^6$ is independently, at each instance, $C_{1-5}$alkyl, $C_{1-4}$haloalkyl, halo, —$OC_{1-6}$alkyl, —$OC_{1-6}$haloalkyl, —$OC_{2-6}$alkylN$R^aR^a$, —$OC_{2-6}$alkylO$R^a$, —$NR^aR^a$, —$NR^aC_{1-6}$haloalkyl, —$NR^aC_{2-6}$alylN$R^aR^a$ or —$NR^aC_{2-6}$alkylO$R^a$, —$C_{1-8}$alkylO$R^a$, —$C_{1-6}$alkylN$R^aR^a$ or —$S(C_{1-6}$alkyl).

In another embodiment, in conjunction with any one of the above and below embodiments, $R^6$ is a phenyl ring substituted with 1, 2, or 3 substituents independently selected from $R^{14}$ and halo.

In another embodiment, in conjunction with any one of the above and below embodiments, $R^6$ is a saturated or unsaturated 5- or 6-membered ring heterocycle containing 1, 2 or 3 atoms selected from O, N and S substituted with 0, 1, 2, or 3 substituents independently selected from $R^{14}$ and halo.

In another embodiment, in conjunction with any one of the above and below embodiments, $R^6$ is H.

In another embodiment, in conjunction with any one of the above and below embodiments, $R^7$ is independently, at each instance, H, $C_{1-8}$alkyl, $C_{1-4}$haloalkyl, halo, cyano —$OC_{1-6}$alkyl, —$OC_{1-4}$haloalkyl, —$OC_{2-6}$alkylN$R^aR^a$, —$OC_{2-6}$alkylO$R^a$, —$NR^aR^a$, —$NR^aC_{1-4}$haloalkyl, —$NR^aC_{2-6}$alkylN$R^aR^a$, —$NR^aC_{2-6}$alkylO$R^a$, —$C_{1-8}$alkylO$R^a$, —$C_{1-6}$alkylN$R^aR^a$ or —$S(C_{1-6}$alkyl); or $R^7$ is a saturated or unsaturated 4- or 5-membered ring heterocycle containing a single nitrogen atom, wherein the ring is substituted with 0, 1 or 2 substituents independently selected from halo, $C_{1-2}$haloalkyl and $C_{1-3}$alkyl.

Embodiment H: In another embodiment, in conjunction with any one of the above and below embodiments, $R^7$ is independently, at each instance, $C_{1-8}$alkyl, $C_{1-4}$haloalkyl, halo, cyano, —$OR^e$, —$OC_{1-4}$haloalkyl, —$OC_{2-6}$alkylN$R^aR^a$, —$OC_{2-6}$alkylO$R^a$, —$NR^aR^a$, —$NR^aC_{1-4}$haloalkyl, —$NR^aC_{2-6}$alkylN$R^aR^a$, —$NR^aC_{2-6}$alkylO$R^a$, —$C_{1-8}$alkylO$R^a$, —$C_{1-6}$alkylN$R^aR^a$ or —$S(C_{1-6}$alkyl); or $R^7$ is a saturated or unsaturated 4- or 5-membered ring heterocycle containing a single nitrogen atom, wherein the ring is substituted with 0, 1 or 2 substituents independently selected from halo, $C_{1-2}$haloalkyl and $C_{1-3}$alkyl.

In another embodiment, in conjunction with any one of the above and below embodiments, $R^7$ is H.

In another embodiment, in conjunction with any one of the above and below embodiments, $R^7$ is a saturated or unsaturated 4- or 5-membered ring heterocycle containing a single nitrogen atom, wherein the ring is substituted with 0, 1 or 2 substituents independently selected from halo, $C_{1-2}$haloalkyl and $C_{1-3}$alkyl.

In another embodiment, in conjunction with any one of the above and below embodiments, $R^7$ is independently, at each instance, acyclic$C_{1-8}$alkyl, $C_{1-4}$haloalkyl, halo, —$OC_{1-6}$alkyl, —$OC_{1-4}$haloalkyl, —$OC_{2-6}$alkylN$R^aR^a$, —$OC_{2-6}$alkylO$R^a$, —$NR^aR^a$, —$NR^aC_{1-4}$haloalkyl, —$NR^aC_{2-6}$alkylN$R^aR^a$, —$NR^aC_{2-6}$alkylO$R^a$, —$C_{1-8}$alkylO$R^a$, —$C^{1-6}$alkylN$R^aR^a$ or —$S(C_{1-6}$alkyl).

In another embodiment, in conjunction with any one of the above and below embodiments, $R^7$ is independently, at each instance, acyclic$C_{1-8}$alkyl, $C_{1-4}$haloalkyl, Br, or Cl.

In another embodiment, in conjunction with any one of the above and below embodiments, $R^7$ is independently, at each instance, acyclic$C_{1-8}$alkyl or $C_{1-4}$haloalkyl.

Embodiment I: In another embodiment, in conjunction with any one of the above and below embodiments, $R^7$ is independently, at each instance, $C_{3-5}$alkyl or $C_{1-2}$haloalkyl.

In another embodiment, in conjunction with any one of the above and below embodiments, $R^7$ is $C_{3-5}$alkyl.

In another embodiment, in conjunction with any one of the above and below embodiments, $R^7$ is —$C(CH_3)_3$.

In another embodiment, in conjunction with any one of the above and below embodiments, $R^7$ is —$CF_3$.

In another embodiment, in conjunction with any one of the above and below embodiments, $R^8$ is independently, at each instance, H, $C_{1-5}$alkyl, $C_{1-4}$haloalkyl, halo, nitro, —$OC_{1-6}$alkyl, —$OC_{1-4}$haloalkyl, —$OC_{2-6}$alkylN$R^aR^a$, —$OC_{2-6}$alkylO$R^a$, —$NR^aR^a$, —$NR^aC_{1-4}$haloalkyl, —$NR^aC_{2-6}$alkylN$R^aR^a$, —$NR^aC_{2-6}$alkylO$R^a$, —$C_{1-8}$alkylO$R^a$, —$C_{1-6}$alkylN$R^aR^a$, —$S(C_{1-6}$alkyl), a phenyl ring substituted with 1, 2, or 3 substituents independently selected from $R^{14}$ and halo, or $R^8$ is a saturated or unsaturated 5- or 6-membered ring heterocycle containing 1, 2 or 3 atoms selected from O, N and S substituted with 0, 1, 2, or 3 substituents independently selected from $R^{14}$ and halo.

In another embodiment, in conjunction with any one of the above and below embodiments, $R^8$ is H.

In another embodiment, in conjunction with any one of the above and below embodiments, $R^8$ is independently, at each instance, $C_{1-5}$alkyl, $C_{1-4}$haloalkyl, halo, nitro, —$OC_{1-6}$alkyl, —$OC_{1-4}$haloalkyl, —$OC_{2-6}$alkylN$R^aR^a$, —$OC_{2-6}$alkylO$R^a$, —$NR^aR^a$, —$NR^aC$, haloalkyl, —$NR^aC_{2-6}$alkylN$R^aR^a$, —$NR^aC_{2-6}$alkylO$R^a$, —$C_{1-8}$alkylO$R^a$, —$C_{1-6}$alkylN$R^aR^a$, —$S(C_{1-6}$alkyl), a phenyl ring substituted with 1, 2, or 3 substituents independently selected from $R^{14}$ and halo, or $R^8$ is a saturated or unsaturated 5- or 6-membered ring heterocycle containing 1, 2 or 3 atoms selected from O, N and S substituted with 0, 1, 2, or 3 substituents independently selected from $R^{14}$ and halo.

In another embodiment, in conjunction with any one of the above and below embodiments, $R^8$ is independently, at each instance, $C_{1-5}$alkyl, $C_{1-4}$haloalkyl, halo, nitro, —$OC_{1-6}$alkyl, —$OC_{1-4}$haloalkyl, —$OC_{2-6}$alkylN$R^aR^a$, —$OC_{2-6}$alkylO$R^a$, —$NR^aR^a$, —$NR^aC$ 1-4haloalkyl, —$NR^aC_{2-6}$alkylN$R^aR^a$, —$NR^aC_{2-6}$alkylO$R^a$, —$C_{1-8}$alkylO$R^a$, —$C_{1-6}$alkylN$R^aR^a$ or —$S(C_{1-6}$alkyl).

In another embodiment, in conjunction with any one of the above and below embodiments, $R^8$ is a phenyl ring substituted with 1, 2, or 3 substituents independently selected from $R^{14}$ and halo.

In another embodiment, in conjunction with any one of the above and below embodiments, $R^8$ is a saturated or unsaturated 5- or 6-membered ring heterocycle containing 1, 2 or 3 atoms selected from O, N and S substituted with 0, 1, 2, or 3 substituents independently selected from $R^{14}$ and halo.

Embodiment J: In another embodiment, in conjunction with any one of the above and below embodiments, $R^9$ is independently, at each instance, $R^f$, $R^g$, halo, nitro, cyano, —$OR^f$, —$OR^h$, —$OC_{2-6}$alkylN$R^aR^f$, —$OC_{2-6}$alkylO$R^f$, —$NR^aR^f$, —$NR^aR^h$, —$NR^aC_{2-6}$alkylN$R^aR^f$, —$NR^fC_{2-6}$alkylO$R^f$, naphthyl, —$CO_2R^e$, —$OC(=O)R^e$, —$C(=O)R^e$, —$C(=O)NR^aR^f$, —$C(=O)NR^aR^f$, —$NR^fC(=O)R^e$, —$NR^fC(=O)R^h$, —$NR^fC(=O)NR^aR^f$, —$NR^fCO_2R^e$, —$C_{1-8}$alkylO$R^f$, —$C_{1-6}$alkylN$R^aR^f$, —$S(=O)_nR^e$, —$S(=O)_2NR^aR^h$, —$NR^aS(=O)_2R^e$, —$OS(=O)_2R^e$, —$OC(=O)NR^aR^f$, —$OR^h$, —$OC_{2-6}$alkylNR, —$OC_{2-6}$alkylO$R^f$, —$NR^aR^h$, —$NR^fC_{2-6}$alkylN$R^aR^h$, —$NR^hC_{2-6}$alkylN$R^aR^f$, —$NR^hC_{2-6}$alkylO$R^f$, —$NR^fC_{2-6}$alkylO$R^h$, —$CO_2R^h$, —$OC(=O)R^h$, —$C(=O)R^h$, —$C(=O)NR^aR^h$, —$NR^fC(=O)R^h$, —$NR^hC(=O)R^f$, —$NR^hC(=O)NR^aR^f$, —NR$^f$C(=O)NR$^a$R$^h$, —NR$^h$CO$_2$R$^e$, —NR$^f$CO$_2$R$^h$, —C$_{1-8}$alkylOR$^h$, —C$_{1-6}$alkylNR$^a$R$^h$, —S(=O)$_n$R$^h$, —S(=O)$_2$NR$^a$R$^h$, —NR$^a$S(=O)$_2$R$^h$, —NR$^h$S(=O)$_2$R$^e$, —OS(=O)$_2$R$^h$, —OC(=O)NR$^a$R$^h$, a phenyl ring substituted with 0, 1, 2, or 3 substituents independently selected from R$^{14}$ and halo; or R$^9$ is a saturated or unsaturated 5- or 6-membered ring heterocycle containing 1, 2 or 3 atoms selected from O, N and S substituted with 0, 1, 2, or 3 substituents independently selected from R$^{14}$ and halo; or R$^9$ is a saturated or unsaturated 4- or 5-membered ring heterocycle containing a single nitrogen atom, wherein the ring is substituted with 0, 1 or 2 substituents independently selected from halo, C$_{1-2}$haloalkyl and C$_{1-3}$alkyl.

Embodiment K: In another embodiment, in conjunction with any one of the above and below embodiments, R$^9$ is H.

Embodiment L: In another embodiment, in conjunction with any one of the above and below embodiments, R$^9$ is independently, at each instance, R$^e$, R$^g$, halo, nitro, cyano, —OR$^f$, —OR$^h$, —OC$_{2-6}$alkylNR$^a$R$^f$, —OC$_{2-6}$alkylOR$^f$, —NR$^a$R$^f$, —NR$^a$R$^h$, —NR$^f$C$_{2-6}$alkylNR$^a$R$^f$, —NR$^f$C$_{2-6}$alkylOR$^f$, naphthyl, —CO$_2$R$^e$, —OC(=O)R$^e$, —C(=O)R$^e$, —C(=O)NR$^a$R$^f$, —C(=O)NR$^a$R$^h$, —NR$^f$C(=O)R$^e$, —NR$^f$C(=O)R$^h$, —NR$^f$C(=O)NR$^a$R$^f$, —NR$^f$CO$_2$R$^e$, —C$_{1-8}$alkylOR$^f$, —C$_{1-6}$alkylNR$^a$R$^f$, —S(=O)$_n$R$^e$, —S(=O)$_2$NR$^a$R$^f$, —NR$^a$S(=O)$_2$R$^e$, —OS(=O)$_2$R$^e$, —OC(=O)NR$^a$R$^f$, —OR$^h$, —OC$_{2-6}$alkylNR$^a$R$^h$, —OC$_{2-6}$alkylOR$^f$, —NR$^a$R$^h$, —NR$^f$C$_{2-6}$alkylNR$^a$R$^h$, —NR$^h$C$_{2-6}$alkylNR$^a$R$^f$, —NR$^h$C$_{2-6}$alkylOR$^f$, —NR$^f$C$_{2-6}$alkylOR$^h$, —CO$_2$R$^h$, —OC(=O)R$^h$, —C(=O)R$^h$, —C(=O)NR$^a$R$^h$, —NR$^f$C(=O)R$^h$, —NR$^h$C(=O)R$^f$, —NR$^h$C(=O)NR$^a$R$^f$, —NR$^f$C(=O)NR$^a$R$^h$, —NR$^h$CO$_2$R$^e$, —NR$^f$CO$_2$R$^h$, —C$_{1-8}$alkylOR$^h$, —C$_{1-6}$alkylNR$^a$R$^h$, —S(=O)$_n$R$^h$, —S(=O)$_2$NR$^a$R$^f$, —NR$^a$S(=O)$_2$R$^h$, —NR$^h$S(=O)$_2$R$^e$, —OS(=O)$_2$R$^h$, —OC(=O)NR$^a$R$^h$, a phenyl ring substituted with 0, 1, 2, or 3 substituents independently selected from R$^{14}$ and halo; or R$^9$ is a saturated or unsaturated 5- or 6-membered ring heterocycle containing 1, 2 or 3 atoms selected from O, N and S substituted with 0, 1, 2, or 3 substituents independently selected from R$^{14}$ and halo; or R$^9$ is a saturated or unsaturated 4- or 5-membered ring heterocycle containing a single nitrogen atom, wherein the ring is substituted with 0, 1 or 2 substituents independently selected from halo, C$_{1-2}$haloalkyl and C$_{1-3}$alkyl.

In another embodiment, in conjunction with any one of the above and below embodiments, R$^9$ is independently, at each instance, R$^e$.

In another embodiment, in conjunction with any one of the above and below embodiments, R$^9$ is independently, at each instance, R$^g$.

In another embodiment, in conjunction with any one of the above and below embodiments, R$^9$ is independently, at each instance, halo, nitro, cyano, —OR$^e$, —OR$^g$, —OC$_{2-6}$alkylNR$^a$R$^f$, —OC$_{2-6}$alkylOR$^f$, —NR$^a$R$^f$, —NR$^a$R$^g$, —NR$^f$C$_{2-6}$alkylNR$^a$R$^f$, —NR$^f$C$_{2-6}$alkylOR$^f$, —CO$_2$R$^e$, —C(=O)R$^e$, —C(=O)NR$^a$R$^f$, —C(=O)NR$^a$R$^g$, —NR$^f$C(=O)R$^e$, —NR$^f$C(=O)R$^g$, —NR$^f$C(=O)NR$^a$R$^f$, —NR$^f$CO$_2$R$^e$, —C$_{1-8}$alkylOR$^f$, —C$_{1-6}$alkylNR$^a$R$^f$, —S(=O)$_n$R$^e$, —S(=)$_2$NR$^a$R$^f$, —NR$^a$S(=O)$_2$R$^e$ or —OC(=O)NR$^a$R$^f$.

In another embodiment, in conjunction with any one of the above and below embodiments, R$^9$ is independently, at each instance, a phenyl ring substituted with 0, 1, 2, or 3 substituents independently selected from R$^{14}$ and halo; or R$^9$ is a saturated or unsaturated 5- or 6-membered ring heterocycle containing 1, 2 or 3 atoms selected from O, N and S substituted with 0, 1, 2, or 3 substituents independently selected from R$^{14}$ and halo.

In another embodiment, in conjunction with any one of the above and below embodiments, R$^9$ is a saturated or unsaturated 4- or 5-membered ring heterocycle containing a single nitrogen atom, wherein the ring is substituted with 0, 1 or 2 substituents independently selected from halo, C$_{1-2}$haloalkyl and C$_{1-3}$alkyl.

In another embodiment, in conjunction with any one of the above and below embodiments, at least one of R$^5$, R$^6$, R$^7$, R$^8$ and R$^9$ is R$^e$, R$^h$, halo, nitro, cyano, —OR$^h$, —NR$^a$R$^f$, —NR$^a$R$^h$, —NR$^f$C$_{2-6}$alkylNR$^a$R$^f$, —NR$^f$C$_{2-6}$alkylOR$^f$, naphthyl, —CO$_2$R$^e$, —C(=O)R$^e$, —OC(=O)R$^e$, —C(=O)NR$^a$R$^f$, —C(=O)NR$^a$R$^f$, —NR$^f$C(=O)R$^e$, —NR$^f$C(=O)R$^h$, —NR$^f$C(=O)NR$^a$R$^f$, —NR$^f$CO$_2$R$^e$, —C$_{2-6}$alkylOR$^f$, —C$_{1-6}$alkylNR$^a$R$^f$, —S(=O)$_n$R$^e$, —S(=O)$_2$NR$^a$R$^f$, —NR$^a$S(=O)$_2$R$^e$, —OS(=O)$_2$R$^e$, —OC(=O)NR$^a$R$^f$, —OR$^h$, —OC$_{2-6}$alkylNR$^a$R$^h$, —NR$^f$C$_{2-6}$alkylNR$^a$R$^h$, —NR$^i$C$_2$alkylNR$^a$R$^f$, —NR$^h$C$_{2-6}$alkylOR$^f$, —NR$^f$C$_{2-6}$alkylOR$^h$, —CO$_2$R$^h$, —OC(=O)R$^h$, —C(=O)R$^h$, —C(=O)NR$^a$R$^h$, —NR$^f$C(=O)R$^h$, —NR$^h$C(=O)R$^f$, —NR$^h$C(=O)NR$^a$R$^f$, —NR$^f$C(=O)NR$^a$R$^h$, —NR$^h$CO$_2$R$^e$, —NR$^f$CO$_2$R$^h$, —C$_{1-8}$alkylOR$^h$, —C$_{1-6}$alkylNR$^a$R$^h$, —S(=O)$_n$R$^h$, —S(=O)$_2$NR$^a$R$^h$, —NR$^a$S(=O)$_2$R$^h$, —NR$^h$S(=O)$_2$R$^e$, —OS(=O)$_2$R$^h$, —OC(=O)NR$^a$R$^h$, or —OC$_{1-8}$alkyl substituted by 1, 2 or 3 substituents independently selected from R$^f$, R$^h$, halo, nitro, cyano, —OR$^f$, —OR$^h$, —OC$_{2-6}$alkylNR$^a$R$^f$, —OC$_{2-6}$alkylOR$^f$, —NR$^a$R$^f$, —NR$^a$R$^f$, —NR$^f$C$_{2-6}$alkylNR$^a$R$^f$, —NR$^f$C$_{2-6}$alkylOR$^f$, naphthyl, —CO$_2$R$^e$, —OC(=O)R$^e$, —C(=O)R$^e$, —C(=O)NR$^a$R$^f$, —C(=O)NR$^a$R$^h$, —NR$^f$C(=O)R$^e$, —NR$^f$C(=O)R$^h$, —NR$^f$C(=O)NR$^a$R$^f$, —NR$^f$CO$_2$R$^e$, —C$_{1-8}$alkylOR$^f$, —C$_{1-6}$alkylNR$^a$R$^f$, —S(=O)$_n$R$^e$, —S(=O)$_2$NR$^a$R$^f$, —NR$^a$S(=O)$_2$R$^e$, —OS(=O)$_2$R$^e$, —OC(=O)NR$^a$R$^f$, —OR$^h$, —OC$_{2-6}$alkylNR$^a$R$^h$, —OC$_{2-6}$alkylOR$^h$, —NR$^a$R$^h$, —NR$^f$C$_{2-6}$alkylNR$^a$R$^h$, —NR$^h$C$_{2-6}$alkylNR$^a$R$^f$, —NR$^h$C$_{2-6}$alkylOR$^f$, —NR$^f$C$_{2-6}$alkylOR$^h$, —CO$_2$R$^h$, —OC(=O)R$^h$, —C(=O)R$^h$, —C(=O)NR$^a$R$^h$, —R$^f$C(=O)R$^h$, —NR$^h$C(=O)R$^f$, —NR$^h$C(=O)NR$^a$R$^f$, —NR$^f$C(=O)NR$^a$R$^h$, —NR$^h$CO$_2$R$^e$, —NR$^f$CO$_2$R$^h$, —C$_{1-8}$alkylOR$^h$, —C$_{1-6}$alkylNR$^a$R$^h$, —S(=O)$_n$R$^h$, —S(=O)$_2$NR$^a$R$^h$, —NR$^a$S(=O)$_2$R$^h$, —NR$^h$S(=O)$_2$R$^e$, —OS(=O)$_2$R$^h$ and —OC(=O)NR$^a$R$^h$.

In another embodiment, in conjunction with any one of the above and below embodiments, at least one of wherein at least one of R$^5$, R$^6$, R$^7$, R$^8$ and R$^9$ is R$^e$, R$^h$, halo, nitro, cyano, —NR$^a$R$^f$, —NR$^a$R$^h$, —NR$^f$C$_{2-6}$alkylNR$^a$R$^f$, —NR$^f$C$_{2-6}$alkylOR$^f$, naphthyl, —CO$_2$R$^e$, —C(=O)R$^e$, —OC(=O)R$^e$, —C(=O)NR$^a$R$^f$, —C(=O)NR$^a$R$^h$, —NR$^f$C(=O)R$^e$, —NR$^f$C(=O)R$^e$, —NR$^f$C(=O)NR$^a$R, —NR$^f$CO$_2$R$^e$, —C$_{1-8}$alkylOR$^f$, —C$_{1-6}$alkylNR$^a$R$^f$, —S(=O)$_n$R$^e$, —S(=O)$_2$NR$^a$R$^f$, —NR$^a$S(=O)$_2$R$^e$, —OS(=O)$_2$R$^e$, —OC(=O)NR$^a$R$^f$, —OR$^h$, —OC$_{2-6}$alkylNR$^a$R$^h$, —OC$_{2-6}$alkylOR$^h$, —NR$^a$R$^h$, —NR$^f$C$_{2-6}$alkylNR$^a$R$^h$, —NR$^h$C$_{2-6}$alkylNR$^a$R$^f$, —NR$^f$C$_{2-6}$alkylOR$^f$, —NR$^f$C$_{2-6}$alkylOR$^h$, —CO$_2$R$^h$, —OC(=O)R$^h$, —C(=O)R$^h$, —C(=O)NR$^a$R$^h$, —NR$^f$C(=O)R$^h$, —NR$^h$C(=O)R$^f$, —NR$^h$C(=O)NR$^a$R$^f$, —NR$^f$C(=O)NR$^a$R$^h$, —NR$^h$CO$_2$R$^e$, —NR$^f$CO$_2$R$^h$, —C$_{1-8}$alkylOR$^h$, —C$_{1-6}$alkylNR$^a$R$^h$, —S(=O)$_n$R$^h$, —S(=O)$_2$NR$^a$R$^h$, —NR$^a$S(=O)$_2$R$^h$, —NR$^h$S(=O)$_2$R$^e$, —OS(=O)$_2$R$^h$ or —OC(=O)NR$^a$R$^h$.

In another embodiment, in conjunction with any one of the above and below embodiments, at least one of R$^5$, R$^6$, R$^7$, R$^8$ and R$^9$ is tert-butyl or CF$_3$.

In another embodiment, in conjunction with any one of the above and below embodiments, R$^{10}$ is independently, at each instance, selected from H, C$_{1-5}$alkyl, C$_{1-4}$haloalkyl, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —C(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; or R$^{10}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein there are no more than 2 N atoms, and wherein the ring is fused with 0 or 1 benzo groups and 0 or 1 saturated or unsaturated 5-, 6- or 7-membered heterocyclic ring containing 1, 2 or 3 atoms selected from N, O and S; wherein the ring is substituted by 0, 1 or 2 oxo or thioxo groups, wherein the ring is substituted by 0, 1, 2 or 3 groups selected from C$_{1-8}$alkyl, C$_{1-4}$haloalkyl, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^e$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; or R$^{10}$ is C$_{1-4}$alkyl substituted by 0, 1, 2 or 3 groups selected from C$_{1-4}$haloalkyl, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$.

Embodiment M: In another embodiment, in conjunction with any one of the above and below embodiments, R$^{10}$ is H.

In another embodiment, in conjunction with any one of the above and below embodiments, R$^{10}$ is independently, at each instance, selected from C$_{1-5}$ alkyl, C$_{1-4}$haloalkyl, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; or R$^{10}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein there are no more than 2 N atoms, and wherein the ring is fused with 0 or 1 benzo groups and 0 or 1 saturated or unsaturated 5-, 6- or 7-membered heterocyclic ring containing 1, 2 or 3 atoms selected from N, O and S; wherein the ring is substituted by 0, 1 or 2 oxo or thioxo groups, wherein the ring is substituted by 0, 1, 2 or 3 groups selected from C$_{1-8}$alkyl, C$_{1-4}$haloalkyl, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$NR$^h$C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; or R$^{10}$ is C$_{1-4}$alkyl substituted by 0, 1, 2 or 3 groups selected from C$_{1-4}$haloalkyl, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^l$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$.

In another embodiment, in conjunction with any one of the above and below embodiments, R$^{11}$ is independently, at each instance, selected from H, C$_{1-8}$alkyl, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^b$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; or R$^{11}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the ring is substituted by 0, 1 or 2 oxo or thioxo groups, wherein the ring is substituted by 0, 1 or 2 groups selected from C$_{1-8}$alkyl, C$_{1-4}$haloalkyl, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^3$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; or R$^{10}$ and R$^{11}$ together are a saturated or unsaturated 3-, 4- or 5-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from oxo, thioxo, R$^c$, R$^e$, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^f$, —C(=O)NR$^a$R, —C(=NR$^a$)NR$^a$R$^h$, —OR$^h$, —OC(=O)R$^h$, —OC(=O)NR$^a$R$^h$, —OC(=O)N (R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O) R$^e$, —S(=O)$_2$N(R$^a$)C(=O)R$^h$, —S(=O)$_2$N(R$^h$)C(=O) OR$^f$, —S(=O)$_2$N(R$^a$)C(=O)OR$^h$, —S(=O)$_2$N(R$^h$)C(=O) NR$^a$R$^f$, —S(=O)$_2$N(R$^a$)C(=O)NR$^a$R$^h$, —NR$^a$R$^h$, —N(R$^h$) C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C (=O)NR$^a$R$^h$, —N(R$^h$)C(=NR$^a$)NR$^a$R$^f$, —N(R$^a$)C(=NR$^a$) NR$^a$R$^h$, —N(R$^h$)S(=O)$_2$R$^e$, —N(R$^a$)S(=O)$_2$R$^h$, —N(R$^h$)S (=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; or R$^{10}$ and R$^{11}$ together are a saturated or partially unsaturated 3-, 4- or 5-carbon bridge, wherein the bridge is substituted by 0, 1 or 2 substituents selected from oxo, thioxo, R$^c$, R$^e$, halo, cyano, nitro, —C(=O)R$^e$, —C(=O)OR$^f$, —C(=O)NR$^a$R$^f$, —C(=NR$^a$) NR$^a$R$^f$, —OR$^f$, —OC(=O)R$^e$, —OC(=O)NR$^a$R$^f$, —OC (=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O) R$^e$, —N(R$^a$)C(=O)OR$^f$, —N(R$^a$)C(=O)NR$^a$R$^f$, —N(R$^a$)C (=NR$^a$)NR$^a$R$^f$, —N(R$^a$)S(=O)$_2$R$^e$, —N(R$^a$)S(=O)$_2$ NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O) NR$^a$R$^h$, —OC(=O)N(R$^a$)S(=O)$_2$R$^h$, —OC(=O)N(R$^h$)S (=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N (R$^h$)C(=O)R$^e$, —S(=O)$_2$N(R$^a$)C(=O)R$^h$, —S(=O)$_2$N (R$^h$)C(=O)OR$^f$, —S(=O)$_2$N(R$^a$)C(=O)OR$^h$, —S(=O)$_2$N (R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$) C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$) C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; and when R$^{10}$ and R$^{11}$ together form a bridge, R$^{12}$ may additionally be halo or —CF$_3$, R$^{13}$ may additionally be halo or —OR$^a$ or cyano or nitro, and R$^{14}$ may additionally be halo.

In another embodiment, in conjunction with any one of the above and below embodiments, R$^{11}$ is independently, at each instance, selected from C$_{1-8}$alkyl, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N (R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O) R$^e$, —N(R$^a$)C(=O)OR$^f$, —N(R$^a$)C(=O)NR$^a$R$^f$, —N(R$^a$)C (=NR$^a$)NR$^a$R$^f$, —N(R$^a$)S(=O)$_2$R$^e$, —N(R$^a$)S(=O)$_2$ NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O) NR$^a$R$^h$, —OC(=O)N(R$^a$)S(=O)$_2$R$^h$, —OC(=O)N(R$^h$)S (=O)$_2$R$^e$, —OC$_{2-6}$alkylNR$^a$R$^h$, —OC$_{2-6}$alkylOR, —SR$^h$, —S(=O)R$^h$, —S(=O)$_2$R$^h$, —S(=O)$_2$NR$^a$R$^h$, —S(=O)$_2$N (R$^h$)C(=O)R$^e$, —S(=O)$_2$N(R$^a$)C(=O)R$^h$, —S(=O)$_2$N (R$^h$)C(=O)OR$^f$, —S(=O)$_2$N(R$^a$)C(=O)OR$^h$, —S(=O)$_2$N (R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$) C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$) C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; or R$^{11}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the ring is substituted by 0, 1 or 2 oxo or thioxo groups, wherein the ring is substituted by 0, 1, 2 or 3 groups selected from C$_{1-8}$alkyl, C$_{1-4}$haloalkyl, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N (R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O) R$^e$, —N(R$^a$)C(=O)OR$^f$, —N(R$^a$)C(=O)NR$^a$R$^f$, —N(R$^a$)C (=NR$^a$)NR$^a$R$^f$, —N(R$^a$)S(=O)$_2$R$^e$, —N(R$^a$)S(=O)$_2$ NR$^a$R$^f$, —NR$^a$C$_{2-6}$alkylNR$^a$R$^f$, —NR$^a$ C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O) NR$^a$R$^h$, —OC(=O)N(R$^a$)S(=O)$_2$R$^h$, —OC(=O)N(R$^h$)S (=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N (R$^h$)C(=O)R$^e$, —S(=O)$_2$N(R$^a$)C(=O)R$^h$, —S(=O)$_2$N (R$^h$)C(=O)OR$^f$, —S(=O)$_2$N(R$^a$)C(=O)OR$^h$, —S(=O)$_2$N (R$^h$)C(=O)NR$^a$R$^f$, —S(=O)$_2$N(R$^a$)C(=O)NR$^a$R$^h$, —NR$^a$R$^e$, —N(R$^h$)C(=O)R$^h$, —N(R$^a$)C(=O)R$^h$, —N(R$^h$) C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$) C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; or R$^h$ is C$_{1-4}$alkyl substituted by 0, 1, 2 or 3 groups selected from C$_{1-4}$haloalkyl, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O) NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N (R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O) NR$^a$R$^f$, —N(R$^a$)C(=NR$^a$)NR$^a$R$^f$, —N(R$^a$)S(=O)$_2$R$^e$ —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O) NR$^a$R$^h$, —OC(=O)N(R$^a$)S(=O)$_2$R$^h$, —OC(=O)N(R$^h$)S (=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N (R$^h$)C(=O)R$^e$, —S(=O)$_2$N(R$^a$)C(=O)R$^h$, —S(=O)$_2$N (R$^h$)C(=O)OR$^f$, —S(=O)$_2$N(R$^a$)C(=O)OR$^h$, —S(=O)$_2$N (R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$) C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$) C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; or R$^{10}$ and R$^{11}$ together are a saturated or unsaturated 3-, 4- or 5-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from oxo, thioxo, R$^c$, R$^e$, halo, cyano, nitro, —C(=O)R$^e$, —C(=O)

OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^e$)C(=O)OR$^f$, —S(=O)$_2$N(R$^a$)C(=O)OR$^h$, —S(=O)$_2$N(R$^a$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; or R$^{10}$ and R$^{11}$ together form a saturated or partially unsaturated 3-, 4- or 5-carbon bridge, wherein the bridge is substituted by 0, 1 or 2 substituents selected from oxo, thioxo, R$^c$, R$^e$, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; and when R$^{10}$ and R$^{11}$ together form a bridge, R$^{12}$ may additionally be halo or —CF$_3$, R$^{13}$ may additionally be halo or —OR$^a$ or cyano or nitro, and R$^{14}$ may additionally be halo.

In another embodiment, in conjunction with any one of the above and below embodiments, R$^{11}$ is independently, at each instance, selected from C$_{1-8}$alkyl, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^e$)C(=O)OR$^f$, —S(=O)$_2$N(R$^a$)C(=O)OR$^h$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^a$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$.

In another embodiment, in conjunction with any one of the above and below embodiments, R$^{11}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the ring is substituted by 0, 1 or 2 oxo or thioxo groups, wherein the ring is substituted by 0, 1, 2 or 3 groups selected from C$_{1-8}$alkyl, C$_{1-4}$haloalkyl, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^{11}$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$.

In another embodiment, in conjunction with any one of the above and below embodiments, R$^{11}$ is C$_{1-4}$alkyl substituted by 0, 1, 2 or 3 groups selected from C$_{1-4}$haloalkyl, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N (R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$.

Embodiment N: In another embodiment, in conjunction with any one of the above and below embodiments, R$^{10}$ and R$^{11}$ together are a saturated or unsaturated 3-, 4- or 5-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from oxo, thioxo, R$^c$, R$^e$, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$ —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; and when R$^{10}$ and R$^{11}$ together form a bridge, R$^{12}$ may additionally be halo or —CF$_3$, R$^{13}$ may additionally be halo or —OR$^a$ or cyano or nitro, and R$^{14}$ may additionally be halo.

In another embodiment, in conjunction with any one of the above and below embodiments, R$^{10}$ and R$^{11}$ together are a saturated or unsaturated 3-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from oxo, thioxo, R$^c$, R$^e$, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; and when R$^{10}$ and R$^{11}$ together form a bridge, R$^{12}$ may additionally be halo or —CF$_3$, R$^{13}$ may additionally be halo or —OR$^a$ or cyano or nitro, and R$^{14}$ may additionally be halo.

In another embodiment, in conjunction with any one of the above and below embodiments, R$^{10}$ and R$^{11}$ together are a saturated or unsaturated 4-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from oxo, thioxo, R$^c$, R$^e$, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^i$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; and when R$^{10}$ and R$^{11}$ together form a bridge, R$^{12}$ may additionally be halo or —CF$_3$, R$^{13}$ may additionally be halo or —OR$^a$ or cyano or nitro, and R$^{14}$ may additionally be halo.

In another embodiment, in conjunction with any one of the above and below embodiments, R$^{10}$ and R$^{11}$ together are a saturated or unsaturated 3-, 4- or 5-atom bridge containing 1, 2 or 3 atoms selected from O, N and S with the remaining atoms being carbon, so long as the combination of O and S atoms is not greater than 2, wherein the bridge is substituted by 1 or 2 substituents selected from R$^c$, R$^e$, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N (R$^h$)C(=O)OR$^f$, —S(=O)$_2$N(R$^a$)C(=O)OR$^h$, —S(=O)$_2$N(R$^h$)C(=O)NR$^a$R$^h$, —S(=O)$_2$N(R$^a$)C(=O)NR$^a$R$^h$, —NR$^a$R$^h$, —N(R$^h$)C(=O)R$^e$, —N(R$^a$)C(=O)R$^f$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_2$alkylNR$^a$R$^h$, —NR$^h$C$_{2-6}$alkylOR$^f$ and —NR$^a$C$_{2-6}$alkylOR$^h$; and when R$^{10}$ and R$^{11}$ together form a bridge, R$^{12}$ may additionally be halo or —CF$_3$, R$^{13}$ may additionally be halo or —OR$^a$ or cyano or nitro, and R$^{14}$ may additionally be halo.

Embodiment O: In another embodiment, in conjunction with any one of the above and below embodiments, R$^{10}$ and R$^{11}$ together are a saturated or unsaturated 3-atom bridge containing 1 or 2 atoms selected from O, N and S with the remaining atoms being carbon, wherein the bridge is substituted by 1 or 2 substituents selected from R$^c$, R$^e$, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^e$)C(=O)R$^h$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; and the bridge is additionally substituted by 0 or 1 substituents selected from R$^e$, oxo, thioxo, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; and when R$^{10}$ and R$^{11}$ together form a bridge, R$^{12}$ may additionally be halo or —CF$_3$, R$^{13}$ may additionally be halo or —OR$^a$ or cyano or nitro, and R$^{14}$ may additionally be halo.

In another embodiment, in conjunction with any one of the above and below embodiments, R$^{10}$ and R$^{11}$ together are a saturated or unsaturated 3-atom bridge containing 1 or 2 atoms selected from O, N and S with the remaining atoms being carbon, wherein the bridge is substituted by a substituents selected from —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; and when R$^{10}$ and R$^{11}$ together form a bridge, R$^{12}$ may additionally be halo or —CF$_3$, R$^{13}$ may additionally be halo or —OR$^a$ or cyano or nitro, and R$^{14}$ may additionally be halo.

In another embodiment, in conjunction with any one of the above and below embodiments, or R$^{10}$ and R$^{11}$ together are a saturated or partially unsaturated 3-, 4- or 5-carbon bridge, wherein the bridge is substituted by 0, 1 or 2 substituents selected from oxo, thioxo, R$^c$, R$^e$, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$.

In another embodiment, in conjunction with any one of the above and below embodiments, R$^{12}$ is independently, at each instance, selected from H, C$_{1-8}$alkyl, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; or R$^{12}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the ring is substituted by 0, 1 or 2 oxo or thioxo groups, wherein the ring is substituted by 0, 1, 2 or 3 groups selected from C$_{1-8}$alkyl, C$_{1-4}$haloalkyl, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O) R$^e$, —N(R$^a$)C(=O)OR$^f$, —N(R$^a$)C(=O)NR$^a$R$^f$, —N(R$^a$)C(=NR$^a$)NR$^a$R$^f$, —N($^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$) C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$, and additionally substituted by 0, 1 or 2 halo groups; or R$^{11}$ and R$^{12}$ together are a saturated or unsaturated 3-, 4- or 5-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from oxo, thioxo, R$^c$, R$^e$, halo, cyano, nitro, —C(=O)R$^e$, —C(=O)OR$^f$, —C(=O) NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O) NR$^a$R$^f$, N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R, —C(=NR$^a$)NR$^a$R$^h$, —OR$^h$, —OC(=O)R$^h$, —OC(=O)

NR$^a$R$^h$, —OC(=O)N(R$^a$)S(=O)$_2$R$^e$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^i$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^f$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; wherein when R$^3$ is NH$_2$, then —R$^{11}$—R$^{12}$— is not —C=C—C=N— or any substituted version thereof, or R$^{11}$ and R$^{12}$ together are a saturated or partially unsaturated 3-, 4- or 5-carbon bridge, wherein the bridge is substituted by 0, 1 or 2 substituents selected from oxo, thioxo, R$^c$, R$^e$, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^e$)C(=O)NR$^a$R, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^h$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; and when R$^{11}$ and R$^{12}$ together form a bridge, R$^{10}$ may additionally be halo, R$^{13}$ may additionally be halo or —OR$^a$ or cyano or nitro, and R$^{14}$ may additionally be halo.

Embodiment Q: In another embodiment, in conjunction with any one of the above and below embodiments, R$^{12}$ is H.

In another embodiment, in conjunction with any one of the above and below embodiments, R$^{12}$ is independently, at each instance, selected from C$_{1-8}$alkyl, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; or R$^{12}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the ring is substituted by 0, 1 or 2 oxo or thioxo groups, wherein the ring is substituted by 0, 1, 2 or 3 groups selected from C$_{1-8}$alkyl, C$_{1-4}$haloalkyl, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$^2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; or R$^{12}$ is C$_{1-4}$alkyl substituted by 0, 1, 2 or 3 groups selected from C$_{1-4}$haloalkyl, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$, and additionally substituted by 0, 1 or 2 halo groups; or R$^{11}$ and R$^{12}$ together are a saturated or unsaturated 3-, 4- or 5-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from oxo, thioxo, $R^c$, $R^e$, halo, cyano, nitro, —C(=O)$R^e$, —C(=O)O$R^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; wherein when R$^3$ is NH$_2$, then R$^{11}$R$^{12}$ is not —C=C—C=N— or any substituted version thereof; or R$^{11}$ and R$^{12}$ together are a saturated or partially unsaturated 3-, 4- or 5-carbon bridge, wherein the bridge is substituted by 0, 1 or 2 substituents selected from oxo, thioxo, R$^c$, R$^e$, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; and when R$^{11}$ and R$^{12}$ together form a bridge, R$^{10}$ may additionally be halo, R$^{13}$ may additionally be halo or —OR$^a$ or cyano or nitro, and R$^{14}$ may additionally be halo.

In another embodiment, in conjunction with any one of the above and below embodiments, R$^{12}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the ring is substituted by 0, 1 or 2 oxo or thioxo groups, wherein the ring is substituted by 0, 1, 2 or 3 groups selected from C$_{1-8}$alkyl, C$_{1-4}$haloalkyl, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$.

In another embodiment, in conjunction with any one of the above and below embodiments, R$^{11}$ and R$^{12}$ together are a saturated or unsaturated 3-, 4- or 5-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from oxo, thioxo, R$^c$, R$^e$, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; wherein R$^{11}$R$^{12}$is not —C(NH$_2$)=C—C=N— or any substituted version thereof; or R$^{11}$ and R$^{12}$ together are a saturated or partially unsaturated 3-, 4- or 5-carbon bridge, wherein the bridge is substituted by 0, 1 or 2 substituents selected from oxo, thioxo, R$^c$, R$^e$, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)

$R^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^i$, —NR$^h$C$_{2-6}$alkylNR$^a$R$^f$, —NR$^a$C$_{2-6}$alkylNR$^a$R$^h$—NR$^h$C$_{2-6}$alkylOR$^f$nd —NR$^a$C$_{2-6}$alkylOR$^h$; and when R$^{11}$ and R$^{12}$ together form a bridge, R$^{10}$ may additionally be halo, R$^{13}$ may additionally be halo or —OR$^a$ or cyano or nitro, and R$^{14}$ may additionally be halo.

Embodiment R: In another embodiment, in conjunction with any one of the above and below embodiments, R$^{11}$ and R$^{12}$ together are a saturated or unsaturated 3-, 4- or 5-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from oxo, thioxo, R$^c$, R$^e$, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; wherein when R$^3$ is NH$_2$, then R$^{11}$R$^{12}$ is not —C=C—C=N— or any substituted version thereof, and when R$^{11}$ and R$^{12}$ together form a bridge, R$^{10}$ may additionally be halo, R$^{13}$ may additionally be halo or —OR$^a$ or cyano or nitro, and R$^{14}$ may additionally be halo.

In another embodiment, in conjunction with any one of the above and below embodiments, R$^{11}$ and R$^{12}$ together are a saturated or unsaturated 3-, 4- or -atom bridge containing 1, 2 or 3 atoms selected from O, N and S with the remaining atoms being carbon, so long as the combination of O and S atoms is not greater than 2, and for a 4-atom bridge the first attachment atom in R$^{12}$ is not N, wherein the bridge is substituted by 0, 1 or 2 substituents selected from oxo, thioxo, R$^c$, R$^e$, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; wherein when R$^3$ is NH$_2$, then R$^{11}$R$^{12}$ is not —C=C—C=N— or any substituted version thereof; and when R$^{11}$ and R$^{12}$ together form a bridge, R$^{10}$ may additionally be halo, R$^{13}$ may additionally be halo or —OR$^a$ or cyano or nitro, and R$^{14}$ may additionally be halo.

Embodiment S: In another embodiment, in conjunction with any one of the above and below embodiments, R$^{11}$ and R$^{12}$ together are a saturated or unsaturated 3-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from oxo, thioxo, R$^c$, R$^e$, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; and when R$^{11}$ and R$^{12}$ together form a bridge, R$^{10}$ may additionally be halo, R$^{13}$ may additionally be halo or —OR$^a$ or cyano or nitro, and R$^{14}$ may additionally be halo.

In another embodiment, in conjunction with any one of the above and below embodiments, $R^{11}$ and $R^{12}$ together are a saturated or unsaturated 3-atom bridge containing 1 or 2 atoms selected from O, N and S with the remaining atoms being carbon, wherein the bridge is substituted by 0, 1 or 2 substituents selected from oxo, thioxo, $R^c$, $R^e$, halo, cyano, nitro, —C(=O)$R^e$, —C(=O)O$R^f$, —C(=O)N$R^aR^f$, —C(=N$R^a$)N$R^aR^f$, —O$R^f$, —OC(=O)$R^e$, —OC(=O)N$R^aR^f$, —OC(=O)N($R^a$)S(=O)$_2R^e$, —OC$_{2-6}$alkylN$R^aR^f$, —OC$_{2-6}$alkylO$R^f$, —S$R^e$, —S(=O)$R^e$, —S(=O)$_2R^e$, —S(=O)$_2$N$R^aR^f$, —S(=O)$_2$N($R^a$)C(=O)$R^e$, —S(=O)$_2$N($R^a$)C(=O)O$R^f$, —S(=O)$_2$N($R^a$)C(=O)N$R^aR^f$, —N$R^aR^f$, —N($R^a$)C(=O)$R^e$, —N($R^a$)C(=O)O$R^f$, —N($R^a$)C(=O)N$R^aR^f$, —N($R^a$)C(=N$R^a$)N$R^aR^f$, —N($R^a$)S(=O)$_2R^e$, —N($R^a$)S(=O)$_2$N$R^aR^f$, —N$R^aC_{2-6}$alkylN$R^aR^f$, —N$R^aC_{2-6}$alkylO$R^f$, —C(=O)$R^h$, —C(=O)O$R^h$, —C(=O)N$R^aR^h$, —C(=N$R^a$)N$R^aR^h$, —O$R^h$, —OC(=O)$R^h$, —OC(=O)N$R^aR^h$, —OC(=O)N($R^a$)S(=O)$_2R^h$, —OC(=O)N($R^h$)S(=O)$_2R^e$, —OC$_{2-6}$alkylN$R^aR^h$, —OC$_{2-6}$alkylO$R^h$, —S$R^h$, —S(=O)$R^h$, —S(=O)$_2R^h$, —S(=O)$_2$N$R^aR^h$, —S(=O)$_2$N($R^h$)C(=O)$R^e$, —S(=O)$_2$N($R^a$)C(=O)$R^h$, —S(=O)$_2$N($R^h$)C(=O)O$R^f$, —S(=O)$_2$N($R^a$)C(=O)O$R^h$, —S(=O)$_2$N($R^h$)C(=O)N$R^aR^f$, —S(=O)$_2$N($R^a$)C(=O)N$R^aR^h$, —N$R^aR^h$, —N($R^h$)C(=O)$R^e$, —N($R^a$)C(=O)$R^h$, —N($R^h$)C(=O)O$R^f$, —N($R^a$)C(=O)O$R^h$, —N($R^h$)C(=O)N$R^aR^f$, —N($R^a$)C(=O)N$R^aR^h$, —N($R^h$)C(=N$R^a$)N$R^aR^f$, —N($R^a$)C(=N$R^a$)N$R^aR^h$, —N($R^h$)S(=O)$_2R^e$, —N($R^a$)S(=O)$_2R^h$, —N($R^h$)S(=O)$_2$N$R^aR^f$, —N($R^a$)S(=O)$_2$N$R^aR^h$, —N$R^hC_{2-6}$alkylN$R^aR^f$, —N$R^aC_{2-6}$alkylN$R^aR^h$, —N$R^hC_{2-6}$alkylO$R^f$ and —N$R^aC_{2-6}$alkylO$R^h$; and when $R^{11}$ and $R^{12}$ together form a bridge, $R^{10}$ may additionally be halo, $R^{13}$ may additionally be halo or —O$R^a$ or cyano or nitro, and $R^{14}$ may additionally be halo.

In another embodiment, in conjunction with any one of the above and below embodiments, $R^{11}$ and $R^{12}$ together are a saturated or unsaturated 3-atom bridge containing 1 or 2 atoms selected from O, N and S with the remaining atoms being carbon, wherein the bridge is substituted by 1 or 2 substituents selected from oxo, thioxo, $R^c$, $R^e$, halo, cyano, nitro, —C(=O)$R^e$, —C(=O)O$R^f$, —C(=O)N$R^aR^f$, —C(=N$R^a$)N$R^aR^f$, —O$R^f$, —OC(=O)$R^e$, —OC(=O)N$R^aR^f$, —OC(=O)N($R^a$)S(=O)$_2R^e$, —OC$_{2-6}$alkylN$R^aR^f$, —OC$_{2-6}$alkylO$R^f$, —S$R^e$, —S(=O)$R^e$, —S(=O)$_2R^e$, —S(=O)$_2$N$R^aR^f$, —S(=O)$_2$N($R^a$)C(=O)$R^e$, —S(=O)$_2$N($R^a$)C(=O)O$R^f$, —S(=O)$_2$N($R^a$)C(=O)N$R^aR^f$, —N$R^aR^f$, —N($R^a$)C(=O)$R^e$, —N($R^a$)C(=O)O$R^f$, —N($R^a$)C(=O)N$R^aR^f$, —N($R^a$)C(=N$R^a$)N$R^aR^f$, —N($R^a$)S(=O)$_2R^e$, —N($R^a$)S(=O)$_2$N$R^aR^f$, —N$R^aC_{2-6}$alkylN$R^aR^f$, —N$R^aC_{2-6}$alkylO$R^f$, —C(=O)$R^h$, —C(=O)O$R^h$, —C(=O)N$R^aR^h$, —C(=N$R^a$)N$R^aR^h$, —O$R^h$, —OC(=O)$R^h$, —OC(=O)N$R^aR^h$, —OC(=O)N($R^a$)S(=O)$_2R^h$, —OC(=O)N($R^h$)S(=O)$_2R^e$, —OC$_{2-6}$alkylN$R^aR^h$, —OC$_{2-6}$alkylO$R^h$, —S$R^h$, —S(=O)$R^h$, —S(=O)$_2R^h$, —S(=O)$_2$N$R^aR^h$, —S(=O)$_2$N($R^h$)C(=O)$R^e$, —S(=O)$_2$N($R^a$)C(=O)$R^h$, —S(=O)$_2$N($R^h$)C(=O)O$R^f$, —S(=O)$_2$N($R^a$)C(=O)O$R^h$, —S(=O)$_2$N($R^h$)C(=O)N$R^aR^f$, —S(=O)$_2$N($R^a$)C(=O)N$R^aR^h$, —N$R^aR^h$, —N($R^h$)C(=O)$R^e$, —N($R^a$)C(=O)$R^h$, —N($R^h$)C(=O)O$R^f$, —N($R^a$)C(=O)O$R^h$, —N($R^h$)C(=O)N$R^aR^f$, —N($R^a$)C(=O)N$R^aR^h$, —N($R^h$)C(=N$R^a$)N$R^aR^f$, —N($R^a$)C(=N$R^a$)N$R^aR^h$, —N($R^h$)S(=O)$_2R^e$, —N($R^a$)S(=O)$_2R^h$, —N($R^h$)S(=O)$_2$N$R^aR^f$, —N($R^a$)S(=O)$_2$N$R^aR^h$, —N$R^hC_{2-6}$alkylN$R^aR^f$, —N$R^aC_{2-6}$alkylN$R^aR^h$, —N$R^hC_{2-6}$alkylO$R^f$ and —N$R^aC_{2-6}$alkylO$R^h$; and when $R^{11}$ and $R^{12}$ together form a bridge, $R^{10}$ may additionally be halo, $R^{13}$ may additionally be halo or —O$R^a$ or cyano or nitro, and $R^{14}$ may additionally be halo.

In another embodiment, in conjunction with any one of the above and below embodiments, $R^{11}$ and $R^{12}$ together are a saturated or unsaturated 3-atom bridge containing 1 or 2 atoms selected from O, N and S with the remaining atoms being carbon, wherein the bridge is substituted by $R^e$, $R^c$, —C(=O)$R^e$, —C(=O)O$R^f$, —C(=O)N$R^aR^f$, —C(=N$R^a$)N$R^aR^f$, —O$R^f$, —OC(=O)$R^e$, —OC(=O)N$R^aR^f$, —OC(=O)N($R^a$)S(=O)$_2R^e$, —OC$_{2-6}$alkylN$R^aR^f$, —OC$_{2-6}$alkylO$R^f$, —S$R$, —S(=O)$R^e$, —S(=O)$_2R^e$, —S(=O)$_2$N$R^aR^f$, —S(=O)$_2$N($R^a$)C(=O)$R^e$, —S(=O)$_2$N($R^a$)C(=O)O$R^f$, —S(=O)$_2$N($R^a$)C(=O)N$R^aR^h$, —N$R^aR^h$, —N($R^h$)C(=O)$R^e$, —N($R^a$)C(=O)$R^f$, —N($R^h$)C(=O)N$R^aR^f$, —N($R^a$)C(=N$R^a$)N$R^aR^f$, —N($R^h$)S(=O)$_2R^e$, —N($R^a$)S(=O)$_2$N$R^aR^f$, —N$R^aC_{2-6}$alkylO$R^aR^f$, —N$R^aC_{2-6}$alkylO$R^f$, —C(=O)$R^h$, —C(=O)O$R^h$, —C(=O)N$R^aR^h$, —C(=N$R^a$)N$R^aR^h$, —O$R^h$, —OC(=O)$R^h$, —OC(=O)N$R^aR^h$, —OC(=O)N($R^a$)S(=O)$_2R^h$, —OC(=O)N($R^h$)S(=O)$_2R^e$, —OC$_{2-6}$alkylN$R^aR^h$, —OC$_{2-6}$alkylO$R^h$, —S$R^h$, —S(=O)$R^h$, —S(=O)$_2R^h$, —S(=O)$_2$N$R^aR^h$, —S(=O)$_2$N($R^h$)C(=O)$R^e$, —S(=O)$_2$A($R^a$)C(=O)$R^h$, —S(=O)$_2$N($R^h$)C(=O)O$R^f$, —S(=O)$_2$N($R^a$)C(=O)O$R^h$, —S(=O)$_2$N($R^h$)C(=O)N$R^aR^f$, —S(=O)$_2$N($R^a$)C(=O)N$R^aR^i$, —N$R^aR^h$, —N($R^h$)C(=O)$R^e$, —N($R^a$)C(=O)$R^h$, —N($R^e$)C(=O)O$R^f$, —N($R^a$)C(=O)O$R^h$, —N($R^h$)C(=O)N$R^aR^f$, —N($R^a$)C(=O)N$R^aR^h$, —N($R^h$)C(=N$R^a$)N$R^aR^f$, —N($R^a$)C(=N$R^a$)N$R^aR^h$, —N($R^h$)S(=O)$_2R^e$, —N($R^a$)S(=O)$_2R^h$, —N($R^e$)S(=O)$_2$N$R^aR$, —N($R^a$)S(=O)$_2$N$R^aR^i$, —N$R^hC_{2-6}$alkyN$R^aR^f$, —N$R^aC_{2-6}$alkylN$R^aR^h$, —N$R^hC_{2-6}$alkylO$R^f$ and —N$R^aC_{2-6}$alkylO$R^h$; and when $R^{11}$ and $R^{12}$ together form a bridge, $R^{10}$ may additionally be halo, $R^{13}$ may additionally be halo or —O$R^a$ or cyano or nitro, and $R^{14}$ may additionally be halo.

In another embodiment, in conjunction with any one of the above and below embodiments, $R^{11}$ and $R^{12}$ together are a saturated or unsaturated 4-atom bridge containing 1, 2 or 3 atoms selected from O, N and S with the remaining atoms being carbon, so long as the combination of O and S atoms is not greater than 2 and first attachment atom in $R^{12}$ is not N, wherein the bridge is substituted by 0, 1 or 2 substituents selected from oxo, thioxo, $R^c$, $R^e$, halo, cyano, nitro, —C(=O)$R^e$, —C(=O)O$R^f$, —C(=O)N$R^aR^f$, —C(=N$R^a$)N$R^aR^h$, —O$R^f$, —OC(=O)$R^e$, —OC(=O)N$R^aR^f$, —OC(=O)N($R^a$)S(=O)$_2R^e$, —O$C_{2-6}$alkylN$R^aR^f$, —O$C_{2-6}$alkylO$R^f$, —S$R^e$, —S(=O)$R^e$, —S(=O)$_2R^e$, —S(=O)$_2$N$R^aR^f$, —S(=O)$_2$N($R^a$)C(=O)$R^e$, —S(=O)$_2$N($R^a$)C(=O)O$R^f$, —S(=O)$_2$N($R^a$)C(=O)N$R^aR^f$, —N$R^aR^f$, —N($R^a$)C(=O)$R^e$, —N($R^a$)C(=O)O$R^f$, —N($R^a$)C(=O)N$R^aR^f$, —N($R^a$)C(=N$R^a$)N$R^aR^f$, N($R^a$)S(=O)$_2R^e$, —N($R^a$)S(=O)$_2$N$R^aR^f$, —N$R^aC_{2-6}$alkylN$R^aR^f$, —N$R^aC_{2-6}$alkylO$R^f$, —C(=O)$R^h$, —C(=O)O$R^f$, —C(=O)N$R^aR^h$, —C(=N$R^a$)N$R^aR^h$, —O$R^h$, —OC(=O)$R^h$, —OC(=O)N$R^aR^h$, —OC(=O)N($R^a$)S(=O)$_2R^h$, —OC(=O)N($R^h$)S(=O)$_2R^e$, —O$C_{2-6}$alkylN$R^aR^h$, —O$C_{2-6}$alkylO$R^h$, —S$R^h$, —S(=O)$R^h$, —S(=O)$_2R^h$, —S(=O)$_2$N$R^aR^h$, —S(=O)$_2$N($R^h$)C(=O)$R^e$, —S(=O)$_2$N($R^a$)C(=O)$R^h$, —S(=O)$_2$N($R^h$)C(=O)O$R^f$, —S(=O)$_2$N($R^a$)C(=O)O$R^h$, —S(=O)$_2$N($R^h$)C(=O)N$R^aR^f$, —S(=O)$_2$N($R^a$)C(=O)N$R^aR^h$, —N$R^aR^h$, —N($R^h$)C(=O)$R^e$, —N($R^a$)C(=O)$R^h$, —N($R^h$)C(=O)O$R^f$, —N($R^a$)C(=O)O$R^h$, —N($R^h$)C(=O)N$R^aR^f$, —N($R^a$)C(=O)N$R^aR^h$, —N($R^h$)C(=N$R^a$)N$R^aR^f$, —N($R^a$)C(=N$R^a$)N$R^aR^h$, —N($R^h$)S(=O)$_2R^e$, —N($R^a$)S(=O)$_2R^h$, —N($R^h$)S(=O)$_2$N$R^aR^f$, —N($R^a$)S(=O)$_2$N$R^aR^h$, —N$R^hC_{2-6}$alkylN$R^aR^f$, —N$R^aC_{2-6}$alkylN$R^aR^h$, —N$R^hC_{2-6}$alkylO$R^f$ and —N$R^aC_{2-6}$alkylO$R^h$; and when $R^{11}$ and $R^{12}$ together form a bridge, $R^{10}$ may additionally be halo, $R^{13}$ may additionally be halo or —O$R^a$ or cyano or nitro, and $R^{14}$ may additionally be halo.

Embodiment T: In another embodiment, in conjunction with any one of the above and below embodiments, $R^{11}$ and $R^{12}$ together form a —$R^{11}$—$R^{12}$— bridge selected from —O—C≡C—O—, —N—C≡C—C— and —N=C—C=C—, wherein the bridge is substituted by 0, 1 or 2 substituents selected from oxo, thioxo, $R^c$, $R^e$, halo, cyano, nitro, —C(=O)$R^e$, —C(=O)O$R^f$, —C(=O)N$R^aR^f$, —C(=N$R^a$)N$R^aR$, —O$R^f$, —C(=O)$R^e$, —OC(=O)N$R^aR^f$, —OC(=O)N($R^a$)S(=O)$_2R^e$, —O$C_{2-6}$alkylN$R^aR^f$, —O$C_{2-6}$alkylO$R^f$, —S$R^h$, —S(=O)$R^e$, —S(=O)$_2R^e$, —S(=O)$_2$N$R^aR^f$, —S(=O)$_2$N($R^a$)C(=O)$R^e$, —S(=O)$_2$N($R^a$)C(=O)O$R^f$, —S(=O)$_2$N($R^a$)C(=O)N$R^aR^f$, —N$R^aR^f$, —N($R^a$)C(=O)$R^e$, —N($R^a$)C(=O)O$R^f$, —N($R^a$)C(=O)N$R^aR^f$, —N($R^a$)C(=N$R^a$)N$R^aR^f$, N($R^a$)S(=O)$_2R^e$, —N($R^a$)S(=O)$_2$N$R^aR^f$, —N$R^aC_{2-6}$alkyl N$R^aR^f$, —N$R^aC_{2-6}$ alkylO$R^f$, —C(=O)$R^h$, —C(=O)O$R^h$, —C(=O)N$R^aR^h$, —C(=N$R^a$)N$R^aR^h$, —O$R^h$, —OC(=O)$R^h$, —OC(=O)N$R^aR^h$, —OC(=O)N($R^a$)S(=O)$_2R^e$, —OC(=O)N($R^e$)S(=O)$_2R^e$, —O$C_{2-6}$alkylN$R^aR^h$, —O$C_{2-6}$alkylO$R^h$, —S$R^h$, —S(=O)$R^e$, —S(=O)$_2R^h$, —S(=O)$_2$N$R^aR^i$, —S(=O)$_2$N($R^e$)C(=O)$R^e$, —S(=O)$_2$N($R^a$)C(=O)$R^h$, —S(=O)$_2$N($R^h$)C(=O)O$R^f$, —S(=O)$_2$N($R^a$)C(=O)O$R^h$, —S(=O)$_2$N($R^h$)C(=O)N$R^aR^f$, —S(=O)$_2$N($R^a$)C(=O)N$R^aR^h$—N$R^aR^h$, —N($R^h$)C(=O)$R^e$, —N($R^a$)C(=O)$R^h$, —N($R^h$)C(=O)O$R^f$, —N($R^a$)C(=O)O$R^h$, —N($R^h$)C(=O)N$R^aR$, —N($R^a$)C(=O)N$R^aR^h$, —N($R^h$)C(=N$R^a$)N$R^aR^f$, —N($R^a$)C(=N$R^a$)N$R^aR^h$, —N($R^h$)S(=O)$_2$ $R^e$, —N($R^a$)S(=O)$_2R^h$, —N($R^h$)S(=O)$_2$N$R^aR^f$, —N($R^a$)S(=O)$_2$N$R^aR^h$, —N$R^hC_{2-6}$alkylN$R^aR^f$, —N$R^aC_{2-6}$ alkylN$R^aR^h$, —N$R^hC_{2-6}$alkylO$R^f$ an-N$R^aC_{2-6}$alkylO$R^a$ and when $R^{11}$ and $R^{12}$ together form a bridge, $R^{10}$ may additionally be halo, $R^{13}$ may additionally be halo or —O$R^a$ or cyano or nitro, and $R^{14}$ may additionally be halo.

$R^{11}$ and $R^{12}$ together form a —$R^{11}$—$R^{12}$— bridge selected from —O—C—C—O—, —N—C—C—C— and —N=C—C=C—, wherein the bridge is substituted by 1 or 2 substituents selected from oxo, thioxo, $R^c$, $R^e$, halo, cyano, nitro, —C(=O)$R^e$, —C(=O)O$R^f$, —C(=O)N$R^aR^f$, —C(=N$R^a$)N$R^aR^f$, —O$R^f$, —OC(=O)$R^e$, —OC(=O)N$R^aR^f$, —OC(=O)N($R^a$)S(=O)$_2R^e$, —O$C_{2-6}$alkylN$R^aR^f$, —O$C_{2-6}$alkylO$R^f$, —S$R^e$, —S(=O)$R^e$, —S(=O)$_2R^e$, —S(=O)$_2$N$R^aR^f$, —S(=O)$_2$N($R^a$)C(=O)$R^e$, —S(=O)$_2$N($R^a$)C(=O)O$R^f$, —S(=O)$_2$N($R^a$)C(=O)N$R^aR^f$, —N$R^aR^f$, —N($R^a$)C(=O)$R^e$, —N($R^a$)C(=O)O$R^f$, —N($R^a$)C(=O)N$R^aR^f$, —N($R^a$)C(=N$R^a$)N$R^aR^f$, —N($R^a$)S(=O)$_2R^e$, —N($R^a$)S(=O)$_2$N$R^aR^f$, —N$R^aC_{2-6}$alkylN$R^aR^f$, —N$R^aC_{2-6}$alkylO$R^f$, —C(=O)$R^h$, —C(=O)O$R^e$, —C(=O)N$R^aR^h$, —C(=N$R^a$)N$R^aR^h$, —O$R^h$, —OC(=O)$R^h$, —OC(=O)N$R^aR^h$, —OC(=O)N($R^a$)S(=O)$_2R^h$, —OC(=O)N($R^h$)S(=O)$_2R^e$, —O$C_{2-6}$alkylN$R^aR^h$, —O$C_{2-6}$alkylO$R^h$, —S$R^h$, —S(=O)$R^h$, —S(=O)$_2R^h$, —S(=O)$_2$N$R^aR^h$, —S(=O)$_2$N($R^h$)C(=O)$R^e$, —S(=O)$_2$N($R^a$)C(=O)$R^h$, —S(=O)$_2$N($R^1$)C(=O)O$R^f$, —S(=O)$_2$N($R^a$)C(=O)O$R^h$, —S(=O)$_2$N($R^h$)C(=O)N$R^aR^f$, —S(=O)$_2$N($R^a$)C(=O)N$R^aR^h$, —N$R^aR$, —N($R^h$)C(=O)$R^e$, —N($R^a$)C(=O)$R^h$, —N($R^h$)C(=O)O$R^f$, —N($R^a$)C(=O)O$R^h$, —N($R^e$)C(=O)N$R^aR^f$, —N($R^a$)C(=O)N$R^aR^h$ —N($R^h$)C(=N$R^a$)N$R^aR^f$, —N($R^a$)C(=N$R^a$)N$R^aR^h$, —N($R^h$)S(=O)$_2R^e$, —N($R^a$)S(=O)$_2R^h$, —N($R^h$)S(=O)$_2$N$R^aR^f$, —N($R^a$)S(=O)$_2$N$R^aR^h$, —N$R^hC_{2-6}$alkylN$R^aR^f$, —N$R^aC_{2-6}$alkylN$R^aR^h$, —N$R^hC_{2-6}$alkylO$R^f$ and —N$R^aC_{2-6}$alkylO$R^h$; and when $R^{11}$ and $R^{12}$ together form a bridge, $R^{10}$ may additionally be halo, $R^{13}$ may additionally be halo or —O$R^a$ or cyano or nitro, and $R^{14}$ may additionally be halo.

In another embodiment, in conjunction with any one of the above and below embodiments, or $R^{10}$ and $R^{11}$ together are a saturated or partially unsaturated 3-, 4- or 5-carbon bridge, wherein the bridge is substituted by 0, 1 or 2 substituents selected from oxo, thioxo, $R^c$, $R^e$, halo, cyano, nitro, —C(=O)$R^e$, —C(=O)O$R^f$, —C(=O)N$R^aR^f$, —C(=N$R^a$)N$R^aR^f$, —O$R^f$, —OC(=O)$R^e$, —OC(=O)N$R^aR^f$, —OC(=O)N($R^a$)S(=O)$_2R^e$, —O$C_{2-6}$alkylN$R^aR^f$, —O$C_{2-6}$alkylO$R^f$, —S$R^e$, —S(=O)$R^e$, —S(=O)$_2R^e$, —S(=O)$_2$N$R^aR^f$, —S(=O)$_2$N($R^a$)C(=O)$R^e$, —S(=O)$_2$N($R^a$)C(=O)O$R^f$, —S(=O)$_2$N($R^a$)C(=O)N$R^aR^f$, —N$R^aR^f$, —N($R^a$)C(=O)$R^e$, —N($R^a$)C(=O)O$R^f$, —N($R^a$)C(=O)N$R^aR^f$, —N($R^a$)C(=N$R^a$)N$R^aR^f$, —N($R^a$)S(=O)$_2R^e$, —N($R^a$)S(=O)$_2$N$R^aR^f$, —N$R^aC_{2-6}$alkylN$R^aR^f$, —N$R^aC_{2-6}$alkylO$R^f$, —C(=O)$R^h$, —C(=O)O$R^h$, —C(=O)N$R^aR^h$, —C(=N$R^a$)N$R^aR^h$, —O$R^h$, —OC(=O)$R^h$, —OC(=O)N$R^aR^h$, —OC(=O)N($R^a$)S(=O)$_2R^h$, —OC(=O)N($R^h$)S(=O)$_2R^e$, —O$C_{2-6}$alkylN$R^aR^h$, —O$C_{2-6}$alkylO$R^h$, —S$R^h$, —S(=O)$R^h$, —S(=O)$_2R^h$, —S(=O)$_2$N$R^aR^h$, —S(=O)$_2$N($R^h$)C(=O)$R^e$, —S(=O)$_2$N($R^a$)C(=O)$R^h$, —S(=O)$_2$N($R^h$)C(=O)O$R^f$, —S(=O)$_2$N($R^a$)C(=O)O$R^h$, —S(=O)$_2$N($R^h$)C(=O)N$R^aR^f$, —S(=O)$_2$N($R^a$)C(=O)N$R^aR^h$, —N$R^aR^h$, —N($R^h$)C(=O)$R^e$, —N($R^a$)C(=O)$R^h$, —N($R^h$)C(=O)O$R^f$, —N($R^a$)C(=O)O$R^h$, —N(h)C(=O)N$R^aR^h$, —N($R^a$)C(=O)N$R^aR^h$, —N($R^h$)C(=N$R^a$)N$R^aR$, —N($R^a$)C(=N$R^a$)N$R^aR^h$, —N($R^h$)S(=O)$_2R^e$, —N($R^a$)S(=O)$_2R^h$, —N($R^h$)S(=O)$_2$N$R^aR^f$, —N($R^a$)S(=O)$_2$N$R^aR^h$, —N$R^hC_{2-6}$alkylN$R^aR^f$, —N$R^aC_{2-6}$alkylN$R^aR^h$, —N$R^hC_{2-6}$alkylO$R^f$ and —N$R^aC_{2-6}$alkylO$R^h$.

In another embodiment, in conjunction with any one of the above and below embodiments, $R^{13}$ is independently, at each instance, selected from H, $C_{1-8}$alkyl, —C(=O)$R^e$, —C(=O)OR, —C(=O)N$R^aR^f$, —C(=N$R^a$)N$R^aR$, —OR, —OC(=O)$R^e$, —OC(=O)N$R^aR^f$, —OC(=O)N($R^a$)S(=O)$_2R^e$, —O$C_{2-6}$alkylN$R^aR^f$, —O$C_{2-6}$alkylO$R^f$, —S$R^e$, —S(=O)$R^e$, —S(=O)$_2R^e$, —S(=O)$_2$N$R^aR^f$, —S(=O)$_2$N($R^a$)C(=O)$R^e$, —S(=O)$_2$N($R^a$)C(=O)O$R^f$, —S(=O)$_2$N($R^a$)C(=O)N$R^aR^f$, —N$R^aR^f$, —N($R^a$)C(=O)$R^e$, —N($R^a$)

C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^a$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^e$)C(=O)OR$^f$, —N(R$^a$)C(=O)OR$^h$, —N(R$^h$)C(=O)NR$^a$R, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; or R$^{13}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the ring is substituted by 0, 1 or 2 oxo or thioxo groups, wherein the ring is substituted by 0, 1, 2 or 3 groups selected from C$_{1-8}$alkyl, C$_{1-4}$haloalkyl, halo, cyano, nitro, —C(=O)$_k$W, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^{11}$, —C(=O)OR$^h$, —C(=O)NR$^a$R, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^e$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkyNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; or R$^{13}$ is C$_{1-4}$alkyl substituted by 0, 1, 2 or 3 groups selected from C$_{1-4}$haloalkyl, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$ —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, c(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylN-R$^a$R$^h$, —OC$_{2-6}$alkylOR$^h$, —SR$^h$, —S(=O)R$^h$, —S(=O)$_2$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N (R$^a$)C(=O)OR$^h$, —S(=O)$_2$N(R$^h$)C(=O)NR$^a$R$^f$, —S(=O)$_2$ N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^e$C$_{2-6}$ alkylOR$^f$ and —NR$^a$C$_{2-6}$alkylOR$^h$.

In another embodiment, in conjunction with any one of the above and below embodiments, R$^{13}$ is H.

In another embodiment, in conjunction with any one of the above and below embodiments, R$^{13}$ is independently, at each instance, selected from C$_{1-8}$alkyl, —C(=O)R$^e$, —C(=O)OR$^f$, —C(=O)NR$^a$R$^f$, —C(=NR$^a$)NR$^a$R$^f$, —OR, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^h$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$ —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^e$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^l$, —N(R$^e$)C(=O)R$^e$, —N(R$^a$)C(O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^l$, —N(R$^h$)C(=NR$^a$)NR$^a$R, —N(R$^a$)C(=NR$^a$)NR$^a$R$^h$, —N(R$^e$)S(=O)$_2$R$^e$, —N(a)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$.

In another embodiment, in conjunction with any one of the above and below embodiments, R$^{13}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the ring is substituted by 0, 1 or 2 oxo or thioxo groups, wherein the ring is substituted by 0, 1, 2 or 3 groups selected from C$_{1-8}$alkyl, C$_4$haloalkyl, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^e$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)

C(=O)OR$^f$, —N(R$^a$)C(=O)OR$^h$, —N(R$^h$)C(=O)NR$^a$R, —N(R$^a$)C(=O)NR$^a$R$^h$, —N(R$^h$)C(=NR$^a$)NR$^a$R, —N(R$^a$)C(=NR$^a$)NR$^a$R$^h$, —N(R$^a$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$.

In another embodiment, in conjunction with any one of the above and below embodiments, R$^{13}$ is C$_{1-4}$alkyl substituted by 0, 1, 2 or 3 groups selected from C$_{1-4}$haloalkyl, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^e$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^e$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NE$^h$C$_{2-6}$alkylOR$^f$ and —NR$^a$C$_{2-6}$alkylOR$^h$.

In another embodiment, in conjunction with any one of the above and below embodiments, R$^{14}$ is independently, at each instance, selected from H, C$_{1-5}$alkyl, C$_{1-4}$haloalkyl, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^h$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; or R$^{14}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein there are no more than 2 N atoms, and wherein the ring is fused with 0 or 1 benzo groups and 0 or 1 saturated or unsaturated 5-, 6- or 7-membered heterocyclic ring containing 1, 2 or 3 atoms selected from N, O and S; wherein the ring is substituted by 0, 1 or 2 oxo or thioxo groups, wherein the ring is substituted by 0, 1, 2 or 3 groups selected from C$_{1-8}$alkyl, C$_{1-4}$haloalkyl, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; or R$^{14}$ is C$_{1-4}$alkyl substituted by 0, 1, 2 or 3 groups selected from C$_{1-4}$haloalkyl, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —Nr$^h$C$_{2-6}$alkylOR$^f$ and —NR$^a$C$_{2-6}$alkylOR$^h$.

In another embodiment, in conjunction with any one of the above and below embodiments, R$^{14}$ is H.

In another embodiment, in conjunction with any one of the above and below embodiments, R$^{14}$ is independently, at each instance, selected from C$_{1-5}$alkyl, C$_{1-4}$haloalkyl, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)

NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; or R$^{14}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein there are no more than 2 N atoms, and wherein the ring is fused with 0 or 1 benzo groups and 0 or 1 saturated or unsaturated 5-, 6- or 7-membered heterocyclic ring containing 1, 2 or 3 atoms selected from N, O and S; wherein the ring is substituted by 0, 1 or 2 oxo or thioxo groups, wherein the ring is substituted by 0, 1, 2 or 3 groups selected from C$_{1-8}$alkyl, C$_{1-4}$haloalkyl, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^f$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; or R$^{1-4}$ is C$_{1-4}$alkyl substituted by 0, 1 or 2 groups selected from C$_{1-4}$haloalkyl, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C (=NR$^a$)NR$^a$R$^f$, —N(R$^a$)C(=NR$^a$)NR$^a$R$^h$, —N(R$^h$)S(=O)$_2$ R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$ alkylNR$^a$R$^h$, —NR$^h$C$_{2-6}$alkylOR$^f$ and —NR$^a$C$_{2-6}$ alkylOR$^h$.

In another embodiment, in conjunction with any one of the above and below embodiments, at least one of R$^{10}$, R$^{11}$, R$^{12}$, R$^{13}$ and R$^{14}$ is other than H.

In another embodiment, in conjunction with any one of the above and below embodiments, at least two of R$^{10}$, R$^{11}$, R$^{12}$, R$^{13}$ and R$^{14}$ is other than H.

In another embodiment, in conjunction with any one of the above and below embodiments, at least one of R$^{10}$, R$^{11}$, R$^{12}$, R$^{13}$ and R$^{14}$ is selected from C$_{1-5}$ alkyl, C$_{1-4}$haloalkyl, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$_a$R$^f$, —NR$^a$C$_{2-6}$alkylNR$^a$R$^f$, —NR$^a$C$_{2-6}$ alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$ alkylOR$^f$ and —NR$^a$ C$_{2-6}$alkylOR$^h$, or a saturated or unsaturated 5-, 6- or 7-membered monocyclic or 6-, 7-, 8-, 9-, 10- or 11-membered bicyclic ring containing 1, 2 or 3 atoms selected from N, O and S, wherein there are no more than 2 N atoms, and wherein the ring is fused with 0 or 1 benzo groups and 0 or 1 saturated or unsaturated 5-, 6- or 7-membered heterocyclic ring containing 1, 2 or 3 atoms selected from N, O and S; wherein the ring is substituted by 0, 1 or 2 oxo or thioxo groups, wherein the ring is substituted by 0, 1, 2 or 3 groups selected from C$_{1-8}$alkyl, C$_{1-4}$haloalkyl, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$ alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)

C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$,          —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; or a C$_{1-4}$alkyl substituted by 0, 1, 2 or 3 groups selected from C$_{1-4}$haloalkyl, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$NR$^a$C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^l$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$,          —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$,          —N(R$^a$)S(=O)$_2$NR$^a$R$^h$, —NR$^h$C$_{2-6}$alkylNR$^a$R$^f$,          —NR$^a$C$_{2-6}$alkylONR$^a$R$^h$, —NR$^a$C$_{1-2}$alkylOR$^f$ and —NR$^a$C$_{2-6}$alkylOR$^h$ In another embodiment, in conjunction with any one of the above and below embodiments, R$^b$ is a heterocycle selected from the group of thiophene, pyrrole, 1,3-oxazole, 1,3,4-oxadiazole, 1,3,4-thiadiazole, 1,2,3-oxadiazole, 1,2,3-thiadiazole, 1H-1,2,3-triazole, isothiazole, 1,2,4-oxadiazole, 1,2,4-thiadiazole, 1,2,3,4-oxatriazole, 1,2,3,4-thiatriazole, 1H-1,2,3,4-tetraazole, 1,2,3,5-oxatriazole, 1,2,3,5-thiatriazole, furan, imidazol-2-yl, benzimidazole, 1,2,4-triazole, isoxazole, thiolane, pyrrolidine, tetrahydrofuran, 4,5-dihydrothiophene, 2-pyrroline, 4,5-dihydrofuran, pyridazine, pyrimidine, pyrazine, 1,2,3-triazine, 1,2,4-triazine, 1,3,5-triazine, pyridine, 2H-3,4,5,6-tetrahydropyran, thiane, 1,2-diazaperhydroine, 1,3-diazaperhydroine, piperazine, 1,3-oxazaperhydroine, morpholine, 1,3-thiazaperhydroine, 1,4-thiazaperhydroine, piperidine, 2H-3,4-dihydropyran, 2,3-dihydro-4H-thiin, 1,4,5,6-tetrahydropyridine, 2H-5,6-dihydropyran, 2,3-dihydro-6H-thiin, 1,2,5,6-tetrahydropyridine, 3,4,5,6-tetrahydropyridine, 4H-pyran, 4H-thiin, 1,4-dihydropyridine, 1,4-dithiane, 1,4-dioxane, 1,4-oxathiane, 1,2-oxazolidine, 1,2-thiazolidine, pyrazolidine, 1,3-oxazolidine, 1,3-thiazolidine, imidazolidine, 1,2,4-oxadiazolidine, 1,3,4-oxadiazolidine, 1,2,4-thiadiazolidine, 1,3,4-thiadiazolidine, 1,2,4-triazolidine, 2-imidazolin-1-yl, 2-imidazolin-2-yl, 3-imidazoline, 2-pyrazoline, 4-imidazoline, 2,3-dihydroisothiazole, 4,5-dihydroisoxazole, 4,5-dihydroisothiazole, 2,5-dihydroisoxazole, 2,5-dihydroisothiazole, 2,3-dihydroisoxazole, 4,5-dihydrooxazole, 2,3-dihydrooxazole, 2,5-dihydrooxazole, 4,5-dihydrothiazole, 2,3-dihydrothiazole, 2,5-dihydrothiazole, 1,3,4-oxathiazolidine, 1,4,2-oxathiazolidine, 2,3-dihydro-1H-[1,2,3]triazole, 2,5-dihydro-1H-[1,2,3]triazole, 4,5-dihydro-1H-[1,2,3]triazol-1-yl, 4,5-dihydro-1H-[1,2,3]triazol-3-yl, 4,5-dihydro-1H-[1,2,3]triazol-5-yl, 2,3-dihydro-1H-[1,2,4]triazole, 4,5-dihydro-1H-[1,2,4]triazole, 2,3-dihydro-[1,2,4]oxadiazole, 2,5-dihydro-[1,2,4]oxadiazole, 4,5-dihydro-[1,2,4]thiadiazole, 2,3-dihydro-[1,2,4]thiadiazole, 2,5-dihydro-[1,2,4]thiadiazole, 4,5-dihydro-[1,2,4]thiadiazole, 2,5-dihydro-[1,2,4]oxadiazole, 2,3-dihydro-[1,2,4]oxadiazole, 4,5-dihydro-[1,2,4]oxadiazole, 2,5-dihydro-[1,2,4]thiadiazole, 2,3-dihydro-[1,2,4]thiadiazole, 4,5-dihydro-[1,2,4]thiadiazole, 2,3-dihydro-[1,3,4]oxadiazole, 2,3-dihydro-[1,3,4]thiadiazole, [1,4,2]oxathiazole, [1,3,4]oxathiazole, 1,3,5-triazaperhydroine, 1,2,4-triazaperhydroine, 1,4,2-dithiazaperhydroine, 1,4,2-dioxazaperhydroine, 1,3,5-oxadiazaperhydroine, 1,2,5-oxadiazaperhydroine, 1,3,4-thiadiazaperhydroine, 1,3,5-thiadiazaperhydroine, 1,2,5-thiadiazaperhydroine, 1,3,4-oxadiazaperhydroine, 1,4,3-oxathiazaperhydroine, 1,4,2-oxathiazaperhydroine, 1,4,5,6-tetrahydropyridazine, 1,2,3,4-tetrahydropyridazine, 1,2,3,6-tetrahydropyridazine, 1,2,5,6-tetrahydropyrimidine, 1,2,3,4-tetrahydropyrimidine, 1,4,5,6-tetrahydropyrimidine, 1,2,3,6-tetrahydropyrazine, 1,2,3,4-tetrahydropyrazine, 5,6-dihydro-4H-[1,2]oxazine, 5,6-dihydro-2H-[1,2]oxazine, 3,6-dihydro-2H-[1,2]oxazine, 3,4-dihydro-2H-[1,2]oxazine, 5,6-dihydro-4H-[1,2]thiazine, 5,6-dihydro-2H-[1,2] thiazine, 3,6-dihydro-21H-[1,2]thiazine, 3,4-dihydro-2H-[1,2]thiazine, 5,6-dihydro-2H-[1,3]oxazine, 5,6-dihydro-4H-[1,3]oxazine, 3,6-dihydro-2H-[1,3]oxazine, 3,4-dihydro-2H-[1,3]oxazine, 3,6-dihydro-21H-[1,4]oxazine, 3,4-dihydro-2H-[1,4]oxazine, 5,6-dihydro-2H-[1,3]thiazine, 5,6-dihydro-4H-[1,3]thiazine, 3,6-dihydro-2H-[1,3]thiazine, 3,4-dihydro-2H-[1,3]thiazine, 3,6-dihydro-2H-[1,4]thiazine, 3,4-dihydro-2H-[1,4]thiazine, 1,2,3,6-tetrahydro-[1,2,4]triazine, 1,2,3,4-tetrahydro-[1,2,4]triazine, 1,2,3,4-tetrahydro-[1,3,5]triazine, 2,3,4,5-tetrahydro-[1,2,4]triazine, 1,4,5,6-tetrahydro-[1,2,4]triazine, 5,6-dihydro-[1,4,2]dioxazine, 5,6-dihydro-[1,4,2]dithiazine, 2,3-dihydro-[1,4,2]dioxazine, 3,4-dihydro-2H-[1,3,4]oxadiazine, 3,6-dihydro-2H-[1,3,4]oxadiazine, 3,4-dihydro-2H-[1,3,5]oxadiazine, 3,6-dihydro-2H-[1,3,5]oxadiazine, 5,6-dihydro-2H-[1,2,5]oxadiazine, 5,6-dihydro-4H-[1,2,5]oxadiazine, 3,4-dihydro-2H-[1,3,4]thiadiazine, 3,6-dihydro-2H-[1,3,4]thiadiazine, 3,4-dihydro-2H-[1,3,5]thiadiazine, 3,6-dihydro-2H-[1,3,5]thiadiazine, 5,6-dihydro-2H-[1,2,5]thiadiazine, 5,6-dihydro-4H-[1,2,5]thiadiazine, 5,6-dihydro-2H-[1,2,3]oxadiazine, 3,6-dihydro-2H-[1,2,5]oxadiazine, 5,6-dihydro-4H-[1,3,4]oxadiazine, 3,4-dihydro-2H-[1,2,5]oxadiazine, 5,6-dihydro-2H-[1,2,3]thiadiazine, 3,6-dihydro-2H-[1,2,5]thiadiazine, 5,6-dihydro-4H-[1,3,4]thiadiazine, 3,4-dihydro-2H-[1,2,5]thiadiazine, 5,6-dihydro-[1,4,3]oxathiazine, 5,6-dihydro-[1,4,2]oxathiazine, 2,3-dihydro-[1,4,3]oxathiazine, 2,3-dihydro-[1,4,2]oxathiazine, 3,4-dihydropyridine, 1,2-dihydropyridine, 5,6-dihydropyridine, 2H-pyran, 2H-thiin, 3,6-dihydropyridine, 2,3-dihydropyridazine, 2,5-dihydropyridazine, 4,5-dihydropyridazine, 1,2-dihydropyridazine, 1,4-dihydropyrimidin-1-yl, 1,4-dihydropyrimidin-4-yl, 1,4-dihydropyrimidin-5-yl, 1,4-dihydropyrimidin-6-yl, 2,3-dihydropyrimidine, 2,5-dihydropyrimidine, 5,6-dihydropyrimidine, 3,6-dihydropyrimidine, 5,6-dihydropyrazine, 3,6-dihydropyrazine, 4,5-dihydropyrazine, 1,4-dihydropyrazine, 1,4-dithiin, 1,4-dioxin, 2H-1,2-oxazine, 6H-1,2-oxazine, 4H-1,2-oxazine, 2H-1,3-oxazine, 4H-1,3-oxazine, 6H-1,3-oxazine, 2H-1,4-oxazine, 4H-1,4-oxazine, 2H-1,3-thiazine, 2H-1,4-thiazine, 4H-1,2-thiazine, 6H-1,3-thiazine, 4H-1,4-thiazine, 2H-1,2-thiazine, 6H-1,2-thiazine, 1,4-oxathiin, 2H,5H-1,2,3-triazine, 1H,4H-1,2,3-triazine, 4,5-dihydro-1,2,3-triazine, 1H,6H-1,2,3-triazine, 1,2-dihydro-1,2,3-triazine, 2,3-dihydro-1,2,4-triazine, 3H,6H-1,2,4-triazine, 1H,6H-1,2,4-triazine, 3,4-dihydro-1,2,4-triazine, 1H,4H-1,2,4-triazine, 5,6-dihydro-1,2,4-triazine, 4,5-dihydro-1,2,4-triazine, 2H,5H-1,2,4-triazine, 1,2-dihydro-1,2,4-triazine, 1H,4H-1,3,5-triazine, 1,2-dihydro-1,3,5-triazine, 1,4,2-dithiazine, 1,4,2-dioxazine, 2H-1,3,4-oxadiazine, 2H-1,3,5-oxadiazine, 6H-1,2,5-oxadiazine, 4H-1,3,4-oxadiazine, 4H-1,3,5-oxadiazine, 4H-1,2,5-oxadiazine, 2H-1,3,5-thiadiazine, 6H-1,2,5-thiadiazine, 4H-1,3,4- thiadiazine, 4H-1,3,5-thiadiazine, 4H-1,2,5-thiadiazine, 2H-1,3,4-thiadiazine, 6H-1,3,4-thiadiazine, 6H-1,3,4-oxadiazine, and 1,4,2-oxathiazine, wherein the heterocycle is optionally fused with a vicinally saturated or unsaturated 5-, 6- or 7-membered ring containing 0, 1 or 2 atoms independently selected from N, O and S.

In another embodiment, the compound is selected from:

(2R)-2-hydroxy-N-[4-({6-[4-(trifluoromethyl)phenyl]pyrimidin-4-yl}oxy)-1,3-benzothiazol-2-yl]propanamide;

(2S)-2-hydroxy-N-[4-({6-[4-(trifluoromethyl)phenyl]pyrimidin-4-yl}oxy)-1,3-benzothiazol-2-yl]propanamide;

(2S)-3-[2-[6-(quinolin-7-yloxy)pyrimidin-4-yl]-5-(trifluoromethyl)phenoxy]propane-1,2-diol;

[7-({6-[4-(trifluoromethyl)phenyl]pyrimidin-4-yl}oxy)quinolin-3-yl]methanol;

1-[7-({6-[4-(trifluoromethyl)phenyl]pyrimidin-4-yl}oxy)quinolin-3-yl]ethanol;

1-methyl-5-({6-[4-(trifluoromethyl)phenyl]pyrimidin-4-yl}oxy)quinoxalin-2 (1H)-one;

2-({6-[4-(trifluoromethyl)phenyl]pyrimidin-4-yl}oxy)quinoline;

2-(4-methyl-1,4-diazepan-1-yl)-4-({6-[4-(trifluoromethyl)phenyl]pyrimidin-4-yl}oxy)-1,3-benzothiazole;

2-(6-{[2-(acetylamino)-1,3-benzothiazol-4-yl]oxy}pyrimidin-4-yl)-5-(trifluoromethyl)phenyl trifluoromethanesulfonate;

2-[6-(quinolin-7-yloxy)pyrimidin-4-yl]-5-(trifluoromethyl)aniline;

2-[6-(quinolin-7-yloxy)pyrimidin-4-yl]-5-(trifluoromethyl)phenol;

2-[6-(quinolin-7-yloxy)pyrimidin-4-yl]phenol;

2-[7-({6-[4-(trifluoromethyl)phenyl]pyrimidin-4-yl}oxy)quinolin-3-yl]propan-2-ol;

2-{6-[(2-amino-1,3-benzothiazol-4-yl)oxy]pyrimidin-4-yl}-5-(trifluoromethyl)phenol;

2-bromo-4-({6-[4-(trifluoromethyl)phenyl]pyrimidin-4-yl}oxy)-1,3-benzothiazole;

2-chloro-4-({6-[4-(trifluoromethyl)phenyl]pyrimidin-4-yl}oxy)-1,3-benzothiazole;

2-chloro-7-({6-[4-(trifluoromethyl)phenyl]pyrimidin-4-yl}oxy)quinoline;

2-chloro-8-({6-[4-(trifluoromethyl)phenyl]pyrimidin-4-yl}oxy)quinoline;

2-hydroxy-2-methyl-N-[4-({6-[4-(trifluoromethyl)phenyl]pyrimidin-4-yl}oxy)-1,3-benzothiazol-2-yl]propanamide;

2-hydroxy-2-phenyl-N-[4-({6-[4-(trifluoromethyl)phenyl]pyrimidin-4-yl}oxy)-1,3-benzothiazol-2-yl]acetamide;

2-hydroxy-N-[4-({6-[4-(trifluoromethyl)phenyl]pyrimidin-4-yl}oxy)-1,3-benzothiazol-2-yl]propanamide;

2-hydroxy-N-[4-({6-[4-(trifluoromethyl)phenyl]pyrimidin-4-yl}oxy)-1,3-benzothiazol-2-yl]acetamide;

2-iodo-4-({6-[4-(trifluoromethyl)phenyl]pyrimidin-4-yl}oxy)-1,3-benzothiazole;

2-methyl-5-({6-[4-(trifluoromethyl)phenyl]pyrimidin-4-yl}oxy)-1,3-benzothiazole;

2-methyl-5-({6-phenyl-5-[4-(trifluoromethyl)phenyl]pyridazin-3-yl}oxy)-1,3-benzothiazole;

2-methyl-8-({6-[4-(trifluoromethyl)phenyl]pyrimidin-4-yl}oxy)quinoxaline;

2-morpholin-4-yl-N-[4-({6-[4-(trifluoromethyl)phenyl]pyrimidin-4-yl}oxy)-1,3-benzothiazol-2-yl]acetamide;

2-phenyl-N-[4-({6-[4-(trifluoromethyl)phenyl]pyrimidin-4-yl}oxy)-1,3-benzothiazol-2-yl]acetamide;

2-pyridin-4-yl-4-({6-[4-(trifluoromethyl)pyrimidin-4-yl}oxy)-1,3-benzothiazole;

3-({6-[4-(trifluoromethyl)phenyl]pyrimidin-4-yl}oxy)isoquinoline;

3-({6-[4-(trifluoromethyl)phenyl]pyrimidin-4-yl}oxy)pyridin-2-amine;

3-amino-5-({6-[4-(trifluoromethyl)phenyl]pyrimidin-4-yl}oxy)quinoxalin-2 (1H)-one;

4-({6-[2-(methoxymethoxy)-4-(trifluoromethyl)phenyl]pyrimidin-4-yl}oxy)-1,3-benzothiazol-2-amine;

4-({6-[4-(trifluoromethyl)phenyl]pyrimidin-4-yl}oxy)-1,3-benzothiazol-2-amine;

4-({6-[4-(trifluoromethyl)phenyl]pyrimidin-4-yl}oxy)-1,3-benzothiazole;

4-({6-[4-(trifluoromethyl)phenyl]pyrimidin-4-yl}oxy)-1,3-benzothiazole-2,6-diamine;

4-({6-[4-(trifluoromethyl)phenyl]pyrimidin-4-yl}oxy)-1,3-benzothiazole-2-carboxamide;

4-({6-[4-(trifluoromethyl)phenyl]pyrimidin-4-yl}oxy)-1,3-benzoxazol-2-amine;

4-({6-[4-(trifluoromethyl)phenyl]pyrimidin-4-yl}oxy)isoquinoline;

4-({6-[4-(trifluoromethyl)piperidin-1-yl]pyrimidin-4-yl}oxy)-1,3-benzothiazol-2-amine;

4-(1-benzothien-4-yloxy)-6-[4-(trifluoromethyl)phenyl]pyrimidine;

4-(2,3-dihydro-1,4-benzodioxin-6-yloxy)-6-[4-(trifluoromethyl)phenyl]pyrimidine;

4-(2-naphthyloxy)-6-[4-(trifluoromethyl)phenyl]pyrimidine;

4-(2-pyridin-2-ylethoxy)-6-[4-(trifluoromethyl)phenyl]pyrimidine;

4-(3-methoxyphenoxy)-6-[4-(trifluoromethyl)phenyl]pyrimidine;

4-(4-tert-butylphenyl)-6-(3-methoxyphenoxy)pyrimidine;

4-(4-tert-butylphenyl)-6-(quinolin-7-yloxy)pyrimidin-2-amine;

4-[(6-{4-[3-(trifluoromethyl)pyridin-2-yl]piperazin-1-yl}pyrimidin-4-yl)oxy]-1,3-benzothiazol-2-amine;

4-[6-(quinolin-7-yloxy)pyrimidin-4-yl]benzonitrile;

4-{[6-(2,2-dimethyl-2,3-dihydro-1-benzofuran-6-yl)pyrimidin-4-yl]oxy}-1,3-benzothiazol-2-amine;

4-{[6-(4-bromophenyl)pyrimidin-4-yl]oxy}-1,3-benzothiazol-2-amine;

4-{[6-(4-cycloheptylpiperazin-1-yl)pyrimidin-4-yl]oxy}-1,3-benzothiazol-2-amine;

4-{[6-(4-phenylpiperazin-1-yl)pyrimidin-4-yl]oxy}-1,3-benzothiazol-2-amine;

4-{6-[(2-aminoquinolin-8-yl)oxy]pyrimidin-4-yl}benzonitrile;

4-chloro-7-({6-[4-(trifluoromethyl)phenyl]pyrimidin-4-yl}oxy)quinoline;

4-methyl-8-({6-[4-(trifluoromethyl)phenyl]pyrimidin-4-yl}oxy)quinoline;

5-({5,6-bis[4-(trifluoromethyl)phenyl]pyridazin-3-yl}oxy)-2-methyl-1,3-benzothiazole;

5-({6-(isoquinolin-5-yloxy)-4-[4-(trifluoromethyl)phenyl]pyridazin-3-yl}oxy)isoquinoline;

5-({6-[4-(trifluoromethyl)phenyl]pyrimidin-4-yl}oxy)-3,4-dihydroquinoxalin-2 (1H)-one;

5-({6-[4-(trifluoromethyl)phenyl]pyrimidin-4-yl}oxy)isoquinoline;

5-({6-[4-(trifluoromethyl)phenyl]pyrimidin-4-yl}oxy)quinoline;

5-({6-[4-(trifluoromethyl)phenyl]pyrimidin-4-yl}oxy)quinoxalin-2-ol;

5-({6-[4-(trifluoromethyl)phenyl]pyrimidin-4-yl}oxy)quinoxalin-2-amine;

5-({6-[4-(trifluoromethyl)phenyl]pyrimidin-4-yl}oxy)quinoxaline;

5-{[6-(4-tert-butylphenyl)pyrimidin-4-yl]oxy}-2-methyl-1,3-benzothiazole;

6-({6-[4-(trifluoromethyl)phenyl]pyrimidin-4-yl}oxy)-1H-indole;

6-({6-[4-(trifluoromethyl)phenyl]pyrimidin-4-yl}oxy)isoquinoline;

6-({6-[4-(trifluoromethyl)phenyl]pyrimidin-4-yl}oxy)quinoxaline;

7-({6-(2-naphthyl)-5-[4-(trifluoromethyl)phenyl]pyridazin-3-yl}oxy)quinoline;

7-({6-(3-fluorophenyl)-5-[4-(trifluoromethyl)phenyl]pyridazin-3-yl}oxy)quinoline;

7-({6-(4-fluorophenyl)-5-[4-(trifluoromethyl)phenyl]pyridazin-3-yl}oxy)quinoline;

7-({6-(isoquinolin-7-yloxy)-4-[4-(trifluoromethyl)phenyl]pyridazin-3-yl}oxy)isoquinoline;

7-({6-(quinolin-7-yloxy)-4-[4-(trifluoromethyl)phenyl]pyridazin-3-yl}oxy)quinoline;

7-({6-[2-(benzyloxy)-4-(trifluoromethyl)phenyl]pyrimidin-4-yl}oxy)quinoline;

7-({6-[2-(cyclohexylmethoxy)-4-(trifluoromethyl)phenyl]pyrimidin-4-yl}oxy)quinoline;

7-({6-[2-(methoxymethoxy)-4-(trifluoromethyl)phenyl]pyrimidin-4-yl}oxy)quinoline;

7-({6-[2,4-bis(trifluoromethyl)phenyl]pyrimidin-4-yl}oxy)quinoline;

7-({6-[2-bromo-4-(trifluoromethyl)phenyl]pyrimidin-4-yl}oxy)quinoline;

7-({6-[2-chloro-6-(trifluoromethyl)pyridin-3-yl]pyrimidin-4-yl}oxy)quinoline;

7-({6-[2-piperidin-1-yl-6-(trifluoromethyl)pyridin-3-yl]pyrimidin-4-yl}oxy)quinoline;

7-({6-[2-pyridin-3-yl-4-(trifluoromethyl)phenyl]pyrimidin-4-yl}oxy)quinoline;

7-({6-[3-(methylsulfanyl)phenyl]pyrimidin-4-yl}oxy)quinoline;

7-({6-[3-(trifluoromethoxy)phenyl]pyrimidin-4-yl}oxy)quinoline;

7-({6-[4-(trifluoromethoxy)phenyl]-5-[4-(trifluoromethyl)phenyl]pyridazin-3-yl}oxy)quinoline;

7-({6-[4-(trifluoromethoxy)phenyl]pyrimidin-4-yl}oxy)quinoline;

7-({6-[4-(trifluoromethyl)-2-vinylphenyl]pyrimidin-4-yl}oxy)quinoline;

7-({6-[4-(trifluoromethyl)phenyl]pyrimidin-4-yl}oxy)-3,4-dihydronaphthalen-1(2H)-one;

7-({6-[4-(trifluoromethyl)phenyl]pyrimidin-4-yl}oxy)isoquinoline;

7-({6-[4-(trifluoromethyl)phenyl]pyrimidin-4-yl}oxy)quinolin-2-amine;

7-({6-[4-(trifluoromethyl)phenyl]pyrimidin-4-yl}oxy)quinolin-2-ol;

7-({6-[4-(trifluoromethyl)phenyl]pyrimidin-4-yl}oxy)quinoline;

7-({6-[4'-fluoro-5-(trifluoromethyl)-1,1'-biphenyl-2-yl]pyrimidin-4-yl}oxy)quinoline;

7-({6-[5-(trifluoromethyl)-1,1'-biphenyl-2-yl]pyrimidin-4-yl}oxy)quinoline;

7-({6-phenyl-5-[4-(trifluoromethyl)phenyl]pyridazin-3-yl}oxy)quinoline;

7-[(6-phenylpyrimidin-4-yl)oxy]quinoline;

7-{[6-(1-acetyl-3,3-dimethyl-2,3-dihydro-1H-indol-6-yl)pyrimidin-4-yl]oxy}quinoline;

7-{[6-(1-benzofuran-5-yl)pyrimidin-4-yl]oxy}quinoline;

7-{[6-(1-methyl-1H-indol-5-yl)pyrimidin-4-yl]oxy}quinoline;

7-{[6-(2,4-dichlorophenyl)pyrimidin-4-yl]oxy}quinoline;

7-{[6-(2-naphthyl)pyrimidin-4-yl]oxy}quinoline;

7-{[6-(3,4-difluorophenyl)pyrimidin-4-yl]oxy}quinoline;

7-{[6-(3-chloro-4-fluorophenyl)pyrimidin-4-yl]oxy}quinoline;

7-{[6-(3-fluoro-4-methylphenyl)pyrimidin-4-yl]oxy}quinoline;

7-{[6-(3-nitrophenyl)pyrimidin-4-yl]oxy}quinoline;

7-{[6-(3-piperidin-1-ylphenyl)pyrimidin-4-yl]oxy}quinoline;

7-{[6-(3-pyrrolidin-1-ylphenyl)pyrimidin-4-yl]oxy}quinoline;

7-{[6-(4-bromophenyl)pyrimidin-4-yl]oxy}quinoline;

7-{[6-(4-chlorophenyl)pyrimidin-4-yl]oxy}quinoline;

7-{[6-(4-fluorophenyl)pyrimidin-4-yl]oxy}quinoline;

7-{[6-(4-tert-butylphenyl)pyrimidin-4-yl]oxy}quinoline;

7-{[6-(6-chloropyridin-3-yl)pyrimidin-4-yl]oxy}quinoline;

7-{[6-(6-methoxypyridin-3-yl)pyrimidin-4-yl]oxy}quinoline;

7-pyridin-4-yl-4-({6-[4-(trifluoromethyl)phenyl]pyrimidin-4-yl}oxy)-1,3-benzothiazol-2-amine;

8-({6-[2-amino-4-(trifluoromethyl)phenyl]pyrimidin-4-yl}oxy)quinolin-2-amine;

8-({6-[3-(trifluoromethoxy)phenyl]pyrimidin-4-yl}oxy)quinolin-2-amine;

8-({6-[4-(trifluoromethyl)phenyl]pyrimidin-4-yl}oxy)-3,4-dihydroquinoxalin-2 (1H)-one;

8-({6-[4-(trifluoromethyl)phenyl]pyrimidin-4-yl}oxy)imidazo[1,2-a]pyridine;

8-({6-[4-(trifluoromethyl)phenyl]pyrimidin-4-yl}oxy)isoquinoline;

8-({6-[4-(trifluoromethyl)phenyl]pyrimidin-4-yl}oxy)quinazolin-2-amine;

8-({6-[4-(trifluoromethyl)phenyl]pyrimidin-4-yl}oxy)quinoline;

8-({6-[4-(trifluoromethyl)phenyl]pyrimidin-4-yl}oxy)quinoxalin-2-amine;

8-({6-phenyl-5-[4-(trifluoromethyl)phenyl]pyridazin-3-yl}oxy)quinolin-2-amine;

8-[6-(4-Trifluoromethyl-phenyl)-pyrimidin-4-yloxy]-quinolin-2-ylamine;

methyl 2-(6-{[2-(acetylamino)-1,3-benzothiazol-4-yl]oxy}pyrimidin-4-yl)-5-(trifluoromethyl)benzoate;

methyl 4-({6-[4-(trifluoromethyl)phenyl]pyrimidin-4-yl}oxy)-1,3-benzothiazol-2-ylcarbamate;

methyl 7-({6-[4-(trifluoromethyl)phenyl]pyrimidin-4-yl}oxy)quinoline-3-carboxylate;

N-(4-{[6-(2,2-dimethyl-2,3-dihydro-1-benzofuran-6-yl)pyrimidin-4-yl]oxy}-1,3-benzothiazol-2-yl)acetamide;

N-(4-{[6-(3-phenylpyrrolidin-1-yl)pyrimidin-4-yl]oxy}-1,3-benzothiazol-2-yl)acetamide;

N-(4-{[6-(4-benzylpiperazin-1-yl)pyrimidin-4-yl]oxy}-1,3-benzothiazol-2-yl)acetamide;

N-(4-{[6-(4-bromophenyl)pyrimidin-4-yl]oxy}-1,3-benzothiazol-2-yl)acetamide;

N-(4-{[6-(4-phenylpiperazin-1-yl)pyrimidin-4-yl]oxyl}-1,3-benzothiazol-2-yl)acetamide;

N-(4-{[6-(4-phenylpiperidin-1-yl)pyrimidin-4-yl]oxy}-1,3-benzothiazol-2-yl)acetamide;

N-(4-tert-butylbenzyl)-N-[2-[6-(quinolin-7-yloxy)pyrimidin-4-yl]-5-(trifluoromethyl)phenyl]amine;

N-(cyclohexylmethyl)-3-[6-(quinolin-7-yloxy)pyrimidin-4-yl]-6-(trifluoromethyl)pyridin-2-amine;

N-(cyclohexylmethyl)-N-[2-[6-(quinolin-7-yloxy)pyrimidin-4-yl]-5-(trifluoromethyl)phenyl]amine;

N-(pyridin-4-ylmethyl)-N-[2-[6-(quinolin-7-yloxy)pyrimidin-4-yl]-5-(trifluoromethyl)phenyl]amine;

N,N-dimethyl-4-({6-[4-(trifluoromethyl)phenyl]pyrimidin-4-yl}oxy)-1,3-benzothiazole-2-carboxamide;

N-[2-(6-{[2-(acetylamino)-1,3-benzothiazol-4-yl]oxy}pyrimidin-4-yl)-5-(trifluoromethyl)phenyl]cyclohexanecarboxamide;

N-[2-(6-{[2-(acetylamino)-1,3-benzothiazol-4-yl]oxy}pyrimidin-4-yl)-5-(trifluoromethyl)phenyl]-4-(trifluoromethyl)benzamide;

N-[2-(6-{[2-(acetylamino)-1,3-benzothiazol-4-yl]oxy}pyrimidin-4-yl)-5-(trifluoromethyl)phenyl]-2,2-dimethylpropanamide;

N-[2-(6-{[2-(acetylamino)-1,3-benzothiazol-4-yl]oxy}pyrimidin-4-yl)-5-(trifluoromethyl)phenyl]-2-cyclohexylacetamide;

N-[2-(6-{[2-(acetylamino)-1,3-benzothiazol-4-yl]oxy}pyrimidin-4-yl)-5-(trifluoromethyl)phenyl]nicotinamide;

N-[2-(6-{[2-(acetylamino)-1,3-benzothiazol-4-yl]oxy}pyrimidin-4-yl)-5-(trifluoromethyl)phenyl]isonicotinamide;

N-[2-(6-{[2-(acetylamino)-1,3-benzothiazol-4-yl]oxy}pyrimidin-4-yl)-5-(trifluoromethyl)phenyl]acetamide;

N-[2-[6-(quinolin-7-yloxy)pyrimidin-4-yl]-5-(trifluoromethyl)phenyl]benzenesulfonamide;

N-[2-[6-(quinolin-7-yloxy)pyrimidin-4-yl]-5-(trifluoromethyl)phenyl]acetamide;

N-[2-[6-(quinolin-7-yloxy)pyrimidin-4-yl]-5-(trifluoromethyl)phenyl]methanesulfonamide;

N-[3-({6-[4-(trifluoromethyl)phenyl]pyrimidin-4-yl}oxy)phenyl]acetamide;

N-[4-({5-(4-fluorophenyl)-4-[4-(trifluoromethyl)phenyl]pyridin-2-yl}oxy)-1,3-benzothiazol-2-yl]acetamide;

N-[4-({5-[4-(trifluoromethoxy)phenyl]-4-[4-(trifluoromethyl)phenyl]pyridin-2-yl}oxy)-1,3-benzothiazol-2-yl]acetamide;

N-[4-({5-bromo-4-[4-(trifluoromethyl)phenyl]pyridin-2-yl}oxy)-1,3-benzothiazol-2-yl]acetamide;

N-[4-({5-chloro-4-[4-(trifluoromethyl)phenyl]pyridin-2-yl}oxy)-1,3-benzothiazol-2-yl]acetamide;

N-[4-({6-[2-(benzyloxy)-4-(trifluoromethyl)phenyl]pyrimidin-4-yl}oxy)-1,3-benzothiazol-2-yl]acetamide;

N-[4-({6-[2-(hydroxymethyl)-4-(trifluoromethyl)phenyl]pyrimidin-4-yl}oxy)-1,3-benzothiazol-2-yl]acetamide;

N-[4-({6-[2-(methoxymethoxy)-4-(trifluoromethyl)phenyl]pyrimidin-4-yl}oxy)-1,3-benzothiazol-2-yl]acetamide;

N-[4-({6-[2-[(cyclohexylmethyl)amino]-4-(trifluoromethyl)phenyl]pyrimidin-4-yl}oxy)-1,3-benzothiazol-2-yl]acetamide;

N-[4-({6-[2-[(piperidin-4-ylmethyl)amino]-4-(trifluoromethyl)phenyl]pyrimidin-4-yl}oxy)-1,3-benzoxazol-2-yl]acetamide;

N-[4-({6-[2-amino-4-(trifluoromethyl)phenyl]pyrimidin-4-yl}oxy)-1,3-benzothiazol-2-yl]acetamide;

N-[4-({6-[2-bromo-4-(trifluoromethyl)phenyl]pyrimidin-4-yl}oxy)-1,3-benzothiazol-2-yl]acetamide;

N-[4-({6-[2-chloro-4-(trifluoromethyl)phenyl]pyrimidin-4-yl}oxy)-1,3-benzothiazol-2-yl]acetamide;

N-[4-({6-[2-hydroxy-4-(trifluoromethyl)phenyl]pyrimidin-4-yl}oxy)-1,3-benzothiazol-2-yl]acetamide;

N-[4-({6-[2-iodo-4-(trifluoromethyl)phenyl]pyrimidin-4-yl}oxy)-1,3-benzothiazol-2-yl]acetamide;

N-[4-({6-[4-(1-phenylethyl)piperazin-1-yl]pyrimidin-4-yl}oxy)-1,3-benzothiazol-2-yl]acetamide;

N-[4-({6-[4-(2,6-dimethylphenyl)piperazin-1-yl]pyrimidin-4-yl}oxy)-1,3-benzothiazol-2-yl]acetamide;

N-[4-({6-[4-(trifluoromethyl)-2-vinylphenyl]pyrimidin-4-yl}oxy)-1,3-benzothiazol-2-yl]acetamide;

N-[4-({6-[4-(trifluoromethyl)phenyl]pyrimidin-4-yl}oxy)-1,3-benzothiazol-2-yl]acetamide;

N-[4-({6-[4-(trifluoromethyl)phenyl]pyrimidin-4-yl}oxy)-1,3-benzoxazol-2-yl]acetamide;

N-[4-({6-phenyl-5-[4-(trifluoromethyl)phenyl]pyridazin-3-yl}oxy)-1,3-benzothiazol-2-yl]aczetamide;

N-[6-(dimethylamino)-4-({6-[4-(trifluoromethyl)phenyl]pyrimidin-4-yl}oxy)-1,3-benzothiazol-2-yl]acetamide;

N-[8-({6-[4-(trifluoromethyl)phenyl]pyrimidin-4-yl}oxy)quinolin-2-yl]acetamide;

N-[8-({6-[4-(trifluoromethyl)phenyl]pyrimidin-4-yl}oxy)quinoxalin-2-yl]acetamide;

N-{4-[(6-{4-[2-(trifluoromethyl)phenyl]piperazin-1-yl}pyrimidin-4-yl)oxy]-1,3-benzothiazol-2-yl}acetamide;

N-{4-[(6-{4-[3-(trifluoromethyl)pyridin-2-yl]piperazin-1-yl}pyrimidin-4-yl)oxy]-1,3-benzothiazol-2-yl}acetamide;

N-2~,N-2~-dimethyl-N-1~-[4-({6-[4-(trifluoromethyl)phenyl]pyrimidin-4-yl}oxy)-1,3-benzothiazol-2-yl]glycinamide;

N-benzyl-N-[2-[6-(quinolin-7-yloxy)pyrimidin-4-yl]-5-(trifluoromethyl)phenyl]amine;

N-butyl-8-({6-[4-(trifluoromethyl)phenyl]pyrimidin-4-yl}oxy)quinazolin-4-amine;

N-methyl-4-({6-[4-(trifluoromethyl)phenyl]pyrimidin-4-yl}oxy)-1,3-benzothiazol-2-amine;

N-methyl-8-({6-[4-(trifluoromethyl)phenyl]pyrimidin-4-yl}oxy)quinolin-2-amine;

N-pentyl-N-[2-[6-(quinolin-7-yloxy)pyrimidin-4-yl]-5-(trifluoromethyl)phenyl]amine;

N-pyridin-2-yl-4-({6-[4-(trifluoromethyl)phenyl]pyrimidin-4-yl}oxy)-1,3-benzothiazol-2-amine;

tert-butyl 2-(6-{[2-(acetylamino)-1,3-benzothiazol-4-yl]oxy}pyrimidin-4-yl)-5-(trifluoromethyl)phenylcarbamate;

tert-butyl 2-[6-(quinolin-7-yloxy)pyrimidin-4-yl]-5-(trifluoromethyl)phenylcarbamate;

tert-butyl 2-{6-[(2-aminoquinolin-8-yl)oxy]pyrimidin-4-yl}-5-(trifluoromethyl)phenylcarbamate;

tert-butyl 4-({[2-(6-{[2-(acetylamino)-1,3-benzothiazol-4-yl]oxy}pyrimidin-4-yl)-5-(trifluoromethyl)phenyl]amino}methyl)piperidine-1-carboxylate;

tert-butyl 4-(6-{[2-(acetylamino)-1,3-benzothiazol-4-yl]oxy}pyrimidin-4-yl)piperazine-1-carboxylate; and tert-butyl 4-(6-{[2-(acetylamino)-1,3-benzothiazol-4-yl]oxy}pyrimidin-4-yl)-3,6-dihydropyridine-1 (2H)-carboxylate, or any pharmaceutically-acceptable salt thereof.

As stated above, the above embodiments may be used in conjuction with other embodiments listed. The following table is a non-exclusive, non-limiting list of some of the combinations of embodiments. Although the following embodiment sets are meant to be used with any of the above embodiments, they are also considered wherein $R^5$, $R^6$, $R^8$, $R^{13}$ and $R^{14}$ are all H.

Where X is N and Y is CH:

| Emb. # | $R^1$ | $R^4$ | $R^7$ | $R^9$ | $R^{10}$ | $R^{11}$ | $R^{12}$ |
|---|---|---|---|---|---|---|---|
| 1001 | C | E | — | — | N | N | Q |
| 1002 | C | E | — | — | O | O | Q |
| 1003 | C | E | — | — | P | P | Q |
| 1004 | C | E | — | — | M | R | R |
| 1005 | C | E | — | — | M | S | S |
| 1006 | C | E | — | — | M | T | T |
| 1007 | C | D | — | — | — | — | — |
| 1008 | C | F | — | — | — | — | — |
| 1009 | C | G | — | — | — | — | — |
| 1010 | A | E | H | J | N | N | Q |
| 1011 | A | E | H | J | O | O | Q |
| 1012 | A | E | H | J | P | P | Q |
| 1013 | A | E | H | J | M | R | R |
| 1014 | A | E | H | J | M | S | S |
| 1015 | A | E | H | J | M | T | T |
| 1016 | A | D | H | J | — | — | — |
| 1017 | A | F | H | J | — | — | — |
| 1018 | A | G | H | J | — | — | — |
| 1019 | A | E | H | K | N | N | Q |
| 1020 | A | E | H | K | O | O | Q |
| 1021 | A | E | H | K | P | P | Q |
| 1022 | A | E | H | K | M | R | R |
| 1023 | A | E | H | K | M | S | S |
| 1024 | A | E | H | K | M | T | T |
| 1025 | A | D | H | K | — | — | — |
| 1026 | A | F | H | K | — | — | — |
| 1027 | A | G | H | K | — | — | — |
| 1028 | A | E | H | L | N | N | Q |
| 1029 | A | E | H | L | O | O | Q |
| 1030 | A | E | H | L | P | P | Q |
| 1031 | A | E | H | L | M | R | R |
| 1032 | A | E | H | L | M | S | S |
| 1033 | A | E | H | L | M | T | T |
| 1034 | A | D | H | L | — | — | — |
| 1035 | A | F | H | L | — | — | — |
| 1036 | A | G | H | L | — | — | — |
| 1037 | A | E | I | J | N | N | Q |
| 1038 | A | E | I | J | O | O | Q |
| 1039 | A | E | I | J | P | P | Q |
| 1040 | A | E | I | J | M | R | R |
| 1041 | A | E | I | J | M | S | S |
| 1042 | A | E | I | J | M | T | T |
| 1043 | A | D | I | J | — | — | — |
| 1044 | A | F | I | J | — | — | — |
| 1045 | A | G | I | J | — | — | — |
| 1046 | A | E | I | K | N | N | Q |
| 1047 | A | E | I | K | O | O | Q |
| 1048 | A | E | I | K | P | P | Q |
| 1049 | A | E | I | K | M | R | R |
| 1050 | A | E | I | K | M | S | S |
| 1051 | A | E | I | K | M | T | T |
| 1052 | A | D | I | K | — | — | — |
| 1053 | A | F | I | K | — | — | — |
| 1054 | A | G | I | K | — | — | — |
| 1055 | A | E | I | L | N | N | Q |
| 1056 | A | E | I | L | O | O | Q |
| 1057 | A | E | I | L | P | P | Q |
| 1058 | A | E | I | L | M | R | R |
| 1059 | A | E | I | L | M | S | S |
| 1060 | A | E | I | L | M | T | T |
| 1061 | A | D | I | L | — | — | — |
| 1062 | A | F | I | L | — | — | — |

-continued

| Emb. # | $R^1$ | $R^4$ | $R^7$ | $R^9$ | $R^{10}$ | $R^{11}$ | $R^{12}$ |
| --- | --- | --- | --- | --- | --- | --- | --- |
| 1063 | A | G | I | L | — | — | — |
| 1064 | B | E | H | J | N | N | Q |
| 1065 | B | E | H | J | O | O | Q |
| 1066 | B | E | H | J | P | P | Q |
| 1067 | B | E | H | J | M | R | R |
| 1068 | B | E | H | J | M | S | S |
| 1069 | B | E | H | J | M | T | T |
| 1070 | B | D | H | J | — | — | — |
| 1071 | B | F | H | J | — | — | — |
| 1072 | B | G | H | J | — | — | — |
| 1073 | B | E | H | K | N | N | Q |
| 1074 | B | E | H | K | O | O | Q |
| 1075 | B | E | H | K | P | P | Q |
| 1076 | B | E | H | K | M | R | R |
| 1077 | B | E | H | K | M | S | S |
| 1078 | B | E | H | K | M | T | T |
| 1079 | B | D | H | K | — | — | — |
| 1080 | B | F | H | K | — | — | — |
| 1081 | B | G | H | K | — | — | — |
| 1082 | B | E | H | L | N | N | Q |
| 1083 | B | E | H | L | O | O | Q |
| 1084 | B | E | H | L | P | P | Q |
| 1085 | B | E | H | L | M | R | R |
| 1086 | B | E | H | L | M | S | S |
| 1087 | B | E | H | L | M | T | T |
| 1088 | B | D | H | L | — | — | — |
| 1089 | B | F | H | L | — | — | — |
| 1090 | B | G | H | L | — | — | — |
| 1091 | B | E | I | J | N | N | Q |
| 1092 | B | E | I | J | O | O | Q |
| 1093 | B | E | I | J | P | P | Q |
| 1094 | B | E | I | J | M | R | R |
| 1095 | B | E | I | J | M | S | S |
| 1096 | B | E | I | J | M | T | T |
| 1097 | B | D | I | J | — | — | — |
| 1098 | B | F | I | J | — | — | — |
| 1099 | B | G | I | J | — | — | — |
| 1100 | B | E | I | K | N | N | Q |
| 1101 | B | E | I | K | O | O | Q |
| 1102 | B | E | I | K | P | P | Q |
| 1103 | B | E | I | K | M | R | R |
| 1104 | B | E | I | K | M | S | S |
| 1105 | B | E | I | K | M | T | T |
| 1106 | B | D | I | K | — | — | — |
| 1107 | B | F | I | K | — | — | — |
| 1108 | B | G | I | K | — | — | — |
| 1109 | B | E | I | L | N | N | Q |
| 1110 | B | E | I | L | O | O | Q |
| 1111 | B | E | I | L | P | P | Q |
| 1112 | B | E | I | L | M | R | R |
| 1113 | B | E | I | L | M | S | S |
| 1114 | B | E | I | L | M | T | T |
| 1115 | B | D | I | L | — | — | — |
| 1116 | B | F | I | L | — | — | — |
| 1117 | B | G | I | L | — | — | — | where X is CH and Y is N:

| Emb. # | $R^1$ | $R^4$ | $R^7$ | $R^9$ | $R^{10}$ | $R^{11}$ | $R^{12}$ |
| --- | --- | --- | --- | --- | --- | --- | --- |
| 2001 | C | E | — | — | N | N | Q |
| 2002 | C | E | — | — | O | O | Q |
| 2003 | C | E | — | — | P | P | Q |
| 2004 | C | E | — | — | M | R | R |
| 2005 | C | E | — | — | M | S | S |
| 2006 | C | E | — | — | M | T | T |
| 2007 | C | D | — | — | — | — | — |
| 2008 | C | F | — | — | — | — | — |
| 2009 | C | G | — | — | — | — | — |
| 2010 | A | E | H | J | N | N | Q |
| 2011 | A | E | H | J | O | O | Q |
| 2012 | A | E | H | J | P | P | Q |
| 2013 | A | E | H | J | M | R | R |
| 2014 | A | E | H | J | M | S | S |
| 2015 | A | E | H | J | M | T | T |
| 2016 | A | D | H | J | — | — | — |
| 2017 | A | F | H | J | — | — | — |
| 2018 | A | G | H | J | — | — | — |
| 2019 | A | E | H | K | N | N | Q |
| 2020 | A | E | H | K | O | O | Q |
| 2021 | A | E | H | K | P | P | Q |
| 2022 | A | E | H | K | M | R | R |
| 2023 | A | E | H | K | M | S | S |
| 2024 | A | E | H | K | M | T | T |
| 2025 | A | D | H | K | — | — | — |
| 2026 | A | F | H | K | — | — | — |
| 2027 | A | G | H | K | — | — | — |
| 2028 | A | E | H | L | N | N | Q |
| 2029 | A | E | H | L | O | O | Q |
| 2030 | A | E | H | L | P | P | Q |
| 2031 | A | E | H | L | M | R | R |
| 2032 | A | E | H | L | M | S | S |
| 2033 | A | E | H | L | M | T | T |
| 2034 | A | D | H | L | — | — | — |
| 2035 | A | F | H | L | — | — | — |
| 2036 | A | G | H | L | — | — | — |
| 2037 | A | E | I | J | N | N | Q |
| 2038 | A | E | I | J | O | O | Q |
| 2039 | A | E | I | J | P | P | Q |
| 2040 | A | E | I | J | M | R | R |
| 2041 | A | E | I | J | M | S | S |
| 2042 | A | E | I | J | M | T | T |
| 2043 | A | D | I | J | — | — | — |
| 2044 | A | F | I | J | — | — | — |
| 2045 | A | G | I | J | — | — | — |
| 2046 | A | E | I | K | N | N | Q |
| 2047 | A | E | I | K | O | O | Q |
| 2048 | A | E | I | K | P | P | Q |
| 2049 | A | E | I | K | M | R | R |
| 2050 | A | E | I | K | M | S | S |
| 2051 | A | E | I | K | M | T | T |
| 2052 | A | D | I | K | — | — | — |
| 2053 | A | F | I | K | — | — | — |
| 2054 | A | G | I | K | — | — | — |
| 2055 | A | E | I | L | N | N | Q |
| 2056 | A | E | I | L | O | O | Q |
| 2057 | A | E | I | L | P | P | Q |
| 2058 | A | E | I | L | M | R | R |
| 2059 | A | E | I | L | M | S | S |
| 2060 | A | E | I | L | M | T | T |
| 2061 | A | D | I | L | — | — | — |
| 2062 | A | F | I | L | — | — | — |
| 2063 | A | G | I | L | — | — | — |
| 2064 | B | E | H | J | N | N | Q |
| 2065 | B | E | H | J | O | O | Q |
| 2066 | B | E | H | J | P | P | Q |
| 2067 | B | E | H | J | M | R | R |
| 2068 | B | E | H | J | M | S | S |
| 2069 | B | E | H | J | M | T | T |
| 2070 | B | D | H | J | — | — | — |
| 2071 | B | F | H | J | — | — | — |
| 2072 | B | G | H | J | — | — | — |
| 2073 | B | E | H | K | N | N | Q |
| 2074 | B | E | H | K | O | O | Q |
| 2075 | B | E | H | K | P | P | Q |
| 2076 | B | E | H | K | M | R | R |
| 2077 | B | E | H | K | M | S | S |
| 2078 | B | E | H | K | M | T | T |
| 2079 | B | D | H | K | — | — | — |
| 2080 | B | F | H | K | — | — | — |
| 2081 | B | G | H | K | — | — | — |
| 2082 | B | E | H | L | N | N | Q |
| 2083 | B | E | H | L | O | O | Q |
| 2084 | B | E | H | L | P | P | Q |
| 2085 | B | E | H | L | M | R | R |
| 2086 | B | E | H | L | M | S | S |
| 2087 | B | E | H | L | M | T | T |
| 2088 | B | D | H | L | — | — | — |
| 2089 | B | F | H | L | — | — | — |

-continued

| Emb. # | R¹ | R⁴ | R⁷ | R⁹ | R¹⁰ | R¹¹ | R¹² |
|---|---|---|---|---|---|---|---|
| 2090 | B | G | H | L | — | — | — |
| 2091 | B | E | I | J | N | N | Q |
| 2092 | B | E | I | J | O | O | Q |
| 2093 | B | E | I | J | P | P | Q |
| 2094 | B | E | I | J | M | R | R |
| 2095 | B | E | I | J | M | S | S |
| 2096 | B | E | I | J | M | T | T |
| 2097 | B | D | I | J | — | — | — |
| 2098 | B | F | I | J | — | — | — |
| 2099 | B | G | I | J | — | — | — |
| 2100 | B | E | I | K | N | N | Q |
| 2101 | B | E | I | K | O | O | Q |
| 2102 | B | E | I | K | P | P | Q |
| 2103 | B | E | I | K | M | R | R |
| 2104 | B | E | I | K | M | S | S |
| 2105 | B | E | I | K | M | T | T |
| 2106 | B | D | I | K | — | — | — |
| 2107 | B | F | I | K | — | — | — |
| 2108 | B | G | I | K | — | — | — |
| 2109 | B | E | I | L | N | N | Q |
| 2110 | B | E | I | L | O | O | Q |
| 2111 | B | E | I | L | P | P | Q |
| 2112 | B | E | I | L | M | R | R |
| 2113 | B | E | I | L | M | S | S |
| 2114 | B | E | I | L | M | T | T |
| 2115 | B | D | I | L | — | — | — |
| 2116 | B | F | I | L | — | — | — |
| 2117 | B | G | I | L | — | — | — |

One aspect of the current invention relates to compounds having the general structure:

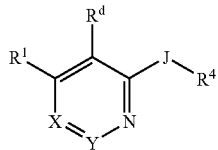

or any pharmaceutically-acceptable salt thereof, wherein:
X is C(R²) and Y is C(R³); or X is N and Y is C(R³); or X is C(R²) and Y is N;
J is O or S;
n is independently, at each instance, 0, 1 or 2.
R¹ is

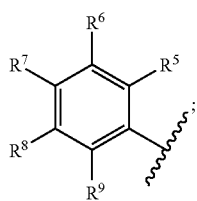

or R¹ is a naphthyl substituted by 0, 1, 2 or 3 substituents independently selected from R⁵; or R¹ is R$^b$ substituted by 1, 2 or 3 substituents independently selected from R⁵;

R² is, independently, in each instance, R¹⁰, C$_{1-8}$alkyl substituted by 0, 1 or 2 substituents selected from R¹⁰, —(CH$_2$)$_n$phenyl wherein the phenyl is substituted by 0, 1, 2 or 3 substituents independently selected from R¹⁰, or a saturated or unsaturated 5- or 6-membered ring heterocycle containing 1, 2 or 3 heteroatoms independently selected from N, O and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, the heterocycle and bridge being substituted by 0, 1, 2 or 3 substituents independently selected from R¹⁰;

R³ is, independently, in each instance, H, halo, —NH$_2$, —NHC$_{1-3}$alkyl, —N(C$_{1-3}$alkyl)C$_{1-3}$alkyl, —OC$_{1-3}$alkyl, —C$_{1-2}$haloalkyl, —OC$_{1-2}$haloalkyl or C$_{1-3}$alkyl;

R⁴ is

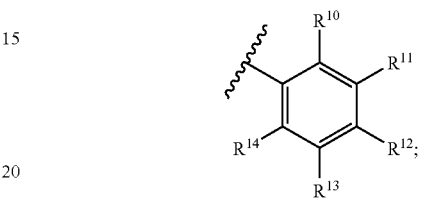

wherein when R¹ is bromophenyl, methylphenyl or trifluoromethylphenyl, R⁴ is not trifluoromethylphenyl or trifluoromethylhalophenyl; or R⁴ is a saturated or unsaturated 5- or 6-membered ring heterocycle containing 1, 2 or 3 atoms selected from O, N and S, so long as the combination of O and S atoms is not greater than 2, wherein each of the carbon atoms of the heterocycle is substituted by H, C$_{1-9}$alkyl, C$_{1-4}$haloalkyl, halo, cyano, oxo, —OR$^a$, —S(=O)$_n$C$_{1-6}$alkyl, —OC$_{1-4}$haloalkyl, —OC$_{2-6}$alkyNR$^a$R$^a$, —OC$_{2-6}$alkylOR$^a$, —OC$_{1-6}$alkylC(=O)OR$^a$, —NR$^a$R$^a$, —NR$^a$C$_{1-4}$haloalkyl, —NR$^a$ C$_{2-6}$alkylNR$^a$R$^a$, —NR$^a$C$_{2-6}$alkylOR$^a$, —C(=O)C$_{1-6}$alkyl, —C(=O)OC$_{1-6}$alkyl, —OC(=O)C$_{1-6}$alkyl, —C(=O)NR$^a$C$_{1-6}$alkyl or —NR$^a$C(=O)C$_{1-6}$alkyl; and unsaturated carbon atoms may be additionally substituted by =O; and each of the nitrogen atoms in the heterocycle are substituted by H, —C$_{1-6}$alkylOR$^a$, —C$_{1-6}$alkyl, —C$_{1-6}$alkylNR$^a$R$^a$, —C$_{1-3}$alkylC(=O)OR$^a$, —C$_{1-3}$alkylC(=O)NR$^a$R$^a$, —C$_{1-3}$alkylOC(=O)C$_{1-6}$alkyl, —C$_{1-3}$alkylNR$^a$C(=O)C$_{1-6}$alkyl, —C(=O)R$^c$ or —C$_{1-3}$alkylR$^c$; or R⁴ is an 8-, 9-, 10- or 11-membered bicyclic ring, containing 0, 1, 2, 3 or 4 N atoms and 0, 1 or 2 atoms selected from S and O with the remainder being carbon atoms, wherein each of the carbon atoms of the ring is substituted by H, C$_{1-9}$alkyl, C$_{1-4}$haloalkyl, halo, cyano, oxo, —OR$^a$, —S(=O)$_n$C$_{1-6}$alkyl, —OC$_{1-4}$haloalkyl, —OC$_{2-6}$alkylNR$^a$R$^a$, —OC$_{2-6}$alkylOR$^a$, —OC$_{1-6}$alkylC(=O)OR$^a$, —NR$^a$R$^a$, —NR$^a$C$_{1-4}$haloalkyl, —NR$^a$C$_2$-alkylNR$^a$R$^a$, —NR$^a$C$_{2-6}$alkylOR$^a$, —C(=O)C$_{1-6}$alkyl, —C(=O)OC$_{1-6}$alkyl, —OC(=O)C$_{1-6}$alkyl, —C(=O)NR$^a$C$_{1-6}$alkyl or —NR$^a$C(=O)C$_{1-6}$alkyl; and unsaturated carbon atoms may be additionally substituted by =O; and any available nitrogen atoms in the ring are substituted by H, —C$_{1-6}$alkylOR$^a$, —C$_{1-6}$alkyl, —C$_{1-6}$alkylNR$^a$R$^a$, —C$_{1-3}$alkylC(=O)OR$^a$, —C$_{1-3}$alkylC(O)NR$^a$R$^a$, —C$_{1-3}$alkylOC(=O)C$_{1-6}$alkyl, —C$_{1-3}$alkylNR$^a$C(=O)C$_{1-6}$alkyl, —C(=O)R$^c$ or —C$_{1-3}$alkylR$^c$;

R⁵ is independently, at each instance, H, C$_{1-5}$alkyl, C$_{1-4}$haloalkyl, halo, nitro, —OC$_{1-6}$ alkyl, —OC$_{1-4}$haloalkyl, —OC$_{2-6}$alkylNR$^a$R$^a$, —OC$_{2-6}$alkylOR$^a$, —NR$^a$R$^a$, —NR$^a$C$_{1-4}$haloalkyl, —NR$^a$C$_{2-6}$alkylNR$^a$R$^a$, —NR$^a$C$_{2-6}$alkylOR$^a$, naphthyl, —CO$_2$(C$_{1-6}$alkyl), —C(=O)(C$_{1-6}$alkyl), —C(=O)NR$^a$R$^a$, —NR$^a$C(=O)R$^a$, —NR$^a$C(=O)NR$^a$R$^a$, —NR$^a$CO$_2$(C$_{1-6}$alkyl), —C$_{1-8}$alkylOR$^a$, —C$_{1-6}$alkylNR$^a$R$^a$, —S(=O)$_n$(C$_{1-6}$alkyl), —S(=O)$_2$NR$^a$R$^a$, —NR$^a$S(=O)$_2$(C$_{1-6}$alkyl), —OC(=O)NR$^a$R$^a$, a phenyl ring substituted with 0, 1, 2, or 3 substituents independently selected from R$^{10}$; or R$^5$ is a saturated or unsaturated 5- or 6-membered ring heterocycle containing 1, 2 or 3 atoms selected from O, N and S, substituted with 0, 1, 2, or 3 substituents independently selected from R$^{10}$;

R$^6$ is independently, at each instance, H, C$_{1-5}$alkyl, C$_{1-4}$haloalkyl, halo, —OC$_{1-6}$alkyl, —OC$_{1-4}$haloalkyl, —OC$_{2-6}$alkyl NR$^a$R$^a$, —NR$^a$C$_{1-4}$haloalkyl, —NR$^a$C$_{2-6}$alkylNR$^a$R$^a$ or —NR$^a$C$_{2-6}$alkylOR$^a$, —C$_{1-8}$ OR$^a$, —C$_{1-6}$alkylNR$^a$R$^a$, —S(C$_{1-6}$alkyl), a phenyl ring substituted with 1, 2, or 3 substituents independently selected from R$^{10}$; or R$^6$ is a saturated or unsaturated 5- or 6-membered ring heterocycle containing 1, 2 or 3 atoms selected from O, N and S substituted with 0, 1, 2, or 3 substituents independently selected from R$^{10}$;

R$^7$ is independently, at each instance, H, C$_{1-5}$alkyl, C$_{1-4}$haloalkyl, bromo, —OC$_{1-6}$alkyl, —OC$_{1-4}$haloalkyl, —OC$_{2-6}$alkylNR$^a$R$^a$, —OC$_{2-6}$alkylOR$^a$, —NR$^a$R$^a$, —NR$^a$C$_{1-4}$haloalkyl, —NR$^a$C$_{2-6}$alkylNR$^a$R$^a$, —NR$^a$C$_{2-6}$alkylOR$^a$, —C$_{1-8}$alkylOR$^a$, —C$_{1-6}$alkylNR$^a$R$^a$ or —S(C$_{1-6}$alkyl); or R$^7$ is a saturated or unsaturated 4- or 5-membered ring heterocycle containing a single nitrogen atom, wherein the ring is substituted with 0, 1 or 2 substituents independently selected from halo, C$_{1-2}$haloalkyl and C$_{1-3}$alkyl;

R$^8$ is independently, at each instance, H, C$_{1-5}$alkyl, C$_{1-4}$haloalkyl, halo, —OC$_{1-6}$alkyl, —OC$_{1-4}$haloalkyl, —OC$_{2-6}$alkylNR$^a$R$^a$, —OC$_{2-6}$alkylOR$^a$, —NR$^a$R$^a$, —NR$^a$C$_{1-4}$ haloalkyl, —NR$^a$C$_{2-6}$alkylNR$^a$R$^a$, —NR$^a$C$_{2-6}$alkylOR$^a$, —C$_{1-8}$alkylOR$^a$, —C$_6$alkylNR$^a$R$^a$, —S(C$_{1-6}$alkyl), a phenyl ring substituted with 1, 2, or 3 substituents independently selected from R$^{10}$, or R$^8$ is a saturated or unsaturated 5- or 6-membered ring heterocycle containing 1, 2 or 3 atoms selected from O, N and S substituted with 0, 1, 2, or 3 substituents independently selected from R$^{10}$;

R$^9$ is independently, at each instance, H, C$_{1-8}$alkyl, C$_{1-4}$haloalkyl, halo, nitro, —OC$_{1-6}$alkyl, —OC$_{1-4}$haloalkyl, —OC$_{2-6}$alkylNR$^a$R$^a$, —OC$_{2-6}$alkylOR$^a$, —NR$^a$R$^a$, —NR$^a$C$_{1-4}$ haloalkyl, —NR$^a$C$_{2-6}$alkylNR$^a$R$^a$ or —NR$^a$C$_{2-6}$alkylOR$^a$, —CO$_2$(C$_{1-6}$alkyl), —C(=O)(C$_{1-6}$alkyl), —C(=O)NR$^a$R$^a$, —NR$^a$C(=O)(C$_{1-6}$alkyl), —NR$^a$C(=O)NR$^a$R$^a$, —NR$^a$CO$_2$(C$_{1-6}$alkyl), —C$_{1-8}$alkylOR$^a$, —C$_{1-6}$alkylNR$^a$R$^a$, —S(=O)$_n$(C$_{1-6}$alkyl), —S(=O)$_2$NR$^a$R$^a$, —NR$^a$S(=O)$_2$(C$_{1-6}$alkyl), —OC(=O)NR$^a$R$^a$, a phenyl ring substituted with 0, 1, 2, or 3 substituents independently selected from R$^{10}$; or R$^9$ is a saturated or unsaturated 5- or 6-membered ring heterocycle containing 1, 2 or 3 atoms selected from O, N and S substituted with 0, 1, 2, or 3 substituents independently selected from R$^{10}$; wherein at least one of R$^5$, R$^6$, R$^7$, R$^8$ and R$^9$ is C$_{1-8}$alkyl, C$_{1-4}$haloalkyl, halo, —OC$_{1-4}$haloalkyl, —R$^9$ is C$_{1-8}$alkyl, C$_{1-4}$haloalkyl, halo, —OC$_{1-4}$haloalkyl, —OC$_{2-6}$alkylNR$^a$R$^a$, —OC$_{2-6}$alkylOR$^a$, —NR$^a$C$_{1-4}$haloalkyl —NR$^a$C$_{2-6}$alkylNR$^a$R$^a$, —NR$^a$C$_{2-6}$alkylOR$^a$, —C$_{1-8}$alkylNR$^a$R$^a$ or —S(C$_{1-6}$alkyl); or R$^9$ is a saturated or unsaturated 4- or 5-membered ring heterocycle containing a single nitrogen atom, wherein the ring is substituted with 0, 1 or 2 substituents independently selected from halo, C$_{1-2}$haloalkyl and C$_{1-3}$alkyl;

R$^{10}$ is independently, at each instance, selected from H, C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^{10}$ is a saturated or unsaturated 5-, 6- or 7-membered monocyclic or 6-, 7-, 8-, 9-, 10- or 11-membered bicyclic ring containing 1 or 2 atoms selected from N, O and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the carbon atoms of the ring are substituted by 0, 1 or 2 oxo groups, wherein the ring is substituted by 0, 1, 2 or 3 groups selected from C$_{1-8}$ alkyl, C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$-OC$_{2-6}$alkylOR$^a$, —SR$^a$, —S(=O)(C$_8$alkyl), —S(=O)$_2$(C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^{10}$ is C$_{1-4}$alkyl substituted by 0, 1, 2 or 3 groups selected from C$_{1-4}$haloalkyl, halo, cyano, nitro, —C(=O)(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-4}$alkylOR$^a$;

R$^{11}$ is independently, at each instance, selected from H, C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-4}$alkylNR$^a$R$^a$, —OC$_2$ alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^{11}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —S(=O)$_2$NR$^a$R$^a$, —S(=O)$_2$N(R$^a$)C(=O)(C$_{1-8}$ alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O) (Cz 8alkyl), —N(R$^a$)C(=O)O(C$_{1-8}$alkyl), —N(R$^a$)C(=O)

NR$^a$R$^a$, —N(R$^a$)C(=NR$^a$)NR$^a$R$^a$, —N(R$^a$)S(=O)$_2$(C$_{1-8}$ alkyl), —N(R$^a$)S(=O)$_2$NR$^a$R$^a$, and —NR$^a$C$_{2-6}$alkylOR$^a$; or R$^{11}$ is C$_{1-4}$ alkyl substituted by 0, 1, 2 or 3 groups selected from C$_{1-4}$haloalkyl, halo, cyano, nitro, —C(=O)(C$_{1-8}$ alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$ alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$) NR$^a$R$^a$, —N(R$^a$)S(=O)$_2$(C$_{1-8}$alkyl), —N(R$^a$)S(=O)$_2$ NR$^a$R$^a$, —NR$^a$C$_{2-6}$alkylNR$^a$R$^a$ and —NR$^a$C$_{2-6}$alkylOR$^a$;

R$^{12}$ is independently, at each instance, selected from H, C$_{1-8}$alkyl, C$_{1-4}$haloalkyl, halo, cyano, nitro, —C(=O)O (C$_{1-8}$ alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N (R$^a$)S(=O)$_2$(C$_{1-8}$alkyl), —OC$_{2-6}$alkylNR$^a$R$^a$, —OC$_{2-6}$ alkylOR$^a$, —SR$^a$, —S(=O)(C$_{1-8}$alkyl), —S(=O)$_2$(C$_{1-8}$ alkyl), —S(=O)$_2$NR$^a$R$^a$, —S(=O)$_2$N(R$^a$)C(=O)(C$_{1-8}$ alkyl), —S(=O)$_2$N(R$^a$)C(=O)O(C$_{1-8}$alkyl), —S(=O)$_2$N (R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^{12}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$) NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$ (C$_{1-8}$alkyl), —S(=O)$_2$NR$^a$R$^a$, —S(=O)$_2$N(R$^a$)C(=O) (C$_{1-8}$ alkyl), —S(=O)$_2$N(R$^a$)C(=O)O(C$_{1-8}$alkyl) —S(=O)$_2$N(R$^a$)C(=O)NR$^a$R$^a$, —NR$^a$R$^a$, —N(R$^a$)C(=O) (C$_{1-8}$alkyl), —N(R$^a$)C(=O)O(C$_{1-8}$alkyl), —N(R$^a$)C(=O) NR$^a$R$^a$, —N(R$^a$)C(=NR$^a$)NR$^a$R$^a$, —N(R$^a$)S(=O)$_2$(C$_{1-8}$ alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^{12}$ is C$_{1-4}$alkyl substituted by 0, 1, 2 or 3 groups selected from C$_{1-4}$haloalkyl, halo, cyano, nitro, —C(=O)(C$_{1-8}$alkyl), —C(=O)O(C$_{1-8}$alkyl), —C(=O) NR$^a$R$^a$, —C(=NR$^a$)NR$^a$R$^a$, —OR$^a$, —OC(=O)(C$_{1-8}$ alkyl), —OC(=O)NR$^a$R$^a$, —OC(=O)N(R$^a$)S(=O)$_2$(C$_{1-8}$ alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$ NR$^a$R$^a$, —S(=O)$_2$N(R$^a$)C(=O)(C$_{1-8}$alkyl), —S(=O)$_2$N (R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O (C$_{1-8}$alkyl), —N(R$^a$)C(=O)NR$^a$R$^a$, —N(R$^a$)C(=NR$^a$) NR$^a$R$^a$, —N(R$^a$)S(=O)$_2$(C$_{1-8}$alkyl), —N(R$^a$)S(=O)$_2$ NR$^a$R$^a$, —NR$^a$C$_{2-6}$alkylNR$^a$R$^a$ and —NR$^a$C$_{2}$alkylOR$^a$;

R$^{13}$ is independently, at each instance, selected from H, C$_{1-8}$alkyl, C$_{1-4}$haloalkyl, halo, cyano, nitro, —C(=O)(C$_{1-8}$ alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC (=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O) (C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C (=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O (C$_{1-8}$alkyl), —N(R$^a$)C(=O)NR$^a$R$^a$, —N(R$^a$)C(=NR$^a$) NR$^a$R$^a$, —N(R$^a$)S(=O)$_2$(C$_{1-8}$alkyl), —N(R$^a$)S(=O)$_2$ NR$^a$R$^a$, —NR$^a$C$_{2-6}$alkylNR$^a$R$^a$ and —NR$^a$C$_{2-6}$alkylOR$^a$; or R$^{13}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O) (C$_{1-8}$alkyl), —OC(=O)NR$^a$R$^a$, —OC(=O)N(R$^a$)S(=O)$_2$ (C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C(=O)O(C$_{1-8}$alkyl), —S(=O)$_2$N(R$^a$)C (=O)NR$^a$R$^a$, —NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, and —NR$^a$C$_{2-6}$alkylOR$^a$; or R$^{13}$ is C$_{1-4}$alkyl substituted by 0, 1, 2 or 3 groups selected from C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$) NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$ (C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C(=O)O(C$_{1-8}$alkyl), —S(=O)$_2$N (R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$;

R$^{14}$ is independently, at each instance, selected from H, C$_{1-8}$alkyl, C$_{1-4}$haloalkyl, halo, cyano, nitro, —C(=O)(C$_{1-8}$ alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC (=O)NR$^a$R$^a$, —OC(=O)N(R$^a$)S(=O)$_2$(C$_{1-8}$alkyl), —OC$_{2-6}$alkylOR$^a$, —SR$^a$, —S(=O)(C$_{1-8}$alkyl), —S(=O)$_2$ (C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C(=O)O(C$_{1-8}$alkyl), —S(=O)$_2$N (R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^{14}$ is a saturated or unsaturated 5-, 6- or 7-membered monocyclic or 6-, 7-, 8-, 9-, 10- or 11-membered bicyclic ring containing 1 or 2 atoms selected from N, 0 and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the carbon atoms of the ring are substituted by 0, 1 or 2 oxo groups, wherein the ring is substituted by 0, 1, 2 or 3 groups selected from C$_{1-8}$ alkyl, C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$) NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S (=O)$_2$(C$_{1-8}$alkyl), —S(=O)$_2$NR$^a$R$^a$, —S(=O)$_2$N(R$^a$)C (=O)(C$_{1-8}$alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^{14}$ is C$_{1-4}$alkyl substituted by 0, 1, 2 or 3 groups selected from C$_{1-4}$haloalkyl, halo, cyano, nitro, —C(=O)(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$ alkyl), —S(=O)$_2$N(R$^a$)C(=O)O(C$_8$alkyl), —S(=O)$_2$ N(R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$;

R$^a$ is independently, at each instance, H, phenyl, benzyl or C$_{1-6}$alkyl, the phenyl, benzyl and C$_{1-6}$alkyl being substituted by 0, 1, 2 or 3 substituents selected from halo, C$_{1-4}$alkyl, C$_{1-3}$haloalkyl, —OC$_{1-4}$alkyl, —NH$_2$, —NHC$_{1-4}$alkyl, —N(C$_{1-4}$alkyl)C$_{1-4}$alkyl;

R$^b$ is a heterocycle selected from the group of thiophene, pyrrole, 1,3-oxazole, 1,3-thiazol-5-yl, 1,3,4-oxadiazole, 1,3,4-thiadiazole, 1,2,3-oxadiazole, 1,2,3-thiadiazole, 1H-1,2,3-triazole, isothiazole, 1,2,4-oxadiazole, 1,2,4-thiadiazole, 1,2,3,4-oxatriazole, 1,2,3,4-thiatriazole, 1H-1,2,3,4-tetraazole, 1,2,3,5-oxatriazole, 1,2,3,5-thiatriazole, furan, imidazol-1-yl, imidazol-3-yl, imidazol-4-yl, 1,2,4-triazole, 1,2,4-triazole, isoxazole, pyrazol-3-yl, pyrazol-4-yl, pyrazol-5-yl, thiolane, pyrrolidine, tetrahydrofuran, 4,5-dihydrothiophene, 2-pyrroline, 4,5-dihydrofuran, pyridazine, pyrimidine, pyrazine, 1,2,3-triazine, 1,2,4-triazine, 1,3,5-triazine, pyridine, 2H-3,4,5,6-tetrahydropyran, thiane, 1,2-diazaperhydroine, 1,3-diazaperhydroine, piperazine, 1,3-oxazaperhydroine, morpholine, 1,3-thiazaperhydroine, 1,4-thiazaperhydroine, piperidine, 2H-3,4-dihydropyran, 2,3-dihydro-4H-thiin, 1,4,5,6-tetrahydropyridine, 2H-5,6-dihydropyran, 2,3-dihydro-6H-thiin, 1,2,5,6-tetrahydropyridine, 3,4,5,6-tetrahydropyridine, 4H-pyran, 4H-thiin, 1,4-dihydropyridine, 1,4-dithiane, 1,4-dioxane, 1,4-oxathiane, 1,2-oxazolidine, 1,2-thiazolidine, pyrazolidine, 1,3-oxazolidine, 1,3-thiazolidine, imidazolidine, 1,2,4-oxadiazolidine, 1,3,4-oxadiazolidine, 1,2,4-thiadiazolidine, 1,3,4-thiadiazolidine, 1,2,4-triazolidine, 2-imidazolin-1-yl, 2-imidazolin-2-yl, 2-imidazolin-5-yl, 3-imidazoline, 2-pyrazoline, 4-imidazoline, 2,3-dihydroisothiazole, 4,5-dihydroisoxazole, 4,5-dihydroisothiazole, 2,5-dihydroisoxazole, 2,5-dihydroisothiazole, 2,3-dihydroisoxazole, 4,5-dihydrooxazole, 2,3-dihydrooxazole, 2,5-dihydrooxazole, 4,5-dihydrothiazole, 2,3-dihydrothiazole, 2,5-dihydrothiazole, 1,3,4-oxathiazolidine, 1,4,2-oxathiazolidine, 2,3-dihydro-1H-[1,2,3]triazole, 2,5-dihydro-1H-[1,2,3]triazole, 4,5-dihydro-1H-[1,2,3]triazol-1-yl, 4,5-dihydro-1H-[1,2,3]triazol-3-yl, 4,5-dihydro-1H-[1,2,3]triazol-5-yl, 2,3-dihydro-1H-[1,2,4]triazole, 4,5-dihydro-1H-[1,2,4]triazole, 2,3-dihydro-[1,2,4]oxadiazole, 2,5-dihydro-[1,2,4]oxadiazole, 4,5-dihydro-[1,2,4]thiadiazole, 2,3-dihydro-[1,2,4]thiadiazole, 2,5-dihydro-[1,2,4]thiadiazole, 4,5-dihydro-[1,2,4]thiadiazole, 2,5-dihydro-[1,2,4]oxadiazole, 2,3-dihydro-[1,2,4]oxadiazole, 4,5-dihydro-[1,2,4]oxadiazole, 2,5-dihydro-[1,2,4]thiadiazole, 2,3-dihydro-[1,2,4]thiadiazole, 4,5-dihydro-[1,2,4]thiadiazole, 2,3-dihydro-[1,3,4]oxadiazole, 2,3-dihydro-[1,3,4]thiadiazole, [1,3,4]oxathiazole, [1,3,4]oxathiazole, 1,3,5-triazaperhydroine, 1,2,4-triazaperhydroine, 1,4,2-dithiazaperhydroine, 1,4,2-dioxazaperhydroine, 1,3,5-oxadiazaperhydroine, 1,2,5-oxadiazaperhydroine, 1,3,4-thiadiazaperhydroine, 1,3,5-thiadiazaperhydroine, 1,2,5-thiadiazaperhydroine, 1,3,4-oxadiazaperhydroine, 1,4,3-oxathiazaperhydroine, 1,4,2-oxathiazaperhydroine, 1,4,5,6-tetrahydropyridazine, 1,2,3,4-tetrahydropyridazine, 1,2,3,6-tetrahydropyridazine, 1,2,5,6-tetrahydropyrimidine, 1,2,3,4-tetrahydropyrimidine, 1,4,5,6-tetrahydropyrimidine, 1,2,3,6-tetrahydropyrazine, 1,2,3,4-tetrahydropyrazine, 5,6-dihydro-4H-[1,2]oxazine, 5,6-dihydro-2H-[1,2]oxazine, 3,6-dihydro-2H-[1,2]oxazine, 3,4-dihydro-2H-[1,2]oxazine, 5,6-dihydro-4H-[1,2]thiazine, 5,6-dihydro-2H-[1,2] thiazine, 3,6-dihydro-2H-[1,2] thiazine, 3,4-dihydro-2H-[1,2] thiazine, 5,6-dihydro-2H-[1,3]oxazine, 5,6-dihydro-4H-[1,3]oxazine, 3,6-dihydro-2H-[1,3]oxazine, 3,4-dihydro-2H-[1,3]oxazine, 3,6-dihydro-2H-[1,4]oxazine, 3,4-dihydro-2H-[1,4]oxazine, 5,6-dihydro-2H-[1,3]thiazine, 5,6-dihydro-4H-[1,3]thiazine, 3,6-dihydro-2H-[1,3]thiazine, 3,4-dihydro-2H-[1,3]thiazine, 3,6-dihydro-2H-[1,4]thiazine, 3,4-dihydro-2H-[1,4]thiazine, 1,2,3,6-tetrahydro-[1,2,4]triazine, 1,2,3,4-tetrahydro-[1,2,4]triazine, 1,2,3,4-tetrahydro-[1,3,5]triazine, 2,3,4,5-tetrahydro-[1,2,4]triazine, 1,4,5,6-tetrahydro-[1,2,4]triazine, 5,6-dihydro-[1,4,2]dioxazine, 5,6-dihydro-[1,4,2]dithiazine, 2,3-dihydro-[1,4,2]dioxazine, 3,4-dihydro-2H-[1,3,4]oxadiazine, 3,6-dihydro-2H-[1,3,4] oxadiazine, 3,4-dihydro-2H-[1,3,5]oxadiazine, 3,6-dihydro-2H-[1,3,5]oxadiazine, 5,6-dihydro-2H-[1,2,5]oxadiazine, 5,6-dihydro-4H-[1,2,5]oxadiazine, 3,4-dihydro-2H-[1,3,4] thiadiazine, 3,6-dihydro-2H-[1,3,4]thiadiazine, 3,4-dihydro-2H-[1,3,5]thiadiazine, 3,6-dihydro-2H-[1,3,5]thiadiazine, 5,6-dihydro-2H-[1,2,5]thiadiazine, 5,6-dihydro-4H-[1,2,5]thiadiazine, 5,6-dihydro-2H-[1,2,3]oxadiazine, 3,6-dihydro-2H-[1,2,5]oxadiazine, 5,6-dihydro-4H-[1,3,4]oxadiazine, 3,4-dihydro-2H-[1,2,5]oxadiazine, 5,6-dihydro-2H-[1,2,3] thiadiazine, 3,6-dihydro-2H-[1,2,5]thiadiazine, 5,6-dihydro-4H-[1,3,4]thiadiazine, 3,4-dihydro-2H-[1,2,5]thiadiazine, 5,6-dihydro-[1,4,3]oxathiazine, 5,6-dihydro-[1,4,2]oxathiazine, 2,3-dihydro-[1,4,3]oxathiazine, 2,3-dihydro-[1,4,2]oxathiazine, 3,4-dihydropyridine, 1,2-dihydropyridine, 5,6-dihydropyridine, 2H-pyran, 2H-thiin, 3,6-dihydropyridine, 2,3-dihydropyridazine, 2,5-dihydropyridazine, 4,5-dihydropyridazine, 1,2-dihydropyridazine, 1,4-dihydropyrimidin-1-yl, 1,4-dihydropyrimidin-4-yl, 1,4-dihydropyrimidin-5-yl, 1,4-dihydropyrimidin-6-yl, 2,3-dihydropyrimidine, 2,5-dihydropyrimidine, 5,6-dihydropyrimidine, 3,6-dihydropyrimidine, 5,6-dihydropyrazine, 3,6-dihydropyrazine, 2,3-dihydropyrazine, 1,4-dihydropyrazine, 1,4-dithiin, 1,4-dioxin, 2H-1,2-oxazine, 6H-1,2-oxazine, 4H-1,2-oxazine, 2H-1,3-oxazine 4H-1,3-oxazine, 6H-1,3-oxazine, 2H-1,4-oxazine, 4H-1,4-oxazine, 2H-1,3-thiazine, 2H-1,4-thiazine, 4H-1,2-thiazine, 6H-1,3-thiazine, 4H-1,4-thiazine, 2H-1,2-thiazine, 6H-1,2-thiazine, 1,4-oxathiin, 2H,5H-1,2,3-triazine, 1H,4H-1,2,3-triazine, 4,5-dihydro-1,2,3-triazine, 1H,6H-1,2,3-triazine, 1,2-dihydro-1,2,3-triazine, 2,3-dihydro-1,2,4-triazine, 3H,6H-1,2,4-triazine, 1H,6H-1,2,4-triazine, 3,4-dihydro-1,2,4-triazine, 1H,4H-1,2,4-triazine, 5,6-dihydro-1,2,4-triazine, 4,5-dihydro-1,2,4-triazine, 2H,5H-1,2,4-triazine, 1,2-dihydro-1,2,4-triazine, 1H,4H-1,3,5-triazine, 1,2-dihydro-1,3,5-triazine, 1,4,2-dithiazine, 1,4,2-dioxazine, 2H-1,3,4-oxadiazine, 2H-1,3,5-oxadiazine, 6H-1,2,5-oxadiazine, 4H-1,3,4-oxadiazine, 4H-1,3,5-oxadiazine, 4H-1,2,5-oxadiazine, 2H-1,3,5-thiadiazine, 6H-1,2,5-thiadiazine, 4H-1,3,4-thiadiazine, 4H-1,3,5-thiadiazine, 4H-1,2,5-thiadiazine, 2H-1,3,4-thiadiazine, 6H-1,3,4-thiadiazine, 6H-1,3,4-oxadiazine, and 1,4,2-oxathiazine, wherein the heterocycle is optionally vicinally fused with a saturated or unsaturated 5-, 6- or 7-membered ring containing 0, 1 or 2 atoms independently selected from N, O and S;

$R^c$ is phenyl substituted by 0, 1 or 2 groups selected from halo, $C_{1-4}$alkyl, $C_{1-3}$haloalkyl, —$OR^a$ and —$NR^aR^a$; or $R^C$ is a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the carbon atoms of the heterocycle are substituted by 0, 1 or 2 oxo groups, wherein the heterocycle or fused phenyl ring is substituted by 0, 1, 2 or 3 substituents selected from halo, $C_{1-4}$alkyl, $C_{1-3}$haloalkyl, —$OR^a$ and —$NR^aR^a$; and $R^d$ is independently in each instance hydrogen or —$CH_3$.

In another embodiment, in conjunction with any one of the above and below embodiments, $R^1$ is

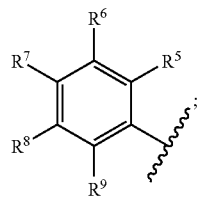

In another embodiment, in conjunction with any one of the above and below embodiments, $R^7$ is $C_{2-6}$alkyl or $C_{1-4}$ haloalkyl.

In another embodiment, in conjunction with any one of the above and below embodiments, $R^1$ is a naphthyl substituted by 0, 1, 2 or 3 substituents independently selected from $R^5$.

In another embodiment, in conjunction with any one of the above and below embodiments, $R^1$ is $R^b$ substituted by 1, 2 or 3 substituents independently selected from $R^5$.

In another embodiment, in conjunction with any one of the above and below embodiments, $R^1$ is 4-tert-butylphenyl or 4-trifluoromethylphenyl.

In another embodiment, in conjunction with any one of the above and below embodiments, $R^b$ is substituted by one substituent selected from halo, $C_{1-4}$haloalkyl and $C_{1-5}$alkyl, and additionally by 0, 1 or 2 substituents independently selected from $R^5$.

In another embodiment, in conjunction with any one of the above and below embodiments, $R^2$ is H.

In another embodiment, in conjunction with any one of the above and below embodiments, $R^2$ is $R^{10}$, $C_{1-8}$alkyl substituted by 0, 1 or 2 substituents selected from $R^{10}$, or a saturated or unsaturated 5- or 6-membered ring heterocycle containing 1, 2 or 3 heteroatoms independently selected from N, O and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, the heterocycle and bridge being substituted by 0, 1, 2 or 3 substituents independently selected from $R^{10}$; or $R^2$ is —$(CH_2)_n$phenyl substituted by 0, 1, 2 or 3 substituents independently selected from H, $C_{1-8}$alkyl, $C_{1-4}$haloalkyl, halo, cyano, nitro, —$C(=O)(C_{1-8}$alkyl), —$C(=O)O(C_{1-8}$alkyl), —$C(=O)NR^aR^a$, $C(=NR^a)$ $NR^aR^a$, —$OC(=O)(C_{1-8}$alkyl), —$OC(=O)NR^aR^a$, —$OC(=O)N(R^a)S(=O)_2(C_{1-8}$alkyl), —$OC_{2-6}$alkylNR^aR^a$, —$OC_{2-6}$alkylOR^a$, —$SR^a$, —$S(=O)(C_{1-8}$alkyl), —$S(=O)_2(C_{1-8}$alkyl), —$S(=O)_2NR^aR^a$, —$S(=O)_2N(R^a)C(=O)$ $(C_{1-8}$ alkyl), —$S(=O)_2N(R^a)C(=O)O(C_{1-8}$alkyl), —$S(=O)_2N(R^a)C(=O)NR^aR^a$, —$NR^aR^a$, —$N(R^a)C(=O)$ $(C_{1-8}$alkyl), —$N(R^a)C(=O)O(C_{1-8}$alkyl), —$N(R^a)C(=O)NR^aR^a$, —$N(R^a)C(=NR^a)NR^aR^a$, —$N(R^a)S(=O)_2(C_{1-8}$alkyl), —$N(R^a)S(=O)_2NR^aR^a$, —$NR^aC_{2-6}$alkylNR^aR^a$, —$NR^aC_{2-6}$alkylOR^a$, and $C_{1-4}$alkyl substituted by 0, 1, 2 or 3 groups selected from $C_{1-4}$haloalkyl, halo, cyano, nitro, —$C(=O)(C_{1-8}$alkyl), —$C(=O)O(C_{8-1}$alkyl), —$C(=O)NR^aR^a$, —$C(=NR^a)NR^aR^a$, —$OR^a$, —$C(=1)_8(C_1$ alkyl), —$OC(=O)NR^aR^a$, —$OC(=O)N(R^a)S(=O)_2(C_{1-8}$alkyl), —$OC_{2-6}$alkylNR^aR^a$, —$OC_{2-6}$alkylOR^a$, —$SR^a$, —$S(=O)(C_{1-8}$alkyl), —$S(=O)_2(C_{1-8}$alkyl), —$S(=O)_2NR^aR^a$, —$S(=O)_2N(R^a)C(=O)$ $(C_{1-8}$ alkyl), —$S(=O)_2N(R^a)C(=O)O(C_{1-8}$alkyl), —$S(=O)_2N(R^a)C(=O)NR^aR^a$, —$NR^aR^a$, —$N(R^a)C(=O)$ $(C_{1-8}$alkyl), —$N(R^a)C(=O)O(C_{1-8}$alkyl), —$N(R^a)C(=O)NR^aR^a$, —$N(R^a)C(=NR^a)NR^aR^a$, —$N(R^a)S(=O)_2(C_{1-8}$alkyl), —$N(R^a)S(=O)_2NR^aR^a$, —$NR^aC_{2-6}$alkylNR^aR^a$ and —$NR^aC_{2-6}$alkylOR^a$.

In another embodiment, in conjunction with any one of the above and below embodiments, $R^3$ is H.

In another embodiment, in conjunction with any one of the above and below embodiments, $R^3$ is halo, —$NHC_{1-3}$ alkyl, —$N(C_{1-3}$alkyl$)C_{1-3}$alkyl, —$OC_{1-3}$alkyl, —$C_{1-2}$haloalkyl, —$OC_{1-2}$haloalkyl or $C_{1-3}$alkyl.

In another embodiment, in conjunction with any one of the above and below embodiments, $R^4$ is

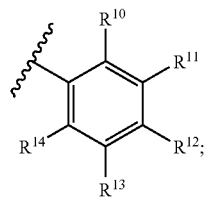

wherein at least one of $R^{10}$, $R^{11}$, $R^{12}$, $R^{13}$ and $R^{14}$ is other than $C_{1-4}$haloalkyl or halo.

In another embodiment, in conjunction with any one of the above and below embodiments, at least one of $R^{10}$, $R^{11}$, $R^{12}$, $R^{13}$ and $R^{14}$ is —$OR^a$ or —$NR^aR^a$.

In another embodiment, in conjunction with any one of the above and below embodiments, $R^4$ is a saturated or unsaturated 5- or 6-membered ring heterocycle containing 1, 2 or 3 atoms selected from O, N and S, so long as the combination of O and S atoms is not greater than 2, wherein each of the carbon atoms of the heterocycle is substituted by H, $C_{1-9}$alkyl, $C_{1-4}$haloalkyl, halo, cyano, oxo, $OR^a$, —$S(=O)_nC_{1-6}$alkyl, —$OC_{1-4}$haloalkyl, —$OC_{2-6}$alkylNR^aR^a$, —$OC_{2-6}$alkylOR^a$, —$OC_{1-6}$alkylC(=O)OR^a$, —$NR^aR^a$, —$NR^aC_{1-4}$haloalkyl, —$NR^aC_{2-6}$alkylNR^aR^a$, —$NR^aC_{2-6}$alkylOR^a$, —$C(=O)C_{1-6}$alkyl, —$C(=O)OC_{1-6}$ alkyl, —$OC(=O)C_{1-6}$alkyl, —$C(=O)NR^aC_{1-6}$alkyl or —$NR^aC(=O)C_{1-6}$alkyl; and unsaturated carbon atoms may be additionally substituted by =O; and any available nitrogen atoms in the heterocycle are substituted by H, —$C_{1-6}$alkylOR^a$, —$C_{1-6}$alkylNR^aR^a$, —$C_{1-3}$alkylC(=O)OR^a$, —$C_{1-3}$alkylC(=O)NR^aR^a$, —$C_{1-3}$alkylOC(=O)C_{1-6}$alkyl, —$C_{1-3}$alkylNR^aC(=O)C_{1-6}$alkyl, —$C(=O)R^c$ or —$C_{1-3}$ alkyl$R^c$.

In another embodiment, in conjunction with any one of the above and below embodiments, $R^4$ is a saturated or unsaturated 5- or 6-membered ring heterocycle containing 1 or 2 atoms selected from O, N and S, wherein each of the carbon atoms of the heterocycle is substituted by H, $C_{1-9}$alkyl, $C_{1-4}$haloalkyl, halo, cyano, oxo, —$OR^a$, —$S(=O).C_1$ alkyl, —$OC_{1-4}$haloalkyl, —$OC_{2-6}$alkylNR^aR^a$, —OC$_{2-6}$alkylOR$^a$, —OC$_{1-6}$alkylC(=O)O R$^a$, —NR$^a$R$^a$, —NR$^a$C$_4$haloalkyl, —NR$^a$C$_{2-6}$alkylNR$^a$, —NR$^a$C$_{2-6}$alkylOR$^a$, —C(=O)C$_{1-6}$alkyl, —C(=O)OC$_{1-6}$alkyl, —OC(=O)C$_{1-6}$alkyl, —C(=O)NR$^a$C$_{1-6}$alkyl or —NR$^a$C(=O)C$_{1-6}$alkyl; and unsaturated carbon atoms may be additionally substituted by =O; and any available nitrogen atoms in the chain are substituted by H, —C$_{1-6}$alkylOR$^a$, —C$_{1-6}$alkyl, —C$_{1-6}$alkylNR$^a$R$^a$, —C$_{1-3}$alkylC(=O)OR$^a$, —C$_{1-3}$alkylC(=O)NR$^a$R$^a$, —C$_{1-3}$alkylOC(=O)C$_{1-6}$alkyl, —C$_{1-3}$alkylNR$^a$C(=O)C$_6$alkyl, —C(=O)R$^c$ or —C$_{1-3}$alkylR$^c$.

In another embodiment, in conjunction with any one of the above and below embodiments, R$^4$ is an 8-, 9-, 10- or 11-membered bicyclic ring, containing 1, 2, 3 or 4 N atoms and 0, 1 or 2 atoms selected from S and O with the remainder being carbon atoms, wherein each of the carbon atoms of the ring is substituted by H, C$_{1-9}$alkyl, C$_{1-4}$haloalkyl, halo, cyano, oxo, —OR$^a$, —S(=O)$_n$C$_{1-6}$alkyl, —OC$_{1-4}$haloalkyl, —OC$_{2-26}$alkylNR$^a$, —OC$_{1-6}$alkylC(=O)OR$^a$, —NR$^a$R$^a$, —NR$^a$C$_{1-4}$haloalkyl, —NR$^a$C 26alkylNR$^a$R$^a$, —NR$^a$C$_{2-6}$alkylOR$^a$, —C(=O)C$_{1-6}$alkyl, —C(=O)OC$_{1-6}$alkyl, —OC(=O)C$_{1-6}$alkyl, —C(=O)NR$^a$C$_{1-6}$alkyl or —NR$^a$C(=O)C$_{1-6}$alkyl; and unsaturated carbon atoms may be additionally substituted by =O; and any available nitrogen atoms in the ring are substituted by H, —C$_{1-6}$alkylOR$^a$, —C$_{1-6}$alkyl, —C$_{1-6}$alkylNR$^a$R$^a$, —C$_{1-3}$alkylC(=O)OR$^a$, —C$_{1-3}$alkylC(=O)NR$^a$R$^a$, —C$_{1-3}$alkylOC(=O)C$_{1-6}$alkyl, —C$_{1-3}$alkylNR$^a$C(=O)C$_{1-6}$alkyl, —C(=O)R$^c$ or —C$_{1-3}$alkylR$^c$.

In another embodiment, in conjunction with any one of the above and below embodiments, R$^4$ is an 8-, 9-, 10- or 11-membered bicyclic ring, containing 1, 2, 3 or 4 N atoms with the remainder being carbon atoms, wherein each of the carbon atoms of the ring is substituted by H, C$_{1-9}$alkyl, C$_{1-4}$haloalkyl, halo, cyano, oxo, —OR$^a$, —S(=O)$_n$C$_{1-6}$alkyl, —OC$_{1-4}$haloalkyl, —OC$_{2-6}$alkylNR$^a$, —OC$_{2-6}$alkylOR$^a$, —OC$_{1-6}$alkylC(=O)OR$^a$, —NR$^a$R$^a$, —NR$^a$C$_{1-4}$haloalkyl, —NR$^a$C$_2$ alkylNR$^a$R$^a$, —NR$^a$C$_{2-6}$alkylOR$^a$, —C(=O)C$_{1-6}$alkyl, —C(=O)OC$_{1-6}$alkyl, —OC(=O)C$_{1-6}$alkyl, —C(=O)NR$^a$C$_{1-6}$alkyl or —NR$^a$C(=O)C$_{1-6}$alkyl; and unsaturated carbon atoms may be additionally substituted by =O; and any available nitrogen atoms in the ring are substituted by H, —C$_{1-6}$alkylOR$^a$, —C$_{1-6}$alkyl, —C$_{1-6}$alkylNR$^a$R$^a$, —C$_{1-3}$alkylC(=O)OR$^a$, —C$_{1-3}$alkylC(=O)NR$^a$R$^a$, —C$_{1-3}$alkylOC(=O)C$_{1-6}$alkyl, —C$_{1-3}$alkylNR$^a$C(=O)C$_{1-6}$alkyl, —C(=O)R$^C$ or —C$_{1-3}$alkylR$^c$.

In another embodiment, in conjunction with any one of the above and below embodiments, R$^4$ is a 9- or 10-membered bicyclic ring, containing 1, 2, 3 or 4 N atoms with the remainder being carbon atoms, wherein each of the carbon atoms of the ring is substituted by H, C$_{1-9}$alkyl, C$_{1-4}$haloalkyl, halo, cyano, oxo, —OR$^a$, —S(=O)$_n$C$_{1-6}$alkyl, —OC$_{1-4}$haloalkyl, —OC$_{2-6}$alkylNR$^a$R$^a$, —OC$_{2-6}$alkylOR$^a$, —OC$_{1-6}$alkylC(=O)OR$^a$, —NR$^a$R$^a$, —NR$^a$C$_{1-4}$haloalkyl, —NR$^a$C$_{2-6}$alkylNR$^a$R$^a$, —NR$^a$C$_{2-6}$alkylOR$^a$, —C(=O)C$_{1-6}$ alkyl, —C(=O)OC$_{1-6}$alkyl, —OC(=O)C$_{1-6}$alkyl, —C(=O)NR$^a$C$_{1-6}$alkyl or —NR$^a$C(=O)C$_{1-6}$alkyl; and unsaturated carbon atoms may be additionally substituted by =O; and any available nitrogen atoms in the ring are substituted by H, —C$_{1-6}$alkylOR$^a$, —C$_{1-6}$alkyl, —C$_{1-6}$alkylNR$^a$R$^a$, —C$_{1-3}$alkylC(=O)OR$^a$, —C$_{1-3}$alkylC(=O)NR$^a$R$^a$, —C$_{1-3}$alkylOC(=O)C$_{1-6}$alkyl, —C$_{1-3}$alkylNR$^a$C(=O)C$_{1-6}$alkyl, —C(=O)R$^c$ or —C$_{1-3}$alkylR$^c$.

In another embodiment, in conjunction with any one of the above and below embodiments, R$^4$ is a 10-membered bicyclic ring, comprising vicinally-fused six-membered aromatic rings, containing 1 or 2 N atoms with the remainder being carbon atoms, wherein each of the carbon atoms of the ring is substituted by H, C$_{1-9}$alkyl, C$_{1-4}$ haloalkyl, halo, cyano, —OR$^a$, —S(=O)$_n$C$_{1-6}$alkyl, —OC$_{1-4}$haloalkyl, —OC$_{2-6}$alkylNR$^a$R$^a$, —OC$_{2-6}$alkylOR$^a$, —OC$_{1-6}$alkylC(=O)OR$^a$, —NR$^a$R$^a$, —NR$^a$C$_{1-4}$haloalkyl, —NC$_{2-6}$alkyl-NR$^a$R$^a$, —NR$^a$C$_{2-6}$alkylOR$_{1-6}$alkyl, —C(=O)OC$_{1-6}$alkyl, —OC(=O)C$_{1-6}$alkyl, —C(=O)NR$^a$C$_{1-6}$alkyl or —NR$^a$C(=O)C$_{1-6}$alkyl.

In another embodiment, in conjunction with any one of the above and below embodiments, R$^4$ is selected from 2-quinolinyl, 3-quinolinyl, 4-quinolinyl, 5-quinolinyl, 7-quinolinyl, 8-quinolinyl, 1-isoquinolinyl, 3-isoquinolinyl, 4-isoquinolinyl, 5-isoquinolinyl, 6-isoquinolinyl, 7-isoquinolinyl, 8-isoquinolinyl, 2-quinazolinyl, 4-quinazolinyl, 5-quinazolinyl, 7-quinazolinyl and 8-quinazolinyl, any of which are substituted by 1 or 2 substituents selected from C$_{1-3}$alkyl, C$_{1-3}$haloalkyl, halo, cyano, —OCH$_3$, —OH, —NH$_2$ and —NHCH$_3$.

In another embodiment, in conjunction with any one of the above and below embodiments, R$^4$ is an 8-, 9-, 10- or 11-membered bicyclic ring, containing 0, 1, 2, 3 or 4 N atoms and 0, 1 or 2 atoms selected from S and O with the remainder being carbon atoms, wherein at least one of the carbon atoms of the ring is substituted by C$_{1-9}$alkyl, C$_{1-4}$haloalkyl, halo, cyano, oxo, —OR$^a$, —S(=O)$_n$C$_{1-6}$alkyl, —OC$_{1-4}$haloalkyl, —OC$_{2-6}$alkylNR$^a$R$^a$, —OC$_{2-6}$alkylOR$^a$—OC$_{1-6}$alkylC(=O)OR$^a$, —NR$^a$R$^a$, —NR$^a$C$_{1-4}$haloalkyl, —NR$^a$C$_{2-6}$alkylNR$^a$R$^a$, —NR$^a$C$_{2-6}$alkylOR$^a$, —C(=O)C$_{1-6}$alkyl, —C(=O)OC$_{1-6}$alkyl, —OC(=O)C$_{1-6}$alkyl, —C(=O)NR$^a$C$_{1-6}$alkyl or —NR$^a$C(=O)C$_{1-6}$alkyl.

In another embodiment, in conjunction with any one of the above and below embodiments, R$^4$ is quinolin-8-yl or quinolin-7-yl wherein each of the carbon atoms of the quinolinyl ring is substituted by H, C$_{1-9}$alkyl, C$_{1-4}$haloalkyl, halo, cyano, oxo, —OR$^a$, —S(=O)$_n$C$_{1-6}$alkyl, —OC$_{1-4}$haloalkyl, —OC$_{2-6}$alkylNR$^a$R$^a$, —OC$_{2-6}$alkylOa —OC$_{1-6}$alkylC(=O)OR$^a$, —NR$^a$R$^a$, —NR$^a$C$_{1-4}$haloalkyl, —NR$^a$C$_{2-6}$alkylNR$^a$R$^a$, —NR$^a$C$_{2-6}$alkylOR$^a$, —C(=O)C$_{1-6}$ alkyl, —C(=O)OC$_{1-6}$alkyl, —OC(=O)C$_{1-6}$alkyl, —C(=O)NR$^a$C$_{1-6}$alkyl or —NR$^a$C(=O)C$_{1-6}$alkyl.

In another embodiment, in conjunction with any one of the above and below embodiments, R$^5$ and R$^9$ are each independently selected from H, C$_{1-4}$haloalkyl, halo, nitro, —OC$_{1-6}$alkyl, —OC$_{1-4}$haloalkyl, —OC$_{2-6}$alkylNR$^a$R$^a$, —OC$_{2-6}$alkylOR$^a$, —NR$^a$R$^a$, —NR$^a$C$_{1-4}$ haloalkyl, —NR$^a$C$_{2-6}$alkylNR$^a$R$^a$, —NR$^a$C$_{2-6}$alkylOR$^a$, —CO$_2$(C$_{1-6}$alkyl), —C(=O)(C$_{1-6}$alkyl), —C(=O)NR$^a$R$^a$, —NR$^a$C(=O)R$^a$, —NR$^a$C(=O)NR$^a$R$^a$, —NR$^a$CO$_2$(C$_{1-6}$alkyl), —C$_{1-8}$alkylOR$^a$, —C$_{1-6}$ alkylNR$^a$R$^a$, —S(=O)$_n$(C$_{1-6}$alkyl), —S(=O)$_2$NR$^a$R$^a$, —NR$^a$S(=O)$_2$(C$_{1-6}$alkyl) and —OC(=O)NR$^a$R$^a$.

In another embodiment, in conjunction with any one of the above and below embodiments, R$^5$ and R$^9$ are both H.

In another embodiment, in conjunction with any one of the above and below embodiments, at least one of R$^5$ and R$^9$ are selected from C$_{1-4}$haloalkyl, halo, nitro, —OC$_{1-6}$alkyl, —OC$_{1-4}$haloalkyl, —OC$_{2-6}$alkylNR$^a$R$^a$, —OC$_{2-6}$alkylOR$^a$, —NR$^a$R$^a$, —NR$^a$Cl$_4$ haloalkyl, —NR$^a$C$_{2-6}$alkylNR$^a$R$^a$, —NR$^a$C$_{2-6}$alkylOR$^a$, —CO$_2$(C$_6$alkyl), —C(=O)(C$_{1-6}$alkyl), —C(=O)NR$^a$R$^a$, —NR$^a$C(=O)R$^a$, —NR$^a$C(=O)NR$^a$R$^a$, —NR$^a$CO$_2$(C$_{1-6}$alkyl), —C$_{1-8}$alkylOR$^a$, C$_{2-6}$alkylNR$^a$R$^a$, —S(=O)$_n$(C$_{1-6}$alkyl), —S(=O)$_2$NR$^a$R$^a$, —NR$^a$S(=O)$_2$(C$_{1-6}$alkyl) and —OC(=O)NR$^a$R$^a$.

In another embodiment, in conjunction with any one of the above and below embodiments, R$^6$ and R$^8$ are each independently selected from H, C$_{1-5}$alkyl, C$_{1-4}$haloalkyl, halo, —OC$_{1-6}$alkyl, —OC$_{1-4}$haloalkyl, —OC$_{2-6}$alkylNR$^a$R$^a$, —OC$_{2-6}$alkylOR$^a$, —NR$^a$R$^a$, —NR$^a$C$_{1-4}$haloalkyl, —NR$^a$C$_{2-6}$alkylNR$^a$R$^a$ or —NR$^a$C$_{2-6}$alkylOR$^a$, —C$_{1-8}$alkylOR$^a$, —C$_{1-6}$ alkylNR$^a$R$^a$ and —S(C$_{1-6}$alkyl).

In another embodiment, in conjunction with any one of the above and below embodiments, R$^6$ and R$^8$ are both H.

In another embodiment, in conjunction with any one of the above and below embodiments, at least one of R$^6$ and R$^8$ is selected from C$_{1-5}$alkyl, C$_{1-4}$haloalkyl, halo, —OC$_{1-6}$alkyl, —OC$_{1-4}$haloalkyl, —OC$_{2-6}$alkylNR$^a$R$^a$, —OC$_{2-6}$alkylOR$^a$, —NR$^a$R$^a$, —NR$^a$C$_{1-4}$haloalkyl, —NR$^a$C$_{2-6}$alkylNR$^a$R$^a$ or —NR$^a$C$_{2-6}$ alkylOR$^a$, —C$_{1-9}$alkylOR$^a$, —C$_{1-6}$ alkylNR$^a$R$^a$ and —S(C$_{1-6}$alkyl).

In another embodiment, in conjunction with any one of the above and below embodiments, R$^7$ is independently, at each instance, C$_{1-8}$alkyl, C$_{1-4}$haloalkyl, —OC$_{1-4}$haloalkyl, —OC$_{2-6}$alkylNR$^a$R$^a$, —NR$^a$R$^a$, —NR$^a$Cl$_4$ haloalkyl, —NR$^a$C$_{2-6}$alkylNR$^a$R$^a$, —NR$^a$C$_{2-6}$alkylOR$^a$, —C$_{1-8}$alkylOR$^a$, —C$_{1-6}$alkylNR$^a$R$^a$ or —S(C$_{1-6}$alkyl).

In another embodiment, in conjunction with any one of the above and below embodiments, R$^7$ is C$_{1-5}$alkyl or C$_{1-3}$haloalkyl.

In another embodiment, in conjunction with any one of the above and below embodiments, R$^{10}$ and R$^{14}$ are each independently selected from H, C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$alkyl)-N(R$^a$)C(=O)NR$^a$R$^a$, N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$ and C$_{1-4}$alkyl substituted by 0, 1, 2 or 3 groups selected from C$_{1-4}$haloalkyl, halo, cyano, nitro, —C(=O)(C$_{1-8}$alkyl), —C(=O)NR$^a$R$^a$, —C(=NR$^a$)NR$^a$R$^a$, —OR$^a$, —OC(=O)(C$_{1-8}$alkyl), —C(=O)NR$^a$R$^a$, —OC(=O)N(R$^a$)S(=O)$_2$(C$_{1-8}$alkyl), —OC$_{2-6}$alkylNR$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$.

In another embodiment, in conjunction with any one of the above and below embodiments, R$^{11}$ and R$^{13}$ are independently, at each instance, selected from H, C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$ alkyl), —S(=O)$_2$N(R$^a$)C(=O)O(C$_{1-8}$alkyl), —S(=O)$_2$N(R$^a$)C(=O)NR$^a$R$^a$, NR$^a$R$^a$, —N(R$^a$)C(=O)O(C$_{1-8}$alkyl), —N(R$^a$)C(=O)NR$^a$R$^a$, N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$, —NR$^a$C$_{2-6}$alkylOR$^a$ and C$_{1-4}$alkyl substituted by 0, 1, 2 or 3 groups selected from C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$ (C$_{1-8}$alkyl), —S(=O)$_2$NR$^a$R$^a$, —S(=O)$_2$N(R$^a$)C(=O) (C$_{1-8}$ alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O) (C$_{1-8}$alkyl), —N(R$^a$)C(=O)O(C$_{1-8}$alkyl), —N(R$^a$)C(=O) NR$^a$R$^a$, —N(R$^a$)C(=NR$^a$)NR$^a$R$^a$, —N(R$^a$)S(=O)$_2$(C$_{1-8}$ alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$.

In another embodiment, in conjunction with any one of the above and below embodiments, R$^{12}$ is independently, at each instance, selected from H, C$_{1-8}$alkyl, C$_{1-4}$haloalkyl, halo, cyano, nitro, —C(=O)O(C$_{1-8}$alkyl), —C(=O) NR$^a$R$^a$, —C(=NR$^a$)NR$^a$R$^a$, —OR$^a$, —OC(=O)(C$_{1-8}$ alkyl), —OC(=O)NR$^a$R$^a$, —OC(=O)N(R$^a$)S(=O)$_2$(C$_{1-8}$ alkyl), —OC$_{2-6}$alkylNR$^a$R$^a$, —OC$_{2-6}$alkylOR, —SR$^a$, —S(=O)(C$_{1-8}$alkyl), —S(=O)$_2$(C$_{1-8}$alkyl), —S(=O)$_2$ NR$^a$R$^a$, —S(=O)$_2$N(R$^a$)C(=O)(C$_{1-8}$alkyl), —S(=O)$_2$N (R$^a$)C(=O)O(C$_{1-5}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O (C$_{1-8}$alkyl), —N(R$^a$)C(=O)NR$^a$R$^a$, —N(R$^a$)C(=NR$^a$) NR$^a$R$^a$, —N(R$^a$)S(=O)$_2$(C$_{1-8}$alkyl), —N(R$^a$)S(=O)$_2$ NR$^a$R$^a$, —NR$^a$C$_{2-6}$alkylNR$^a$R$^a$ and —NR$^a$C$_{2-6}$alkylOR$^a$; or R$^{12}$ is C$_{1-4}$alkyl substituted by 0, 1, 2 or 3 groups selected from C$_{1-4}$haloalkyl, halo, cyano, nitro, —C(=O)(C$_{1-8}$ alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R, —OC$_{2-6}$alkylOR, —SR$^a$, —S(=O) (C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C (=O)O(C$_{1-8}$alkyl), —S(=O)$_2$N(R$^a$)C(=O)NR$^a$R$^a$, —NR$^a$R$^a$, —N(R$^a$)C(=O)(C$_{8-1}$alkyl), —N(R$^a$)C(=O)O (C$_{1-8}$alkyl), —N(R$^a$)C(=O)NR$^a$R$^a$, —N(R$^a$)C(=NR$^a$) NR$^a$R$^a$, —N(R$^a$)S(=O)$_2$(C$_{1-8}$alkyl), —N(R$^a$)S(=O)$_2$ NR$^a$R$^a$, —NR$^a$C$_{2-6}$alkylNR$^a$R$^a$ and —NR$^a$C$_{2-6}$alkylOR$^a$.

In another embodiment, in conjunction with any one of the above and below embodiments, X is N and Y is C(R$^3$).

In another embodiment, in conjunction with any one of the above and below embodiments, X is C(R$^2$) and Y is N.

In another embodiment, in conjunction with any one of the above and below embodiments, X is C(R$^2$) and Y is C(R$^3$).

In another embodiment, in conjunction with any one of the above and below embodiments, J is O.

In another embodiment, in conjunction with any one of the above and below embodiments, J is S.

Another aspect of the invention relates to a method of treating acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, comprising the step of administering a compound according to any of the above embodiments.

Another aspect of the invention relates to a pharmaceutical composition comprising a compound according to any of the above embodiments and a pharmaceutically-acceptable diluent or carrier.

Another aspect of the invention relates to the use of a compound according to any of the above embodiments as a medicament.

Another aspect of the invention relates to the use of a compound according to any of the above embodiments in the manufacture of a medicament for the treatment of acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders.

Another aspect of the invention relates to a method of making a compound according to the above embodiments, comprising the step of: reacting

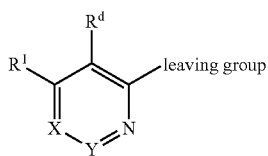

with $R^4JH$ to form

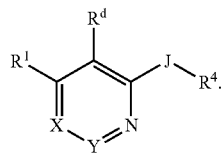

The compounds of this invention may have in general several asymmetric centers and are typically depicted in the form of racemic mixtures. This invention is intended to encompass racemic mixtures, partially racemic mixtures and separate enantiomers and diastereomers.

Unless otherwise specified, the following definitions apply to terms found in the specification and claims: "$C_{\alpha\text{-}\beta}$alkyl" means an alkyl group comprising a minimum of $\alpha$ and a maximum of $\beta$ carbon atoms in a branched, cyclical or linear relationship or any combination of the three, wherein $\alpha$ and $\beta$ represent integers. The alkyl groups described in this section may also contain one or two double or triple bonds. Examples of $C_{1\text{-}6}$alkyl include, but are not limited to the following:

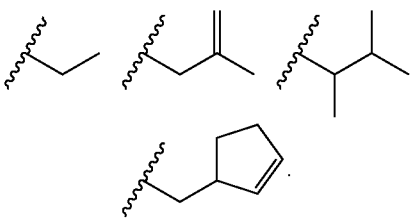

"Benzo group", alone or in combination, means the divalent radical $C_4H_4=$, one representation of which is —CH=CH—CH=CH—, that when vicinally attached to another ring forms a benzene-like ring—for example tetrahydronaphthylene, indole and the like.

The terms "oxo" and "thioxo" represent the groups =O (as in carbonyl) and =S (as in thiocarbonyl), respectively.

"Halo" or "halogen" means a halogen atoms selected from F, Cl, Br and I.

"$C_{v\text{-}w}$haloalkyl" means an alkyl group, as described above, wherein any number—at least one—of the hydrogen atoms attached to the alkyl chain are replaced by F, Cl, Br or I.

"Heterocycle" means a ring comprising at least one carbon atom and at least one other atom selected from N, O and S. Examples of heterocycles that may be found in the claims include, but are not limited to, the following:

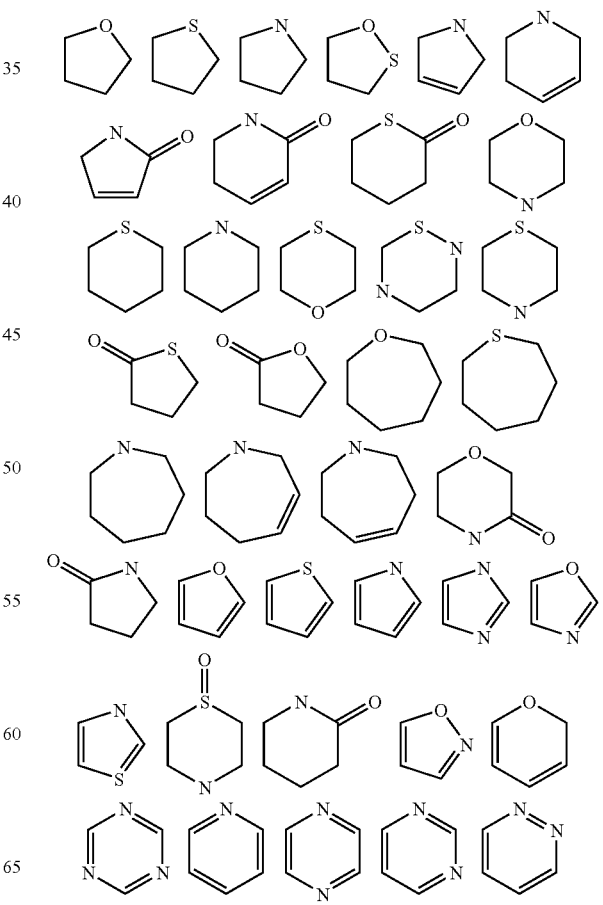

-continued

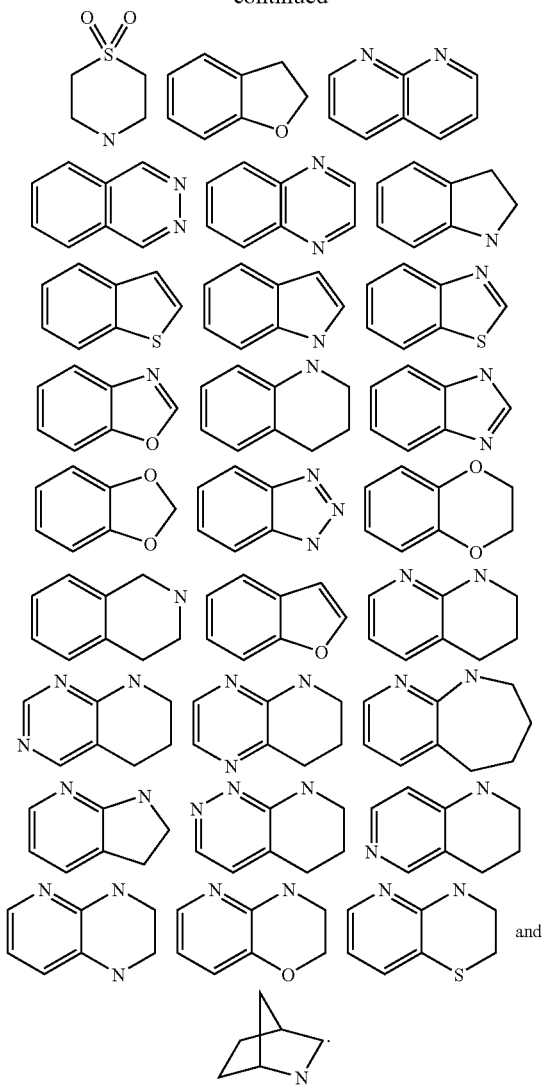

"Available nitrogen atoms" are those nitrogen atoms that are part of a heterocycle and are joined by two single bonds (e.g. piperidine), leaving an external bond available for substitution by, for example, H or $CH_3$.

"Pharmaceutically-acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al., J. Pharm. Sci. 66:1 (1977).

"Saturated or unsaturated" includes substituents saturated with hydrogens, substituents completely unsaturated with hydrogens and substituents partially saturated with hydrogens.

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, trichloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, triisopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-trisilyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'=O, S, NR), and the like, which are illustrated in the following examples:

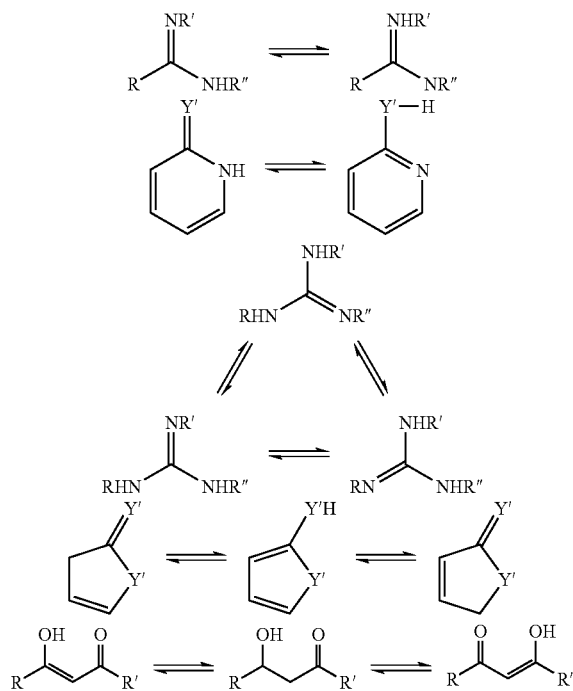

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

The specification and claims contain listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

Experimental

General

Unless otherwise noted, all materials were obtained from commercial suppliers and used without further purification. All parts are by weight and temperatures are in degrees centigrade unless otherwise indicated. All compounds showed NMR spectra consistent with their assigned structures. Melting points were determined on a Buchi apparatus and are uncorrected. Mass spectral data was determined by electrospray ionization technique. All examples were purified to ≧95% purity as determined by high-performance liquid chromatography. Unless otherwise stated, reactions were run at room temperature under a nitrogen atmosphere. Microwave reactions were conducted using a Smith Synthesizer® (Personal Chemistry, Inc., Upssala, Sweden) apparatus.

The following abbreviations are used:
aq.—aqueous
BINAP—2,2'-bis(diphenylphosphino)-1,1'-binaphthyl
cond—concentrated
DMF—N,N-dimethylformamide
DMSO—methyl sulfoxide
Et$_2$O—diethyl ether
EtOAc—ethyl acetate
EtOH—ethyl alcohol
h—hour
min—minutes
MeOH—methyl alcohol
satd—saturated
THF—tetrahydrofuran Generic Schemes for the Preparation of Pyridine Core (I):
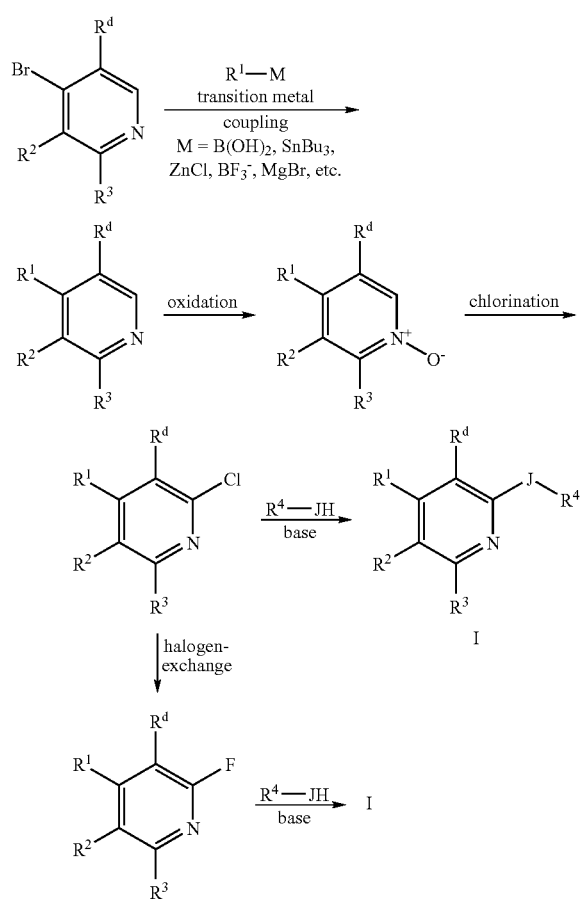
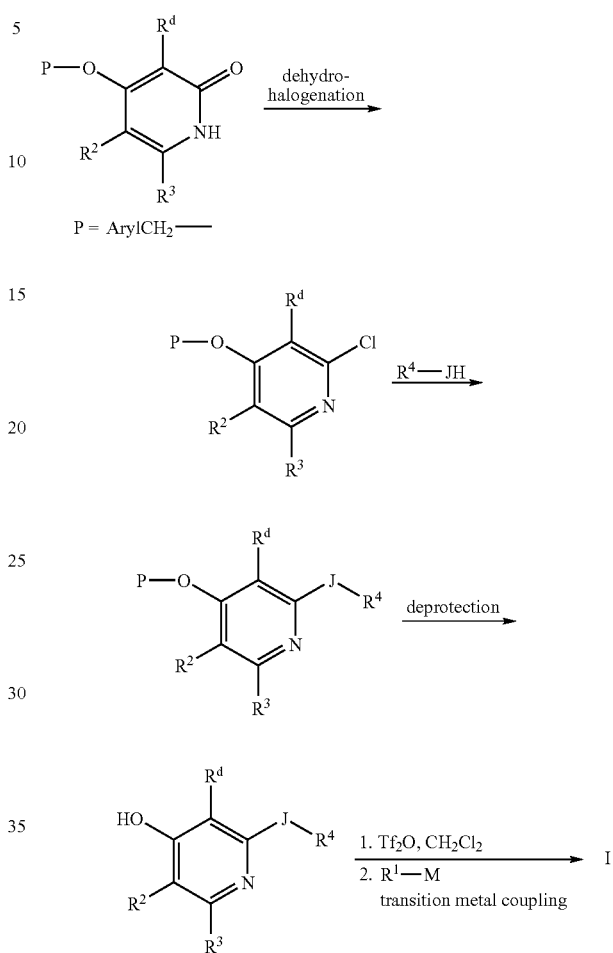
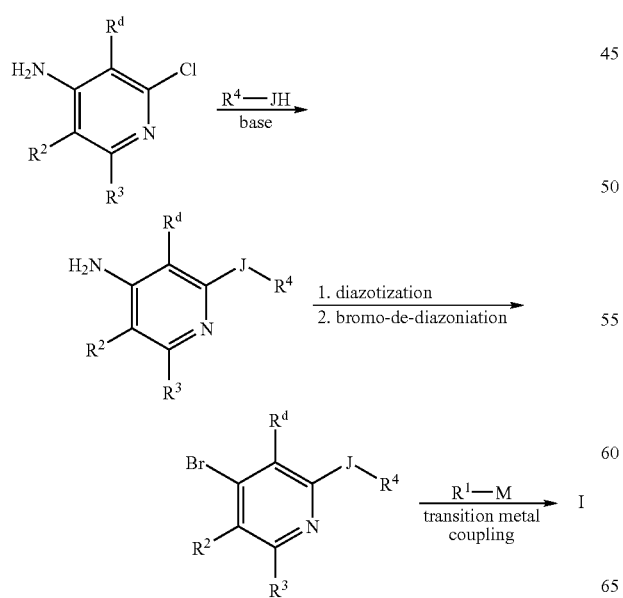
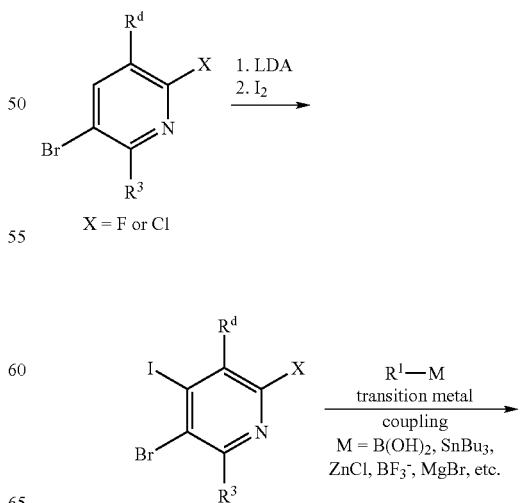

-continued
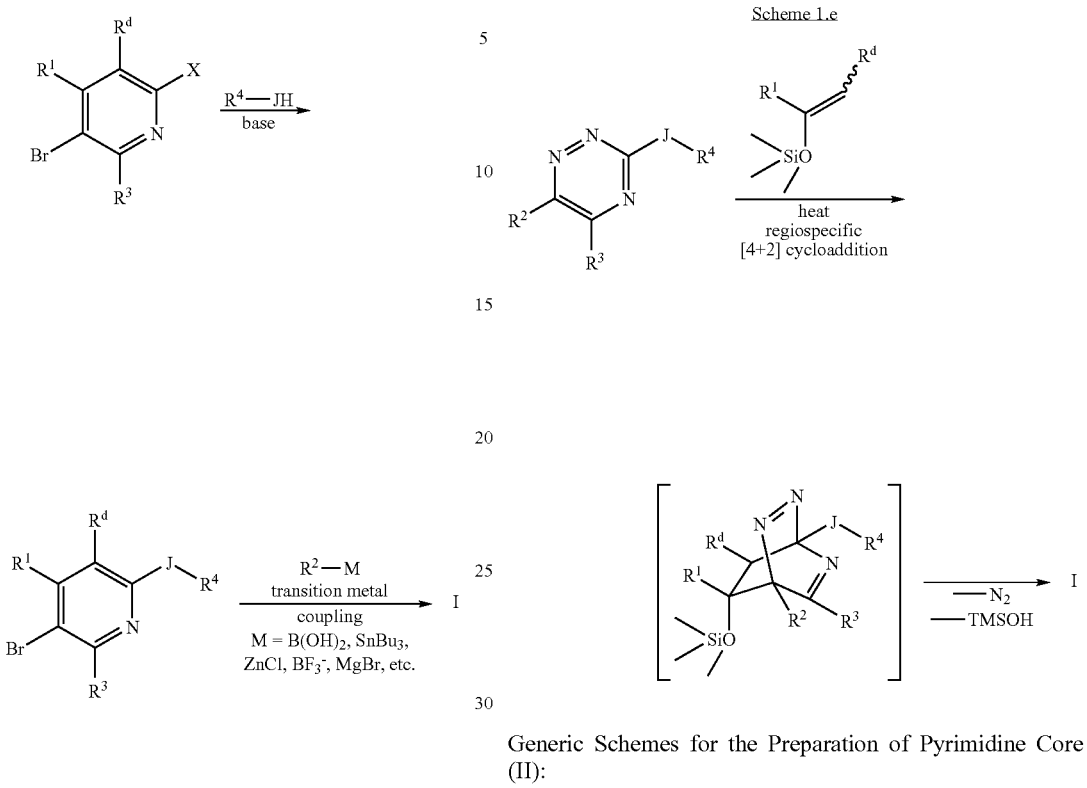
Scheme 1.e
Generic Schemes for the Preparation of Pyrimidine Core (II):
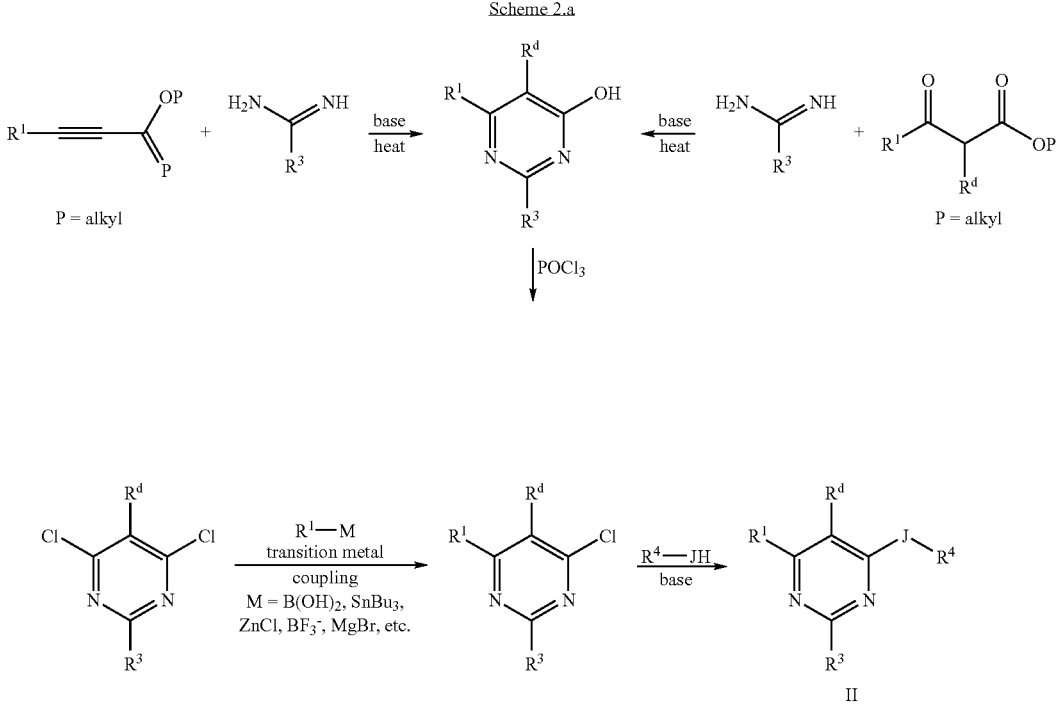
Scheme 2.a Scheme 2.b
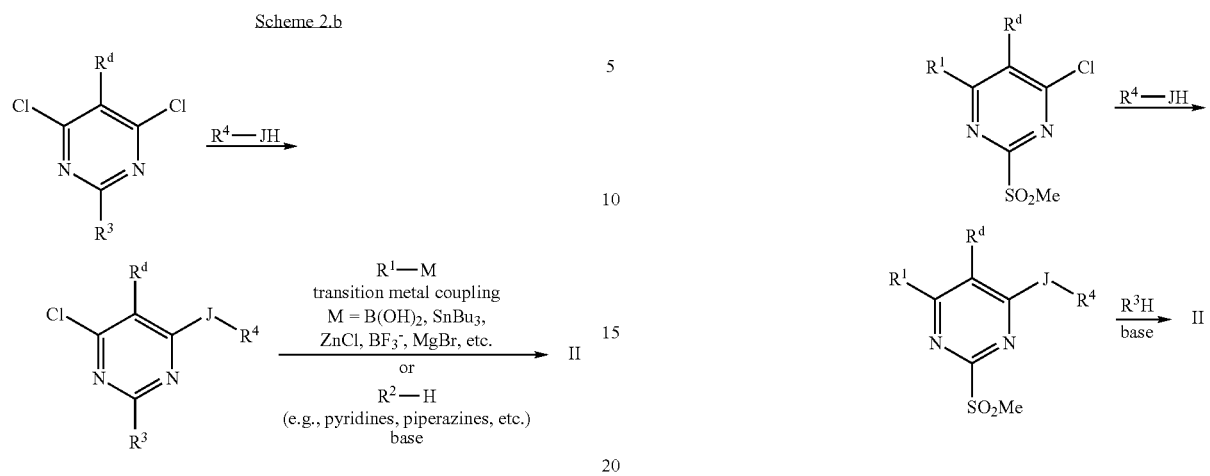
Scheme 2.c
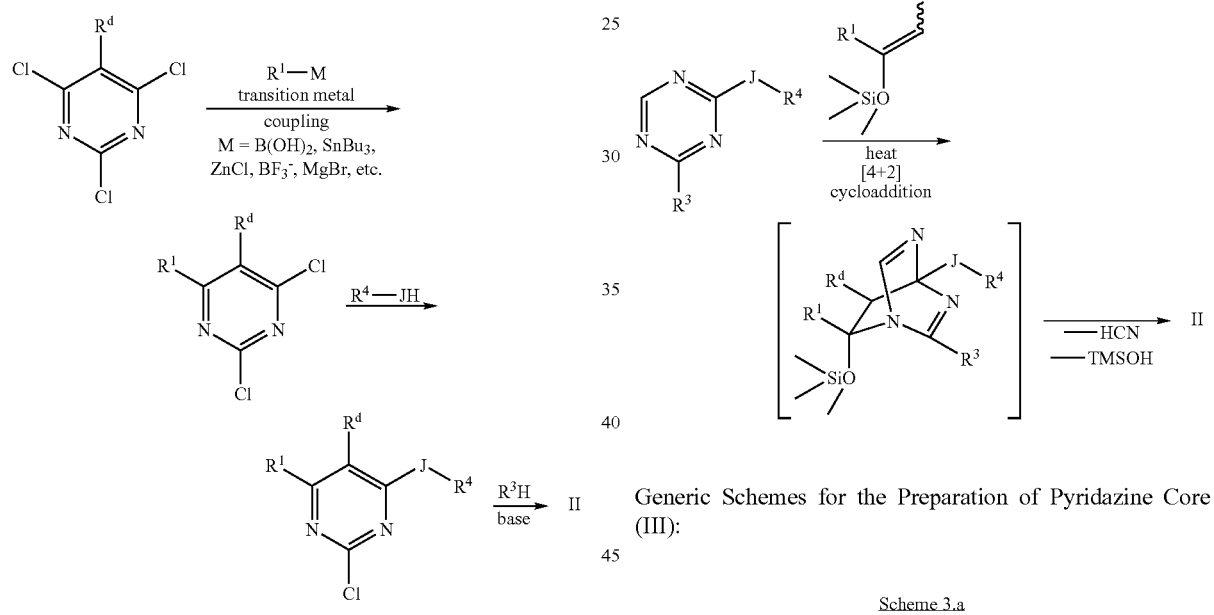
Scheme 2.d
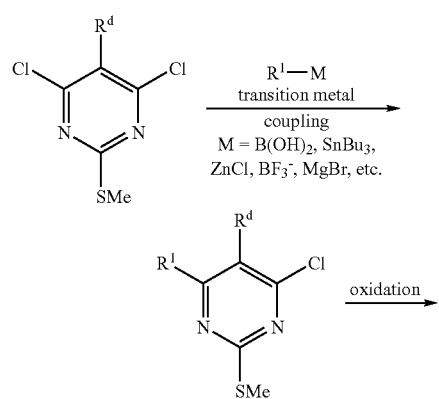
Scheme 2.e
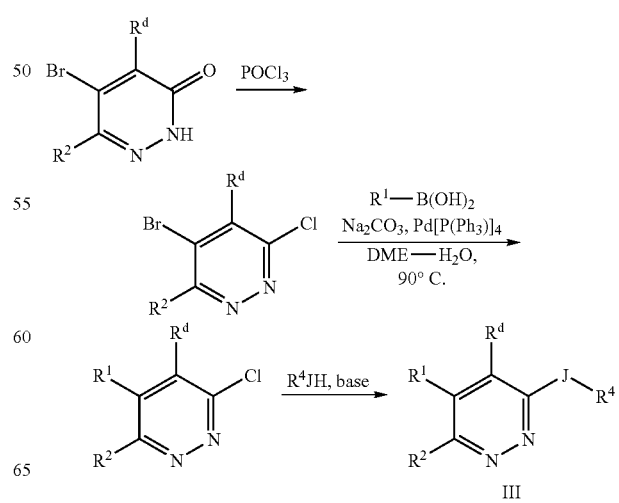
Generic Schemes for the Preparation of Pyridazine Core (III):
Scheme 3.a -continued
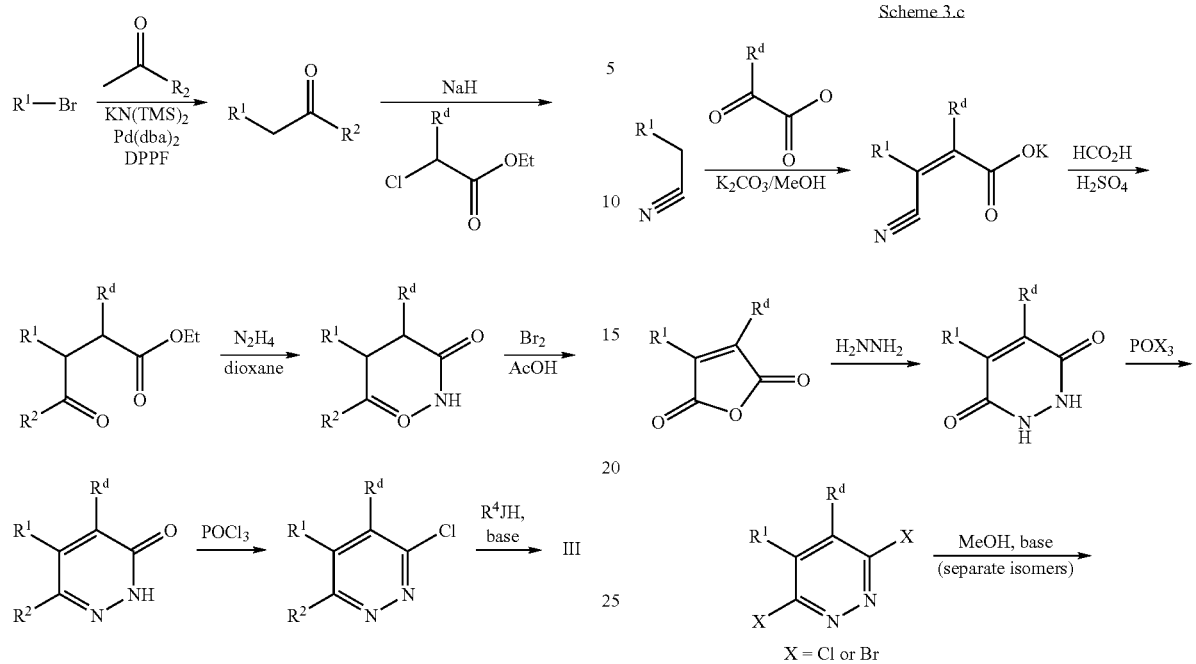
Scheme 3.b
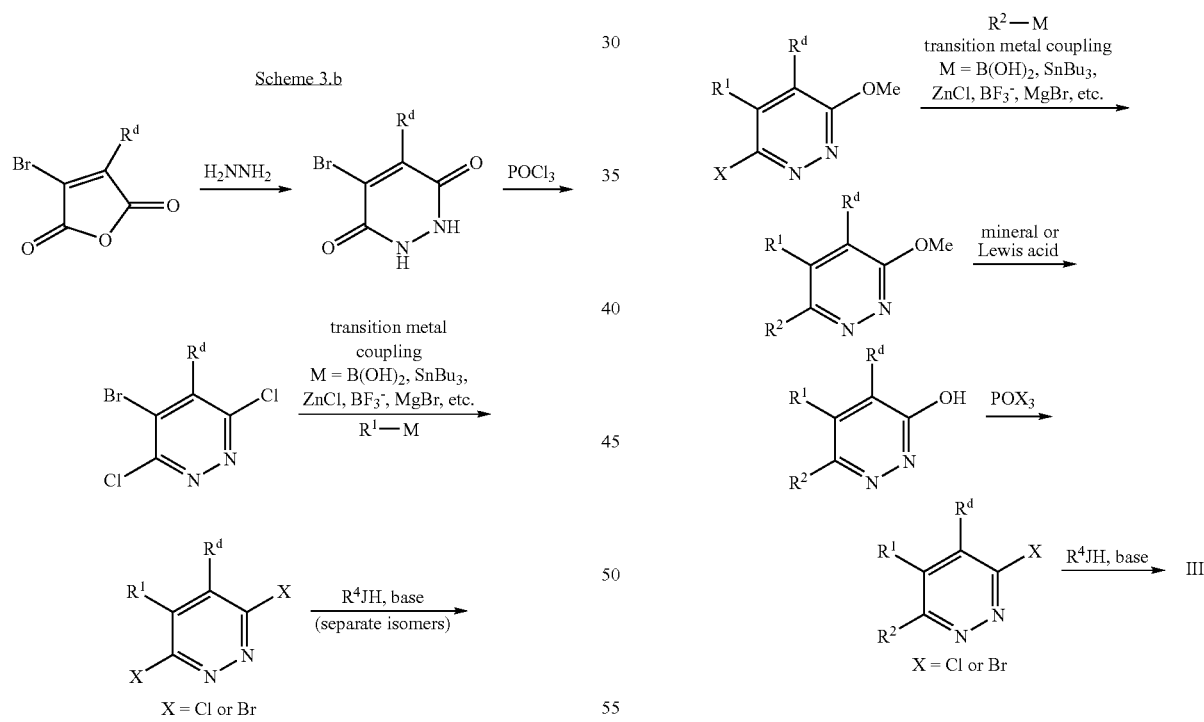
Scheme 3.c
Scheme 3.d
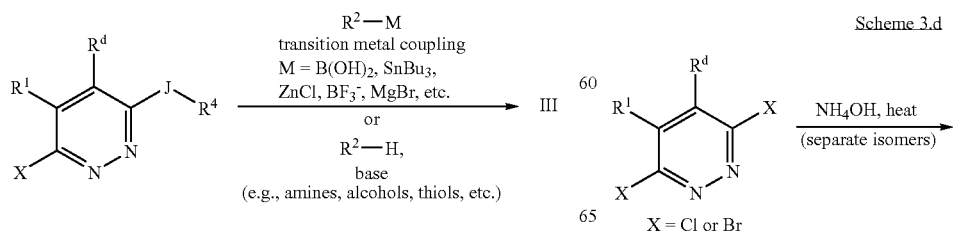

-continued

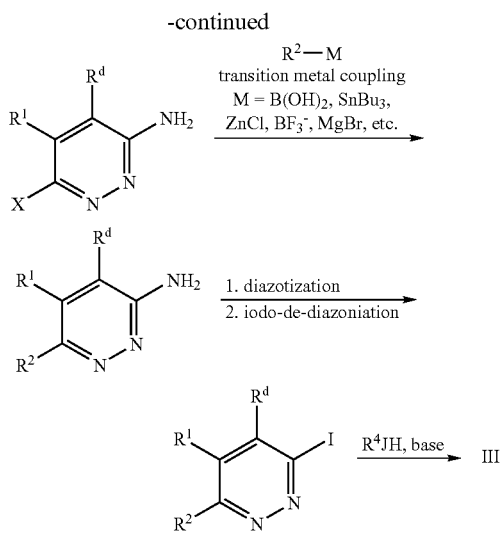

Scheme 3.e

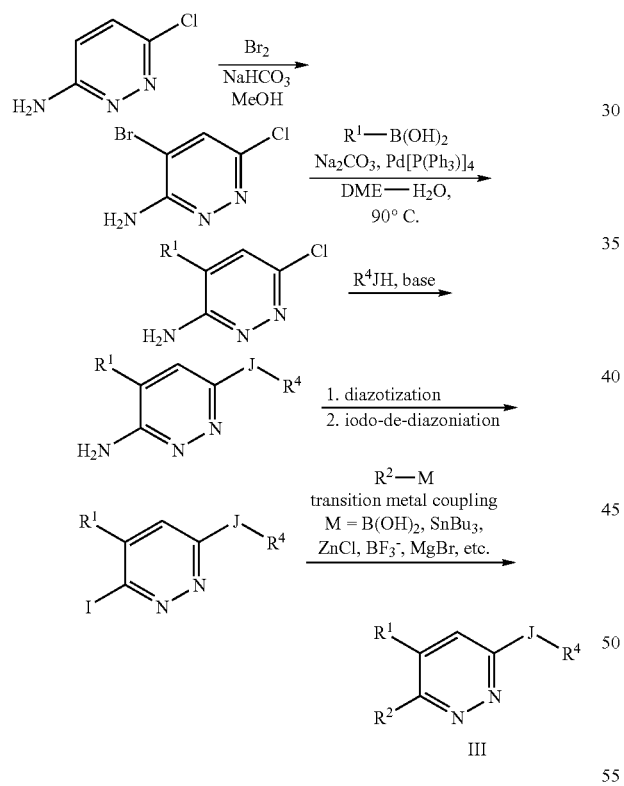

Scheme 3.f

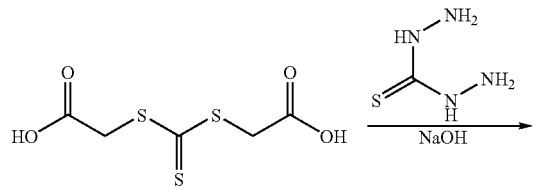

-continued

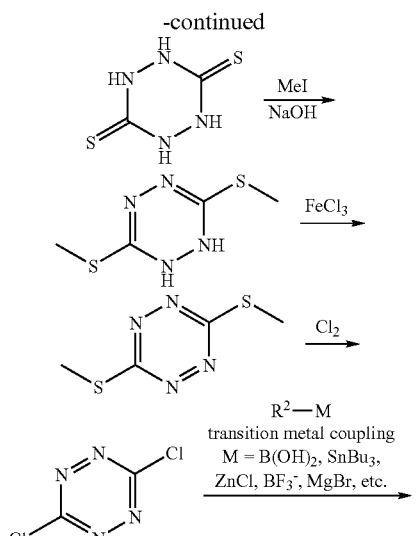

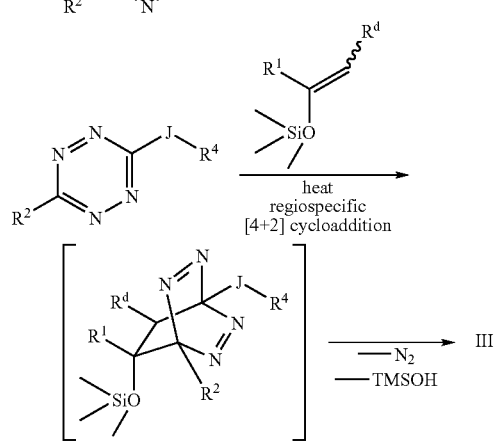

EXAMPLE 1

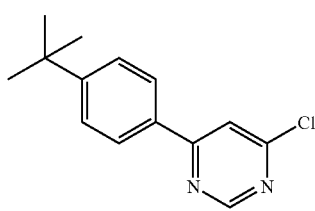

(a) 4-(4-tert-Butyl-phenyl)-6-chloro-pyrimidine. To a 250-mL, round-bottomed flask containing 4,6-dichloropyrimidine (4.0 g, 27 mmol, Aldrich) in $CH_3CN$ (80 mL), was added 4-tert-butylphenylboronic acid (1.9 g, 11 mmol, Aldrich) and $Pd(PPh_3)_4$ (0.62 g, 0.54 mmol, Aldrich). A solution of 10% $Na_2CO_3$ (50 mL) was added, and the mixture was stirred under $N_2$ at 90° C. for 8 h. The reaction mixture was allowed to cool to room temperature and then EtOAc (200 mL) and 5% brine (80 mL) were added. A solid formed and was collected by filtration. The filtrate was poured into a separatory funnel, and the organic layer was collected. The solid that had been previously collected and the organic phase were combined and the resulting solution was concentrated in vacuum. The residue was dissolved in CH₂Cl₂, dried over Na₂SO₄, filtered, and concentrated in vacuum. Silica gel chromatography with hexanes/EtOAc (5:1) gave the title compound as a white solid. MS (ESI, pos. ion.) m/z: 247 (M+1).

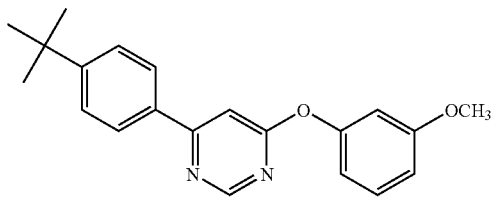

(b) 4-(4-tert-Butyl-phenyl)-6-(3-methoxy-phenoxy)-pyrimidine. To a 25-mL, round-bottomed flask containing 4-(4-tert-butyl-phenyl)-6-chloro-pyrimidine (Example 1a) (0.10 g, 0.41 mmol), 3-methoxyphenol (0.10 g, 0.81 mmol, Aldrich), and DMF (4 mL) at room temperature was added NaH (0.032 g, 0.81 mmol, 60% disp. in oil). The reaction mixture turned green, and gas evolution was observed. The solution was stirred for 20 h under a N₂ atmosphere. The reaction was quenched with H₂O (50 mL), and the solution was extracted with EtOAc (3×25 mL). The combined extracts were washed with H₂O (3×25 mL) and brine, dried over Na₂SO₄, and adsorbed onto silica gel. The crude material was purified by chromatography (0 to 20% ethyl acetate/hexanes) on silica gel to afford the title compound as a white solid. Mp: 73-76° C. MS (ESI, pos. ion.) m/z: 335.1 (M+1).

EXAMPLE 2

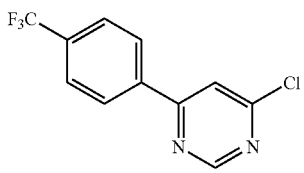

(Method A)

(a) 4-Chloro-6-[4-(trifluoromethyl)phenyl]pyrimidine. To a 500-mL, round-bottomed flask was added 4,6-dichloropyrimidine (14 g, 95 mmol, Aldrich), 4-(trifluoromethyl)phenylboronic acid (6.0 g, 32 mmol, Aldrich), acetonitrile (95 mL), and 1 M sodium carbonate (95 mL). The mixture was sparged with N₂ for 15 min. Pd(PPh₃)₄ (1.9 g, 1.6 mmol, Strem) was then added, and the resulting yellow mixture was heated under a N₂ atmosphere at 80° C. for 15 h. After cooling to 25° C., the solution was concentrated in vacuum, and the solution was diluted with aq. NaHCO₃ and extracted with CH₂Cl₂. The combined organic extracts were dried over Na₂SO₄, filtered and concentrated in vacuum. Purification by silica gel chromatography (gradient, 1.5 to 10% ethyl acetate/hexanes) afforded the title compound as a white solid. MS (ESI, pos. ion) m/z: 259 (M+1).

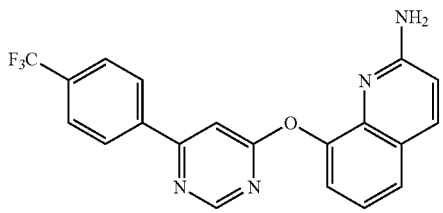

(b) 8-[6-(4-Trifluoromethyl-phenyl)-pyrimidin-4-yloxy]-quinolin-2-ylamine. To a 50-mL, round-bottomed flask was added NaH (175 mg, 4.37 mmol, 60% dispersion in mineral oil, Aldrich) and anhydrous DMF (10 mL). The resulting suspension was stirred under N₂ at 25° C. and treated with 2-amino-8-quinolinol (700 mg, 4.37 mmol, Sigma). After stirring for 10 min at 25° C., the bright-yellow solution was treated with 4-chloro-6-[4-(trifluoromethyl)phenyl]pyrimidine (1.24 g, 4.79 mmol) and stirred in a 50° C. oil bath for 3 h. The reaction mixture was allowed to cool to 25° C., diluted with 1 N NaOH (100 mL), and extracted with EtOAc (200 mL). The organic phase was washed with 1 N NaOH (100 mL), water (50 mL), satd NaCl (50 mL), dried over Na₂SO₄, filtered, and concentrated in vacuum. Purification by silica gel chromatography (98:2 dichloromethane: 2 M NH₃ in MeOH) afforded the title compound as a white solid. MP 203°0 C. MS (ESI, pos. ion) m/z: 383 (M+1).

EXAMPLE 2

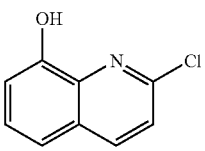

(Method B)

(a) 2-Chloro-quinolin-8-ol. A mixture of 2,8-dihydroxyquinoline (4.0 g, 25 mmol, Fluka) in POCl₃ (20 mL, Aldrich) was stirred at 100° C. for 1 h. The mixture was allowed to cool to room temperature, and poured into a mixture of ice (200 g) and 30% aq. NH₃ (100 mL). A white solid formed that was collected by filtration and washed with water. The white solid was dissolved in 12 N HCl (200 mL), and the resulting mixture was stirred at 100° C for 1 h. The mixture was allowed to cool to room temperature and 30% aq. NH₃ was added until no further precipitation occurred. The resulting white precipitate was collected by filtration and dried in vacuum (25° C., 18 h) to yield the title compound. MS (ESI, pos. ion) m/z: 179.9 (M+1).

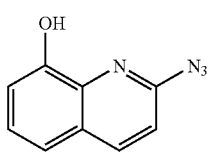

(b) 2-Azido-quinolin-8-ol. A mixture of 2-chloro-quinolin-8-ol (2.5 g, 14 mmol) and sodium azide (4.6 g, 70 mmol, Aldrich) in DMF (20 mL) was stirred at 110° C. for 16 h.

After cooling to room temperature, water (50 mL) was added and the mixture was extracted with EtOAc (2×50 mL). The combined organic phases were washed with water (2×20 mL), brine (20 mL), dried (Na₂SO₄), and filtered. After removing ca. ¾ of the solvent in vacuum, a solid was formed. The solid was collected by filtration, washed with 20% EtOAc/hexanes and dried under house vacuum (25° C., 16 h) to give the title compound. MS (ESI, pos. ion) m/z: 187.2 (M+1).

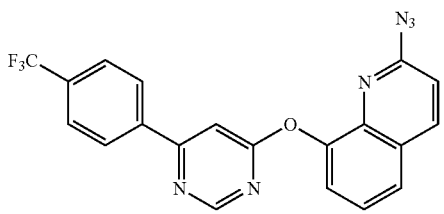

(c) 2-Azido-8-[6-(4-trifluoromethyl-phenyl)-pyrimidin-4-yloxy]-quinoline. A mixture of 4-chloro-6-(4-trifluoromethyl-phenyl)-pyrimidine, (Example 2(a), Method A), (2.0 g, 7.7 mmol), 2-chloro-quinolin-8-ol (3.0 g, 7.0 mmol), and K₂CO₃ (1.9 g, 14 mmol) in DMF (15 mL) was stirred at 80°C for 6 h. After cooling to room temperature, water (50 mL) was added and the mixture was extracted with EtOAc (2×100 mL). The combined organic phases were washed with water (2×30 mL), brine (30 mL), dried (Na₂SO₄), and filtered. After removing ca. ¾ of the solvent in vacuum, a solid formed that was collected by filtration. The solid was washed with 20% EtOAc/hexanes and dried under house vacuum (25° C., 16 h) to give the title compound. MS (ESI, pos. ion) m/z: 409.0 (M+1).

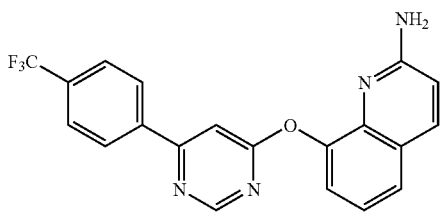

(d) 8-[6-(4-Trifluoromethyl-phenyl)-pyrimidin-4-yloxy]-quinolin-2-ylamine. A mixture of 2-azido-8-[6-(4-trifluoromethyl-phenyl)-pyrimidin-4-yloxy]-quinoline (2.7 g, 6.6 mmol) and triphenylphosphine (3.5 g, 13 mmol, Aldrich) in toluene (50 mL) was heated at reflux for 4 h. The solvent was removed in vacuum, and the residue was dissolved in AcOH:H₂O (2:1, 30 mL), and the resulting mixture was stirred at 50° C. for 18 h. After removing the solvent in vacuum, the residue was purified by silica gel chromatography with 60% EtOAc/hexanes. Following recrystalization from 20% of EtOAc/hexanes the title compound was isolated. M.p. 225.6-227.9° C. MS (ESI, pos. ion) m/z: 382.8 (M+1); Anal. Calcd for C₂₀H₁₃F₃N₄O: C, 62.83; H, 3.43; N, 14.65; found: C, 62.53; H, 3.43; N, 14.74.

EXAMPLE 3

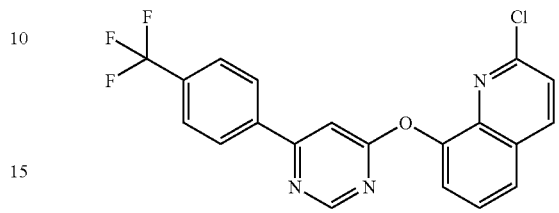

2-Chloro-8-[6-(4-trifluoromethyl-phenyl)-pyrimidin-4-yloxy]-quinoline. To a solution of 4-chloro-6-(4-trifluoromethyl-phenyl)-pyrimidine, (Example 2(a), Method A), (259 mg, 1 mmol) and 2-chloro-quinolin-8-ol (Example 2(a), Method B), (180 mg, 1 mmol) in 2 mL of DMF was added potassium carbonate (276 mg, 2 mmol). The reaction was stirred in a 90° C. oil bath for 2 h. EtOAc and brine were added, and the aqueous layer was extracted with EtOAc. The combined EtOAc layers were washed with brine, dried over Na₂SO₄, filtered, and concentrated in vacuum. Purification by flash chromatography by silica gel chromatography 1:4 of EtOAc/hexanes as eluent gave the title compound as a white solid. MS (ESI, pos. ion) m/z: 402 (M+1). Mp: 171.5-173.0° C. Anal. Calcd for C₂₀H₁₁ClF₃N₃O: C, 59.79; H, 2.76; N, 10.46. Found: C, 60.01; H, 2.80; N, 10.50.

EXAMPLE 4

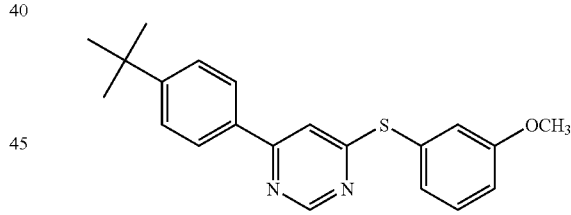

4-(4-tert-Butyl-phenyl)-6-(3-methoxy-phenylsulfanyl)-pyrimidine. To a 25-mL, round-bottomed flask containing 4-(4-tert-butyl-phenyl)-6-chloro-pyrimidine, (Example 1(a)), (0.20 g, 0.82 mmol), 3-methoxybenzenethiol (0.23 g, 1.6 mmol, Aldrich) and DMF (4 mL) under a N₂ atmosphere at room temperature was added NaH (0.066 g, 1.6 mmol, 60% disp. in oil, Aldrich). The mixture turned green and gas evolution was observed. The solution was stirred for 20 h at room temperature under a N₂ atmosphere. The reaction was quenched with H₂O (50 mL), and the resulting solution was extracted with EtOAc (3×25 mL). The combined extracts were washed with H₂O (3×25 mL) and brine, dried over Na₂SO₄, and adsorbed onto silica. The crude material was purified by chromatography (0 to 15% ethyl acetate/hexanes) on silica gel to afford the title compound as a colorless oil. MS (ESI, pos. ion.) m/z: 351.2 (M+1).

EXAMPLE 5

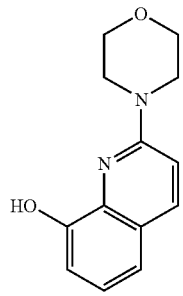

(a) 2-Morpholin-4-yl-quinolin-8-ol. In a 5-mL vial was added 2-chloro-quinolin-8-ol, (Example 2(a), Method B), (180 mg, 1 mmol), morpholine (1.75 mL, 20 mL), and 3 mL of dioxane. The reaction mixtrure was heated in a microwave synthesizer at 220C for 12 min. The mixture was partitioned between 1 N NaOH and EtOAc. The aqueous layer was separated and extracted with EtOAc, and the combined EtOAc layers were washed with brine, dried over $Na_2SO_4$, filtered and concentrated. Recrystallization from MeOH/$H_2O$ provided the title compound as a tan solid. MS (ESI, pos. ion) m/z: 231 (M+1).

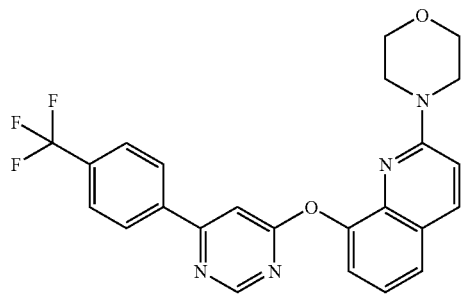

(b) 2-Morpholin-4-yl-8-[6-(4-trifluoromethyl-phenyl)-pyrimidin-4-yloxy]-quinoline. This material was prepared according to the method described in Example 3 using 2-chloro-4-(4-trifluoromethyl-phenyl)-pyrimidine, (Example 2(a), Method A), (196 mg, 0.76 mmol), 2-morpholin-4-yl-quinolin-8-ol (175 mg, 0.76 mmol), and potassium carbonate (210 mg, 1.5 mmol) in DMF (1.5 mL). Purification by silica gel column chromatography (3:1 hexanes: EtOAc) provided the title compound as a white solid. MS (ESI, pos. ion) m/z: 453 (M+1). Mp: 162.8-174.3° C. Anal. Calcd for $C_{24}H_{19}F_3N_4O_2$: C, 63.71; H, 4.23; N, 12.38. Found: C, 63.52; H, 4.24; N, 12.41.

EXAMPLE 6

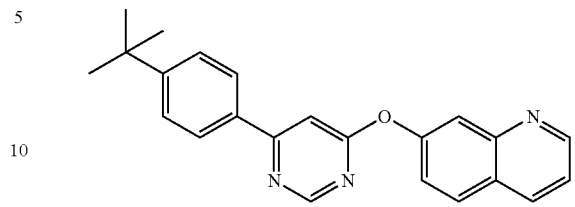

7-[6-(4-tert-Butyl-phenyl)-pyrimidin-4-yloxy]-quinoline. To a 100-mL, round-bottomed flask containing 4-(4-tert-butyl-phenyl)-6-chloro-pyrimidine, (Example 1(a)), (0.15 g, 0.61 mmol) and 7-hydroxyquinoline (0.12 g, 0.85 mmol, Acros) in DMF (4 mL), was added NaH (34 mg, 0.85 mmol, 60% in mineral oil, Aldrich) at room temperature. The solution was then stirred at room temperature for 4 h.

After the solvent was removed in vacuum, the residue was taken up in EtOAc (10 mL), and the organic layers were washed with water (8 mL), dried over $Na_2SO_4$, filtered, and concentrated in vacuum. Silica gel chromatography (3:1 hexanes/EtOAc) gave the title compound as a white solid. Mp: 133-135° C. MS (ESI, pos. ion) m/z: 356 (M+1). Anal. Calcd for $C_{23}H_{21}N_3O$: C, 77.72; H, 5.96; N, 11.82. Found: C, 77.43; H, 5.99; N, 11.74.

EXAMPLE 7

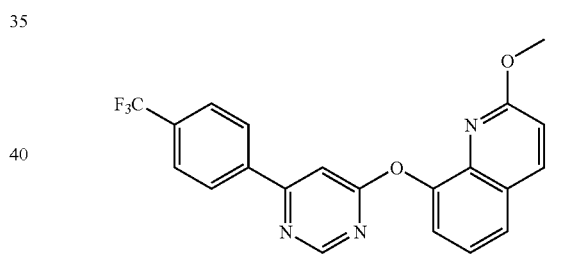

2-Methoxy-8-[6-(4-trifluoromethyl-phenyl)-pyrimidin-4-yloxy]-quinoline. The title compound was prepared from 4-chloro-6-(4-trifluoromethyl-phenyl)-pyrimidine (Example 2(a), Method A) and 2-methoxy-quinolin-8-ol (prepared according to Ataev, A; et al. *Teoreticheskaya i Eksperimental'naya Khimya* 1980, 16 (2), 243-249) under the conditions of Example 6. Mp: 158.5-161° C. MS (ESI, pos. ion) m/z: 398 (M+1).

EXAMPLE 8

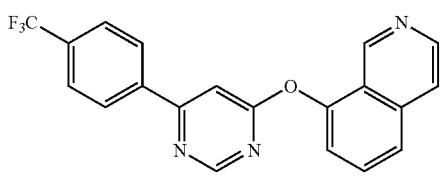

8-[6-(4-Trifluoromethyl-phenyl)-pyrimidin-4-yloxy]-isoquinoline. The title compound was prepared from 4-chloro-6-(4-trifluoromethyl-phenyl)-pyrimidine (Example 2(a), Method A) and isoquinolin-8-ol (MonomerChem) under the conditions of Example 6. Mp: 194-195° C. MS (ESI, pos. ion) m/z: 368.2 (M+1).

EXAMPLE 9

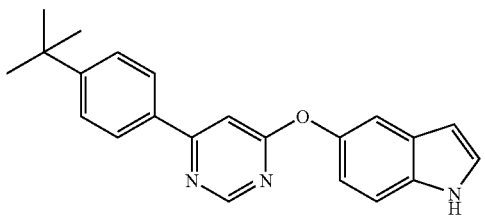

5-[6-(4-tert-Butyl-phenyl)-pyrimidin-4-yloxy]-1H-indole. To a 100-mL, round-bottomed flask containing 4-(4-tert-butyl-phenyl)-6-chloro-pyrimidine, (Example 1(a)), (0.15 g, 0.61 mmol) and 5-hydroxyindole (0.24 g, 1.8 mmol, Aldrich) in 1,4-dioxane (12 mL), was added NaOH (8.0 mL, 8.0 mmol, 1.0 N). The mixture was heated at reflux for 4 h, and after cooling to room temperature, the solvent was removed in vacuum. EtOAc (15 mL) was added to the residue, and the organic layer was washed with 1 N NaOH (10 mL), water (10 mL), dried over $Na_2SO_4$, filtered, and concentrated in vacuum. After purifying the crude product by silica gel chromatography (4:1 hexanes/EtOAc), the resulting solid was dissolved in acetone (3 mL). Water (5 mL) was added dropwise to this mixture, and a white precipitate fell out of solution, which was collected by filtration, washed with water (0.5 mL), and dried under vacuum at 50° C. for 48 h to furnish the title compound. Mp: 143-145° C. MS (ESI, pos. ion) m/z: 344 (M+1). Anal. Calcd for $C_{22}H_{21}N_3O \cdot (H_2O)_{1/8}$: C, 76.44; H, 6.20; N, 12.16. Found: C, 76.63; H, 6.20; N, 12.12.

EXAMPLE 10

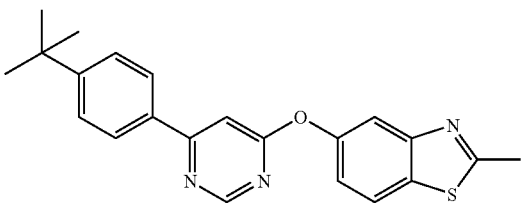

5-[6-(4-tert-Butyl-phenyl)-pyrimidin-4-yloxy]-2-methylbenzothiazole. To a 100-mL, round-bottomed flask containing 4-(4-tert-butyl-phenyl)-6-chloro-pyrimidine, (Example 1(a)), (0.15 g, 0.61 mmol) and 2-methyl-benzothiazol-5-ol (0.14 g, 0.85 mmol, Aldrich) in DMF (10 mL), was added NaH (34 mg, 0.85 mmol, 60% in mineral oil, Aldrich) at room temperature. The solution was then stirred at room temperature for 4 h. After the solvent was removed in vacuum, EtOAc (10 mL) was added to the residue, and the organic layer was washed with water (8 mL), dried over $Na_2SO_4$, filtered, and concentrated in vacuum. After purifying the crude product by silica gel chromatography (4:1 hexanes/EtOAc), the resulting solid was dissolved in acetone (5 mL). Water (8 mL) was added dropwise to this mixture, and a white precipitate fell out of solution, which was collected by filtration, washed with water (0.5 mL), and dried under vacuum at 50° C. for 48 h to furnish the title compound. Mp: 163-165° C. MS (ESI, pos. ion) m/z: 376 (M+1). Anal. Calcd for $C_{23}H_{21}N_3OS \cdot (H_2O)_{1/3}$: C, 69.26; H, 5.72; N, 11.01. Found: C, 69.19; H, 5.61; N, 11.03.

EXAMPLE 11

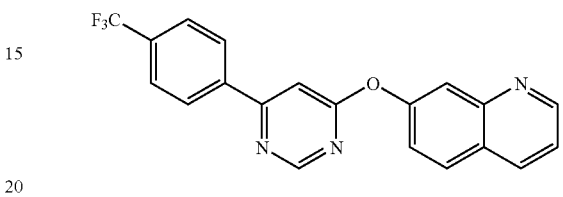

7-[6-(4-Trifluoromethyl-phenyl)-pyrimidin-4-yloxy]-quinoline. To a 250-mL, round-bottomed flask containing 4-chloro-6-(4-trifluoromethyl-phenyl)-pyrimidine, (Example 2(a), Method A), (2.5 g, 9.7 mmol) and 7-hydroxyquinoline (2.0 g, 14 mmol, Acros) in DMF (30 mL), was added NaH (5.4 g, 14 mmol, 60% in mineral oil, Aldrich) at room temperature. The solution was then stirred at room temperature for 4 h. After the solvent was removed in vacuum, EtOAc (100 mL) and water (50 mL) were added to the residue. The solid precipitate was filtered and the filtrate was poured into a separatory funnel. The organic layer was separated, combined with the previously isolated solid, concentrated in vacuum, and purified by silica gel chromatography (2:1 hexanes/EtOAc). The purified product was dissolved in acetone (30 mL) and MeOH (10 mL), and to the solution was added water (30 mL) in small portions. The precipitated solid was filtered, washed with water (5 mL), and dried under vacuum at 50° C. for 48 h to furnish the title compound as a white solid. Mp: 178-180° C. MS (ESI, pos. ion) m/z: 368 (M+1). Anal. Calcd for $C_{20}H_{12}F_3N_3O$: C, 65.40; H, 3.29; N, 11.44. Found: C, 65.42; H, 3.23; N, 11.43.

EXAMPLE 12

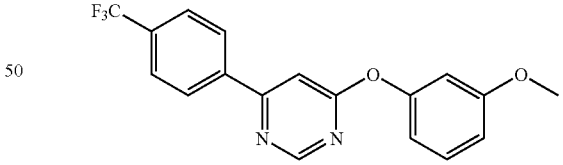

4-(3-Methoxy-phenoxy)-6-(4-trifluoromethyl-phenyl)-pyrimidine. To a 1 00-mL, round-bottomed flask containing 4-chloro-6-(4-trifluoromethyl-phenyl)-pyrimidine, (Example 2(a), Method A), (0.15 g, 0.58 mmol) and 3-methoxyphenol (0.10 g, 0.81 mmol, Aldrich) in DMF (6 mL), was added NaH (32 mg, 0.81 mmol, 60% in mineral oil, Aldrich) at room temperature The solution was then stirred at room temperature for 4 h. After the solvent was removed in vacuum, EtOAc (10 mL) was added to the residue, and the mixture was washed with water (8 mL), dried over $Na_2SO_4$, filtered, and concentrated in vacuum. Silica gel chromatography (5:1 hexanes/EtOAc) afforded the title compound as a white solid. Mp: 87-88° C. MS (ESI, pos. ion) m/z: 347 (M+1). Anal. Calcd for $C_{18}H_{13}F_3N_2O_2$: C, 62.54; H, 3.75; N, 8.09. Found: C, 62.54; H, 3.75; N, 7.99.

EXAMPLE 13

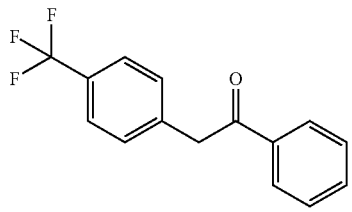

(a) 1-Phenyl-2-(4-trifluoromethyl-phenyl)-ethanone. In a 250-mL, round-bottomed flask were added 1-bromo-4-trifluoromethyl-benzene (10 g, 44 mmol, Aldrich), and THF (50 mL). Potassium bis(trimethylsilyl)amide (176 mL, 88.0 mmol, Aldrich), bis(dibenzylidene)acetone palladium (3.08 g, 3.37 mmol, Acros) and 1,1'-bis(diphenylphosphino)ferrocene (2.2 g, 3.99 mmol, Aldrich) were added to the reaction mixture. After stirring under nitrogen for 10 min, acetophenone (5.4 mL, 46.6 mmol, Aldrich) was added, and the mixture was heated at reflux for 18 h. The reaction mixture was allowed to cool to room temperature, diluted with EtOAc (100 mL) and washed with 0.5 M phosphoric acid (50 mL), $H_2O$ (50 mL) and brine (50 mL). The organic layer was dried over $Na_2SO_4$, filtered and concentrated in vacuum. The crude material was purified by flash silica gel chromatography (5% EtOAc in hexanes) to give the title compound as a dark brown oil. MS (ESI, pos.ion) m/z: 265 (M+1).

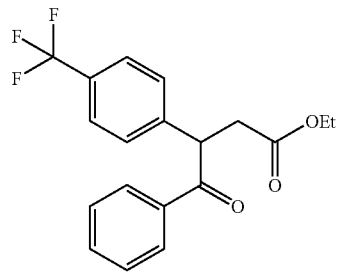

(b) 4-Oxo-4-phenyl-3-(4-trifluoromethyl-phenyl)-butyric acid ethyl ester. In a round-bottomed flask was placed sodium hydride (416 mg, 10.4 mmol, 60% suspension in mineral oil, Aldrich) and washed twice with hexanes. Then 1-phenyl-2-(4-trifluromethyl-phenyl)ethanone (2.0 g, 7.57 mmol) and DMSO (90 mL) were added and the reaction mixture was stirred for 1 h at room temperature. Ethyl chloroacetate (1.05 mL, 10.4 mmol, Aldrich) was then added dropwise and the mixture was stirred at room temperature for 18 h. The reaction mixture was diluted with EtOAc (100 mL) and the organic layer was washed with 0.5 M phosphoric acid (50 mL), $H_2O$ (50 mL) and brine (50 mL). The organic layer was dried over $Na_2SO_4$, filtered and concentrated in vacuum to give the crude title compound as a tan oil. MS (ESI, pos.ion) m/z: 351 (M+1).

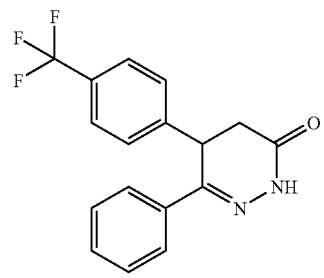

(c) 6-Phenyl-5-(4-trifluoromethyl-phenyl)-4,5-dihydro-2H-pyridazin-3-one. Into a round-bottomed flask was placed 4-oxo-4-phenyl-3-(4-trifluoromethyl-phenyl)-butyric acid ethyl ester (2.0 g, 5.71 mmol), dioxane (5 mL), and hydrazine (0.28 mL, 8.57 mmol, Aldrich), and the reaction mixture was heated at reflux for 18 h. The reaction mixture was then diluted with EtOAc (100 mL) and the organic layer was washed with 0.5 M phosphoric acid (50 mL), $H_2O$ (50 mL) and brine (50 mL). The organic layer was dried over $Na_2SO_4$, filtered and concentrated in vacuum to give the crude title compound as a tan oil. MS (ESI, pos.ion) m/z: 319 (M+1).

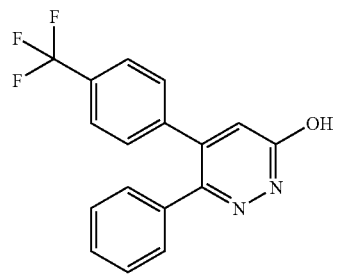

(d) 6-Phenyl-5-(4-trifluoromethyl-phenyl)-pyridazin-3-ol. Bromine (1.00 g, 6.28 mmol) was added to a solution of 6-phenyl-5-(4-trifluoromethyl-phenyl)-4,5-dihydro-2H-pyridazin-3-one (1.00 g, 3.14 mmol) in acetic acid (6 mL) and the mixture was heated at 60C for 10 min. The reaction mixture was allowed to cool to room temperature, diluted with EtOAc (100 mL), washed with satd $NaHCO_3$ (100 mL) and brine (50 mL), dried over $Na_2SO_4$, filtered, and concentrated in vacuum to give the title compound. MS (ESI, pos.ion) m/z: 317 (M+1).

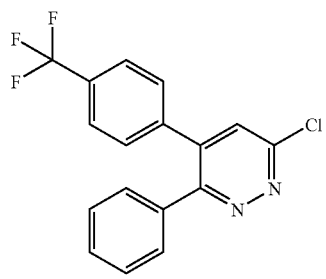

(e) 6-Chloro-3-phenyl-4-(4-trifluoromethyl-phenyl)-pyridazine. A mixture of 6-phenyl-5-(4-trifluoromethyl-phenyl)-pyridazin-3-ol (1.00 g, 3.16 mmol) and $POCl_3$ (6 mL)

was heated at 100° C. for 18 h. After cooling the reaction to room temperature, the volatiles were removed in vacuum and the residue was dissolved in EtOAc (100 mL). The solution was washed with satd NaHCO₃ (100 mL) and brine (50 mL), dried over Na₂SO₄, filtered, and concentrated in vacuum. The crude product was purified by flash silica gel chromatography (10% EtOAc in hexanes) to give the title compound as a brown oil. MS (ESI, pos.ion) m/z: 335 (+1).

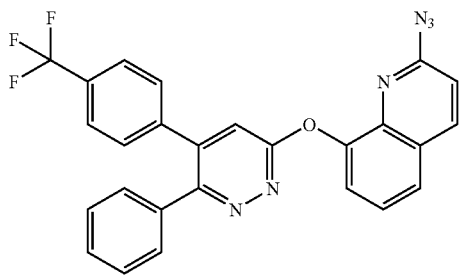

(f) 2-Azido-8-[6-phenyl-5-(4-trifluoromethyl-phenyl)-pyridazin-3-yloxy]-quinoline. Sodium hydride (19.6 mg, 0.816 mmol, 60% suspension in mineral oil, Aldrich) was added to a round-bottomed flask and washed twice with hexanes. 6-Chloro-3-phenyl-4-(4-triflurometthyl-phenyl)-pyridazine (250 mg, 0.749 mmol) was then added, followed by 2-azido-quinolin-8-ol, (Example 2(b)), (123 mg, 0.680 mmol) and DMF (15 mL), and the mixture was heated at 200° C. for 48 h. After cooling to room temperature, the reaction mixture was diluted with EtOAc, washed with H₂O and brine, dried over Na₂SO₄, filtered, and concentrated in vacuum to give the crude title compound as a brown oil. MS (ESI, pos.ion) m/z: 485 (M+1).

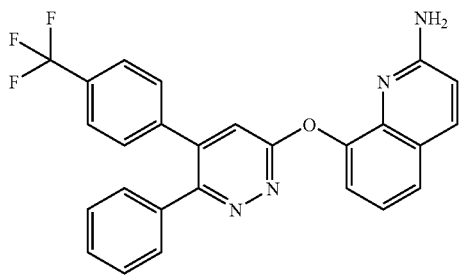

(g) 8-[6-Phenyl-5-(4-trifluoromethyl-phenyl)-pyridazin-3-yloxy]-quinolin-2-ylamine. A mixture of 2-azido-8-[6-phenyl-5-(4-trifluoromethyl-phenyl)-pyridazin-3-yloxy]-quinoline (230 mg, 0.475 mmol), triphenylphosphine (249 mg, 0.950 mmol, Aldrich) and toluene (25 mL) was heated at reflux for 4 h. The solvent was removed in vacuum, the residue was treated with acetic acid and H₂O (10 mL:5 mL) and the mixture was stirred at 50° C. for 18 h. The solvent was removed in vacuum and the residue was purified by silica gel chromatography (2.5% MeOH in dichloromethane) to afford the title compound as a white solid. MS (ESI, pos.ion) m/z: 459 (M+1). Mp: 103-105° C.

EXAMPLE 14

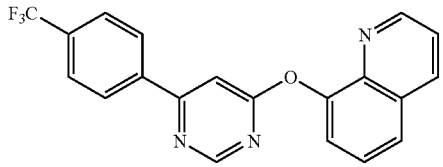

8-[6-(4-Trifluoromethyl-phenyl)-pyrimidin-4-yloxy]-quinoline. To a 100-mL round-bottomed flask containing 4-chloro-6-(4-trifluoromethyl-phenyl)-pyrimidine, (Example 2(a), Method A), (0.30 g, 1.2 mmol) and 8-hydroxyquinoline (0.17 g, 1.2 mmol, Aldrich) in DMF (5 mL), was added NaH (56 mg, 1.4 mmol, 60% in mineral oil, Aldrich) at room temperature and the mixture was then stirred at room temperature for 48 h. After the solvent was removed in vacuum, EtOAc (25 mL) was added to the residue, and the mixture was washed with water (2×15 mL), dried over Na₂SO₄, filtered, and concentrated in vacuum. Silica gel chromatography (4:1 hexanes/EtOAc) afforded the title compound as a white solid. Mp: 155-157° C. MS (ESI, pos. ion) m/z: 368 (M+1). Anal. Calcd for C₂₀H₁₂F₃N₃O: C, 65.40; H, 3.29; N, 11.44. Found: C, 65.29; H, 3.25; N, 11.41.

EXAMPLE 15

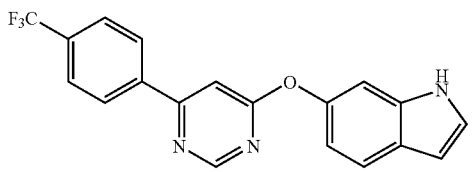

6-[6-(4-Trifluoromethyl-phenyl)-pyrimidin-4-yloxy]-1H-indole. To a 100-mL, round-bottomed flask containing 4-chloro-6-(4-trifluoromethyl-phenyl)-pyrimidine, (Example 2(a), Method A), (0.20 g, 0.77 mmol) and 6-hydroxyindole (0.21 g, 1.5 mmol, Aldrich) in 1,4-dioxane (10 mL), was added NaOH (8.0 mL, 8.0 mmol, 1.0 N). The mixture was heated at reflux for 8 h, and after cooling to room temperature, the reaction mixture was concentrated in vacuum. EtOAc (30 mL) was added, and the organic layer was washed with brine (10 mL), water (15 mL), dried over Na₂SO₄, filtered, and concentrated in vacuum. After the product was purified by silica gel chromatography (5:1 hexanes/EtOAc), the residue was dissolved in acetone (3 mL). Water (4 mL) was then added dropwise to afford a white precipitate, which was collected by filtration, washed with water (0.5 mL), and dried under vacuum at 50° C. for 48 h to furnish the title compound. Mp: 206-209° C. MS (ESI, pos. ion) m/z: 356 (M+1); Anal. Calcd for C₁₉H₁₂F₃N₃O·(H₂O)₀.₂: C, 63.58; H, 3.48; N, 11.71. Found: C, 63.82; H, 3.37; N, 11.61

EXAMPLE 16

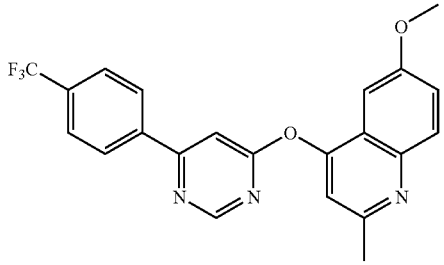

6-Methoxy-2-methyl-4-[6-(4-trifluoromethyl-phenyl)-pyrimidin-4-yloxy]-quinoline. To a 100-mL, round bottomed flask containing 4-chloro-6-(4-trifluoromethyl-phenyl)-pyrimidine, (Example 2(a), Method A), (0.26 g, 1.0 mmol) and 6-methoxy-2-methyl-quinolin-4-ol (0.19 g, 1.0 mmol, Ubichem) in DMF (5 mL), was added NaH (48 mg, 1.2 mmol, 60% in mineral oil, Aldrich) at room temperature The solution was then stirred at room temperature for 24 h. After the solvent was removed in vacuum, EtOAc (30 mL) was added to the residue, and the mixture was washed with brine (2×15 mL), dried over $Na_2SO_4$, filtered, and concentrated in vacuum. After the product was purified by silica gel chromatography (5:1 hexanes/EtOAc), the resulting solid was dissolved in acetone (10 mL) and MeOH (8 mL). Water (15 mL) was then added dropwise to afford a white precipitate, which was collected by filtration, washed with water (2 mL), and dried under vacuum at 50° C. for 48 h to furnish the title compound. Mp: 165-166° C. MS (ESI, pos. ion) m/z: 412; Anal. Calcd for $C_{22}H_{16}F_3N_3O_2$: C, 64.23; H, 3.92; N, 10.21. Found: C, 64.20; H, 3.85; N, 10.14.

EXAMPLE 17

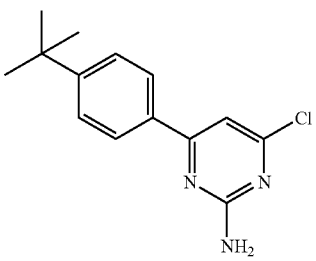

(a) 4-(4-tert-Butyl-phenyl)-6-chloro-pyrimidin-2-ylamine. To a 250-mL, round-bottomed flask was added 2-amino-4,6-dichloropyrimidine (1.4 g, 8.1 mmol, Aldrich), 4-tert-butyl-phenylboronic acid (1.2 g, 6.7 mmol, Aldrich), acetonitrile (30 mL), and 1 M aq. sodium carbonate (25 mL). $Pd(PPh_3)_4$ (0.39 g, 0.34 mmol, Strem) was then added and the resulting yellow mixture was heated under a $N_2$ atmosphere at 90° C. for 15 h. The reaction mixture was allowed to cool to 25° C. and diluted with EtOAc (100 mL). The organic layer was separated, washed with water (30 mL), dried over $Na_2SO_4$, filtered and concentrated in vacuum. Purification of the residue by silica gel chromatography (gradient, 4:1 hexanes:EtOAc) afforded the title compound as clear oil. MS (ESI, pos. ion) m/z: 263 (M+1).

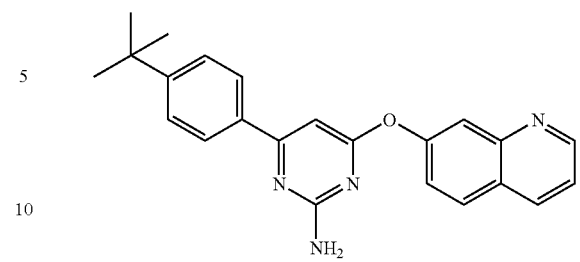

(b) 4-(4-tert-Butyl-phenyl)-6-(quinolin-7-yloxy)-pyrimidin-2-ylamine. To a 50-mL, round-bottomed flask was added 4-(4-tert-butyl-phenyl)-6-chloro-pyrimidin-2-ylamine (0.25 g, 0.96 mmol), 7-hydroxyquinoline (70 mg, 0.48 mmol, Acros), $K_2CO_3$ (66 mg, 0.48 mmol) and anhydrous DMF (10 mL). The resulting suspension was heated at 100° C. for 3 h with stirring under $N_2$. The reaction mixture was allowed to cool to 25° C., diluted with 1 N NaOH (100 mL), and extracted with EtOAc (50 mL). The organic phase was washed with 1 N NaOH (10 mL), water (10 mL), satd NaCl (10 mL), dried over $Na_2SO_4$, filtered, and concentrated in vacuum. Purification of the residue by silica gel chromatography (gradient, 1:1 hexanes:EtOAc) afforded the title compound as a white solid. Mp: 154-157° C. MS (ESI, pos. ion) m/z: 371 (M+1).

EXAMPLE 18

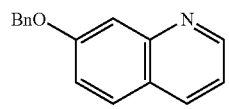

(a) 7-Benzyloxyquinoline. To a 250-mL, round-bottomed flask containing a solution of 7-hydroxyquinoline (2.3 g, 16 mmol, Acros) in DMF (15 mL) was added NaH (0.75 g, 19 mmol, 60% in mineral oil, Aldrich) in small portion with stirring at 0° C. After stirring at 0° C. for 15 min, a solution of benzylbromide (1.9 mL, 16 mmol, Aldrich) in THF (10 mL) was added dropwise over 15 min at 0° C. After the addition, the mixture was stirred at 0° C. for 30 min and diluted with EtOAc (65 mL) and water (30 mL). The organic phase was separated, washed with water (2×20 mL), dried over $Na_2SO_4$, filtered and concentrated in vacuum. Purification of the residue by silica gel chromatography (gradient, 1:1 hexanes:EtOAc) gave the title compound. MS (ESI, pos. ion) m/z: 236 (M+1).

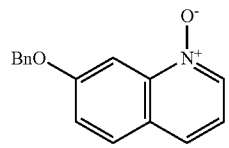

(b) 7-Benzyloxyquinoline 1-oxide. To a 100-mL, round-bottomed flask containing a mixture of 7-benzyloxyquinoline (0.70 g, 3.0 mmol) and $MeReO_3$ (74 mg, 0.30 mmol, Aldrich) in dichloroethane (15 mL) was added dropwise $H_2O_2$ (15 mL, 0.15 mol, 35 wt. % solution in water, Aldrich) over 10 min with stirring at room temperature. The mixture was then stirred at room temperature for 3 h, diluted with water (15 mL) and extracted with $CH_2Cl_2$ (2×30 mL). The combined organic extracts were washed with water (2×20 mL), dried over $Na_2SO_4$, filtered and concentrated in vacuum to give the title compound. MS (ESI, pos. ion) m/z: 252 (M+1).

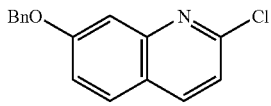

(c) 2-Chloro-7-benzyloxy-quinoline. To a 100-mL, round-bottomed flask was added 7-benzyloxyquinolin 1-oxide (0.72 g, 2.9 mmol) and $POCl_3$ (4.0 mL, 44 mmol, Aldrich) and the mixture was heated at reflux for 3 h under $N_2$. After cooling to room temperature, the solvent was removed in vacuum and the residue was dissolved in EtOAc (50 mL). The solution was washed with 5% $K_2CO_3$ (2×20 mL) and water (2×20 mL), dried over $Na_2SO_4$, filtered, and concentrated in vacuum. Chromatography of the residue over silica gel (gradient: 3:1 hexanes:EtOAc) gave the title compound. MS (ESI, pos. ion) m/z: 270 (M+1).

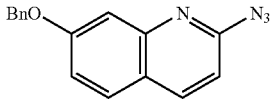

(d) 2-Azido-7-benzyloxy-2-quinoline. To a 100-mL, round-bottomed flask was added 2-chloro-7-benzyloxy-quinoline (0.35 g, 1.3 mmol), $NaN_3$ (0.34 g, 5.2 mmol, Aldrich) and DMSO (10 mL). The mixture was heated at reflux at 110° C. for 2 h, allowed to cool to room temperature, diluted with water (10 mL) and extracted with EtOAc (2×50 mL). The combined organic extracts were washed with water (15 mL), dried over $Na_2SO_4$, filtered, and concentrated in vacuum. Chromatography of the residue over silica gel (gradient: 3:1 hexanes:EtOAc) gave the title compound. MS (ESI, pos. ion) m/z: 277 (M+1).

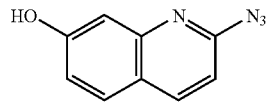

(e) 2-Azido-quinolin-7-ol. To a 100-mL, round-bottomed flask containing a solution of 2-azido-7-benzyloxy-2-quinoline (0.32 g, 1.2 mmol) in $CH_2Cl_2$ (5 mL) was added dropwise a 1.0 M solution of $BBr_3$ in dichloromethane (5.8 mL, 5.8 mmol, Aldrich) with stirring at −40° C. under $N_2$. The reaction mixture was then stirred for 10 h at room temperature and quenched with ice-water (10 mL) with stirring and cooling with an ice bath. Most of the organic solvent was removed in vacuum and the acidity of the aq. residue was adjusted to pH 5 with 2 N NaOH. The precipitated product was extracted with $Et_2O$ (3×40 mL) and the combined organic extracts were washed with water (20 mL), dried over $Na_2SO_4$, filtered and concentrated in vacuum to give the title compound. MS (ESI, pos. ion) m/z: 187 (M+1).

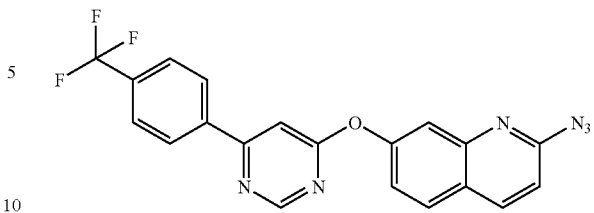

(f) 2-Azido-7-[6-(4-trifluromethyl-phenyl)-pyrimidin-4-yloxy]-quinoline. To a 50-mL, round-bottomed flask was added 4-chloro-6-[4-(trifluoromethyl)phenyl]-pyrimidine, (Example 2(a), Method A), (0.27 g, 1.0 mmol), 2-azido-quinolin-7-ol (0.13 g, 0.69 mmol), $K_2CO_3$ (0.19 g, 1.6 mmol) and anhydrous DMF (15 mL). The resulting suspension was stirred at 90° C. for 3 h under $N_2$. The reaction mixture was allowed to cool to 25° C., diluted with EtOAc (100 mL) and washed with 5% brine (35 mL). The organic phase was dried over $Na_2SO_4$, filtered and concentrated in vacuum. Purification of the residue by silica gel chromatography (gradient: 2:1 hexanes:EtOAc) afforded the title compound. MS (ESI, pos. ion) m/z: 409 (M+1).

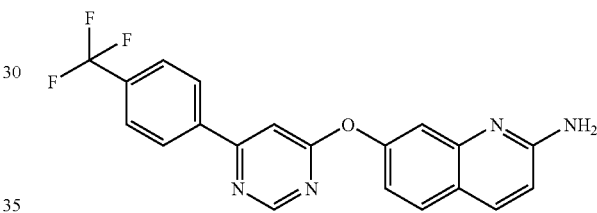

(g) 7-[6-(4-Trifluromethyl-phenyl)-pyrimidin-4-yloxy]-quinolin-2-ylamine. To a 50-mL, round-bottomed flask was added 2-azido-7-[6-(4-trifluromethyl-phenyl)-pyrimidin-4-yloxy]-quinoline (0.20 g, 0.49 mmol), $PPh_3$ (0.26 g, 0.98 mmol, Aldrich), and toluene (10 mL). The mixture was heated at reflux for 4 h, allowed to cool to room temperature and the solvent was removed in vacuum. To the residue was added water (3 mL) and AcOH (6 mL), and the resulting mixture was heated at 50° C. for 5 h. The solvents were removed in vacuum and the residue was dissolved in EtOAc (50 mL), washed with 5% $K_2CO_3$ (25 mL), water (25 mL), dried over $Na_2SO_4$, filtered, and concentrated in vacuum. The residue was suspended in 5:1 $CH_2Cl_2$:MeOH and the title compound was isolated as a solid by filtration. Purification of the filtrate by silica gel chromatography (gradient: 10:1 EtOAc:MeOH) gave additional amounts of the product, which combined with the solid from above afforded the title compound. Mp: 257-259° C. MS (ESI, pos. ion) m/z: 383 (M+1).

EXAMPLE 19

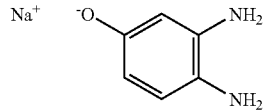

(a) 3,4-Diamino-phenol sodium salt. To a 200-mL, round-bottomed flask containing a solution of 1,2-diamino-4-methoxy-benzene (0.50 g, 3.6 mmol, Avocado) in $CH_2Cl_2$ (5 mL) was added dropwise a solution of $BBr_3$ in $CH_2Cl_2$ (15 mL, 15 mmol, 1.0 M, Aldrich) with stirring at −30° C. under $N_2$. The mixture was stirred at room temperature for 5 h and quenched with ice water (25 mL) by cooling with and ice bath. The mixture was basified to pH 9 with 1 N NaOH and extracted with water (2×8 mL). The combined aq. extracts containing the title compound were used directly in the next reaction. A small portion of the aq. solution was neutralized with 1 N NaOH to give an analytical sample of 3,4-diamino-phenol. MS (ESI, pos. ion) m/z: 125 (M+1).

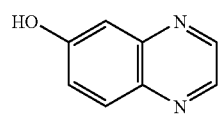

(b) 7-Hydroxy-1,4-quinoxaline. To a 100-mL, round-bottomed flask was added aq. solution of 3,4-diamino-phenol sodium salt from step (a) above (1.6 mmol, 8 mL) and glyoxal (0.70 mL, 4.8 mmol, 40 wt. % solution in water, Aldrich). The mixture was stirred at room temperature for 2 h, acidified to pH 5 with 2 N HCl and extracted with EtOAc:THF (3×20 mL, 1:1). The combined organic extracts were washed with 5% brine (20 mL), dried over $Na_2SO_4$, filtered, and concentrated in vacuum. Purification of the residue by silica gel chromatography (gradient: 2:1 hexanes: EtOAc) afforded the title compound. MS (ESI, pos. ion) m/z: 147 (M+1).

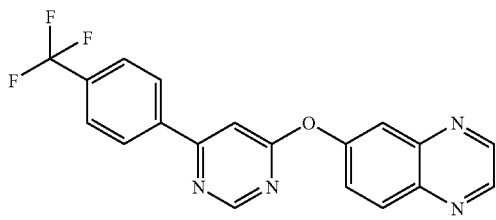

(c) 6-[6-(4-Trifluromethyl-phenyl)-pyrimidin-4-yloxy]-quinoxaline. To a 50-mL, round-bottomed flask was added 4-chloro-6-[4-(trifluoromethyl)phenyl]-pyrimidine, (Example 2(a), Method A), (0.40 g, 1.6 mmol), 7-hydroxy-1,4-quinoxaline (0.19 g, 1.3 mmol), anhydrous DMF (10 mL), and NaH (78 mg, 1.9 mmol, 60% dispersion in mineral oil, Aldrich), and the resulting suspension was stirred at 90° C. for 10 h under $N_2$. The reaction mixture was allowed to cool to room temperature, diluted with EtOAc (50 mL), washed with 5% brine (2×20 mL), dried over $Na_2SO_4$, filtered, and concentrated in vacuum. Purification of the residue by silica gel chromatography (gradient: 3:1 hexanes:EtOAc) afforded the title compound. Mp: 168-170° C. MS (ESI, pos. ion) m/z: 369 (M+1).

EXAMPLE 20

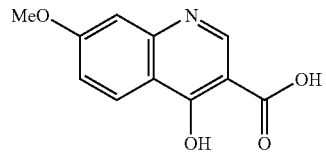

(a) 4-Hydroxy-7-methoxy-quinoline-3-carboxylic acid. To a 200-mL, round-bottomed flask containing 4-hydroxy-7-methoxy-quinoline-3-carboxylic acid ethyl ester (2.6 g, 11 mmol, Aldrich) was added 2 N NaOH (25 mL, 50 mmol) and the mixture was heated at reflux for 3 h. After cooling to room temperature, the mixture was neutralized to pH 7 with 2 N HCl and the white precipitate was filtered and dried under vacuum at 60° C. for 3 days to afford the title compound. MS (ESI, pos. ion) m/z: 220 (M+1).

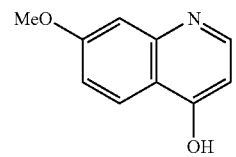

(b) 7-Methoxy-4-hydroxy-quinoline. To a 50-mL, round-bottomed flask was added 4-hydroxy-7-methoxy-quinoline-3-carboxylic acid (1.2 g, 5.5 mmol) and phenyl ether (15 mL). The mixture was heated at 200° C. with stirring under $N_2$ for 1 h. After cooling to room temperature, the mixture was diluted with EtOAc (50 mL) and washed with 1 N NaOH (30 mL). The aqueous phase was separated, acidified to pH 5 with 2 N HCl and extracted with EtOAc (3×40 mL). The combined extracts were dried over $Na_2SO_4$, filtered, and concentrated in vacuum to yield the title compound as yellow oil. MS (ESI, pos. ion) m/z: 176 (M+1).

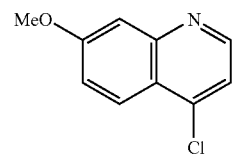

(c) 7-Methoxy-4-chloro-quinoline. To a 100-mL, round-bottomed flask was added 7-methoxy-4-hydroxy-quinoline (0.43 g, 2.5 mmol) and $POCl_3$ (5.0 mL, 55 mmol, Aldrich), and the mixture was heated at reflux for 2 h under $N_2$. After cooling to room temperature, the solvent was removed in vacuum and the residue dissolved in EtOAc (40 mL). The solution was washed with 5% $K_2CO_3$ (2×20 mL) and water (2×20 mL), dried over $Na_2SO_4$, filtered, and concentrated in vacuum. Chromatography of the residue over silica gel (gradient: 3:1 hexanes:EtOAc) gave the title compound MS (ESI, pos. ion) m/z: 194 (M+1).

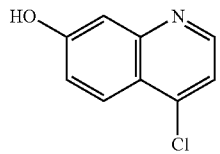

(d) 7-Hydroxy-4-chloro-quinoline. To a 100-mL, round-bottomed flask containing a solution of 7-methoxy-4-chloro-quinoline (0.17 g, 0.86 mmol) in dichloroethane (5 mL) was added dropwise a 1.0 M solution of $BBr_3$ in dichloromethane (6.9 mL, 6.9 mmol, Aldrich) with stirring at −70° C. under $N_2$. The reaction mixture was then stirred for 20 h at room temperature and quenched with ice-water (10 mL) with stirring and cooling with an ice bath. Most of the organic solvent was removed in vacuum and the acidity of the aq. residue was adjusted to pH 6 with 1 N NaOH. The precipitated product was extracted with $Et_2O$ (3×20 mL) and the combined organic extracts were washed with 5% brine (2×10 mL), dried over $Na_2SO_4$, filtered, and concentrated in vacuum to give the title compound. MS (ESI, pos. ion) m/z: 180 (M+1).

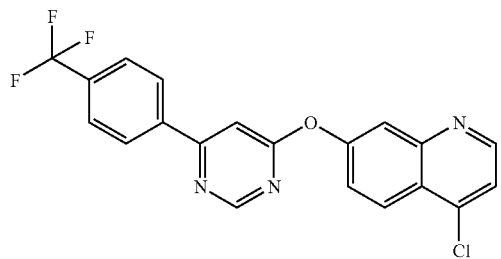

(e) 4-Chloro-7-[6-(4-triflouromethyl-phenyl)-pyrimidin-4-yloxy]-quinoline. To a 150-mL, round-bottomed flask was added 4-chloro-6-[4-(trifluoromethyl)phenyl]-pyrimidine, (Example 2(a), Method A), (0.35 g, 1.4 mmol), 7-hydroxy-4-chloro-quinoline (0.12 g, 0.68 mmol), anhydrous DMF (8 mL), and NaH (54 mg, 1.4 mmol, 60% dispersion in mineral oil, Aldrich). The resulting suspension was stirred at room temperature for 6 h and then diluted with EtOAc (80 mL). The solution was washed with 5% brine (2×20 mL), dried over $Na_2SO_4$, filtered, and concentrated in vacuum. Purification of the residue by silica gel chromatography (gradient: 3:1 hexanes:EtOAc) afforded the title compound. Mp: 205-208° C. MS (ESI, pos. ion) m/z: 402 (M+1).

EXAMPLE 21

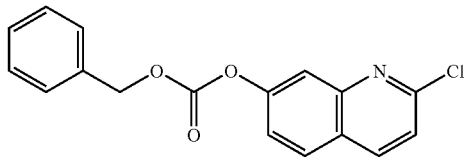

(a) 7-Benzyloxycarbonyloxy-2-chloro-quinoline. The title compound was prepared from 7-hydroxyquinoline (Acros) and benzyl chloroformate (Aldrich) in three steps analogous to the conditions of Example 18 (a), (b) and (c). MS (ESI, pos. ion) m/z: 314 (M+1).

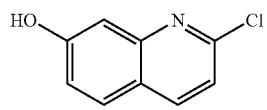

(b) 7-Hydroxy-2-chloro-quinoline. To a 100-mL, round-bottomed flask was added 7-benzyloxycarbonyloxy-2-chloro-quinoline (0.32 g, 1.0 mmol), $NaN_3$ (0.26 mg, 4.0 mmol, Aldrich), and DMF (10 mL) and the mixture was heated at 100° C. for 3 h with stirring under $N_2$. After cooling to room temperature, the mixture was diluted with EtOAc (50 mL) and acidified to pH 4 with 1 N HCl. The organic phase was separated, washed with 5% brine (2×20 mL), dried over $Na_2SO_4$, filtered, and concentrated in vacuum. Chromatography of the residue over silica gel (gradient: 3:1 hexanes:EtOAc) gave the title compound. MS (ESI, pos. ion) m/z: 180 (M+1).

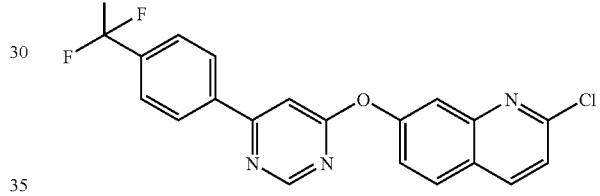

(c) 2-Chloro-7-[6-(4-triflouromethyl-phenyl)-pyrimidin-4-yloxy]-quinoline. To a 50-mL, round-bottomed flask was added 4-chloro-6-[4-(trifluoromethyl)phenyl]-pyrimidine, (Example 2(a), Method A), (0.27 g, 1.0 mmol), 7-hydroxy-2-chloro-quinoline (56 mg, 0.31 mmol), $K_2CO_3$ (42 mg, 0.30 mmol) and anhydrous DMF (6 mL). The resulting suspension was stirred at 90° C. for 4 h under $N_2$. The reaction mixture was allowed to cool to 25° C., diluted with EtOAc (50 mL), washed with 5% brine (15 mL), dried over $Na_2SO_4$, filtered, and concentrated in vacuum. Purification of the residue by silica gel chromatography (gradient: 6:1 hexanes:EtOAc) afforded the title compound. Mp: 171-173° C. MS (ESI, pos. ion) m/z: 402 (M+1).

EXAMPLE 22

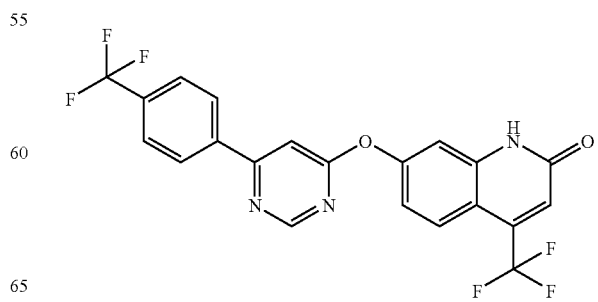

(a) 4-Trifluoromethyl-7-[6-(4-trifluromethyl-phenyl)-pyrimidin-4-yloxy]-1H-quinolin-2-one. To a 250-mL, round-bottomed flask was added 4-chloro-6-[4-(trifluoromethyl) phenyl]-pyrimidine, (Example 2(a), Method A), (1.07 g, 4.1 mmol), 2,7-dihydroxy-4-trifluoromethylquinoline (0.79 g, 3.5 mmol, Aldrich), K$_2$CO$_3$ (0.67 g, 4.8 mmol) and anhydrous DMF (15 mL). The resulting suspension was heated at 90° C. for 4 h with stirring under N$_2$. The reaction mixture was allowed to cool to 25° C., diluted with EtOAc (50 mL) and the white precipitate was filtered to give the title compound. MS (ESI, pos. ion) m/z: 452 (M+1).

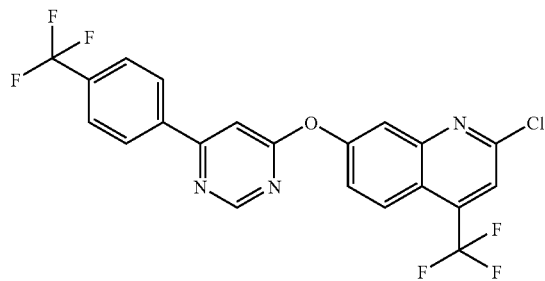

(b) 2-Chloro-4-trifluoromethyl-7-[6-(4-trifluromethyl-phenyl)-pyrimidin-4-yloxy]-quinoline. To a 250-mL, round-bottomed flask containing a solution of 4-trifluoromethyl-7-[6-(4-trifluromethyl-phenyl)-pyrimidin-4-yloxy]-1H-quinolin-2-one (1.1 g, 2.4 mmol) in toluene (20 mL) was added dropwise POCl$_3$ (1.8 mL, 19 mmol, Aldrich) with stirring at 0° C. under N$_2$. The reaction mixture was stirred at room temperature for 0.5 h and heated at reflux for 5 h. The solvent was removed in vacuum and the residue dissolved in EtOAc (200 mL). The solution was washed with 5% K$_2$CO$_3$ (2×40 mL) and water (2×40 mL), dried over Na$_2$SO$_4$, filtered, and concentrated in vacuum. Recrystallization of the residue from CH$_2$Cl$_2$:MeOH (10:1) gave the title compound. Mp: 192-194° C. MS (ESI, pos. ion) m/z: 470 (M+1).

EXAMPLE 23

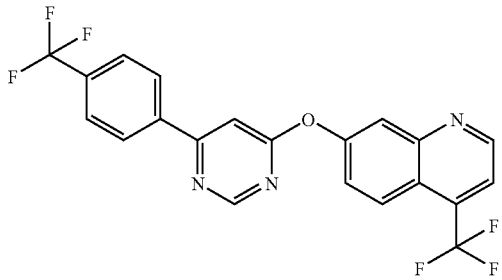

4-Trifluoromethyl-7-[6-(4-trifluromethyl-phenyl)-pyrimidin-4-yloxy]-quinoline. To a 100-mL, round-bottomed flask containing a solution of 2-chloro-4-trifluoromethyl-7-[6-(4-trifluromethyl-phenyl)-pyrimidin-4-yloxy]-quinoline, (Example 22(b)), (0.25 g, 0.53 mmol) in EtOAc (20 mL) was added Zn (0.87 g, 13 mmol, Aldrich), AcOH (61 mg, 1.1 mmol), and water (40 mg, 1.1 mmol). The mixture was heated at 70° C. with stirring for 2.5 h. After cooling to room temperature, 5% aq. Na$_2$CO$_3$ was added and the reaction mixture was extracted with EtOAc (30 mL). The organic phase was washed with water (2×10 mL), dried over Na$_2$SO$_4$, filtered, and concentrated in vacuum. Purification of the residue by silica gel chromatography (gradient: 3:1 hexanes:EtOAc) gave the title compound. Mp: 129-131° C. MS (ESI, pos. ion) m/z: 436 (M+1).

EXAMPLE 24

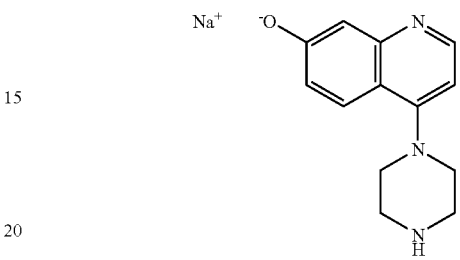

(a) 4-piperazin-1-yl-quinolin-7-ol sodium salt. To a 100-mL, round-bottomed flask containing a solution of 7-methoxy-4-piperazin-quinoline (0.40 g, 1.7 mmol, Ubichem, Plc.) in dichloroethane (15 mL) was added dropwise a 1.0 M solution of BBr$_3$ in dichloromethane (8.2 mL, 8.2 mmol, Aldrich) at −70° C. with stirring under N$_2$. The mixture was stirred at room temperature for 20 h and then quenched with ice water (20 mL) by cooling with an ice bath. Most of the organic solvents were removed under vacuum and the aq. residue was basified with 1 N NaOH to pH 9. The aqueous was washed with EtOAc (30 mL) to give and aq. solution of the title compound, which was used directly in the next reaction. A small portion of the aq. solution was neutralized with 1 N NaOH to give an analytical sample of 4-piperazin-1-yl-quinolin-7-ol. MS (ESI, pos. ion) m/z: 230 (M+1).

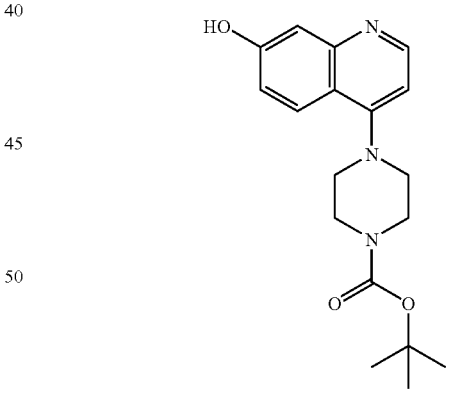

(b) 4-(7-Hydroxy-quinolin-4-yl)-piperazine-1-carboxylic acid tert-butyl ester. To a 100-mL, round-bottomed flask containing the aq. solution of 4-piperazin-1-yl-quinolin-7-ol sodium salt from step (a) above (0.31 g, 1.36 mmol) was added di-tert-butyl dicarbonate (0.42 g, 1.9 mmol, Aldrich), K$_2$CO$_3$ (0.38 g, 2.72 mmol, Aldrich), water (15 mL), and THF (25 mL). The mixture was stirred at room temperature for 1 h, acidified to pH 6 with 2 N HCl and extracted with EtOAc (50 mL). The organic phase was washed with water (20 mL), dried over Na$_2$SO$_4$, filtered, and concentrated in vacuum. Purification of the residue by silica gel chromatography (gradient: 5:5:1 hexanes:EtOAc:MeOH) gave the title compound. MS (ESI, pos. ion) m/z: 330 (M+1).

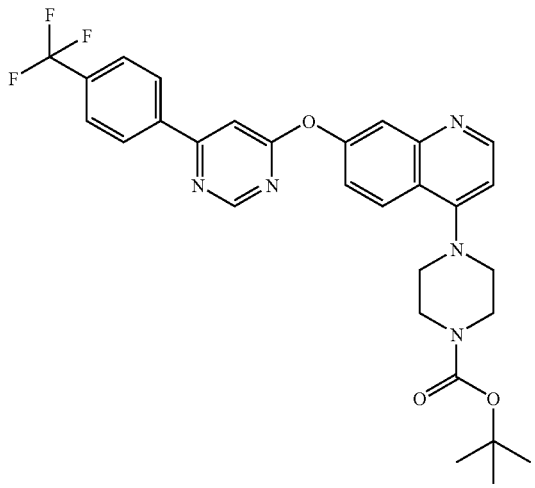

(c) 4-{7-[6-(4-Trifluromethyl-phenyl)-pyrimidin-4-yloxy]-quinolin-4-yloxy}-piperazin-1-carboxylic acid tert-butyl ester. To a 100-mL, round-bottomed flask was added 4-chloro-6-[4-(trifluoromethyl)phenyl]-pyrimidine, (Example 2(a), Method A), (0.40 g, 1.5 mmol), 4-(7-hydroxy-quinolin-4-yl)-piperazine-1-carboxylic acid tert-butyl ester (0.34 g, 1.0 mmol), K$_2$CO$_3$ (0.28 g, 2.0 mmol) and anhydrous DMF (12 mL). The mixture was heated at 90° C. with stirring under N$_2$ for 2 h. The reaction mixture was allowed to cool to 25° C., diluted with EtOAc (80 mL), washed with water (20 mL), dried over Na$_2$SO$_4$, filtered, and concentrated in vacuum. Purification of the residue by silica gel chromatography (gradient: 2:1 hexanes:EtOAc) gave the title compound MS (ESI, pos. ion) m/z: 552 (M+1).

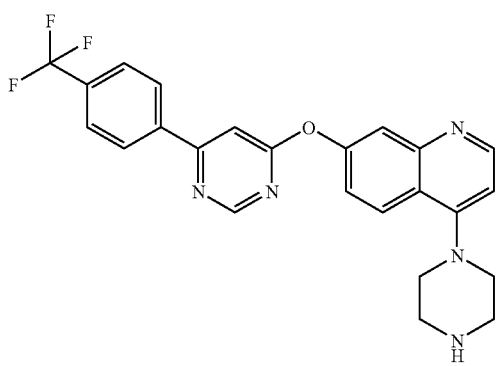

(d) 4-piperazin-1-yl-7-[6-(4-trifluromethyl-phenyl)-pyrimidin-4-yloxy]-quinoline. To a 100-mL, round-bottomed flask containing 4-{7-[6-(4-trifluromethyl-phenyl)-pyrimidin-4-yloxy]-quinolin-4-yloxy}-piperazin-1-carboxylic acid tert-butyl ester (0.41 g, 0.74 mmol) in CH$_2$Cl$_2$ (15 mL), was added CF$_3$COOH (15 mL, 195 mmol, Aldrich). The mixture was stirred at room temperature for 0.5 h and the solvent was removed in vacuum. The residue was dissolved in EtOAc (40 mL), washed with 5% K$_2$CO$_3$ (2×20 mL) and water (2×10 mL), dried over Na$_2$SO$_4$, filtered, and concentrated in vacuum to give the title compound. Mp: 143-145° C. MS (ESI, pos. ion) m/z: 452 (M+1).

EXAMPLE 25

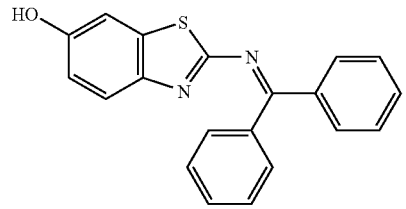

(a) 2-(Benzhydrylidene-amino)-benzothiazol-6-ol. To a 200-mL, round-bottomed flask containing a solution of 2-amino-6-hydroxy-benzothiazol (1.0 g, 6.0 mmol, Astatech, Inc.) in THF (30 mL), was added benzophenone (1.1 g, 6.0 mmol, Aldrich). The mixture was heated at reflux for 3 h, allowed to cool to room temperature and the solvents were evaporated in vacuum to yield the title compound. MS (ESI, pos. ion) m/z: 333 (M+1).

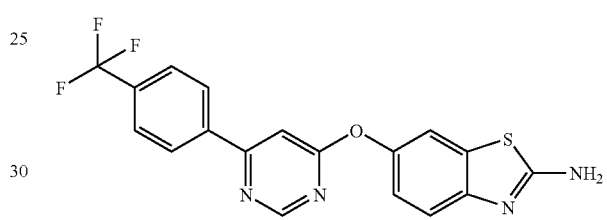

(b) 6-[6-(4-Trifluromethyl-phenyl)-pyrimldin-4-yloxy]-benzothiazol-2-ylamine. To a 100-mL, round-bottomed flask was added 4-chloro-6-[4-(trifluoromethyl)phenyl]-pyrimidine, (Example 2(a), Method A), (0.26 g, 1.0 mmol), 2-(benzhydrylidene-amino)-benzothiazol-6-ol (0.39 g, 1.2 mmol), K$_2$CO$_3$ (0.25 g, 1.8 mmol) and anhydrous DMF (10 mL). The resulting suspension was heated at 50° C. with stirring under N$_2$ for 5 h. The reaction mixture was allowed to cool to 25° C., diluted with EtOAc (45 mL), washed with 5% brine (2×20 mL), dried over Na$_2$SO$_4$, filtered, and concentrated in vacuum. To the residue was added acetone (15 mL) and 1 N NaOH (15 mL), and the mixture was stirred at room temperature for 15 min. The mixture was extracted with EtOAc (40 mL) and the organic phase was separated, washed with 5% brine (2×20 mL), dried over Na$_2$SO$_4$, filtered, and concentrated in vacuum. Purification of the residue by silica gel chromatography (gradient: 20:10:3 hexanes:Et-OAc:MeOH) gave the title compound. Mp: 222-225° C. MS (ESI, pos. ion) m/z: 389 (M+1).

EXAMPLE 26

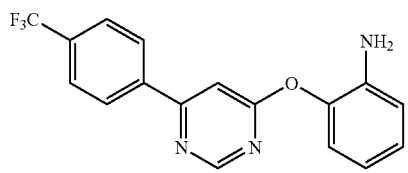

2-[6-(4-Trifluoromethyl-phenyl)-pyrimidin-4-yloxy]-phenylamine. To a mixture of 4-chloro-6-(4-trifluoromethylphenyl)-pyrimidine, (Example 2(a), Method A), (0.52 g, 2.0 mmol) and 2-aminophenol (0.26 g, 2.4 mmol, Aldrich) in DMF (10 mL) was added sodium hydride (0.09 g, 2.2 mmol, 60% dispersion in mineral oil, Aldrich). The mixture was heated at 50° C. for 2 h, allowed to cool to room temperature and diluted with H$_2$O. The resulting solid was filtered, washed with H$_2$O and dried in vacuum at room temperature for 20 h to afford the title compound as a white powder. Mp: 188° C., MS (ESI, pos. ion) m/z: 332 (M+1).

EXAMPLE 27

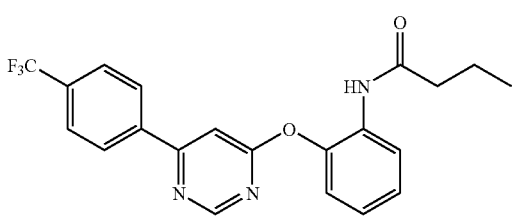

N-{2-[6-(4-Trifluoromethyl-phenyl)-pyrimidin-4-yloxy]-phenyl}-butyramide. To a mixture of 2-[6-(4-trifluoromethyl-phenyl)-pyrimidin-4-yloxy]-phenylamine, (Example 26), (0.33 g, 1.0 mmol), butyryl chloride (0.15 mL, 1.5 mmol, Aldrich), and 4-dimethylaminopyridine (0.006 g, 0.05 mmol, Aldrich) in CH$_2$Cl$_2$ (5 mL) was added Et$_3$N (0.21 mL, 1.5 mmol, Aldrich). The mixture was stirred for 30 min, diluted with hexanes (10 ml) and treated with H$_2$O (2 mL). The resulting solids were filtered, washed with H$_2$O and hexanes, and dried in vacuum for 16 h at room temperature to give the title compound as a white powder. Mp: 112° C., MS (ESI, pos. ion) m/z: 402 (M+1).

EXAMPLE 28

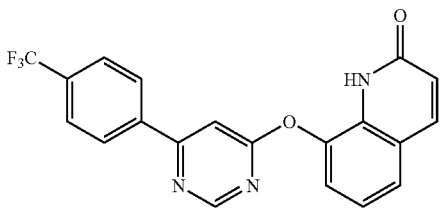

8-[6-(4-Trifluoromethyl-phenyl)-pyrimidin-4-yloxy]-1H-quinolin-2-one. To a mixture of 4-chloro-6-(4-trifluoromethyl-phenyl)-pyrimidine, (Example 2(a), Method A), (0.10 g, 0.39 mmol) and 2,8-quinolinediol (0.075 g, 0.46 mmol, Fluka) in acetonitrile (5 mL) was added 1,8-diazabicyclo[5.4.0]undec-7-ene (0.069 mL, 0.46 mmol, Aldrich). The mixture was heated to reflux for 6 h, allowed to cool to room temperature, and diluted with EtOAc. The solids were filtered, washed with EtOAc and dried in vacuum for 16 h to yield the title compound as long white needles. Mp: 312° C., MS (ESI, pos. ion) m/z: 384 (M+1).

EXAMPLE 29

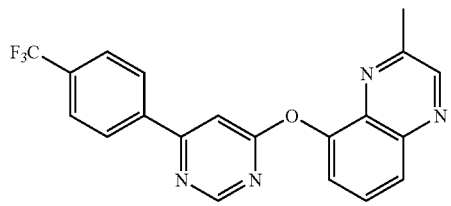

2-Methyl-8-[6-(4-trifluoromethyl-phenyl)-pyrimidin-4-yloxy]-quinoxaline. To a mixture of 4-chloro-6-(4-trifluoromethyl-phenyl)-pyrimidine, (Example 2(a), Method A), (0.20 g, 0.77 mmol) and 3-methyl-quinoxalin-5-ol (0.14 g, 0.85 mmol, prepared according to J. Med. Chem. 1988, 41, 4062-4079.) in DMF (3 mL) was added sodium hydride (0.040 g, 1.0 mmol, 60% dispersion in mineral oil, Aldrich). The reaction was heated at 60° C. for 24 h, allowed to cool to room temperature and partitioned between EtOAc and H$_2$O. The aqueous layer was extracted with EtOAc (4 x). The combined organic layers were dried over MgSO$_4$, filtered and the solvent was removed in vacuum. The residue was purified by flash chromatography (0→75% EtOAc/hexanes) to give the title compound as an ivory powder. Mp: 139-141° C., MS (ESI, pos. ion) m/z: 383 (M+1).

EXAMPLE 30

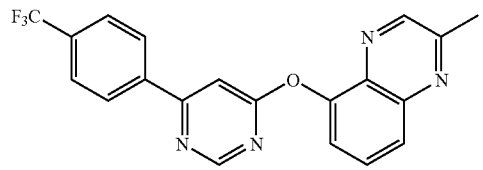

2-Methyl-5-[6-(4-trifluoromethyl-phenyl)-pyrimidin-4-yloxy]-quinoxaline. The title compound was prepared analogous to the procedure in Example 29 using 4-chloro-6-(4-trifluoromethyl-phenyl)-pyrimidine, (Example 2(a), Method A), (0.20 g, 0.77 mmol), 2-methyl-quinoxalin-5-ol (0.14 g, 0.85 mmol, J. Med. Chem, 1988, 41, 4062.) DMF (3 mL), and a 60% dispersion of sodium hydride in mineral oil (0.040 g, 1.0 mmol, Aldrich). Purification by flash chromatography (0→75% EtOAc/hexanes) gave the title compound as an ivory powder. Mp: 135-141° C., MS (ESI, pos. ion) m/z: 383 (M+1).

EXAMPLE 31

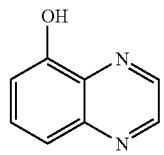

(a) Quinoxalin-5-ol. To a suspension of 2,3-diaminophenol (1.5 g, 12 mmol, Aldrich) in 2 M acetic acid (24 mL) and 4 M sodium acetate (15 mL) was added a solution of 40% aq. glyoxal (1.4 mL, 12.4 mmol, Aldrich). The mixture was heated at 60° C. for 40 min, allowed to cool to room temperature and the pH of the solution was adjusted to pH 8 with satd aq. NaHCO₃. The solution was extracted with CH₂Cl₂ (3×). The combined organic layers were washed with satd aq. NaHCO₃, H₂O, and brine. The orgainic layer was dried over MgSO₄ and concentrated in vacuum. Purification by flash chromatography (0→20% EtOAc/hexanes) gave the title compound as a yellow powder. MS (ESI, pos. ion) m/z: 147 (M+1).

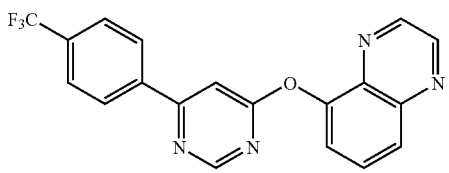

(b) 5-[6-(4-Trifluoromethyl-phenyl)-pyrimidin-4-yloxy]-quinoxaline. The title compound was prepared analogous to the procedure in Example 29 using 4-chloro-6-(4-trifluoromethyl-phenyl)-pyrimidine, (Example 2(a), Method A), (0.30 g, 1.2 mmol), quinoxalin-5-ol (0.19 g, 1.3 mmol) DMF (5 mL), and a 60% dispersion of sodium hydride in mineral oil (0.060 g, 1.5 mmol, Aldrich). Purification by flash chromatography (0→75% EtOAc/hexanes) gave the title compound as a white powder. MS (ESI, pos. ion) m/z: 369 (M+1).

EXAMPLE 32

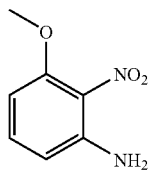

(a) 3-Methoxy-2-nitro-phenylamine. A mixture of 2-amino-3-nitrophenol (25.0 g, 162 mmol, Aldrich) and K₂CO₃ (27 g, 195 mmol) in DMF (65 ml) was stirred at room temperature for 1 h. Methyl iodide (12.2 mL, 195 mmol, Aldrich) was added and the reaction was stirred at room temperature for 30 h. The reaction was diluted with H₂O and extracted with EtOAc (3×). The combined organic layers were dried over Na₂SO₄, filtered and concentrated in vacuum. The dark-red solid was recrystallized from hexanes to yield the title compound as orange needles. MS (ESI, pos. ion) m/z: 169 (M+1).

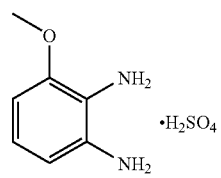

(b) 3-Methoxy-benzene-1,2-diamine sulfate. A mixture of 3-methoxy-2-nitro-phenylamine (4.6 g, 27 mmol), iron powder (10.7 g, 191 mmol, Aldrich), EtOH (130 mL) and H₂O (10 mL) was heated at 50° C. A solution of HCl (12.1 M, 1.7 mL) was added dropwise with stirring. The mixture was heated to reflux for 3 h and allowed to cool to room temperature. After neutralization with NaOH and filtration through Celiteo®, the solvent was removed in vacuum and the residue was partitioned between CH₂Cl₂ and satd aq. NaHCO₃. After extraction with CH₂Cl₂ (3×), the combined organic layers were concentrated. The residue was re-dissolved in of EtOH (30 mL) and treated with concentrated H₂SO₄ until no more precipitate was formed. The resulting solid was removed by filtration, washed with EtOH and dried in vacuum for 20 h at room temperature giving the title compound as an off-white powder. MS (ESI, pos. ion) m/z: 139 (M–HSO₄⁻).

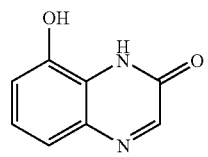

(c) 8-Methoxy-1H-quinoxalin-2-one and 5-Methoxy-1H-quinoxalin-2-one. A solution of 3-methoxy-benzene-1,2-diamine sulfate (4.1 g, 17 mmol) in EtOH (21 mL) and H₂O (48 mL) was neutralized by careful addition of solid NaHCO₃. After addition of ethyl glyoxylate solution (50% in toluene, 3.8 mL, 19 mmol, Fluka) the mixture was heated to reflux for 1 h. The reaction was allowed to cool and partitioned between satd aq. NH₄Cl and 25% i-PrOH/CHCl₃. The aqueous layer was extracted with 25% i-PrOH/CHCl₃ (3×). The combined organic layers were dried over Na₂SO₄, filtered and concentrated in vacuum. Purification by silica gel chromatography (0→2.5% MeOH/CH₂Cl₂) afforded 8-methoxy-1H-quinoxalin-2-one as an off-white powder [MS (ESI, pos. ion) m/z: 177 (M+1)] and 5-methoxy-1H-quinoxalin-2-one as an off-white powder [MS (ESI, pos. ion) m/z: 177 (M+1)].

(d) 8-Hydroxy-1H-quinoxalin-2-one. To a suspension of 8-methoxy-1H-quinoxalin-2-one (0.3 g, 1.7 mmol) in benzene (20 ml) was added AlCl₃ (2.0 g, 15.5 mmol, Aldrich) and the mixture was heated to reflux for 2 h. The reaction was allowed to cool to room temperature and quenched by careful addition of satd aq. NaHCO₃. The resulting mixture was extracted with 25% i-PrOH/CHCl₃ (5×). The combined organic layers were dried over Na₂SO₄, filtered and concentrated in vacuum. Purification by flash chromatography (0→8% MeOH/CH₂Cl₂) afforded the title compound as a brown powder. MS (ESI, pos. ion) m/z: 163 (M+1).

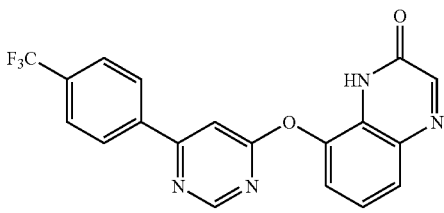

(e) 8-[6-(4-Trifluoromethyl-phenyl)-pyrimidin-4-yloxy]-1H-quinoxalin-2-one. To a suspension of 8-hydroxy-1H-quinoxalin-2-one (0.22 g, 1.4 mmol) and 1,8-diazabicyclo[5.4.0]undec-7-ene (0.25 mL, 1.6 mmol, Aldrich) in CH$_3$CN (20 mL) was added 4-chloro-6-(4-trifluoromethyl-phenyl)-pyrimidine, (Example 2(a), Method A), (0.43 g, 1.6 mmol). The solution was heated to reflux for 18 h, allowed to cool to room temperature and concentrated in vacuum. Purification by flash chromatography (0→80% EtOAc/hexanes) afforded the title compound as as an off-white powder. Mp:>265° C., MS (ESI, pos. ion) m/z: 385 (M+1).

EXAMPLE 33

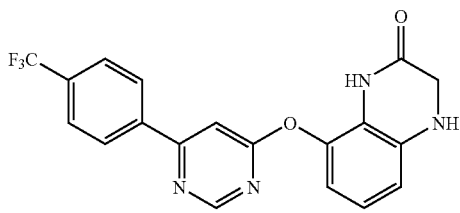

8-[6-(4-Trifluoromethyl-phenyl)-pyrimidin-4-yloxy]-3,4-dihydro-1H-quinoxalin-2-one. To a suspension of 8-[6-(4-trifluoromethyl-phenyl)-pyrimidin-4-yloxy]-1H-quinoxalin-2-one, (Example 32(e)), (0.25 g, 0.65 mmol) in EtOH (5 mL) was added sodium borohydride (0.11 mg, 2.8 mmol, Aldrich). After stirring at room temperature for 2 h, the mixture was quenched with satd aq. NaHCO$_3$ and extracted with 25% i-PrOH/CHCl$_3$ (3×). The combined organic layers were dried over Na$_2$SO$_4$, filtered and concentrated. Purification by flash chromatography (0→1.5% 2M NH$_3$/MeOH in CH$_2$Cl$_2$) gave the title compound as a light-yellow powder. Mp: 305° C., MS (ESI, pos. ion) m/z: 387 (M+1).

EXAMPLE 34

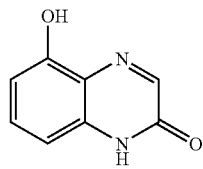

(a) 5-Hydroxy-1H-quinoxalin-2-one. The title compound was prepared analogous to the method used in Example 32(d) using 5-methoxy-1H-quinoxalin-2-one, (Example 32(c)), (0.3 g, 1.7 mmol) and AlCl$_3$ (2.0 g, 15.5 mmol, Aldrich) in benzene (20 mL). Purification by flash chromatography (0→8% MeOH/CH$_2$Cl$_2$) afforded the title compound as a brown powder. MS (ESI, pos. ion) m/z: 163 (M+1).

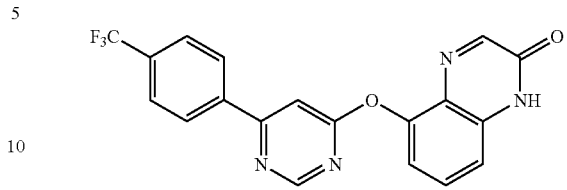

(b) 5-[6-(4-Trifluoromethyl-phenyl)-pyrimidin-4-yloxy]-1H-quinoxalin-2-one. The title compound was prepared analogous to the methods used in Example 32(e) using 4-chloro-6-(4-trifluoromethyl-phenyl)-pyrimidine, (Example 2(a), Method A), (0.38 g, 1.5 mmol), 5-hydroxy-1H-quinoxalin-2-one (0.20 g, 1.2 mmol) and 1,8-diazabicyclo[5.4.0]undec-7-ene (0.22 mL, 1.5 mmol, Aldrich) in CH$_3$CN (20 mL). Purification by flash chromatography (0→80% EtOAc/hexanes) afforded the title compound as an off-white powder. Mp>265° C., MS (ESI, pos. ion) m/z: 385 (M+1).

EXAMPLE 35

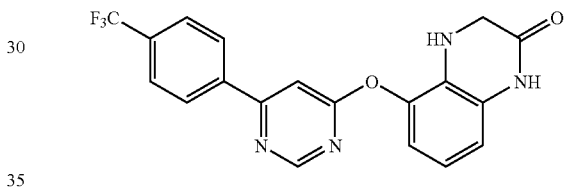

5-[6-(4-Trifluoromethyl-phenyl)-pyrimidin-4-yloxy]-3,4-dihydro-1H-quinoxalin-2-one. The title compound was prepared analogous to the methods used in Example 33 using 5-[6-(4-trifluoromethyl-phenyl)-pyrimidin-4-yloxy]-1H-quinoxalin-2-one, (Example 34(b)), (0.25 g, 0.65 mmol) and sodium borohydride (0.11 mg, 2.8 mmol, Aldrich) in EtOH (5 mL). Purification by flash chromatography (0→1.5% 2M NH$_3$/MeOH in CH$_2$Cl$_2$) gave the title compound as a light-yellow powder. Mp: 305° C., MS (ESI, pos. ion) m/z: 387 (M+1).

EXAMPLE 36

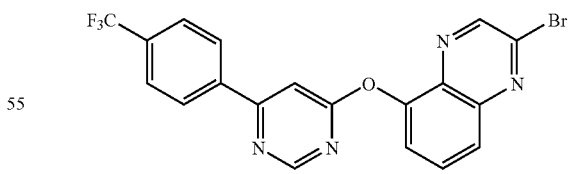

(a) 2-Bromo-5-[6-(4-trifluoromethyl-phenyl)-pyrimidin-4-yloxy]-quinoxaline. A mixture of 5-[6-(4-trifluoromethyl-phenyl)-pyrimidin-4-yloxy]-1H-quinoxalin-2-one, (Example 34(b)), (0.5 g, 1.3 mmol) and POBr$_3$ (10.0 g, 35 mmol, Alfa-Aesar) was heated at 105° C. for 2 h. The mixture was allowed to cool to room temperature, dissolved in CH$_2$Cl$_2$ and carefully treated with satd aq. NaHCO$_3$. The aqueous layer was extracted with CH$_2$Cl$_2$ (4×). The combined organic layers were dried over Na₂SO₄, filtered and concentrated. Purification by flash chromatography (0→1.5% 2M NH₃/MeOH in CH₂Cl₂) gave the title compound as a white powder. Mp: 81° C., MS (ESI, pos. ion) m/z: 447 (M+1).

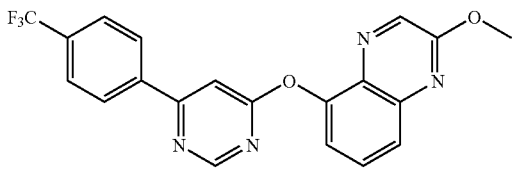

(b) 2-Methoxy-5-[6-(4-trifluoromethyl-phenyl)-pyrimidin-4-yloxy]-quinoxaline. To a solution of 2-bromo-5-[6-(4-trifluoromethyl-phenyl)-pyrimidin-4-yloxy]-quinoxaline (0.12 g, 0.27 mmol) in MeOH (5 mL) was added a solution of sodium methoxide (25% in MeOH, 0.090 ml, 0.33 mmol, Aldrich). The solution was stirred at room temperature for 24 h. Water was added and the product was extracted with 25% i-PrOH/CHCl₃ (4×). The combined organic layers were dried over Na₂SO₄, filtered and concentrated in vacuum. Purification by flash chromatography (0→25% EtOAc/hexanes) gave the title compound as white crystals (0.088 g, 81%). Mp: 162° C., MS (ESI, pos. ion) m/z: 399 (M+1).

EXAMPLE 37

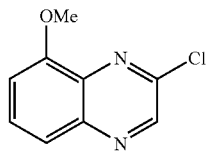

(a) 2-Chloro-8-methoxy-quinoxaline. A mixture of 8-methoxy-1H-quinoxalin-2-one, (Example 32(c)), (0.62 g, 3.5 mmol, and POCl₃ (6.0 mL, 64 mmol, Aldrich) was heated at 105° C. for 4 h. The reaction was allowed to cool to room temperature and concentrated in vacuum. The residue was partitioned between satd aq. NaHCO₃ and CH₂Cl₂ and stirred for 3 h. The aqueous layer was extracted with CH₂Cl₂ (3×). The combined organic layers were dried over Na₂SO₄ and filtered through silica gel, eluting with EtOAc. The solvent was removed in vacuum. MS (ESI, pos. ion) m/z: 195 (M+1).

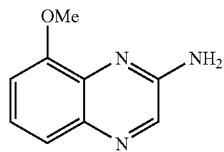

(b) 8-Methoxy-quinoxalin-2-ylamine. A mixture of 2-chloro-8-methoxy-quinoxaline (0.42 g, 2.2 mmol) and CuI (0.21 g, 1.1 mmol, Aldrich) in cond NH₄OH (1.5 mL, Baker) was heated at 140° C. in a microwave synthesizer for 10 min. The reaction was diluted with H₂O and the solids were removed by filtration, and washed with copious amounts of H₂O. The brown powder was dried in vacuum for 20 h at room temperature. MS (ESI, pos. ion) m/z: 176 (M+1).

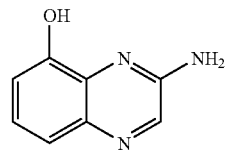

(c) 3-Amino-quinoxalin-5-ol. The title compound was prepared analogous to the methods used in Example 32(d) using 8-methoxy-quinoxalin-2-ylamine (0.12 g, 0.68 mmol) and AlCl₃ (0.82 g, 6.2 mmol, Aldrich) in benzene (10 mL). Purification by flash chromatography (0→7.5% MeOH/CH₂Cl₂) afforded the title compound as a brown powder. MS (ESI, pos. ion) m/z: 162 (M+1).

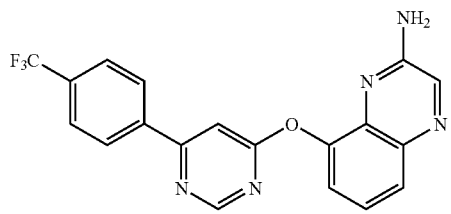

(d) 8-[6-(4-Trifluoromethyl-phenyl)-pyrimidin-4-yloxy]-quinoxa-2-ylamine. The title compound was prepared analogous to the methods used in Example 32(e) using 4-chloro-6-(4-trifluoromethyl-phenyl)-pyriridine, (Example 2(a), Method A), (0.13 g, 0.51 mmol), 3-amino-quinoxalin-5-ol (0.069 g, 0.43 mmol) and 1,8-diazabicyclo[5.4.0]undec-7-ene (0.077 mL, 0.51 mmol, Aldrich) in CH₃CN (5 mL). Purification by flash chromatography (0→75% EtOAc/hexanes) afforded the title compound as an off-white powder. Mp 215° C., MS (ESI, pos. ion) m/z: 384 (M+1).

EXAMPLE 38

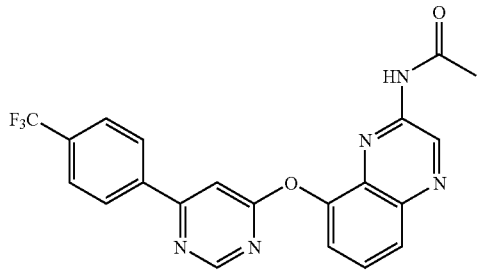

N-{8-[6-(4-Trifluoromethyl-phenyl)-pyrimidin-4-yloxy]-quinoxalin-2-yl}-acetamide. A mixture of 8-[6-(4-trifluoromethyl-phenyl)-pyrimidin-4-yloxy]-quinoxalin-2-ylamine, (Example 37(d)), (0.55 g, 1.4 mmol) and acetic anhydride (0.82 mL, 8.6 mmol, Aldrich) in toluene (15 mL) was heated at 75° C. for 4 h.

After stirring at room temperature for 16 h the mixture was treated with hexanes. The solids were removed by filtration, washed with hexanes and dried in vacuum for 24 h at room temperature to give the title compound as a tan powder. Mp: 237° C., MS (ESI, pos. ion) m/z: 426 (M+1).

EXAMPLE 39

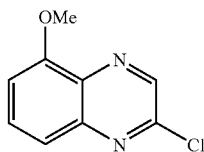

(a) 2-Chloro-5-methoxy-quinoxaline. The title compound was prepared analogous to the methods in Example 37(a) from 5-methoxy-1H-quinoxalin-2-one, (Example 32(c)), (0.47 g, 2.7 mmol) and POCl$_3$ (6.0 mL, 64 mmol, Aldrich). MS (ESI, pos. ion) m/z: 195 (M+1).

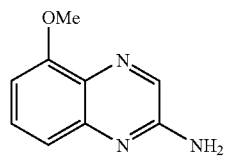

(b) 5-Methoxy-quinoxalin-2-ylamine. The title compound was prepared analogous to the method in Example 37(b) with 2-chloro-5-methoxy-quinoxaline (0.2 g, 1.0 mmol) and CuI (0.098 g, 0.52 mmol, Aldrich) in NH$_4$OH (1.5 mL, Baker) and 15 isolated as a tan powder. MS (ESI, pos. ion) m/z: 176 (M+1).

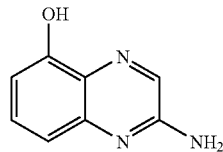

(c) 2-Amino-quinoxalin-5-ol. The title compound was prepared analogous to the methods used in Example 32(d) using 5-methoxy-quinoxalin-2-ylamine (0.15 g, 0.88 mmol) and AlCl$_3$ (1.1 g, 8.0 mmol, Aldrich) in benzene (10 mL). Purification by flash chromatography (0→7.5% MeOH/CH$_2$Cl$_2$) afforded the title compound as a brown powder. MS (ESI, pos. ion) m/z: 162 (M+1).

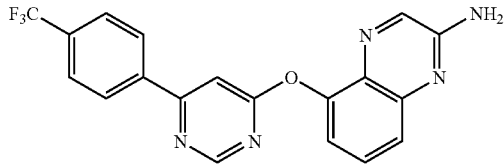

(d) 5-[6-(4-Trifluoromethyl-phenyl)-pyrimidin-4-yloxy]-quinoxalin-2-ylamine. The title compound was prepared analogous to the methods used in Example 32(e) using 4-chloro-6-(4-trifluoromethyl-phenyl)-pyrimidine, (Example 2(a), Method A), (0.2 g, 0.85 mmol), 2-amino-quinoxalin-5-ol (0.11 g, 0.71 mmol) and 1,8-diazabicyclo[5.4.0]undec-7-ene (0.13 mL, 0.85 mmol, Aldrich) in CH$_3$CN (10 mL). Purification by flash chromatography (0→75% EtOAc/hexanes) afforded the title compound as an off-white powder. Mp 225° C., MS (ESI, pos. ion) m/z: 384 (M+1).

EXAMPLE 40

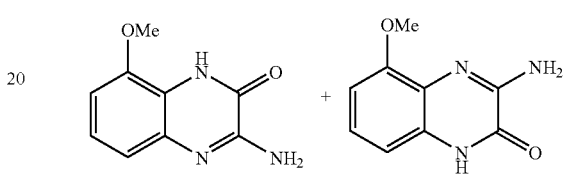

(a) 3-Amino-8-methoxy-1H-quinoxalin-2-one and 3-Amino-5-methoxy-1H-quinoxalin-2-one. To a suspension of 3-methoxy-benzene-1,2-diamine sulfate (Example 32(b)), (2.36 g, 10 mmol) in EtOH (15 mL) and H$_2$O (1 mL) was added NaHCO$_3$ (1.68 g, 20 mmol, J T Baker). When gas evolution was complete, ethoxy-imino-acetic acid ethyl ester (1.6 g, 11 mmol, prepared according to *J. Chem. Soc. Perkin. Trans.* 1, 1999, 1789.) was added and the mixture was stirred at room temperature for 16 h. The reaction was diluted with satd aq. NaHCO$_3$ and extracted with 25% i-PrOH/CHCl$_3$ (5×). The combined organic layers were dried over Na$_2$SO$_4$, filtered and concentrated in vacuum. Purification by flash chromatography (0→5% MeOH/CH$_2$Cl$_2$) afforded 3-amino-8-methoxy-1H-quinoxalin-2-one as a light-brown powder [0.75 g, 39%, MS (ESI, pos. ion) m/z: 192 (M+1)] and 3-amino-5-methoxy-1H-quinoxalin-2-one as a light-brown powder [MS (ESI, pos. ion) m/z: 192 (M+1)].

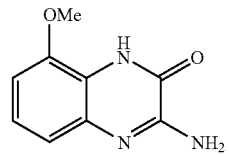

(b) 3-Amino-8-hydroxy-1H-quinoxalin-2-one. The title compound was prepared analogous to the methods used in Example 32(d) using 3-amino-8-methoxy-1H-quinoxalin-2-one (0.75 g, 3.9 mmol) and AlCl$_3$ (4.7 g, 35 mmol, Aldrich) in benzene (50 mL). The reaction was quenched by careful addition of satd aq. NaHCO$_3$ and the solids were removed by filtration through Celite®. The filter cake was washed with H$_2$O and DMSO to remove the product and the filtrate was concentrated in vacuum. The DMSO was removed by azeotropic distillation with H$_2$O to give the title compound. MS (ESI, pos. ion) m/z: 178 (M+1).

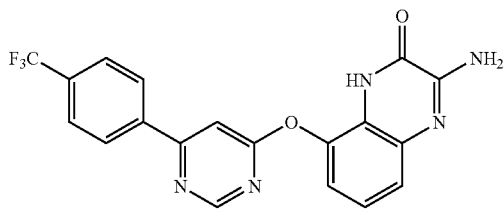

(c) 3-Amino-8-[6-(4-trifluoromethyl-phenyl)-pyrimidin-4-yloxy]-1H-quinoxalin-2-one. The title compound was prepared analogous to the methods used in Example 32(e) using 4-chloro-6-(4-trifluoromethyl-phenyl)-pyrimidine (1.0 g, 3.9 mmol), 3-amino-8-hydroxy-1H-quinoxalin-2-one (0.69 g, 3.9 mmol) and 1,8-diazabicyclo[5.4.0]undec-7-ene (0.70 mL, 4.7 mmol, Aldrich) in CH$_3$CN (50 mL). Purification by flash chromatography (0→2.5% MeOH/CH$_2$Cl$_2$) afforded the title compound as a white powder. Mp 288° C., MS (ESI, pos. ion) m/z: 400 (M+1).

EXAMPLE 41

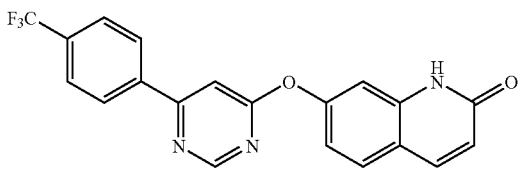

7-[6-(4-Trifluoromethyl-phenyl)-pyrimidin-4-yloxy]-1H-quinolin-2-one. The title compound was prepared analogous to the methods used in Example 32(e) using 4-chloro-6-(4-trifluoromethyl-phenyl)-pyrimidine, (Example 2(a), Method A), (0.50 g, 1.9 mmol), 7-hydroxy-1H-quinolin-2-one (0.37 g, 2.3 mmol, prepared according to *Synthesis* 1997, 87-90) and 1,8-diazabicyclo[5.4.0]undec-7-ene (0.35 mL, 2.3 mmol, Aldrich) in CH$_3$CN (40 mL). Purification by flash chromatography (0→2.5% MeOH/CH$_2$Cl$_2$) afforded the title compound as an off-white powder. Mp 288° C. MS (ESI, pos. ion) m/z: 384 (M+1).

EXAMPLE 42

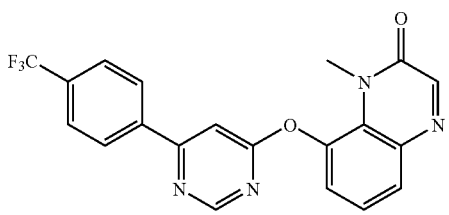

1-Methyl-8-[6-(4-trifluoromethyl-phenyl)-pyrimidin-4-yloxy]-1H-quinoxalin-2-one. To a mixture of 8-[6-(4-trifluoromethyl-phenyl)-pyrimidin-4-yloxy]-1H-quinoxalin-2-one, (Example 32(e)), (0.10 g, 0.26 mmol) and K$_2$CO$_3$ (0.043 g, 0.31 mmol, Aldrich) in DMF (1 mL) was added iodomethane (0.019 mL, 0.31 mmol, Aldrich). The mixture was stirred at room temperature for 20 h, diluted with water and extracted with 25% i-PrOH/CHCl$_3$ (3×). After being concentrated in vacuum, the residue was purified by flash chromatography (0→2% 2M NH$_3$ in MeOH/CH$_2$Cl$_2$) to afford the title compound as an off-white amorphous solid. Mp:158° C. MS (ESI, pos. ion) m/z: 399 (M+1).

EXAMPLE 43

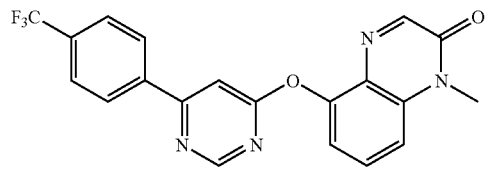

1-Methyl-5-[6-(4-trifluoromethyl-phenyl)-pyrimidin-4-yloxy]-1H-quinoxalin-2-one. The title compound was prepared analogous to the methods used in Example 42 using 5-[6-(4-trifluoromethyl-phenyl)-pyrimidin-4-yloxy]-1H-quinoxalin-2-one, (Example 34(b)), (0.10 g, 0.26 mmol), K$_2$CO$_3$ (0.043 g, 0.31 mmol, Aldrich) and iodomethane (0.019 mL, 0.31 mmol, Aldrich) in DMF (1 mL). Purification by flash chromatography (0→5% 2M NH$_3$ in MeOH/CH$_2$Cl$_2$) afforded the title compound as a white amorphous solid. Mp: 258° C. MS (ESI, pos. ion) m/z: 399 (M+1)

EXAMPLE 44

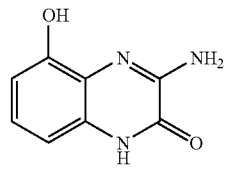

(a) 3-Amino-5-hydroxy-1H-quinoxalin-2-one. The title compound was prepared analogous to the methods used in Example 32(d) using 3-amino-5-methoxy-1H-quinoxalin-2-one, (Example 40(a)), (0.47 g, 2.5 mmol) and AlCl$_3$ (0.97 g, 7.4 mmol, Aldrich) in benzene (25 mL). The reaction was quenched by careful addition of satd aq. NaHCO$_3$ and extracted with 25% i-PrOH/CHCl$_3$ (5×). The combined organic layers were dried over Na$_2$SO$_4$, filtered and concentrated in vacuum to afford the title compound as a brown powder. MS (ESI, pos. ion) m/z: 178 (M+1).

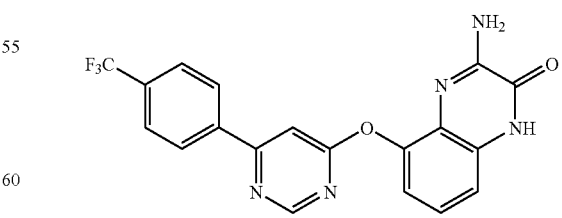

(b) 3-Amino-5-[6-(4-trifluoromethyl-phenyl)-pyrimidin-4-yloxy]-1H-quinoxalin-2-one. A solution of 4-chloro-6-(4-trifluoromethyl-phenyl)-pyrimidine, (Example 2(a), Method A), (0.49 g, 1.9 mmol), 3-amino-5-hydroxy-1H-quinoxalin- 2-one (0.33 g, 1.9 mmol) and K$_2$CO$_3$ (0.31 g, 2.3 mmol, Aldrich) in DMSO (5 mL) was stirred at room temperature for 64 h. The mixture was then heated at 100° C. for 2 h, allowed to cool to room temperature, diluted with H$_2$O, and the solids were collected by filtration. The solids were purified by flash silica gel chromatography (0→2.5% 2M.NH$_3$ in MeOH/CH$_2$Cl$_2$) to afford the title compound as an off-white amorphous solid. Mp: 334° C., MS (ESI, pos. ion) m/z: 400 (M+1).

EXAMPLE 45

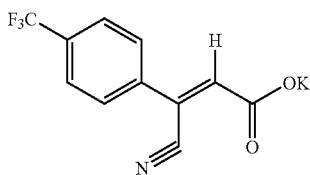

(a) Potassium (Z)-3-(4-trifluoromethylphenyl)-3-cyanopropenoate. (Analogous to the procedure of Dan, W. D. and Blum, D. M. *J. Org. Chem*. 1993, 58, 7916-7917). Glyoxylic acid monohydrate (111.86 g, 1.22 mol, Aldrich) was added portion wise to a suspension of potassium carbonate (284.4 g, 2.06 mol) in methanol (1.6 L) with stirring and cooling with a water bath. To the light-brown suspension was then added 4-trifluoromethylphenylacetonitrile (150 g, 0.81 mol, Aldrich) in small portions, the mixture was stirred for 5 h at room temperature, and the resulting thick solid precipitate was filtered and washed with dichloromethane. Concentration of the filtrate to a 600 mL volume led to the precipitation of additional amount of solid, which was filtered and washed with dichloromethane. The solids were combined and then suspended in cold water (4 L) to remove the excess of potassium carbonate. The precipitate was filtered, washed with water and air-dried to provide the title compound as a white solid, which was used in the next step without additional purification. MS (ESI, pos. ion) m/z: 279 (M).

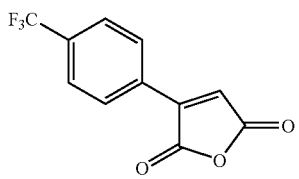

(b) 4-Trifluoromethylphenylmaleic anhydride. (Analogous to the procedure of Dan, W. D. and Blum, D.M. *J. Org. Chem*. 1993, 58, 7916-7917). Potassium (Z)-3-(4-trifluoromethylphenyl)-3-cyanopropenoate (100 g, 358 mmol) was dissolved in 88% formic acid (600 mL, Aldrich) containing cond sulfuric acid (45 mL) and the mixture heated at reflux for 3 h. The reaction mixture was then allowed to cool to room temperature and poured into ice water (1 L). The resulting solid was filtered, washed with water and air dried to give the title compound as a pale-yellow solid, which was used in the next step without additional purification. MS (ESI, pos. ion) m/z: 243 (M+1).

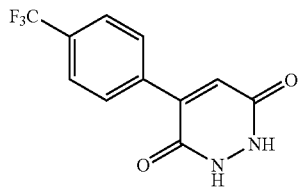

(c) 4-(4-Trifluoromethylphenyl)-1,2-dihydropyridazine-3,6-dione. (Analogous to the procedure of Augustin, M. and Reinemann, P. Z. *Chem*. 1973, 13, 12-13). 4-Trifluoromethylphenylmaleic anhydride (57.2 g, 235.8 mmol) was added to a mixture of water (325 mL) and acetic acid (88 mL), followed by the dropwise addition of hydrazine hydrate (11.44 mL, 235.8 mmol, Aldrich) with stirring at room temperature. To the resulting pale-yellow suspension was then added dropwise cond sulfuric acid (177 mL) with stirring and cooling in an ice bath, which led to the formation of a thick paste. The reaction mixture was heated at 100-115° C. for 3 h with stirring, and then cooled in an ice bath. The precipitate was washed with water until the filtrate showed neutral pH, and then was washed with diethyl ether (2×100 mL) and air-dried to give the title compound as a white solid, which was used in the next step without additional purification. MS (ESI, pos. ion) m/z: 257 (M+1).

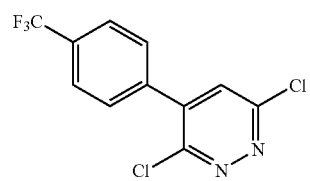

(d) 3,6-Dichloro-4-(4-trifluoromethylphenyl)pyridazine. (Analogous to the procedure of Augustin, M. and Reinemann, P. Z. *Chem*. 1973, 13, 12-13). A mixture of 4-(4-trifluoromethylphenyl)-1,2-dihydropyridazine-3,6-dione (25.6 g, 100 mmol) and phosphorus oxychloride (192 mL) was heated at reflux for 2 h with stirring under nitrogen atmosphere. The reaction mixture was allowed to cool to room temperature and poured in small portions with vigorous stirring into a mixture of water and crushed ice (2.6 L). The product separated as a white precipitate, which was filtered, washed with water (3×50 mL), dried under vacuum and recrystallized from dioxane/methanol to give the title compound as a white solid. MS (ESI, pos. ion) m/z: 293 (M+1).

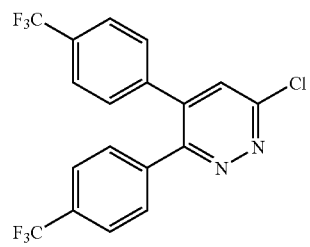

(e) 6-Chloro-3,4-bis-(4-trifluoromethyl-phenyl)-pyridazine. A flask containing 3,6-dichloro-4-(4-trifluoromethyl-phenyl)-pyridazine (996 mg, 3.4 mmol), 4-(trifluoromethyl) phenylboronic acid (647 mg, 3.4 mmol, Aldrich), $Na_2CO_3$ (1.81 g, 17 mmol, Mallinkrodt) and tetrakis(triphenylphosphine)palladium (0) (120 mg, 0.1 mmol, Strem) was evacuated and purged with $N_2$ three times. To the flask was added DME (24 mL) and $H_2O$ (8 mL). The reaction was equipped with an argon balloon and heated at 90° C. for 20 h. The reaction was allowed to cool to room temperature and the solvent was removed in vacuum. The residue was partitioned between $H_2O/CH_2Cl_2$ and the layers were separated. The aqueous layer was extracted with $CH_2Cl_2$ and the combined organic layers were evaporated onto $SiO_2$. Purification by silica gel chromatography with EtOAc/hexanes (0:1→1:9) as eluant afforded the title compound as a tan amorphous solid. MS (ESI, pos. ion) m/z: 403 (M+1).

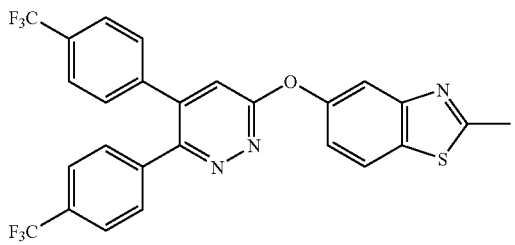

(f) 5-[5,6-Bis-(4-trifluoromethyl-phenyl)-pyridazin-3-yloxy]-2-methyl-benzothiazole. To a solution of 6-chloro-3,4-bis-(4-trifluoromethyl-phenyl)-pyridazine (177 mg, 0.4 mmol) and 2-methyl-5-benzothiazolol (72 mg, 0.4 mmol) in N,N-dimethylacetamide (5 mL) was added NaH (25 mg, 0.6 mmol, 60% suspension in mineral oil, Aldrich) and the mixture was stirred at room temperature for 6 h. The solvent was removed in vacuum and the residue was partitioned between brine/EtOAc. The aqueous layer was separated and extracted with EtOAc. The combined organic layers were evaporated onto $SiO_2$ and purified by flash silica gel chromatography with 2M $NH_3$ in $MeOH/CH_2Cl_2$ (0:1→3:197) as eluant. A second purification by silica gel chromatography with EtOAc/hexanes (0:1→1:4) as eluant gave the title compound as a pale yellow amorphous solid. Mp: 175-177° C. MS (ESI, pos ion.) m/z: 532 (M+1).

EXAMPLE 46

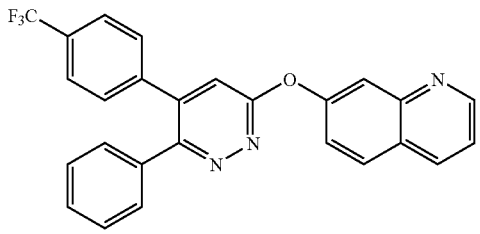

7-[6-Phenyl-5-(4-trifluoromethyl-phenyl)-pyridazin-3-yloxy]-quinoline. To a solution of 6-chloro-3-phenyl-4-(4-trifluoromethyl-phenyl)-pyridazine, (Example 13 (e)), (106 mg, 0.3 mmol) and 7-hydroxyquinoline (55 mg, 0.4 mmol, Acros) in DMF (2.5 mL) was added NaH (22 mg, 0.6 mmol, 60% suspension in mineral oil, Aldrich) and the mixture was stired at room temperature for 15 h. The reaction mixture was then heated at 50° C. for another 28 h, allowed to cool to room temperature and the solvent removed in vacuum. The residue was partitioned between $EtOAc/H_2O$ and the aqueous layer was extracted with EtOAc. The combined organic layers were evaporated onto $SiO_2$ and purified by flash silica gel chromatography with EtOAc/hexanes (0:1→3:7) as eluant to give the title 15 compound as an off-white amorphous solid. Mp: 178-183° C. MS (ESI, pos ion.) m/z: 444 (M+1).

EXAMPLE 47

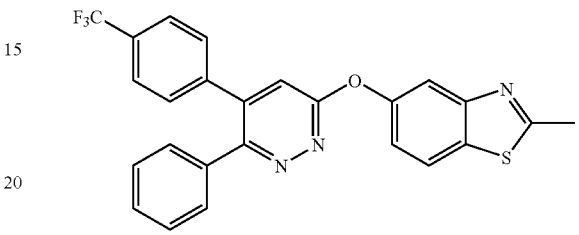

2-Methyl-5-[6-phenyl-5-(4-trifluoromethyl-phenyl)-pyridazin-3-yloxy]-benzothiazole. The title compound was prepared analogous to the procedure used to prepare Example 45(f), using 2-methyl-5-benzothiazolol (117 mg, 0.7 mmol, Aldrich), 6-chloro-3-phenyl-4-(4-trifluoromethyl-phenyl)-pyridazine, (Example 13(e)), (197 mg, 0.6 mmol) and NaH (37 mg, 0.9 mmol, 60% suspension in mineral oil, Aldrich) in DMF (5 mL). Purification by flash silica gel chromatography with 2 M $NH_3$ in $MeOH/CH_2Cl_2$ (0:1→1:49) as eluant gave the title compound as a pale-orange amorphous solid. Mp: 208-209° C. MS (ESI, pos ion.) m/z: 464 (M+1).

EXAMPLE 48

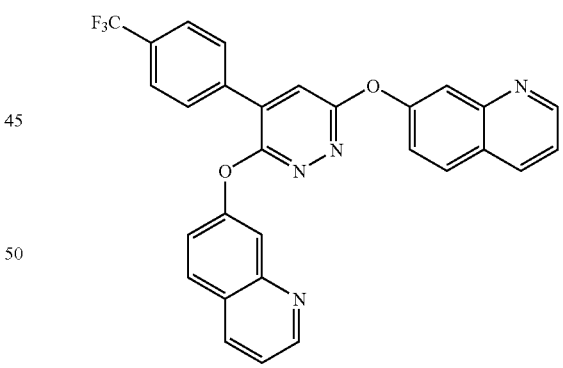

7-[(6-(7-Quinolinyloxy)-4-(4(trifluoromethyl)phenyl)-3-pyridazinyl)oxy]-quinoline. To a solution of 3,6-dichloro-4-(4-trifluoromethyl-phenyl)-pyridazine, (Example 45(d)), (441 mg, 1.5 mmol) and 7-hydroxyquinoline (441 mg, 3.0 mmol, Acros) in DMF (10 mL) was added 60% NaH (150 mg, 3.8 mmol) and the mixture was heated at 80C for 14 h. The solvent was removed in vacuum, the residue was partitioned between $EtOAc/H_2O$ and the aqueous layer was extracted with EtOAc. The combined organic layers were evaporated onto $SiO_2$ and purified by flash silica gel chromatography with EtOAc/hexanes (0:1→1:0) as eluant to give the title compound as an off-white amorphous solid. Mp: 158-162° C. MS (ESI, pos ion.) m/z: 511 (M+1).

EXAMPLE 49

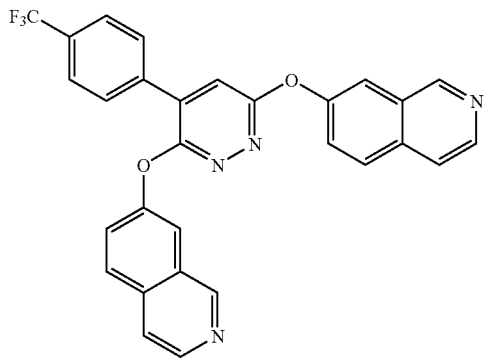

7-[(7-Isoquinolinyloxy)-4-(4-(trifluoromethyl)phenyl)-3-pyridazinyl)oxy]-isoquinoline. The title compound was prepared analogous to the procedure used to prepare Example 48, using 3,6-dichloro-4-(4-trifluoromethyl-phenyl)-pyridazine, (Example 45(d)), (443 mg, 1.5 mmol), 7-hydroxy-isoquinoline (444 mg, 3.1 mmol, Lancaster) and NaH (151 mg, 3.8 mmol, 60% suspension in mineral oil, Aldrich) in DMF (10 mL). Purification by flash silica gel chromatography with 2M $NH_3$ in MeOH/$CH_2Cl_2$ (0:1→1:24) as eluant gave the title compound as a tan amorphous solid. Mp: 82-86° C. MS (ESI, pos ion.) m/z: 511 (M+1).

EXAMPLE 50

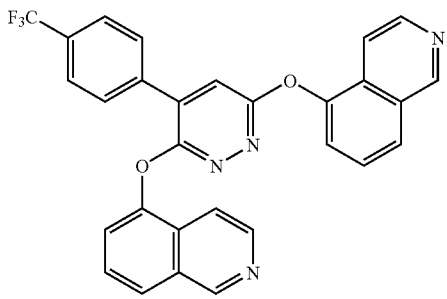

5-((6-(5-Isoquinolinyloxy)-4-(4(trifluoromethyl)phenyl)-3-pyridazinyl)oxy)-isoquinoline. To a solution of 3,6-dichloro-4-(4-trifluoromethyl-phenyl)-pyridazine, (Example 45(d)), (100 mg, 0.3 mmol) and 5-hydroxyisoquinoline (112 mg, 0.7 mmol, Aldrich) in DMF (2.5 mL) was added NaH (32 mg, 0.8 mmol, 60 % suspension in mineral oil, Aldrich) and the reaction mixture was heated at 140° C. for 10 min in a microwave synthesizer. The reaction mixture was allowed to cool to room temperature and partitioned between $H_2O$/$CH_2Cl_2$. The aqueous layer was extracted with $CH_2Cl_2$ and the combined organic layers were concentrated in vacuum. The residue was evaporated onto $SiO_2$ and purified by flash silica gel chromatography with 2M NH3 in MeOH/$CH_2Cl_2$ (0:1→1:49) as eluant to give the title compound as an white amorphous solid. Mp: 197-199° C. MS (ESI, pos ion.) m/z: 511 (M+1).

EXAMPLE 51

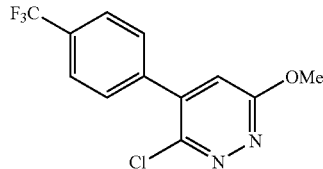

(a) 3-Chloro-6-methoxy-4-(4-trifluoromethyl-phenyl)-pyridazine. To a solution of 3,6-dichloro-4-(4-trifluoromethyl-phenyl)-pyridazine, (Example 45(d)), (4.0 g, 14 mmol) in MeOH (50 mL) was added NaOH (607 mg, 15 mmol) and the mixture was stirred at room temperature for 16 h. The solvent was removed in vacuum and the residue was partitioned between $H_2O$/$CHCl_3$. The aqueous layer was extracted with $CHCl_3$ and the combined organic layers were evaporated onto $SiO_2$. Purification by flash silica gel chromatography with EtOAc/hexanes (0:1→1:9) as eluant gave the title compound as a white amorphous solid. MS (ESI, pos ion.) m/z: 289 (M+1).

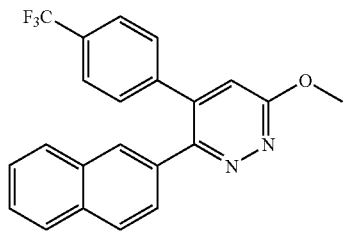

(b) 6-Methoxy-3-naphthalen-2-yl-4-(4-trifluoromethyl-phenyl)-pyridazine. A mixture of 3-chloro-6-methoxy-4-(4-trifluoromethyl-phenyl)-pyridazine (434 mg, 1.5 mmol), 2-napthaleneboronic acid (314 mg, 1.8 mmol, Aldrich), $Na_2CO_3$ (640 mg, 6.0 mmol, Mallinkrodt) and tetrakis(triphenylphosphine)palladium (0) (125 mg, 0.11 mmol, Strem) in $H_2O$ (1 mL) and DME (3 mL) was heated at 140C for 30 min in a microwave synthesizer. The reaction mixture was partitioned between $H_2O$/$CH_2Cl_2$ and the aqueous layer was extracted with $CH_2Cl_2$. The combined organic layers were evaporated onto $SiO_2$ and purified by flash silica gel chromatography with EtOAc/hexanes (0:1→1:9) as eluant to give the title compound as a colorless foam. MS (ESI, pos ion.) m/z: 381 (M+1).

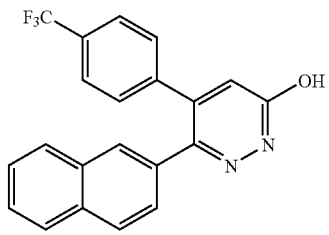

(c) 6-Naphthalen-2-yl-5-(4-trifluoromethyl-phenyl)-pyridazin-3-ol. A mixture of 6-methoxy-3-naphthalen-2-yl-4-(4-trifluoromethyl-phenyl)-pyridazine (389 mg, 1.02 mmol) and 47% HI (3 mL) in MeOH (5 mL) was heated at 65° C.

for 1.5 h then at 75° C. for 6 h. The mixture was allowed to cool to room temperature and the resulting precipitate was filtered, washed with H₂O and dried in vacuum to give the title compound as a white crystalline solid. MS (ESI, pos ion.) m/z: 367 (M+1).

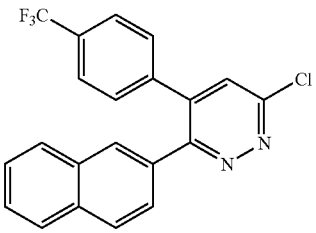

(d) 6-Chloro-3-naphthalen-2-yl-4-(4-trifluoromethyl-phenyl)-pyridazine. A flask charged with 6-naphthalen-2-yl-5-(4-trifluoromethyl-phenyl)-pyridazin-3-ol (300 mg, 0.8 mmol) and POCl₃ (5.0 mL, 54 mmol, Aldrich) was heated at 105° C. for 3.5 h. The reaction was allowed to cool to room temperature and the excess of POCl₃ was removed in vacuum. The residue was dissolved in CH₂Cl₂ and ice was added. The layers were separated and the aqueous layer was extracted with CH₂Cl₂. The combined organic layers were washed with diluted NaHCO₃, dried over Na₂SO₄, filtered and the solvent evaporated in vacuum. Purification of the residue by silica gel chromatography with EtOAc/hexanes (0:1→1:2) afforded the title compound. MS (ESI, pos ion.) m/z: 385 (M+).

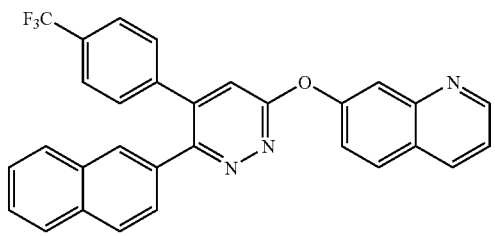

(e) 7-[6-Naphthalen-2-yl-5-(4-trifluoromethyl-phenyl)-pyridazin-3-yloxy]-quinoline. The title compound was prepared analogous to the procedure used to prepare Example 46, using 6-chloro-3-naphthalen-2-yl-4-(4-trifluoromethyl-phenyl)-pyridazine (251 mg, 0.7 mmol), 7-hydroxyquinoline (98 mg, 0.7 mmol, Acros) and NaH (37 mg, 0.9 mmol, 60% suspension in mineral oil, Aldrich) in DMF (2.5 mL). Purification by flash silica gel chromatography with EtOAc/hexanes (0:1→1:2) as eluant gave the title compound as an white amorphous solid. Mp: 194-195° C. MS (ESI, pos ion.) m/z: 494 (M+1).

EXAMPLE 52

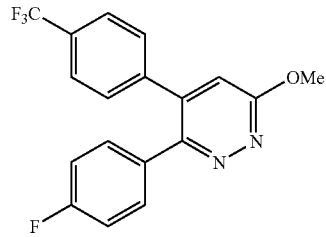

(a) 3-(4-Fluoro-phenyl)-6-methoxy-4-(4-trifluoromethyl-phenyl)-pyridazine. The title compound was prepared analogous to the procedure used to prepare Example 51(b), using 3-chloro-6-methoxy-4-(4-trifluoromethyl-phenyl)-pyridazine, (Example 51(a)), (500 mg, 1.7 mmol), 4-fluorophenylboronic acid (287 mg, 2.1 mmol, Aldrich), Na₂CO₃ (694 mg, 6.5 mmol, Mallinkrodt) and tetrakis(triphenylphosphine)palladium (0) (145 mg, 0.1 mmol, Strem) in H₂O (1.5 mL) and DME (3.5 mL), and heating at 150° C. for 25 min in a microwave synthesizer. This procedure was run in duplicate. The reaction mixtures were combined, partitioned between EtOAc/H₂O and the aqueous layer was extracted with EtOAc. The combined organic layers were evaporated onto SiO₂ and purified by flash silica gel chromatography with EtOAc/hexanes (0:1→3:17) as eluant to give the title compound as an off-white amorphous solid. MS (ESI, pos ion.) m/z: 349 (M+1).

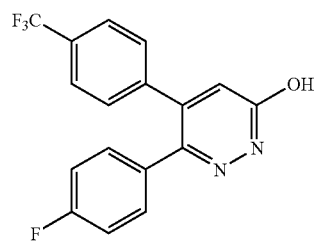

(b) 6-(4-Fluoro-phenyl)-5-(4-trifluoromethyl-phenyl)-pyridazin-3-ol. The title compound was prepared analogous to the procedure used to prepare Example 51(c), using 3-(4-fluoro-phenyl)-6-methoxy-4-(4-trifluoromethyl-phenyl)-pyridazine (384 mg, 1.1 mmol), 47% HI (3 mL) and MeOH (3 mL) and heating to 75° C. for 14 h afforded the title compound as a white amorphous solid. MS (ESI, pos ion.) m/z: 335 (M+1); MS (ESI, neg ion.) m/z: 333 (M−1).

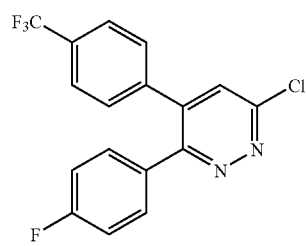

(c) 6-Chloro-3-(4-fluoro-phenyl)-4-(4-trifluoromethyl-phenyl)-pyridazine. The title compound was prepared analogous to the procedure used to prepare Example 51(d), using 6-(4-fluoro-phenyl)-5-(4-trifluoromethyl-phenyl)-pyridazin-3-ol (300 mg, 0.9 mmol) and POCl$_3$ (5.0 mL, 54 mmol, Aldrich). The crude material was passed through a short pad of SiO$_2$ eluting with EtOAc to give the title compound as a light yellow oil. MS (ESI, pos ion.) m/z: 353 (M+1).

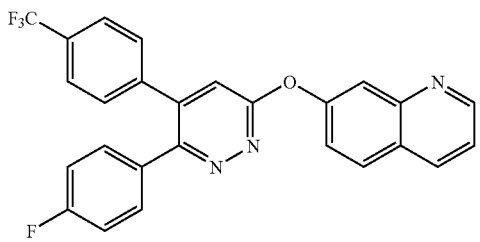

(d) 7-[6-(4-Fluoro-phenyl)-5-(4-trifluoromethyl-phenyl)-pyridazin-3-yloxy]-quinoline. The title compound was prepared analogous to the procedure used to prepare Example 46, using 6-chloro-3-(4-fluoro-phenyl)-4-(4-trifluoromethyl-phenyl)-pyridazine (315 mg, 0.9 mmol), 7-hydroxyquinoline (128 mg, 0.9 mmol, Acros) and NaH (50 mg, 1.25 mmol, 60% suspension in mineral oil, Aldrich) in DMF (2.5 mL). Purification by flash silica gel chromatography with EtOAc/hexanes (0:1→1:1) as eluant gave the title compound as a white amorphous solid. Mp: 191-194° C. MS (ESI, pos ion.) m/z: 462 (M+1).

EXAMPLE 53

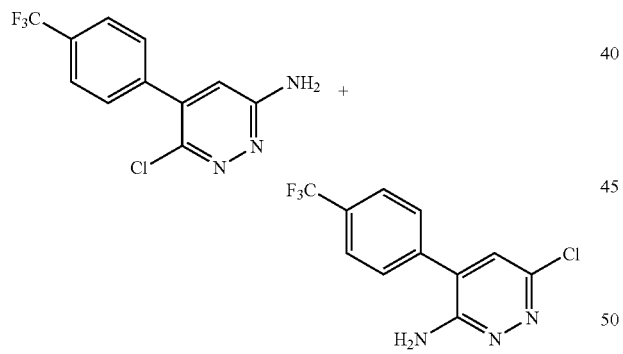

(a) 6-Chloro-5-(4-trifluoromethyl-phenyl)-pyridazin-3-ylamine and 6-Chloro-4-(4-trifluoromethyl-phenyl)-pyridazin-3-ylamine. A mixture of 3,6-dichloro-4-(4-trifluoromethyl-phenyl)-pyridazine, (Example 45(d)), 28-30% aq. NH4OH (13 mL, Baker) and EtOH (1 mL) was heated at 130-140° C. with stirring in a sealed tube for 22 h. The reaction mixture was allowed to cool to room temperature and the light precipitate was filtered, washed with water and dried in the air. The dried precipitate was suspended in Et$_2$O and filtered to give 0.814 g (40%) of 6-chloro-5-(4-trifluoromethyl-phenyl)-pyridazin-3-ylamine as pale-yellow needles. MS (ESI, pos ion.) m/z: 274 (M+1). The filtrate was evaporated in vacuum and the residue purified by flash SiO$_2$ chromatography with EtOAc/hexanes (1:1→1:0) as eluant to give the fast running 6-chloro-4-(4-trifluoromethyl-phenyl)-pyridazin-3-ylamine as a pale-yellow solid. MS (ESI, pos ion.) m/z: 274 (M+1). From the second fraction was isolated 6-chloro-5-(4-trifluoromethyl-phenyl)-pyridazin-3-ylamine.

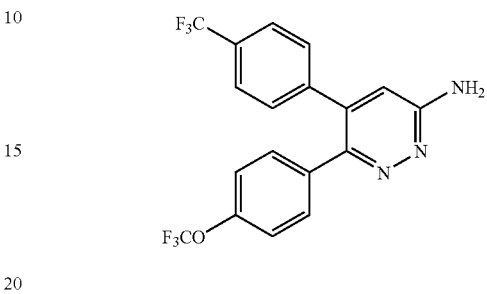

(b) 6-(4-Trifluoromethoxy-phenyl)-5-(4-trifluoromethyl-phenyl)-pyridazin-3-ylamine. A mixture containing 6-chloro-5-(4-trifluoromethyl-phenyl)-pyridazin-3-ylamine from step (a) above (531 mg, 1.9 mmol), 4-(trifluoromethoxy)phenyl-boronic acid (889 mg, 4.3 mmol, Aldrich), Na$_2$CO$_3$ (955 mg, 9.0 mmol, Mallinkrodt) and dichlorobis(triphenylphosphine)palladium (II) (220 mg, 0.3 mmol, Aldrich) in DME (14 mL), H$_2$O. (6 mL) and EtOH (4 mL) was heated at 80° C. with stirring under N$_2$ for 15 h. The reaction was allowed to cool to room temperature, partitioned between EtOAc/H$_2$O and the layers were separated. The aqueous layer was extracted with EtOAc and the combined organic layers were evaporated onto SiO$_2$. Purification by silica gel chromatography with EtOAc/hexanes (0:1→1:0) as eluant afforded the title compound as a tan amorphous solid. MS (ESI, pos. ion) nz/z: 400 (M+1).

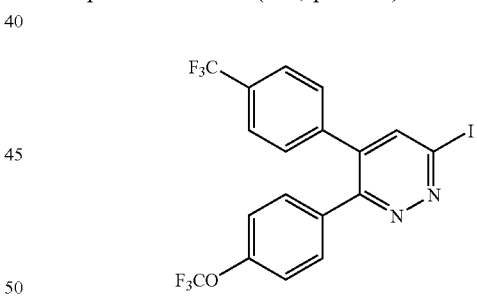

(c) 6-Iodo-3-(4-trifluoromethoxy-phenyl)-4-(4-trifluoromethyl-phenyl)-pyridazine. A mixture of 6-(4-trifluoromethoxy-phenyl)-5-(4-trifluoromethyl-phenyl)-pyridazin-3-ylamine (598 mg, 1.5 mmol), cesium iodide (400 mg, 1.5 mmol, Aldrich), iodine (203 mg, 0.8 mmol, Aldrich), CuI (95 mg, 0.5 mmol, Aldrich) and isoamyl nitrite (1.2 mL, 8.9 mmol, Aldrich)) in DME (10 mL) was heated at 60° C. for 1 h. The reaction mixture was allowed to cool to room temperature and filtered. The filtrate was diluted with toluene (50 mL) and washed with 25% NH$_3$, 5% Na$_2$S$_2$O$_3$, 5% NaCl and dried over MgSO$_4$. The solution was filtered, evaporated onto SiO$_2$ and purified by silica gel chromatography with EtOAc/hexanes (0:1→1:4) as eluant to yield the title compound as a colorless oil. MS (ESI, pos. ion) m/z: 511 (M+1).

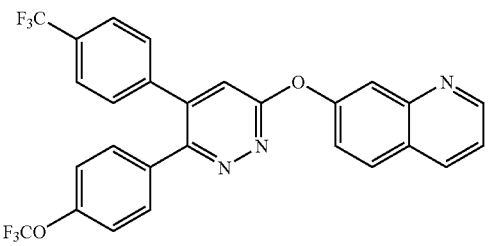

(d) 7-[6-(4-Trifluoromethoxy-phenyl)-5-(4-trifluoromethyl-phenyl)-pyridazin-3-yloxy]-quinoline. The title compound was prepared analogous to the procedure used to prepare Example 46, using 6-iodo-3-(4-trifluoromethoxy-phenyl)-4-(4-trifluoromethyl-phenyl)-pyridazine (377 mg, 0.7 mmol), 7-hydroxyquinoline (130 mg, 0.9 mmol, Acros) and NaH (33 mg, 0.8 mmol, 60% suspension in mineral oil, Aldrich) in DMF (4 mL). Purification by flash silica gel chromatography with EtOAc/hexanes (0:1→7:13) as eluant gave the title compound as a white amorphous solid. MS (ESI, pos ion.) m/z: 528 (M+1).

EXAMPLE 54

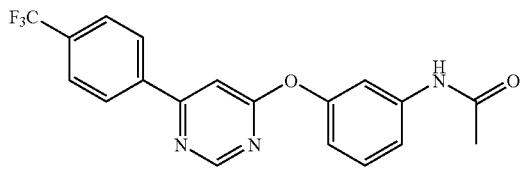

N-{3-[6-(4-Trifluoromethyl-phenyl)-pyrimidin-4-yloxy]-phenyl}-acetamide. A mixture of 4-chloro-6-(4-trifluoromethyl-phenyl)-pyrimidine, (Example 2(a), Method A), (520 mg, 2.0 mmol), 3-acetamidophenol (320 mg, 2.1 mmol, Aldrich) and $K_2CO_3$ (368 mg, 2.7 mmol) in DMF (10 mL) was heated at 80° C. for 8 h. The mixture was allowed to cool to room temperature, poured into $H_2O$, extracted with EtOAc and the combined organic layers were evaporated onto $SiO_2$. Purification by flash silica gel chromatography with EtOAc/hexanes (0:1→2:3) as eluant gave the title compound as a white amorphous solid. Mp: 202-205° C. MS (ESI, pos ion.) m/z: 374 (M+1).

EXAMPLE 55

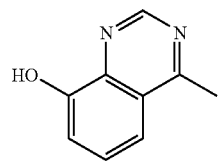

(a) 4-Methyl-quinazolin-8-ol. A mixture of 2'-amino-3'-hydroxyacetophenone (500 mg, 3.3 mmol, TCI America) and formamide (1.0 mL, 25 mmol, Aldrich) was heated at 150° C. for 20 min then 160° C. for 30 min in a microwave synthesizer. The reaction mixture was diluted with $H_2O$ and the solid was filtered and washed with $H_2O$. The solid was dissolved in MeOH, evaporated onto $SiO_2$ and purified by flash silica gel chromatography with EtOAc/hexanes (0:1→2:3) as eluant to give the title compound as an orange amorphous solid. MS (ESI, pos ion.) m/z: 161 (M+1).

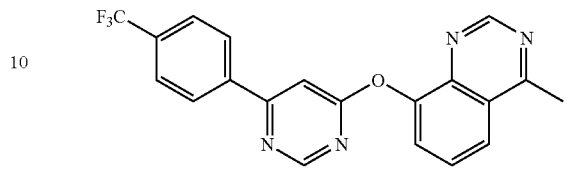

(b) 4-Methyl-8-[6-(4-trifluoromethyl-phenyl)-pyrimidin-4-yloxy]-quinazoline. A mixture of 4-chloro-6-(4-trifluoromethyl-phenyl)-pyrimidine, (Example 2(a), Method A), (102 mg, 0.4 mmol), 4-methyl-quinazolin-8-ol (60 mg, 0.4 mmol) and $K_2CO_3$ (57 mg, 0.4 mmol) in DMF (2 mL) was heated at 80° C. for 1.5 h. The reaction mixture was diluted with $H_2O$ and the solid was filtered and washed with $H_2O$. The solid was dissolved in MeOH, evaporated onto $SiO_2$ and purified by flash silica gel chromatography with EtOAc/hexanes (0:1→1:1) as eluant to give the title compound as an off-white amorphous solid. Mp: 237-240° C. MS (ESI, pos ion.) m/z: 383 (M+1).

EXAMPLE 56

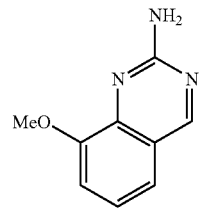

(a) 8-Methoxy-quinazolin-2-ylamine. To a solution of 3-methoxy-2-nitro-benzaldehyde (14.8 g, 81 mmol, Aldrich) and $NH_4Cl$ (4.4 g, 82 mmol, Aldrich) in 80% aq. MeOH (250 mL) was added iron dust (20.5 g, 367 mmol, Aldrich) and the reaction mixture was heated at 60° C. with stirring for 2 h. The reaction mixture was allowed to cool to room temperature and filtered through a pad of Celite®. The filter cake was washed with MeOH and the solution was concentrated in vacuum. The concentrated aq. solution was extracted with $CH_2Cl_2$ and the combined organic layers were washed with brine and dried over $Na_2SO_4$. Purification with EtOAc/Hexanes (0:1→1:4) as eluant gave 3.84 g (31%) of 2-amino-3-methoxy-benzaldehyde as a yellow oil. This oil was heated at 190C for 2.5 h in the presence of guanidine hydrochloride (4.9 g, 51 mmol, Aldrich), $Na_2CO_3$ (5.4 g, 51 mmol) and decalin (55 mL). The reaction was decanted while hot and the solution was allowed to cool to room temperature. The resultant precipitate was stirred with hexanes, filtered, washed with hexanes, and dried in vacuum to give the title compound as a yellow amorphous solid. MS (ESI, pos ion.) m/z: 176 (M+1).

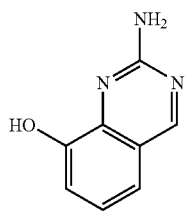

(b) 2-Amino-quinazolin-8-ol. To a cooled to 0° C. slurry of NaH (1.4 g, 35 mmol, 60% suspension in mineral oil, Aldrich) in DMF (100 mL) was added ethanethiol (5.0 mL, 67 mmol, Aldrich) and the reaction mixture was allowed to warm to room temperature. 8-Methoxy-quinazolin-2-ylamine (1.5 g, 8.6 mmol) was then added and the mixture was heated at 80° C. for 14 h. The reaction mixture was allowed to cool to room temperature and the solvent removed in vacuum. The residue was treated with $H_2O$, the volatiles were evaporated in vacuum, and the residue was dissolved in MeOH and evaporated onto $SiO_2$. Purification by flash silica gel chromatography eluting with 2M $NH_3$ in MeOH/$CH_2Cl_2$ (0:1→1:1) gave the title compound as a pale-green amorphous solid. MS (ESI, pos ion.) m/z: 162 (M+1).

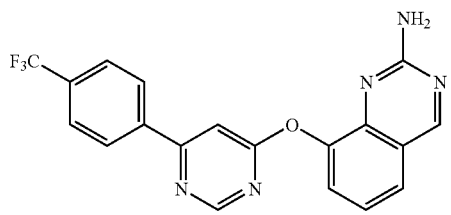

(c) 8-[6-(4-Trifluoromethyl-phenyl)-pyrimidin-4-yloxy]-quinazolin-2-ylamine. The title compound was prepared analogously to the procedure used in Example 46, using 2-amino-quinazolin-8-ol (217 mg, 1.3 mmol), 4-chloro-6-(4-trifluoromethyl-phenyl)-pyrimidine, (Example 2(a), Method A), (386 mg, 1.5 mmol), NaH (65 mg, 1.6 mmol, 60% suspension in mineral oil, Aldrich) and DMF (5 mL). Purification by flash silica gel chromatography eluting with EtOAc/hexanes/2M$NH_3$ in MeOH/$CH_2Cl_2$ (0:1:0:0→2:5:0:0→0:0:0:1→0:0:1:19) gave the title compound as a white amorphous solid. Mp: 251-253° C. MS (ESI, pos ion.) m/z: 384 (M+1).

EXAMPLE 57

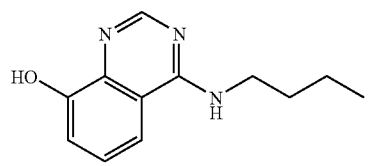

(a) 4-Butylamino-quinazolin-8-ol. The title compound was prepared analogously to the procedure used in Example 56(b), using butyl-(8-methoxy-quinazolin-4-yl)-amine (1.4 g, 6.1 mmol, prepared according to *J. Sci. Ind.Research (India)* 1956, 15C, 1), ethanethiol (3.0 mL, 40 mmol), NaH (1.2 g, 30 mmol, 60% suspension in mineral oil, Aldrich) and DMF (30 mL). Purification by flash silica gel chromatography eluting with MeOH/$CH_2Cl_2$ (0:1→2:23) gave impure material. Further purification by flash silica gel chromatography eluting with EtOAc/hexanes (1:3→1:0) gave the title compound as a light-yellow amorphous solid. MS (ESI, pos ion.) m/z: 218 (M+1).

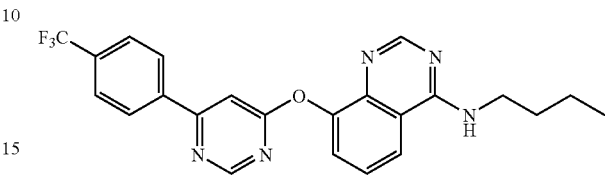

(b) Butyl-{8-[6-(4-trifluoromethyl-phenyl)-pyrimidin-4-yloxy]-quinazolin-4-yl}-amine. The title compound was prepared analogously to the procedure used in Example 46, using 4-butylamino-quinazolin-8-ol (364 mg, 1.7 mmol), 4-chloro-6-(4-trifluoromethyl-phenyl)-pyrimidine, (Example 2(a), Method A), (485 mg, 1.9 mmol), NaH (86 mg, 2.2 mmol, 60% suspension in mineral oil, Aldrich) and DMF (10 mL). Purification by flash silica gel chromatography eluting with EtOAc/hexanes (0:1→2.3) gave the title compound as a light-yellow amorphous solid. MS (ESI, pos ion.) m/z: 440 (M+1).

EXAMPLE 58

(a) Diethyl-(8-methoxy-quinazolin-4-yl)-amine. Two reaction vials each containing 4-chloro-8-methoxy-quinazoline (510 mg, 2.6 mmol, prepared according to *J. Med. Chem.* 1994, 37, 2106), diethylamine (1.0 mL, 9.7 mmol, Aldrich) and benzene (3 mL) were heated at 150° C. for 10 min in a microwave synthesizer. The reaction mixtures were combined, the volatiles were removed in vacuum and the residue was stirred over pentane. The solution was partitioned between EtOAc/satd $NaHCO_3$ and the layers were separated. The organic layer was washed with $H_2O$ and brine and dried over $Na_2SO_4$ to give the title compound as a brown oil. MS (ESI, pos ion.) m/z: 232 (M+1).

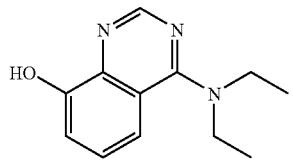

(b) 4-Diethylamino-quinazolin-8-ol. The title compound was prepared analogously to the procedure used in Example 56(b), using diethyl-(8-methoxy-quinazolin-4-yl)-amine (1.0 g, 4.4 mmol), ethanethiol (3.8 mL, 51 mmol), NaH (0.9 g, 23 mmol, 60% suspension in mineral oil, Aldrich) and DMF (27 mL). Purification by flash silica gel chromatography eluting with NH$_4$OH/EtOH/CH$_2$Cl$_2$ (0:0:1→1:7:92) gave the title compound as a gray amorphous solid. MS (ESI, pos ion.) m/z: 218 (M+1).

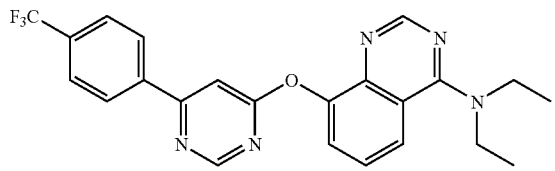

(c) Diethyl-{8-[6-(4-trifluoromethyl-phenyl)-pyrimidin-4-yloxy]-quinazolin-4-yl}-amine. The title compound was prepared analogous to the procedure used in Example 46, using 4-diethylamino-quinazolin-8-ol (444 mg, 2.0 mmol), 4-chloro-6-(4-trifluoromethyl-phenyl)-pyrimidine, (Example 2(a), Method A), (820 mg, 3.2 mmol), NaH (106 mg, 2.7 mmol, 60% suspension in mineral oil, Aldrich) and DMF (20 mL). Purification by flash silica gel chromatography eluting with EtOAc/hexanes (0: 1>2.3) gave the title compound as a white amorphous solid. Mp: 158-162° C. MS (ESI, pos ion.) m/z: 440 (M+1).

EXAMPLE 59

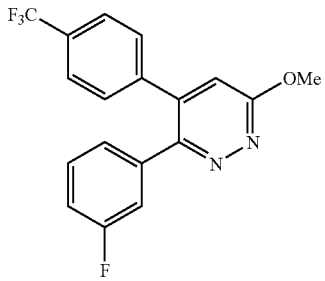

(a) 3-(3-Fluoro-phenyl)-6-methoxy-4-(4-trifluoromethyl-phenyl)-pyridazine. Analogous to the procedure used in Example 51(b), a mixture of 3-chloro-6-methoxy-4-(4-trifluoromethyl-phenyl)-pyridazine, (Example 51(a)), (0.50 g, 1.7 mmol, 3-fluorobenzeneboronic acid (0.29 g, 2.1 mmol, Lancaster), tetrakis(triphenylphosphine)-palladium(0) (0.15 g, 0.13 mmol, Lancaster) and Na$_2$CO$_3$ (0.69 g, 6.5 mmol, Mallinckrodt) in DME (3.5 mL) and H$_2$O (1.5 mL) was heated at 150° C. in a microwave synthesizer for 25 min. The reaction mixture was allowed to cool to room temperature, partitioned between H$_2$O and EtOAc and the aqueous layer was extracted with EtOAc (3×). The combined organic layers were concentrated. Purification by flash chromatography (0→15% EtOAc/hexanes) gave the title compound. MS (ESI, pos. ion) m/z: 349 (M+1).

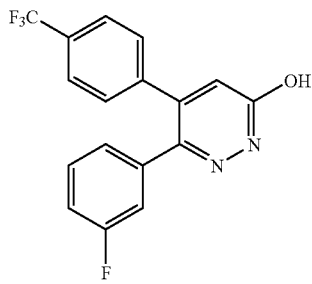

(b) 6-(3-Fluoro-phenyl)-5-(4-trifluoromethyl-phenyl)-pyridazin-3-ol. Analogous to the method used in Example 51(c), a mixture of 3-(3-fluoro-phenyl)-6-methoxy-4-(4-trifluoromethyl-phenyl)-pyridazine (0.27 g, 0.78 mmol) and HI (47% in H$_2$O, 2 mL, Aldrich) in MeOH (2 mL) was heated at 75° C. for 16 h. The reaction mixture was allowed to cool to room temperature, diluted with H$_2$O and filtered. The white solid was dried in vacuum at room temperature for 4 h to give the title compound. MS (ESI, pos. ion) m/z: 335 (M+1).

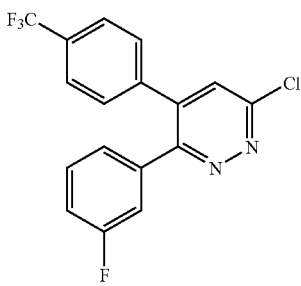

(c) 6-Chloro-3-(3-fluoro-phenyl)-4-(4-trifluoromethyl-phenyl)-pyridazine. The title compound was prepared analogous to the method used in Example 51(d), using 6-(3-fluoro-phenyl)-5-(4-trifluoromethyl-phenyl)-pyridazin-3-ol (0.20 g, 0.58 mmol) and POCl$_3$ (3.0 mL, Aldrich). After concentration in vacuum, the residue was stirred with CH$_2$Cl$_2$ and satd aq. NaHCO$_3$ for 3 h. The aqueous layer was extracted with CH$_2$Cl$_2$ (3×) and the combined organic layers were dried over Na$_2$SO$_4$ and filtered through a pad of SiO$_2$, eluting with EtOAc. The solvent was removed in vacuum to yield the title compound as a light-yellow oil. MS (ESI, pos. ion) m/z: 353 (M+1).

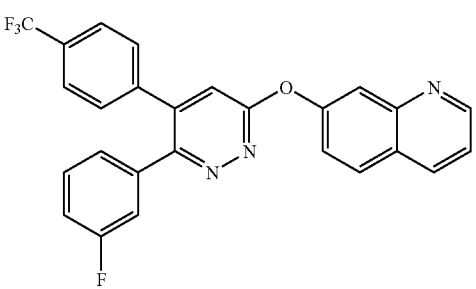

(d) 7-[6-(3-Fluoro-phenyl)-5-(4-trifluoromethyl-phenyl)-pyridazin-3-yloxy]-quinoline. The title compound was prepared analogous to the procedure in Example 29 using 6-chloro-3-(3-fluoro-phenyl)-4-(4-trifluoromethyl-phenyl)-pyridazine (0.22 g, 0.62 mmol), 7-hydroxyquinoline (0.099 g, 0.68 mmol, Acros), DMF (3 mL), and NaH (0.033 g, 0.81 mmol, 60% suspension in mineral oil, Aldrich). Purification by flash chromatography (0→50% EtOAc/hexanes) gave the title compound as a white powder. Mp: 165° C., MS (ESI, pos. ion) m/z: 462 (M+1).

EXAMPLE 60

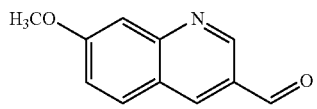

(a) 7-Methoxyquinoline-3-carbaldehyde. A solution of ethyl 7-methoxyquinoline-3-carboxylate (2.0 g, 8.6 mmol, prepared according to Erickson, E. H. et al. *J. Med. Chem.* 1979, 22(7), 816-823) in anhydrous THF (60 mL) was magnetically stirred under $N_2$ in a −23° C. bath and treated dropwise with diisobutylaluminum hydride (12 mL, 18 mmol, 1.5 M in toluene, Aldrich). The reaction mixture was stirred at −23° C. for 45 min, then treated with an additional aliquot of diisobutylaluminum hydride (12 mL, 18 mmol, 1.5 M in toluene, Aldrich). The reaction was stirred at −23° C. for 10 min, then quenched by the dropwise addition of satd $NH_4Cl$ (10 mL) followed by the addition of satd aq. solution of Rochelle's salt (100 mL). The mixture was stirred vigorously for 20 min at 25° C. and concentrated in vacuum to ~110 mL volume. The aqueous phase was extracted with EtOAc (3×100 mL). The combined organic extracts were washed with water (100 mL), satd NaCl (50 mL), dried over $Na_2SO_4$, filtered and concentrated in vacuum to provide 1.9 g of a mixture of two major products. The products were separated by silica gel chromatography (gradient: 0-10% MeOH in EtOAc) to provide an earlier eluting fraction [380 mg, 23%; MS (ESI, pos. ion.) m/z: 192 (M+1)] and a later eluting fraction [745 mg, 46%; MS (ESI, pos. ion.) m/z: 190 (M+1)]. The two products were combined in 2:1 $CH_2Cl_2$:hexanes (30 mL), magnetically stirred at 25° C., and treated with manganese (IV) oxide (10 g, 115 mmol, Aldrich). The suspension was stirred in a 40° C. oil bath for 1 h, allowed to cool to room temperature and filtered through a pad of Celite®. The pad was washed with $CH_2Cl_2$ (200 mL) and the combined filtrate was concentrated in vacuum to afford the title compound as a white solid. MS (ESI, pos. ion.) m/z: 188 (M+1).

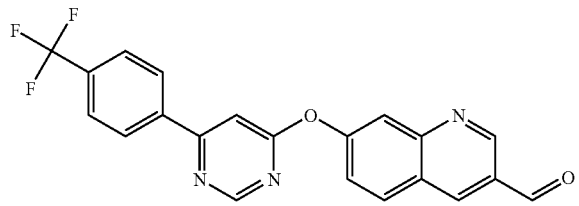

(b) 7-{6-[4-(Trifluoromethyl)phenyl]pyrimidin-4-yloxy}quinoline-3-carbaldehyde. A solution of 7-methoxyquinoline-3-carbaldehyde (790 mg, 4.2 mmol) in 48% aq. hydrobromic acid (10 mL, Aldrich) was distributed equally into two separate microwave-safe, 10-mL, glass reaction vessels equipped with stir bars. The reaction vessels were heated in a microwave synthesizer at 180° C. for 15 min each, then recombined and concentrated in vacuum to afford a tan solid (1.1 g). The solid was treated with 4-chloro-6-[4-(trifluoromethyl)-phenyl]pyrimidine, (Example 2(a), Method A), (1.2 g, 4.6 mmol), methylsulfoxide (10 mL, Aldrich), and cesium carbonate (6.8 g, 21 mmol, Aldrich). The reaction mixture was magnetically stirred under $N_2$ in an 80° C. oil bath for 18 h, then allowed to cool to room temperature and partitioned between EtOAc (200 mL) and water (200 mL). The aqueous phase was extracted with EtOAc (2×100 mL) and the combined organic phases were washed with water (100 mL), satd NaCl (50 mL), dried over $Na_2SO_4$, filtered and concentrated in vacuum. Purification by silica gel chromatography (gradient: 10-35% EtOAc/hexanes, followed by 35% EtOAc/hexanes) provided the title compound as an off-white solid. MS (ESI, pos. ion.) m/z: 396 (M+1).

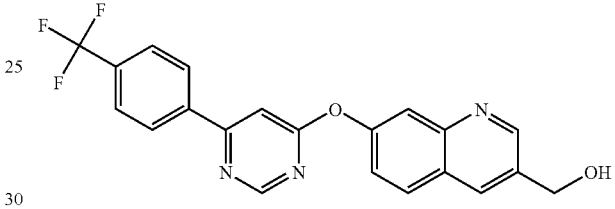

(c) (7-{6-[4-(Trifluoromethyl)phenyl]pyrimidin-4-yloxy}-3-quinolyl)methan-1-ol. A suspension of 7-{6-[4-(trifluoromethyl)phenyl]pyrimidin-4-yloxy}quinoline-3-carbaldehyde (210 mg, 0.53 mmol) in EtOH (20 mL) was stirred at 0° C. and treated with sodium borohydride (20 mg, 0.53 mmol, Aldrich) resulting in a yellow solution. The reaction mixture was allowed to stir at 25° C. for 5 min, then quenched with water (5 mL) and concentrated in vacuum. The residue was partitioned between EtOAc (100 mL) and 10% $Na_2CO_3$ (50 mL). The organic layer was separated and washed with 10% $Na_2CO_3$ (50 mL), satd NaCl (50 mL), dried over $Na_2SO_4$, filtered and concentrated in vacuum. Purification by silica gel chromatography (gradient: 75-95% EtOAc/hexanes) provided the title compound as a white solid. Mp: 181° C. MS (ESI, pos. ion.) m/z: 398 (M+1). Anal. Calcd for $C_{21}H_{14}F_3N_3O_2$: C, 63.48; H, 3.55; N, 10.58; F, 14.34. Found: C, 63.43; H, 3.62; N, 10.46; F, 14.23.

EXAMPLE 61

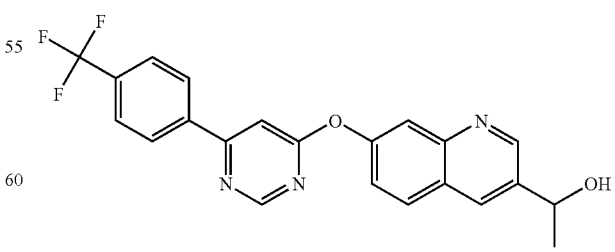

1-(7-{6-[4-(Trifluoromethyl)phenyl]pyrimidin-4-yloxy}-3-quinolyl)ethan-1-ol. A solution of 7-{6-[4-(trifluoromethyl)phenyl]pyrimidin-4-yloxy}quinoline-3-carbaldehyde, (Example 60b), (220 mg, 0.56 mmol) in anhydrous THF (10 mL) was magnetically stirred under N₂ in a −78° C. bath while methylmagnesium bromide (0.22 mL, 0.66 mmol, 3.0 M in Et₂O, Aldrich) was added quickly. The reaction mixture was stirred at −78° C. for 5 min, then treated with satd NH₄Cl (5 mL). The bath was removed and the mixture was stirred for 5 min, then diluted with EtOAc (60 mL) and washed with satd NH₄Cl (20 mL), water (20 mL), satd NaHCO₃ (20 mL), satd NaCl (20 mL), dried over Na₂SO₄, filtered and concentrated in vacuum. Purification by silica gel chromatography (gradient: 60-85% EtOAc in hexanes) provided the title compound as an off-white solid. Mp: 156-157° C. MS (ESI, pos. ion.) m/z: 412 (M+1). Anal. Calcd for C₂₂H₁₆F₃N₃O₂: C, 64.23; H, 3.92; N, 10.21; F, 13.85. Found: C, 63.99; H, 4.05; N, 10.01; F, 13.63.

EXAMPLE 62

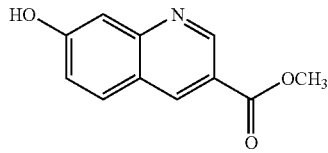

(a) Methyl 7-hydroxyquinoline-3-carboxylate. A solution of ethyl 7-methoxyquinoline-3-carboxylate (500 mg, 2.1 mmol, prepared according to Erickson, E. et al. *J. Med. Chem.* 1979, 22(7), 816-823) in 48% aq. hydrobromic acid (2.5 mL, Aldrich) was added to a microwave-safe, 1 0-mL, glass reaction vessel equipped with a stir bar. The reaction vessel was heated in a microwave synthesizer at 160° C. for 20 min. An additional aliquot of 48% aq. hydrobromic acid (1.0 mL, Aldrich) was added and the mixture heated at 160° C. for an additional 35 min. The resulting solid precipitate was collected by filtration, washed with water (10 mL) and dried in vacuum at 60° C. to afford a solid (255 mg). The filtrate was concentrated in vacuum to afford an additional 260 mg product. The solid products were combined in MeOH (250 mL), stirred in an ice bath and treated in portions with diazomethane (80 mL total, 0.2 M in Et₂O, prepared according to Black, T. H. *Ald. Acta* 1983, 16(1), 3-10). The reaction was followed closely by HPLC-MS to avoid over-alkylation. The reaction mixture was concentrated in vacuum to provide the title compound. MS (ESI, pos. ion.) m/z: 204 (M+1).

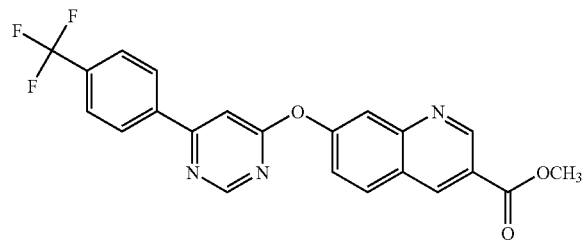

(b) Methyl 7-{6-[4-(trifluoromethyl)phenyl]pyrimidin-4-yloxy}quinoline-3-carboxylate. Methyl 7-hydroxyquinoline-3-carboxylate (350 mg, 1.7 mmol) was treated with 4-chloro-6-[4-(trifluoromethyl)-phenyl]pyrimidine, (Example 2(a), Method A), (490 mg, 1.9 mmol), methylsulfoxide (10 mL, Aldrich), and cesium carbonate (1.7 g, 5.2 mmol, Aldrich). The reaction mixture was magnetically stirred under N₂ in a 50° C. oil bath for 5 h, then allowed to cool to room temperature and partitioned between EtOAc (300 mL) and water (150 mL). The organic phase was washed with water (2×100 mL), satd NaCl (50 mL), dried over Na₂SO₄, filtered and concentrated in vacuum. Purification by silica gel chromatography (gradient: 10-25% EtOAc in hexanes, followed by 25% EtOAc in hexanes) provided the title compound as a white solid; Mp: 216-217° C. MS (ESI, pos. ion.) m/z: 426 (M+1).

EXAMPLE 63

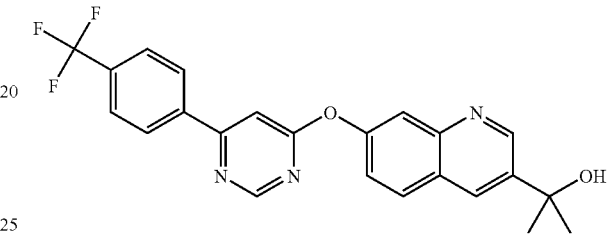

2-(7-{6-[4-(Trifluoromethyl)phenyl]pyrimidin-4-yloxy}-3-quinolyl)propan-2-ol. A solution of methyl 7-{6-[4-(trifluoromethyl)phenyl]pyrimidin-4-yloxy}quinoline-3-carboxylate, (Example 62b), (150 mg, 0.35 mmol) in anhydrous THF (10 mL) was magnetically stirred in a 0° C. bath and treated dropwise with methyllithium (0.63 mL, 1.0 mmol, 1.6 M in Et₂O, Aldrich). After addition was complete, the reaction was quenched with satd NH₄Cl (5 mL), then diluted with EtOAc (120 mL) and washed with water (30 mL). The organic phase was washed with satd NaCl (10 mL), dried over Na₂SO₄, filtered and concentrated in vacuum. Purification by silica gel chromatography (gradient: 50-60% EtOAc/hexanes) provided the title compound as a yellow amorphous solid. MS (ESI, pos. ion.) m/z: 426 (M+1).

EXAMPLE 64

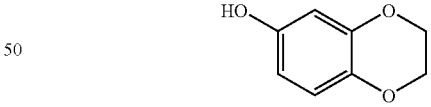

(a) 2H,3H-Benzo[e]1,4-dioxan-6-ol. A solution of 2,3-dihydro-1,4-benzodioxin-6-ylacetate (1.35 g, 6.95 mmol, prepared according to Besson, T. et al. *Tetrahedron* 1995, 55, 3197-3204) in MeOH (20 mL) was treated with 1 N NaOH (5 mL) and stirred at 25° C. for 30 min. The reaction mixture was concentrated in vacuum to a volume of ~5 mL and acidified to pH 1 with 1 N HCl. The aqueous mixture was extracted with EtOAc (3×50 mL). The combined organic extracts were washed with water (50 mL), satd NaCl (50 mL), dried over MgSO₄, filtered and concentrated in vacuum to afford the title compound as a viscous, brown oil. MS (ESI, pos. ion.) m/z: 153 (M+1).

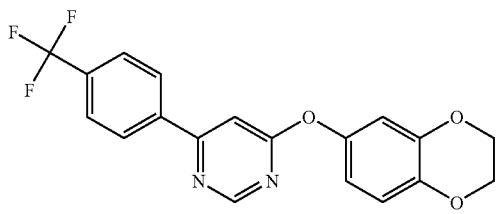

(b) 6-{6-[4-(Trifluoromethyl)phenyl]pyrimidin-4-yloxy}-2H,3H-benzo[e]1,4-dioxane. A solution of 2H,3H-benzo[e]1,4-dioxan-6-ol (300 mg, 2.0 mmol) and 4-chloro-6-[4-(trifluoromethyl)-phenyl]pyrimidine, (Example 2(a), Method A), (560 mg, 2.2 mmol) in acetonitrile (10 mL) was treated with 1,8-diazabicyclo[5.4.0]undec-7-ene (0.60 mL, 4.0 mmol, Aldrich). The reaction mixture was magnetically stirred in an 85° C. oil bath, under a reflux condenser, for 1 h, then allowed to cool to room temperature. The mixture was diluted with EtOAc (75 mL), washed with 1 N HCl (30 mL), satd NaHCO$_3$ (30 mL), water (30 mL), satd NaCl (20 mL), dried over Na$_2$SO$_4$, filtered and concentrated in vacuum. Purification by silica gel chromatography (gradient: 10-20% EtOAc/hexanes, followed by 20% EtOAc/hexanes) provided the title compound as a white solid. Mp: 163.6-163.7° C. MS (ESI, pos. ion.) m/z: 375 (M+1). Anal. Calcd for C$_{19}$H$_{13}$F$_3$N$_2$O$_3$: C, 60.97; H, 3.50; N, 7.48; F, 15.23. Found: C, 60.56; H, 3.36; N, 7.29; F, 15.56.

EXAMPLE 65

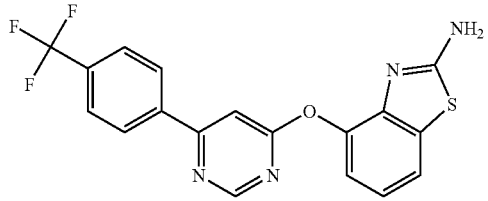

4-[6-(4-Trifluoromethyl-phenyl)-pyrimidin-4-yloxy]-benzothiazol-2-ylamine. To a solution of 4-chloro-6-(4-trifluoromethyl-phenyl)-pyrimidine, (Example 2(a), Method A), ((0.13 g, 0.5 mmol) and 2-amino-4-hydroxybenzothiazole (83 mg, 0.5 mmol, Astatech) in DMF (1 mL) was added potassium carbonate (0.14 g, 1 mmol) and the mixture was heated at 80° C. for 16 h with sirring. The reaction mixture was allowed to cool to room temperature and partitioned between EtOAc and brine. The layers were separated and the aq. layer was extracted with EtOAc. The combined organic extracts were dried over Na$_2$SO$_4$, filtered and concentrated under vacuum. Purification of the residue by silica gel chromatography (2:1 hexanes: EtOAc) provided the title compound as a white solid. MS (ESI, pos. ion) m/z: 389 (M+1). Mp: 232.0-233.5° C. Anal. Calcd for C$_{18}$H$_{11}$F$_3$N$_4$O$_S$: C, 55.67; H, 2.85; N, 14.43; S, 8.26. Found: C, 55.52; H, 3.08; N, 14.23; S, 8.36.

EXAMPLE 66

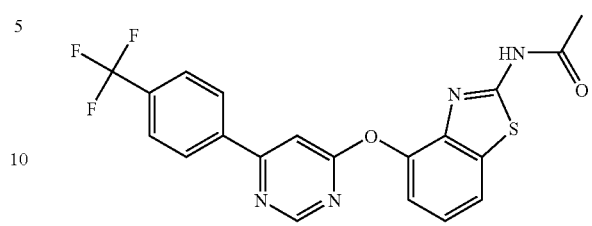

N-{4-[6-(4-Trifluoromethyl-phenyl)-pyrimidin-4-yloxy]-benzothiazol-2-yl}-acetamide. A mixture of 4-[6-(4-trifluoromethyl-phenyl)-pyrimidin-4-yloxy]-benzothiazol-2-ylamine, (Example 65), (97 mg, 0.25 mmol) and acetic anhydride (0.24 mL, 2.5 mmol) was heated in a 105° C. oil bath for 8 h. The solvent was evaporated and the solid that formed was recrystallized from EtOAc/hexanes, and dried under vacuum to give the title compound. MS (ESI, pos. ion) m/z: 431 (M+1). Mp: 219.0-220.5° C. Anal. Calcd for C$_{20}$H$_{13}$F$_3$N$_4$O$_2$S0.75H$_2$O: C, 54.11; H, 3.29; N, 12.62; S, 7.22. Found: C, 54.12; H, 3.07; N, 12.61; S, 7.30.

EXAMPLE 67

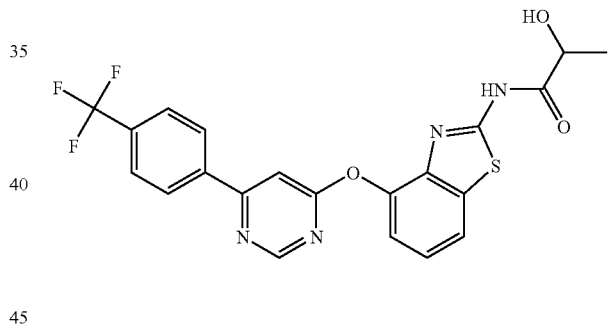

2-Hydroxy-N-{4-[6-(4-trifluoromethyl-phenyl)-pyrimidin-4-yloxy]-benzothiazol-2-yl}-propionamide. A mixture of (+/−)-2-acetoxypropionic acid (56 uL, 0.5 mmol, Fluka) in thionyl chloride (1 mL) was heated at reflux for 3 h. After evaporation of the solvent, the residue was dissolved in THF, and treated with 4-[6-(4-trifluoromethyl-phenyl)-pyrimidin-4-yloxy]-benzothiazol-2-ylamine, (Example 65), (97 mg, 0.25 mmol) and 2-tert-butylimino-2-diethylamino-1,3-dimethyl-perhydro-1,3,2-diazaphosphorine, polymer bound (BEMP resin) (0.17 g, 0.38 mmol, Aldrich). The reaction mixture was stirred at 25° C. for 16 h. The insoluble material was filtered off and washed with CH$_2$Cl$_2$. The filtrate was concentrated and then dissolved in MeOH. Potassium carbonate (69 mg, 0.5 mmol) was added and the reaction mixture was stirred at 25° C. for 2 h. The solvent was evaporated in vacuum and to the residue was added CH$_2$Cl$_2$ (30 mL). After stirring for 5 min, the precipitate was collected by filtration and purified by silica gel chromatography (3:1 of EtOAc/hexanes) to give the title compound. MS (ESI, pos. ion) m/z: 461 (M+1).

EXAMPLE 68

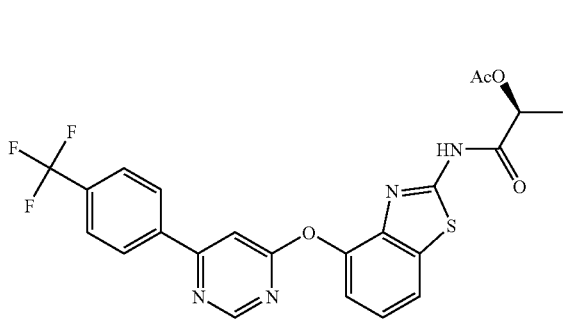

(a) (S)-Acetic acid 1-{4-[6-(4-trifluoromethyl-phenyl)-pyrimidin-4-yloxy]-benzothiazol-2-ylcarbamoyl}-ethyl ester. According to the procedure described in Example 67, the title compound was prepared by using 4-[6-(4-trifluoromethyl-phenyl)-pyrimidin-4-yloxy]-benzothiazol-2-ylamine, (Example 65), (0.39 g, 1 mmol), (S)-(−)-2-acetoxypropionyl chloride (0.25 mL, 2 mmol, Aldrich) and 2-tert-butylimino-2-diethylamino-1,3-dimethyl-perhydro-1,3,2-diazaphosphorine, polymer bound (BEMP resin) (0.68 g, 1.5 mmol, Aldrich) in THF (10 mL). Purification by silica gel chromatography (1:3 of EtOAc/hexanes) provided the title compound. MS (ESI, pos. ion) m/z: 503 (M+1).

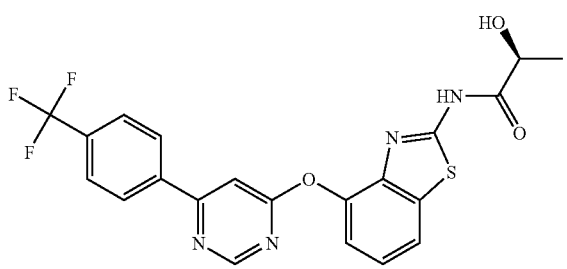

(b) 2-(S)-Hydroxy-N-{4-[6-(4-trifluoromethyl-phenyl)-pyrimidin-4-yloxy]-benzothiazol-2-yl}-propionamide. To a solution of (S)-acetic acid 1-{4-[6-(4-trifluoromethyl-phenyl)-pyrimidin-4-yloxy]-benzothiazol-2-ylcarbamoyl}-ethyl ester (0.19 g, 0.38 mmol) in MeOH (4 mL) was added potassium carbonate (0.11 g, 0.76 mmol) and the mixture was stirred at 25° C. for 2 h. The solvent was evaporated in vacuum and the residue was purified by silica gel chromatography (EtOAc/hexanes=1:2) to give the title compound as a white solid. Chiral LC purification on Chiralpak AD column with 80:20:0.2 of hexanes: IPA: diethylamine gave the desired isomer as a white solid. MS (ESI, pos. ion) m/z: 461 (M+1).

EXAMPLE 69

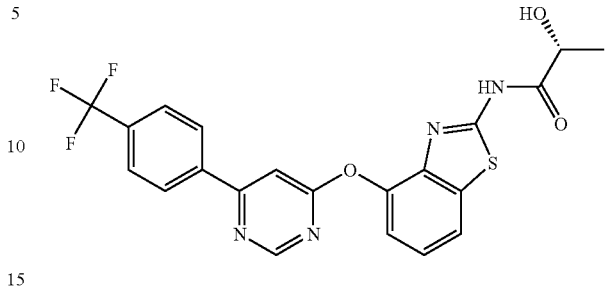

2-(R)-Hydroxy-N-{4-[6-(4-trifluoromethyl-phenyl)-pyrimidin-4-yloxy]-benzothiazol-2-yl}-propionamide. The chiral LC separation of the reaction product of Example 68(b) also gave small amount of the ($R^1$)-isomer as a white solid. MS (ESI, pos. ion) m/z: 461 (M+1).

EXAMPLE 70

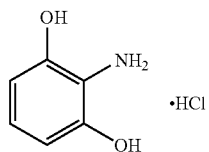

(a) 2-Amino-benzene-1,3-diol hydrochloride. To a solution of 2-nitroresorcinol (0.79 g, 5 mmol, Aldrich) in EtOH (50 mL) was added 10% palladium on carbon (0.26 g) and cond HCl (0.4 mL), and the reaction mixture was stirred under 1 atm of $H_2$ for 3 h. The mixture was filtered through a pad of Celite®, the filter cake was washed with EtOH, and the filtrate was concentrated in vacuum to give the title compound as an off-white solid, which was used in the next step without additional purification. MS (ESI, pos. ion) m/z: 126 (M+1).

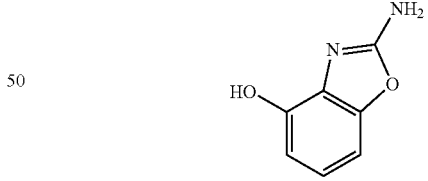

(b) 2-Amino-benzooxazol-4-ol. 2-Amino-benzene-1,3-diol hydrochloride (crude, 5 mmol) was dissolved in water (3 mL) and neutralized with $NaHCO_3$ (0.42 g, 5 mmol). Cyanogen bromide (0.48 g, 4.5 mmol, Aldrich) was then added portion wise to the solution, with stirring at room temperature. The mixture was left to stand at 25° C. for 2 days. The insoluble material was filtered off and the filtrate was neutralized with aq. $Na_2CO_3$ to pH 5. The precipitate was collected by filtration, washed with water (1 mL) and dried under vacuum to give the title compound as a tan solid. MS (ESI, pos. ion) m/z: 151 (M+1).

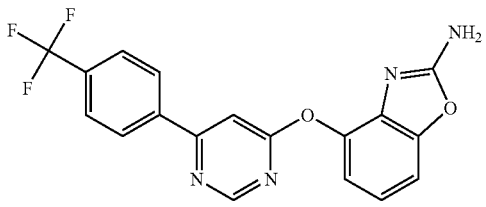

(c) 4-[6-(4-Trifluoromethyl-phenyl)-pyrimidin-4-yloxy]-benzooxazol-2-ylamine. This material was prepared according to the method described in Example 3 using 4-chloro-6-(4-trifluoromethyl-phenyl)-pyrimidine, (Example 2(a), Method A), (0.78 g, 3 mmol), 2-amino-benzooxazol-4-ol (0.3 g, 2 mmol), and $K_2CO_3$ (0.83 g, 6 mmol) in DMF (6 mL). The precipitate formed was collected by filtration, washed with ether (4 mL) and dried to give the title compound as an off-white solid. MS (ESI, pos. ion) m/z: 373 (M+1). Mp: 235.0-247.9° C.

EXAMPLE 71

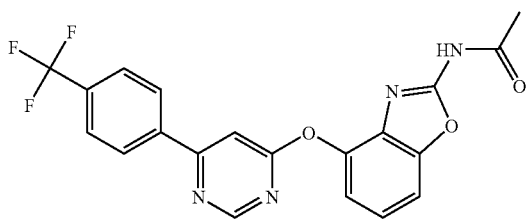

N-{4-[6-(4-Trifluoromethyl-phenyl)-pyrimidin-4-yloxy]-benzooxazol-2-yl}-acetamide. This material was prepared according to the method described in Example 66 using 4-[6-(4-trifluoromethyl-phenyl)-pyrimidin-4-yloxy]-benzooxazol-2-ylamine, (Example 70(c)), (0.27 g, 0.72 mmol) and acetic anhydride (82 uL, 0.87 mmol) in pyridine (3 mL). Purification by silica gel chromatography (1:1.5 of EtOAc/hexanes) provided the title compound as a white solid. MS (ESI, pos. ion) m/z: 415 (M+1). Mp: 205.1-205.2° C.

EXAMPLE 72

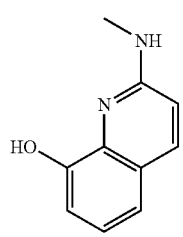

(a) 2-Methylamino-quinolin-8-ol. This material was prepared according to the method described in Example 5(a) using 2-chloro-quinolin-8-ol, (Example 2(a), Method B), (0.18 g, 1 mmol) and methylamine (10 mL, 20 mmol, 2M in THF, ALdrich) in dioxane (3 mL). Recrystallization from MeOH/$H_2O$ provided the title compound as a light-yellow solid. MS (ESI, pos. ion) m/z: 175 (M+1).

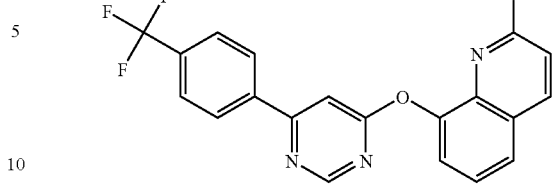

(b) Methyl-{8-[6-(4-trifluoromethyl-phenyl)-pyrimidin-4-yloxy]-quinolin-2-yl}-amine. This material was prepared according to the method described in Example 3 using 4-chloro-6-(4-trifluoromethyl-phenyl)-pyrimidine, (Example 2(a), Method A), (0.22 g, 0.85 mmol), 2-methylamino-quinolin-8-ol (0.12 g, 0.71 mmol), and potassium carbonate (0.2 g, 1.4 mmol) in DMF (1.5 mL). Purification by silica gel chromatography (5:1 hexanes: EtOAc) provided the title compound as a white solid. MS (ESI, pos. ion) m/z: 397 (M+1). Mp: 163.0-165.0° C. Anal. Calcd for $C_{21}H_{15}F_3N_4O \cdot 0.25\ H_2O$: C, 62.92; H, 3.90; N, 13.98. Found: C, 62.98; H, 3.83; N, 13.77.

EXAMPLE 73

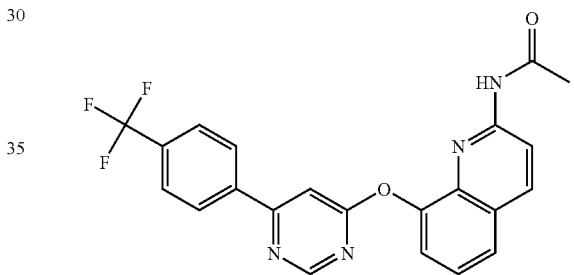

N-{8-[6-(4-Trifluoromethyl-phenyl)-pyrimidin-4-yloxy]-quinolin-2-yl}-acetamide. This material was prepared according to the method described in Example 66 using 8-[6-(4-trifluoromethyl-phenyl)-pyrimidin-4-yloxy]-quinolin-2-ylamine, (Example 2(d), Method B), (0.79 g, 2.1 mmol) and acetic anhydride (2.5 mL, 2.6 mmol). Purification by silica gel chromatography (2:1 hexanes: EtOAc) provided the title compound as a white solid. MS (ESI, pos. ion) m/z: 425 (M+1). Mp: 203.8-206.0° C. Anal. Calcd for $C_{22}H_{15}F_3N_4O_2$: C, 62.26; H, 3.56; N, 13.20. Found: C, 62.28; H, 3.51; N, 13.15.

EXAMPLE 74

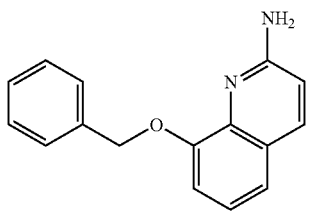

(a) 8-Benzyloxy-quinolin-2-ylamine. To 2-amino-8-hydroxyquinoline (0.96 g, 6 mmol, Fluka) dissolved in acetone (30 mL) was added potassium carbonate (1.2 g, 9 mmol) and the reaction mixture was stirred at 25° C. for 10 min. Benzyl bromide (1.1 mL, 9 mmol, Aldrich) was then added dropwise and the reaction mixture was heated at 50° C. for 16 h. After cooling to room temperature, the precipitate was filtratered, washed with acetone and water, and dried under vacuum to give the title compound as an off-white solid. MS (ESI, pos. ion) m/z: 251 (M+1).

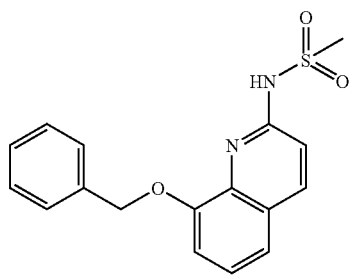

(b) N-(8-Benzyloxy-quinolin-2-yl)-methanesulfonamide. To 8-benzyloxy-quinolin-2-ylamine suspended in THF (6 mL) and DMF (1 mL) was added NaH (0.14 g, 3.6 mmol, 60% suspension in mineral oil, Aldrich). After stirring for 10 min at 25° C., methanesulfonyl chloride (0.26 mL, 3.3 mmol, Aldrich) was added. The reaction mixture was stirred at room temperature for 16 h and then partitioned between EtOAc and 10% citric acid. The aqueous layer was separated, saturated with NaCl and extracted with a mixture of MeOH and EtOAc. The combined organic layers were washed with brine, dried over $Na_2SO_4$ and concentrated in vacuum. Purificaton of the residue by silica gel chromatography (1.5:1 hexanes: EtOAc) provided the title compound as an off-white solid. MS (ESI, pos. ion) m/z: 329 (M+1).

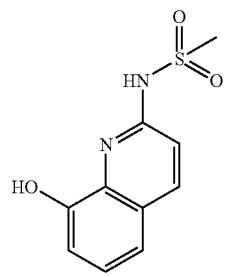

(c) N-(8-Hydroxy-quinolin-2-yl)-methanesulfonamide. To N-(8-benzyloxy-quinolin-2-yl)-methanesulfonamide (0.18 g, 0.54 mmol) suspended in EtOH (2.5 mL) was added 10% palladium on carbon (0.18 g, Aldrich), followed by cyclohexadiene (0.51 mL, 5.4 mmol, Aldrich). The reaction mixture was stirred at 25° C. for 2 h, filtered through a pad of Celite®, and the filtrate was concentrated in vacuum to give the title compound as an off-white solid. MS (ESI, pos. ion) m/z: 239 (M+1).

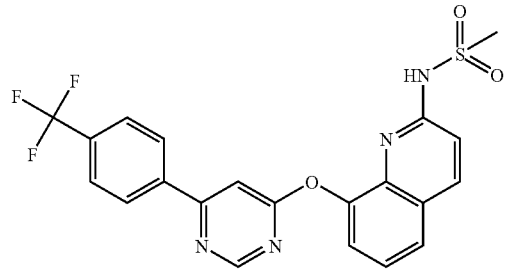

(d) N{8-[6-(4-Trifluoromethyl-phenyl)-pyrimidin-4-yloxy]-quinolin-2-yl)}-methanesulfonamide. This material was prepared according to the method described in Example 3 using 4-chloro-6-(4-trifluoromethyl-phenyl)-pyrimidine, (Example 2(a), Method A), (0.18 g, 0.69 mmol), N-(8-hydroxy-quinolin-2-yl)-methanesulfonamide (0.11 g, 0.46 mmol), and potassium carbonate (0.13 g, 0.92 mmol) in DMF (0.5 mL). Purification by silica gel chromatography (1:1 hexanes: EtOAc) provided the title compound as a white solid. MS (ESI, pos. ion) m/z: 461 (M+1). Mp: 216.7-219.7° C. Anal. Calcd for $C_{21}H_{15}F_3N_4O_3S$: C, 54.78, H. 3.28; N. 12.17, S. 6.96. Found: C, 54.69; H. 3.35, N. 12.06, S. 7.11.

EXAMPLE 75

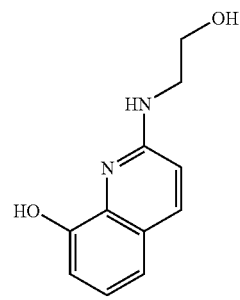

(a) 2-(2-Hydroxy-ethylamino)-quinolin-8-ol. This material was prepared according to the method described in Example 5(a) using 2-chloro-quinolin-8-ol, (Example 2(a), Method B), (0.12 g, 0.67 mmol) and ethanolamine (0.8 mL, 13 mmol, Aldrich) in dioxane (2 mL). Recrystallization from MeOH/$H_2O$ provided the title compound as a yellow solid. MS (ESI, pos. ion) m/z: 205 (M+1).

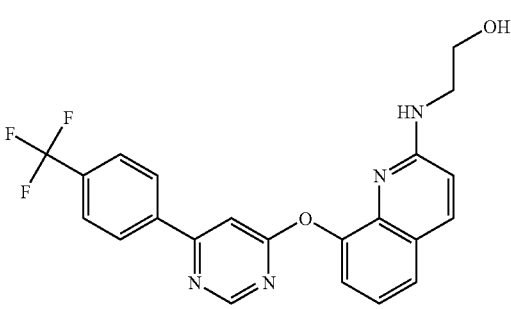

(b) 2-{8-[6-(4-Trifluoromethyl-phenyl)-pyrimidin-4-yloxy]-quinolin-2-ylamino}-ethanol. This material was prepared according to the method described in Example 3 using 4-chloro-6-(4-trifluoromethyl-phenyl)-pyrimidine, (Example 2(a), Method A), (0.14 g, 0.56 mmol), 2-(2-hydroxy-ethylamino)-quinolin-8-ol (95 mg, 0.47 mmol), and potassium carbonate (0.16 g, 1.1 mmol) in DMF (1.5 mL). Purification by silica gel chromatography (1:1 hexanes: EtOAc) provided the title compound as a white solid. MS (ESI, pos. ion) m/z: 427 (M+1). Mp:157.5-160.5° C. Anal. Calcd for $C_{22}H_{17}F_3N_4O_2$: C, 61.97; H, 4.02; N, 13.14. Found: C, 61.93; H, 4.02; N, 13.17.

EXAMPLE 76

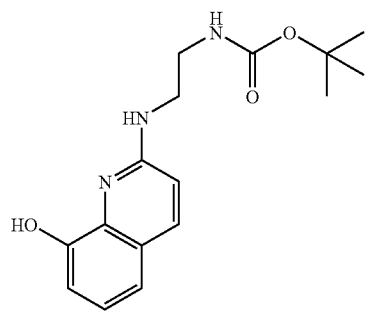

(a) [2-(8-Hydroxy-quinolin-2-ylamino)-ethyl]-carbamic acid tert-butyl ester. This material was prepared according to the method described in Example 5(a) using 2-chloro-quinolin-8-ol (0.18 g, 1 mmol) and tert-butyl N-(2-aminoethyl)carbamate (3.2 g, 20 mmol, Aldrich) in dioxane (3 mL). Recrystallization from MeOH/H₂O provided the title compound as a tan solid. MS (ESI, pos. ion) m/z: 304 (M+1).

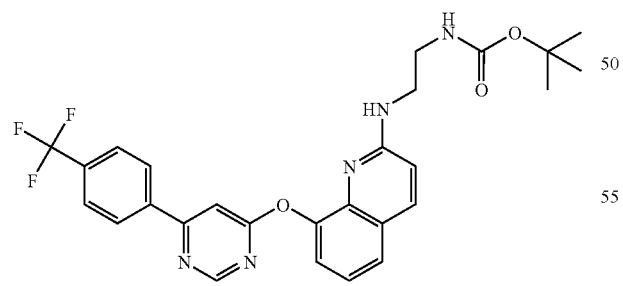

(b) (2-{8-[6-(4-Trifluoromethyl-phenyl)-pyrimidin-4-yloxy]-quinolin-2-ylamino}-ethyl)-carbamic acid tert-butyl ester. This material was prepared according to the method described in Example 3 using 4-chloro-6-(4-trifluoromethyl-phenyl)-pyridine, (Example 2(a), Method A), (0.17 g, 0.65 mmol), [2-(8-hydroxy-quinolin-2-ylamino)-ethyl]-carbamic acid tert-butyl ester (0.16, 0.54 mmol), and potassium carbonate (0.15 g, 1.1 mmol) in DMF (1.5 mL). Purification by silica gel chromatography (3:1 hexanes: EtOAc) provided the title compound as a white solid. MS (ESI, pos. ion) m/z: 526 (M+1).

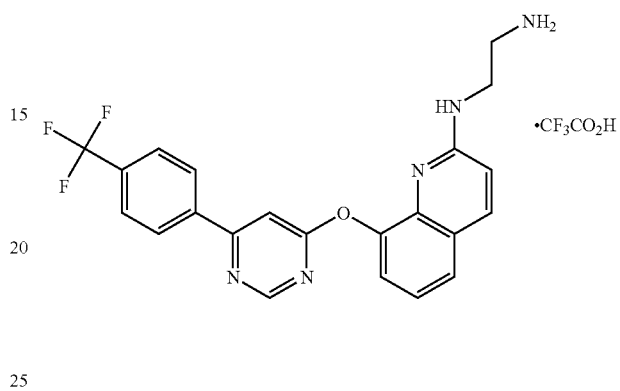

(c) N1-{8-[6-(4-Trifluoromethyl-phenyl)-pyrimidin-4-yloxy]-quinolin-2-yl}-ethane-1,2-diamine trifluoroacetate. To (2-{8-[6-(4-trifluoromethyl-phenyl)-pyrimidin-4-yloxy]-quinolin-2-ylamino}-ethyl)-carbamic acid tert-butyl ester (60 mg, 0.11 mmol) suspended in CH₂Cl₂ (1 mL) was added dropwise trifluoroacetic acid (0.5 mL, Aldrich). The reaction mixture was stirred at 25° C. for 2 h, the solvent was evaporated and the residue was recrystallized from MeOH to give the title compound as a white solid. MS (ESI, pos. ion) m/z: 426 (M+1). Mp: 161.0-163.0° C. Anal. Calcd for $C_{22}H_{18}F_3N_5O2CF_3CO_2H2H_2O$: C, 45.29; H, 3.51; N, 10.16. Found: C, 45.24; H, 3.51; N, 10.06.

EXAMPLE 77

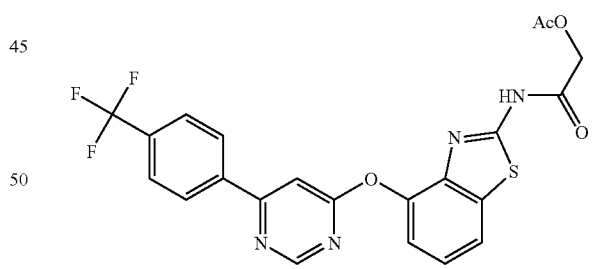

(a) Acetic acid {4-[6-(4-trifluoromethyl-phenyl)-pyrimidin-4-yloxy]-benzothiazol-2-ylcarbamoyl}-methyl ester. According to the procedure described in Example 67, the title compound was prepared by using 4-[6-(4-trifluoromethyl-phenyl)-pyrimidin-4-yloxy]-benzothiazol-2-ylamine, (Example 65), (0.39 g, 1 mmol), acetoxyacetyl chloride (0.22 mL, 2 nmol, Aldrich) and 2-tert-butylimino-2-diethylamino-1,3-dimethyl-perhydro-1,3,2-diazaphorine, polymer bound (BEMP resin) (0.68 g, 1.5 mmol) in THF (10 mL). Purification by silica gel chromatography (1:3 of EtOAc/hexanes) provided the title compound as a white solid. MS (ESI, pos. ion) m/z: 489 (M+1).

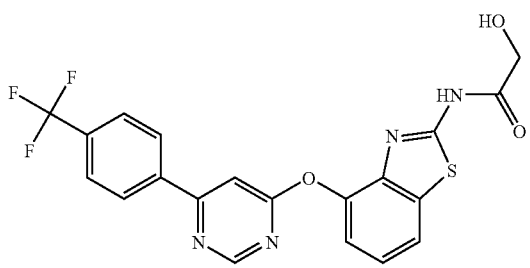

(b) 2-Hydroxy-N-{4-[6-(4-trifluoromethyl-phenyl)-pyrimidin-4-yloxy]-benzothiazol-2-yl}-acetamide. This material was prepared according to the procedure described in Example 68(b) using acetic acid {4-[6-(4-trifluoromethyl-phenyl)-pyrimidin-4-yloxy]-benzothiazol-2-ylcarbamoyl}-methyl ester (0.1 g, 0.2 mmol) and potassium carbonate (57 mg, 0.4 mmol) in a mixture of MeOH (2 mL) and CH$_2$Cl$_2$ (2 mL). Purification by silica gel chromatography (1:1.5 of EtOAc/hexanes) provided the title compound as a white solid. MS (ESI, pos. ion) m/z: 447 (M+1).

EXAMPLE 8

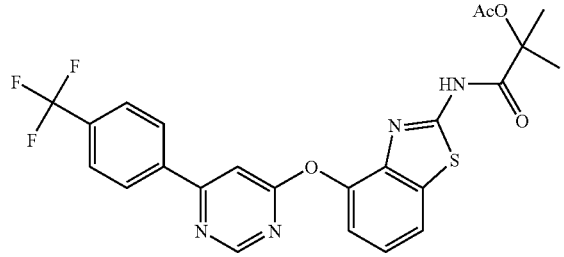

(a) Acetic acid 1-methyl-1-{4-[6-(4-trifluoromethyl-phenyl)-pyrimidin-4-yloxy]-benzothiazol-2-ylcarbamoyl}-ethyl ester. To 4-[6-(4-trifluoromethyl-phenyl)-pyrimidin-4-yloxy]-benzothiazol-2-ylamine, (Example 65), (0.39 g, 1 mmol) suspended in dioxane (3 mL) was added triethylamine (0.27 mL, 2 mmol, Aldrich), followed by 1-chlorocarbonyl-1-methyl-ethyl acetate (0.29 mL, 2 mmol). The reaction mixture was heated at 100° C. for 16 h, allowed to cool to room temperature and partitioned between EtOAc and brine. The layers were separated and the aqueous layer extracted with EtOAc. The combined organic layers were dried over Na$_2$SO$_4$, filtered and concentrated under vacuum. Purification of the residue by silica gel chromatography (3:1 hexanes: EtOAc) provided the title compound as a white foam. MS (ESI, pos. ion) m/z: 517 (M+1).

(b) 2-Hydroxy-2-methyl-N-{4-[6-(4-trifluoromethyl-phenyl)-pyrimidin-4-yloxy]-benzothiazol-2-yl}-propionamide. This material was prepared according to the procedure described in Example 68(b) using acetic acid 1-methyl-1-{4-[6-(4-trifluoromethyl-phenyl)-pyrimidin-4-yloxy]-benzothiazol-2-ylcarbamoyl}-ethyl ester (0.5 g, 1 mmol) and potassium carbonate (0.27 g, 1.9 mmol) in MeOH (10 mL). Purification by silica gel chromatography (1:3 of EtOAc/hexanes) provided the title compound as a white solid. MS (ESI, pos. ion) m/z: 475 (M+1). Mp: 213.1-215.6° C.

EXAMPLE 79

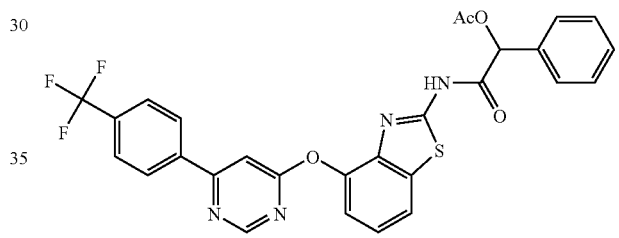

Acetic acid {4-[6-(4-trifluoromethyl-phenyl)-pyrimidin-4-yloxy]-benzothiazol-2-ylcarbamoyl}-methyl ester. This material was prepared according to the procedure described in Example 78(a) using 4-[6-(4-trifluoromethyl-phenyl)-pyrimidin-4-yloxy]-benzothiazol-2-ylamine, (Example 65), (0.36 g, 0.9 mmol), O-acetyl mandelic acid (0.41 mL, 1.8 mmol, Heico Chemicals, Inc.) and triethylamine (0.25 mL, 1.8 mmol) in dioxane (3 mL). Purification by silica gel chromatography (3:1 hexanes: EtOAc) provided the title compound as a light-yellow foam. MS (ESI, pos. ion) m/z: 565 (M+1). Mp: 118.6-138.4° C.

EXAMPLE 80

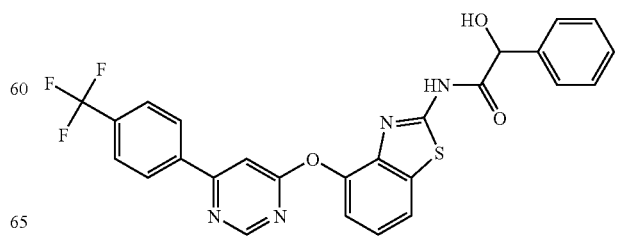

2-Hydroxy-2-phenyl-N-{4-[6-(4-trifluoromethyl-phenyl)-pyrimidin-4-yloxy]-benzothiazol-2-yl}-acetamide. This material was prepared according to the procedure described in Example 68(b) using acetic acid phenyl-{4-[6-(4-trifluoromethyl-phenyl)-pyrimidin-4-yloxy]-benzothiazol-2-ylcarbamoyl}-methyl ester, (Example 79), (0.44 g, 0.78 mmol) and potassium carbonate (0.22 g, 1.6 mmol) in MeOH (8 mL). Purification by silica gel chromatography (1:2 of EtOAc/hexanes) provided the title compound as a white solid. MS (ESI, pos. ion) m/z: 523 (M+1). Mp: 197.7-205.4° C.

EXAMPLE 81

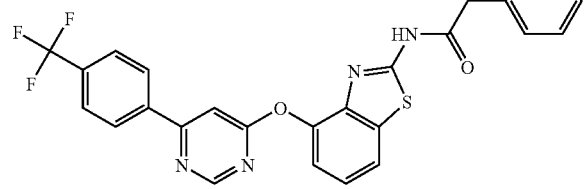

2-Phenyl-N-{4-[6-(4-trifluoromethyl-phenyl)-pyrimidin-4-yloxy]-benzothiazol-2-yl}-acetamide. According to the procedure described in Example 67, the title compound was prepared by using 4-[6-(4-trifluoromethyl-phenyl)-pyrimidin-4-yloxy]-benzothiazol-2-ylamine, (Example 65), (0.19 g, 0.5 mmol), phenylacetyl chloride (0.13 mL, 1 mmol, Aldrich), and 2-tert-butylimino-2-diethylamino-1,3-dimethyl-perhydro-1,3,2-diazaphosphorine, polymer bound (BEMP resin) (0.34 g, 0.75 mmol) in THF (5 mL). Purification by silica gel chromatography (1:4 of EtOAc/hexanes) provided the title compound as a white solid. MS (ESI, pos. ion) m/z: 507 (M+1). Mp: 188.6-191.0° C.

EXAMPLE 2

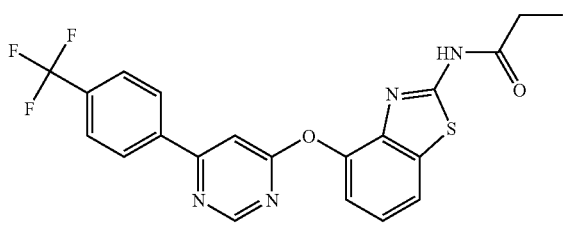

N-{4-[6-(4-Trifluoromethyl-phenyl)-pyrimidin-4-yloxy]-benzothiazol-2-yl}-propionamide. According to the procedure described in Example 67, the title compound was prepared by using 4-[6-(4-trifluoromethyl-phenyl)-pyrimidin-4-yloxy]-benzothiazol-2-ylamine, (Example 65), (0.19 g, 0.5 mmol), propionyl chloride (87 uL, 1 mmol, Aldrich), and 2-tert-butylimino-2-diethylamino-1,3-dimethyl-perhydro-1,3,2-diazaphosphorine, polymer bound (BEMP resin), (0.34 g, 0.75 mmol) in THF (5 mL). Purification by silica gel chromatography (1:4 of EtOAc/hexanes) provided the title compound as a white solid. MS (ESI, pos. ion) m/z: 445 (M+1). Mp: 196.9-197.6° C.

EXAMPLE 83

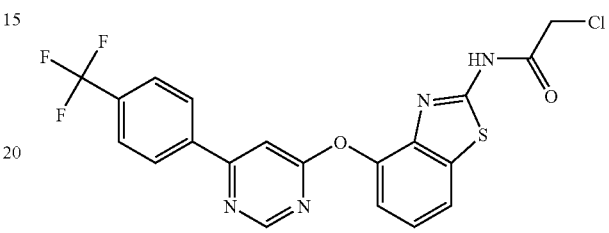

(a) 2-Chloro-N-{4-[6-(4-trifluoromethyl-phenyl)-pyrimidin-4-yloxy]-benzothiazol-2-yl}-acetamide. To a mixture of 4-[6-(4-trifluoromethyl-phenyl)-pyrimidin-4-yloxy]-benzothiazol-2-ylamine, (Example 65), (0.39 g, 1 mmol) and pyridine (97 uL, 1.2 mmol) in toluene (3.5 mL) was added chloroacetyl chloride (96 uL, 1.2 mmol, Aldrich) at 10° C. The reaction mixture was stirred at 10° C. for 1 h, then at 25° C. for 16 h and partitioned between EtOAc and water. The layers were separated and the aqueous layer was extracted with EtOAc. The combined organic layers were washed with brine, dried over Na₂SO₄, filtered and concentrated in vacuum to give the title compound. MS (ESI, pos. ion) m/z: 465 (M+1).

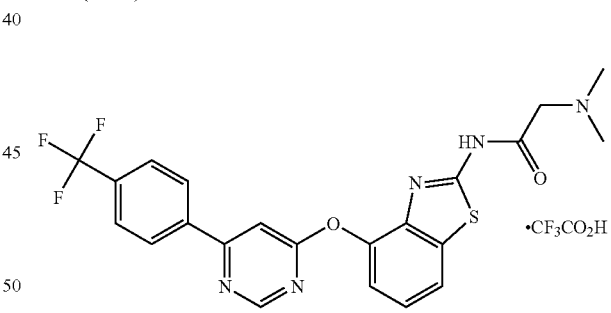

(b) 2-Dimethylamino-N-{4-[6-(4-trifluoromethyl-phenyl)-pyrimidin-4-yloxy]-benzothiazol-2-yl}-acetamide trifluoroacetate. To 2-chloro-N-{4-[6-(4-trifluoromethyl-phenyl)-pyrimidin-4-yloxy]-benzothiazol-2-yl}-acetamide (0.15 g, 0.33 mmol) suspended in CH₂Cl₂ (1.5 mL) was added 2 M solution of dimethylamine in MeOH (0.41 mL, 0.82 mmol, Aldrich) and the reaction mixture was stirred at 25° C. for 16 h. The solvent was evaporated and the residue was purified by silica gel chromatography (1:1 of EtOAc/hexanes), followed by preparative HPLC separation (10-90% 0.1% TFA acetonitrile in 0.1% TFA water for 20 min) to give the title compound as an off-white solid. MS (ESI, pos. ion) m/z: 474 (M+1). Mp: 67.9-68.0° C.

EXAMPLE 84

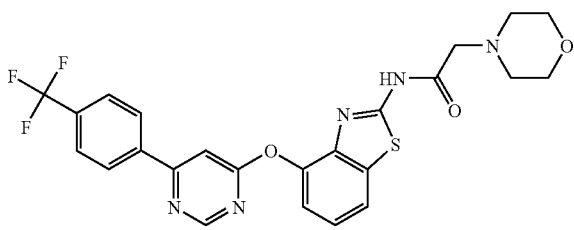

2-Morpholin-4-yl-N-{4-[6-(4-trifluoromethyl-phenyl)-pyrimidin-4-yloxy]-benzothiazol-2-yl}-acetamide. This material was prepared according to the procedure described in Example 83(b) using 2-chloro-N-{4-[6-(4-trifluoromethyl-phenyl)-pyrimidin-4-yloxy]-benzothiazol-2-yl}-acetamide, (Example 83(a)), (0.17 g, 0.33 mmol) and morpholine (72 uL, 0.82 mmol, Aldrich) in $CH_2Cl_2$ (1.5 mL). Purification by silica gel chromatography (1:1 of EtOAc/hexanes) provided the title compound as a white solid. MS (ESI, pos. ion) m/z: 516 (M+1). Mp:177.8-181.7° C.

EXAMPLE 85

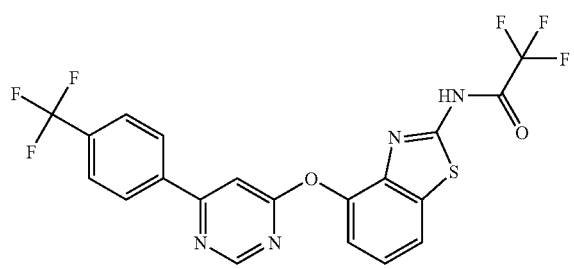

(a) 2,2,2-Trifluoro-N-{4-[6-(4-trifluoromethyl-phenyl)-pyrimidin-4-yloxy]-benzothiazol-2-yl}-acetamide. A suspension of 4-[6-(4-trifluoromethyl-phenyl)-pyrimidin-4-yloxy]-benzothiazol-2-ylamine, (Example 65), (0.15 g, 0.38 mmol) and pyridine (33 uL, 0.41 mmol) in $CH_2Cl_2$ (2 mL) was treated with trifluoroacetic anhydride (58 uL, 0.41 mmol, Aldrich) at 0° C. under nitrogen atmosphere. The reaction mixture was stirred at 0° C. for 2 h and partitioned between $CH_2Cl_2$ and brine. The layers were separated and the aqueous layer was extracted with EtOAc. The combined organic layers were dried over $Na_2SO_4$, filtered and concentrated in vacuum to give the title compound as a white solid. MS (ESI, pos. ion) m/z: 485 (M+1).

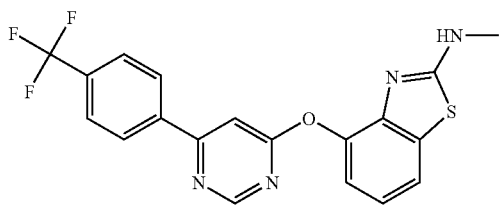

(b) Methyl-{4-[6-(4-trifluoromethyl-phenyl)-pyrimidin-4-yloxy]-benzothiazol-2-yl}-amine. To 2,2,2-trifluoro-N-{4-[6-(4-trifluoromethyl-phenyl)-pyrimidin-4-yloxy]-benzothiazol-2-yl}-acetamide (0.18 g, 0.37 mmol) dissolved in DMF (1 mL) was added iodomethane (51 uL, 0.82 mmol, Aldrich) and cesium carbonate (0.25 g, 0.78 mmol, Aldrich). The reaction mixture was heated at 70° C. for 22 h, allowed to cool to room temperature and partitioned between EtOAc and brine. The layers were separated and the aqueous layer was extracted with EtOAc. The combined organic layers were dried over $Na_2SO_4$, filtered and concentrated in vacuum. Purification of the residue by silica gel chromatography (1:1 of EtOAc/hexanes) provided the title compound as an off-white solid. MS (ESI, pos. ion) m/z: 403 (M+1).

EXAMPLE 86

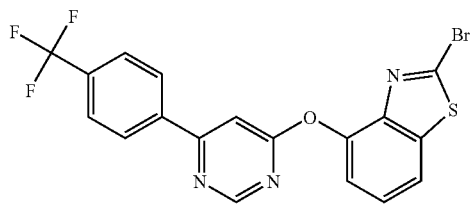

2-Bromo-4-[6-(4-trifluoromethyl-phenyl)-pyrimidin-4-yloxy]-benzothiazole. To a suspension of anhydrous $CuBr_2$ (0.54 g, 2.4 mmol, Aldrich) in dry acetonitrile (4 mL) was added isoamyl nitrite (0.4 mL, 3 mmol, Aldrich) dropwise and the mixture was stirred at room temperature for 10 min. 4-[6-(4-trifluoromethyl-phenyl)-pyrimidin-4-yloxy]-benzothiazol-2-ylamine (0.78 g, 2 mmol) was added in small portions and the reaction mixture was stirred at 25° C. for 1 h, and then heated at 65° C. for 1.5 h. The mixture was filtered through a pad of Celite® and washed with acetonitrile. The filtrate was concentrated in vacuum and purified by silica gel chromatography (1:6 of EtOAc/hexanes) to give the title compound as a white solid. MS (ESI, pos. ion) nvz: 453 (M+1).

EXAMPLE 87

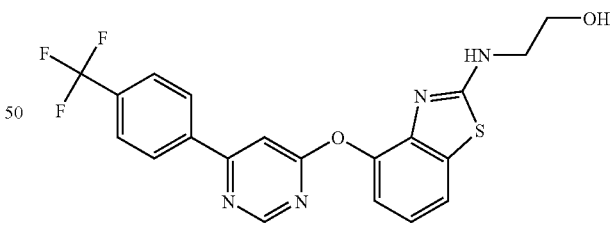

2-{4-[6-(4-Trifluoromethyl-phenyl)-pyrimidin-4-yloxy]-benzothiazol-2-ylamino}-ethanol. To 2-bromo-4-[6-(4-trifluoromethyl-phenyl)-pyrimidin-4-yloxy]-benzothiazole, (Example 86), (90 mg, 0.2 mmol) dissolved in dioxane (1 mL) was added ethanolamine (0.06 mL, 1 mmol, Aldrich). The reaction mixture was heated in microwave synthesizer at 200° C. for 10 min, allowed to cool to room temperature and evaporated in vacuum. Purification of the residue by silica gel chromatography (1:1 of EtOAc/hexanes) provided the title compound as a white solid. MS (ESI, pos. ion) m/z: 433 (M+1).

EXAMPLE 88

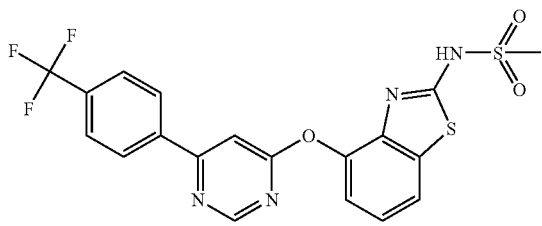

N-{4-[6-(4-Trifluoromethyl-phenyl)-pyrimidin-4-yloxy]-benzothiazol-2-yl} methanesulfonamide. To a solution of 4-[6-(4-trifluoromethyl-phenyl)-pyrimidin-4-yloxy]-benzothiazol-2-ylamine, (Example 65), (0.19 g, 0.5 mmol) in DMF (1.5 mL) was added methanesulfonyl chloride (92 uL, 1.2 mmol) and triethylamine (0.2 mL, 1.5 mmol). The reaction mixture was stirred at 60C for 1 h, at 110° C. for 16 h, allowed to cool to room temperature and partitioned between EtOAc and brine. The layers were separated and the aqueous layer was extracted with EtOAc. The combined organic layers were dried over $Na_2SO_4$, filtered and concentrated under vacuum. Purification of the residue by silica gel chromatography (1:1 of EtOAc/hexanes) provided the title compound as an off-white solid. MS (ESI, pos. ion) m/z: 467 (M+1).

EXAMPLE 89

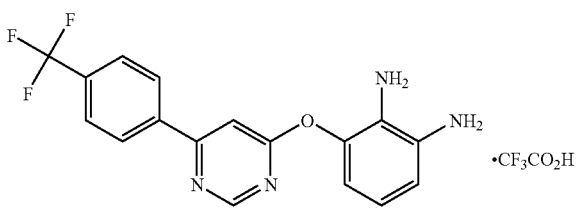

(a) 3-[6-(4-Trifluoromethyl-phenyl)-pyrimidin-4-yloxy]-benzene-1,2-diamine trifluoroacetate. $K_2CO_3$ (138 mg, 1 mmol) was added to a solution of 2,3-diamino-phenol (100 mg, 0.81 mmol, Aldrich), 4-chloro-6-(4-trifluoromethyl-phenyl)-pyrimidine, (Example 2(a), Method A), (202 mg, 0.80 mmol) and DMF (2 mL), and the resulting mixture was irradiated at 180° C. for 10 min in a microwave synthesizer. The solvent was removed under reduced pressure and purified by prep. LC (10-90% $CH_3CN/H_2O$ modified with 0.1% TFA) to give the title compound as a black oil. MS (ESI, pos. ion.) m/z: 347 (M+1).

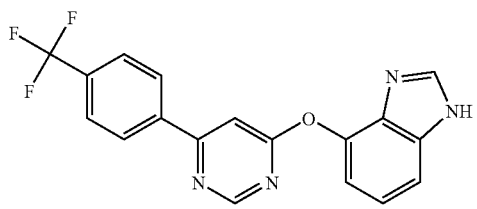

(b) 4-[6-(4-Trifluoromethyl-phenyl)-pyrimidin-4-yloxy]-1H-benzoimidazole. A solution of 3-[6-(4-trifluoromethyl-phenyl)-pyrimidin-4-yloxy]-benzene-1,2-diamine (50 mg, 0.14 mmol), EtOH (1 mL), ethyl formate (1 mL, Aldrich) and HOAc (50 uL) was irradiated at 160° C. for 10 min in a microwave synthesizer. The reaction mixture was left at room temperature for 2 h and the resulting precipitate was filtered, washed with ethyl formate and dried under vacuum to give the title compound as an off-white solid. MS (ESI, pos. ion.) m/z: 357 (M+1).

EXAMPLE 90

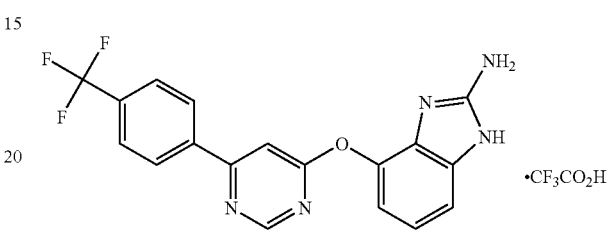

4-[6-(4-Trifluoromethyl-phenyl)-pyrimidin-4-yloxy]-1H-benzoimidazol-2-ylamine trifluoroacetate. Cyanogen bromide (16 mg, 0.15 mmol, Aldrich) was added to a solution of 3-[6-(4-trifluoromethyl-phenyl)-pyrimidin-4-yloxy]-benzene-1,2-diamine, (Example 89), (50 mg, 0.14 mmol) in EtOH (2 mL). After stirring for 3 days the solvent was removed under reduced pressure and the mixture was purified by prep. LC (10-90% $CH_3CN/H_2O$ modified with 0.1% TFA) to give the title compound as a white solid. MS (ESI, pos. ion.) m/z: 372 (M+1).

EXAMPLE 91

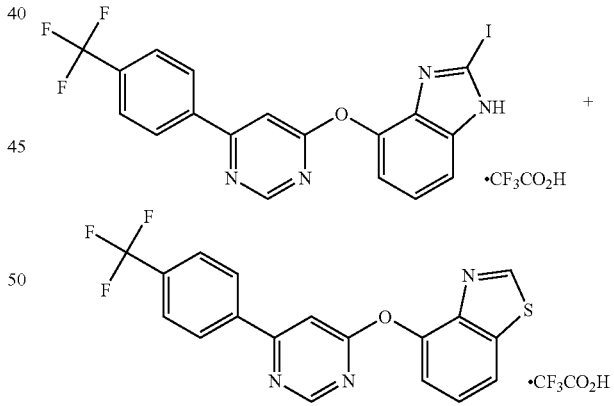

2-Iodo-4-[6-(4-trifluoromethyl-phenyl)-pyrimidin-4-yloxy]-benzothiazole trifluoroacetate and 4-[6-(4-Trifluoromethyl-phenyl)-pyrimidin-4-yloxy]-benzothiazole trifluoroacetate. A mixture of 4-[6-(4-trifluoromethyl-phenyl)-pyrimidin-4-yloxy]-benzothiazol-2-ylamine, (Example 65), (100 mg, 0.26 mmol), isoamyl nitrite (0.21 mL, 1.6 mmol, Aldrich), CsI (68 mg, 0.26 mmol, Aldrich), $I_2$ (33 mg, 0.13 mol, Aldrich), CuI (15 mg, 0.079 mmol, Aldrich) and DME (5 mL) was heated at 65° C. for 1.5 h. The mixture was allowed to cool to room temperature and the solvent was removed under reduced pressure. The resulting mixture was purified by prep. LC (10-90% CH₃CN/H₂O modified with 0.1% TFA) to give 2-iodo-4-[6-(4-trifluoromethyl-phenyl)-pyrimidin-4-yloxy]-benzothiazole as a white solid [(30 mg, 23%), MS (ESI, pos. ion.) m/z: 500 (M+1)] and 4-[6-(4-trifluoromethyl-phenyl)-pyrimidin-4-yloxy]-benzothiazole as a brown solid [MS (ESI, pos. ion.) m/z: 374 (M+1)].

EXAMPLE 92

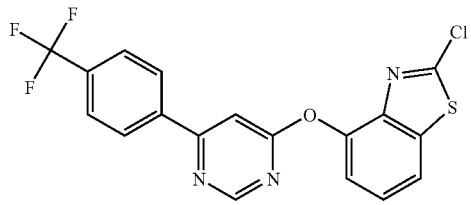

2-Chloro-4-[6-(4-trifluoromethyl-phenyl)-pyrimidin-4-yloxy]-benzothiazole. The title compound was prepared in an analogous manner to the conditions of Example 91 by reacting 4-[6-(4-trifluoromethyl-phenyl)-pyrimidin-4-yloxy]-benzothiazol-2-ylamine (Example 65) with CsCl and CuCl. MS (ESI, pos. ion.) m/z: 408 (M+1).

EXAMPLE 93

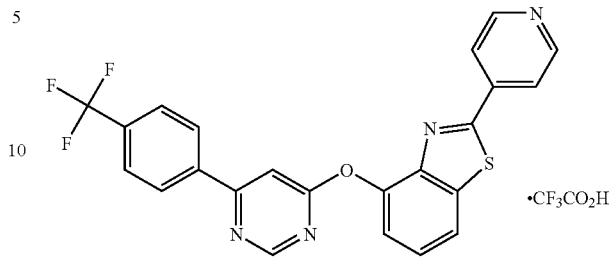

2-Pyridin-4-yl-4-[6-(4-trifluoromethyl-phenyl)-pyrimidin-4-yloxy]-benzothiazole trifluoroacetate. A mixture of 2-iodo-4-[6-(4-trifluoromethyl-phenyl)-pyrimidin-4-yloxy]-benzothiazole, (Example 91), (35 mg, 0.070 mmol), 4-pyridyl boronic acid (13 mg, 0.11 mmol), Pd(PPh₃)₄ (12 mg, 0.010 mmol) Na₂CO₃ (0.20 mL, 2M aq. solution) and dioxane (1 mL) was irradiated at 200° C. for 10 min in a microwave synthesizer. The solvent was removed under reduced pressure, and the residue was purified by prep. LC (10-90% CH₃CN/H₂O modified with 0.1% TFA) to give the title compound as a white powder. MS (ESI, pos. ion.) m/z: 451 (M+1).

ADDITIONAL EXAMPLES

Following the procedure described above in Example 93, or with slight modifications thereof, and following procedures familiar to one of ordinary skill in the art, the following examples were prepared from commercially available reagents:

| Example | Structure | MS (ESI, pos. ion) m/z |
|---|---|---|
| 94 | 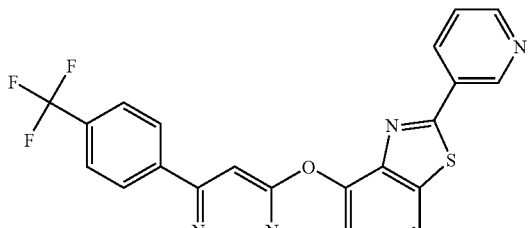 | 451 (M + 1) |
| 95 | 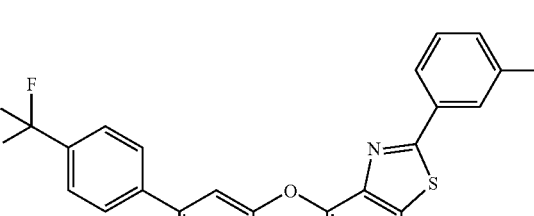 | 518 (M + 1) |

| Example | Structure | MS (ESI, pos. ion) m/z |
|---|---|---|
| 96 | 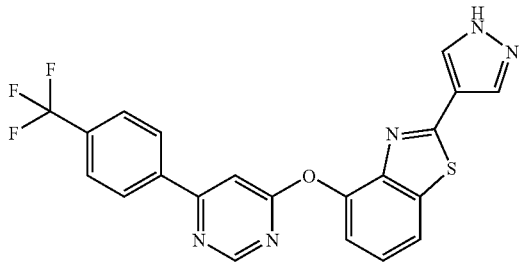 | 440 (M + 1) |

EXAMPLE 97

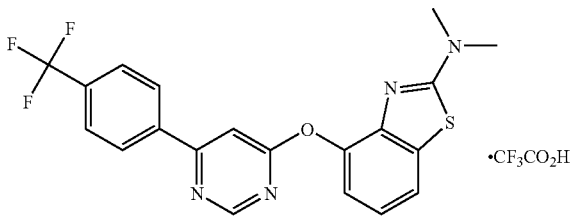

Dimethyl-{4-[6-(4-trifluoromethyl-phenyl)-pyrimidin-4-yloxy]-benzothiazol-2-yl}-amine trifluoroacetate. A mixture of 2-bromo-4-[6-(4-trifluoromethyl-phenyl)-pyrimidin-4-yloxy]-benzothiazole, (Example 86), (24 mg, 0.053 mmol) and dimethyl amine (2M in THF, 0.7 mL, 1.4 mmol, Aldrich) was irradiated at 100° C. for 2 min in a microwave synthesizer. The resulting mixture was evaporated under reduced pressure and the residue purified by prep. LC (20-100% $CH_3CN/H_2O$ modified with 0.1% TFA) to give the title compound as a white solid. MS (ESI, pos. ion.) m/z: 417 (M+1).

ADDITIONAL EXAMPLES

Following the procedure described above in Example 97, or with slight modifications thereof, and following procedures familiar to one of ordinary skill in the art, the following examples were prepared from commercially available reagents:

| Example | Structure | MS (ESI, pos. ion) m/z |
|---|---|---|
| 98 | 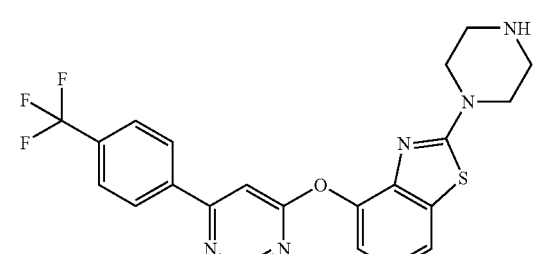 | 458 (M + 1) |
| 99 | 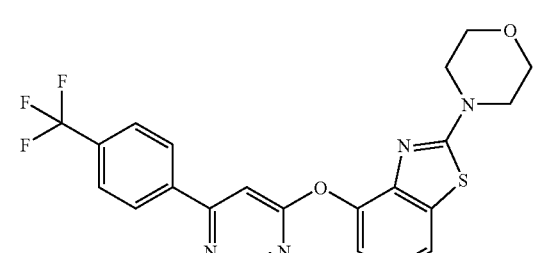 | 459 (M + 1) |

| Example | Structure | MS (ESI, pos. ion) m/z |
|---|---|---|
| 100 | 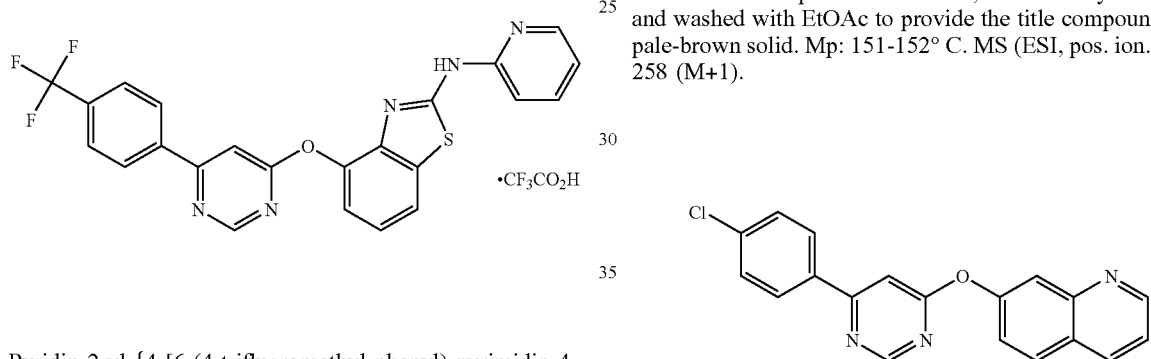 | 486 (M + 1) |

EXAMPLE 101

Pyridin-2-yl-{4-[6-(4-trifluoromethyl-phenyl)-pyrimidin-4-yloxy]-benzothiazol-2-yl}-amine trifluoroacetate. A mixture of 2-iodo-4-[6-(4-trifluoromethyl-phenyl)-pyrimidin-4-yloxy]-benzothiazole, (Example 91), (25 mg, 0.050 mmol), 2-aminopyridine (6 mg, 0.06 mmol, Aldrich), tris(dibenzylideneacetone)dipalladium(0) (5 mg, 0.005 mmol, Aldrich), sodium t-butoxide (7 mg, 0.07 mmol, Aldrich), 2-dicyclohexylphosphino-2'-(N,N-dimethylamino)biphenyl (8 mg, 0.02 mmol, Acros) and dioxane/NMP (3/1, 1.5 mL) was heated at 200° C. for 10 min in a microwave synthesizer. The solvent was removed in vacuum and the residue was purified by prep. LC (10-90% CH$_3$CN/H$_2$O modified with 0.1% TFA) to give the title compound as a white solid. MS (ESI, pos. ion.) m/z: 466 (M+1).

EXAMPLE 102

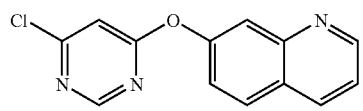

(a) 7-(6-Chloro-pyrimidin-4-yloxy)-quinoline. To a 100-mL, round-bottomed flask containing 4,6-dichloropyrimidine (5.1 g, 35 mmol, Aldrich), 7-hydroxyquinoline (5.0 g, 35 mmol, Aldrich), and DMF (30 mL) at room temperature was added potassium carbonate (4.8 g, 35 mmol, Aldrich). The suspension was stirred at 80° C. for 20 h under a N$_2$ atmosphere. The reaction was diluted with H$_2$O (200 mL) and the solution was extracted with dichloromethane (2×200 mL). The combined extracts were dried over Na$_2$SO$_4$, filtered and concentrated under vacuum. The crude material was suspended in EtOAc, collected by filtration, and washed with EtOAc to provide the title compound as a pale-brown solid. Mp: 151-152° C. MS (ESI, pos. ion.) m/z: 258 (M+1).

(b) 7-[6-(4-Chloro-phenyl)-pyrimidin-4-yloxy]-quinoline. To a 50-mL, round-bottomed flask containing 7-(6-chloro-pyrimidin-4-yloxy)-quinoline (1.5 g, 9.9 mmol) and ethylene glycol dimethyl ether (20 mL) was added 4-chlorophenylboronic acid (1.7 g, 6.6 mmol, Lancaster) and 1 N sodium carbonate (20 mL). The solution was purged with N$_2$ at room temperature for 15 min and palladium(0)-tetrakis-triphenylphosphine (0.38 g, 0.33 mmol, Strem Chemical) was added. The reaction mixture was heated at 100° C. for 16 h under a N$_2$ atmosphere and diluted at room temperature with water (50 mL). The reaction mixture was extracted with EtOAc (2×100 mL), the organic phase was dried over sodium sulfate, and concentrated under vacuum. The crude material was purified by silica gel chromatography (gradient: 1-5% 2 N ammonia in methanol/dichloromethane) to obtain the title compound as a white solid. Mp: 184-185° C. MS (ESI, pos. ion.) mn/z: 334 (M+1).

ADDITIONAL EXAMPLES

Following the procedure described above for Example 102 (b), or with slight modifications thereof, and following procedures familiar to one of ordinary skill in the art, the following examples were prepared:

| Example | Structure | MS (ESI, pos. ion) m/z | Melting Point ° C. |
|---|---|---|---|
| 103 | 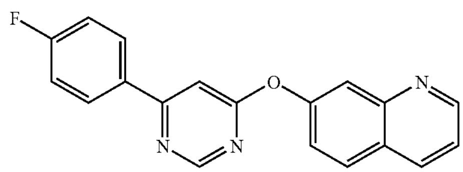 | 318.1 (M + 1) | 167.6-168.8 |
| 104 | 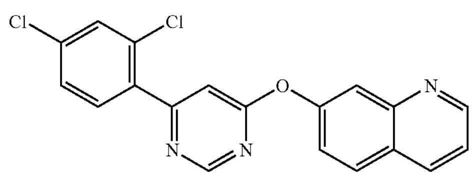 | 370.2 (M + 1) | 186.2-188.1 |
| 105 | 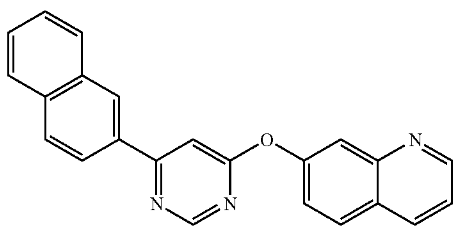 | 350.1 (M + 1) | 164.1-165.9 |
| 106 | 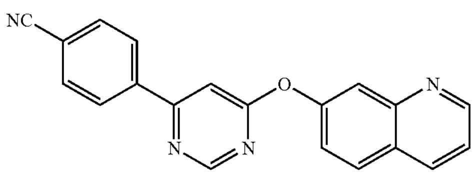 | 325.2 (M + 1) | 232.6-234.2 |
| 107 | 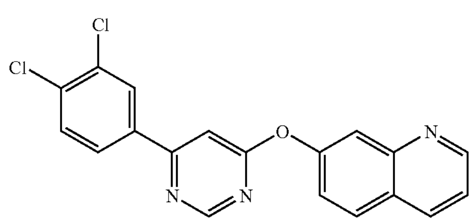 | 367.5 (M + 1) | 236.5-238 |
| 108 | 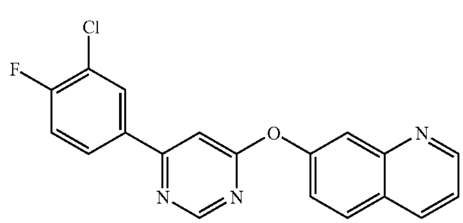 | 352.2 (M + 1) | 240.6-242.8 |
| 109 | 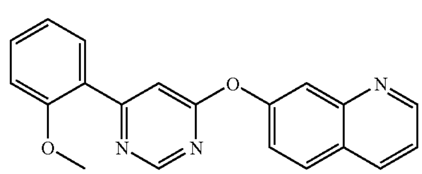 | 330.2 (M + 1) | 115.1 |

| Example | Structure | MS (ESI, pos. ion) m/z | Melting Point ° C. |
|---------|-----------|------------------------|--------------------|
| 110 | 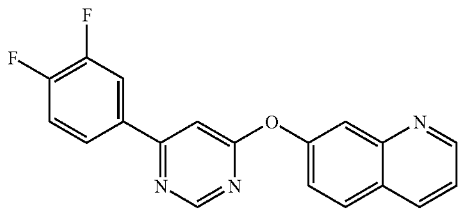 | 335.8 (M + 1) | 194.4-196.2 |

EXAMPLE 111

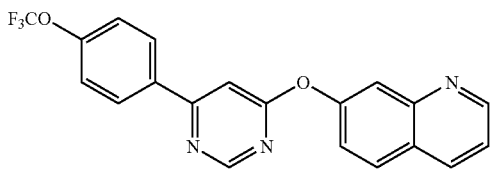

7-[6-(4-Trifluoromethoxy-phenyl)-pyrimidin-4-yloxy]-quinoline. To a 5-mL, microwave vial containing 7-(6-chloro-pyrimidin-4-yloxy)-quinoline, (Example 102(a)), (0.30 g, 1.2 mmol) and 1:1 toluene:EtOH (2.5 mL) was added 4-trifluoromethoxyphenylboronic acid (0.30 g, 1.9 mmol, Aldrich), 2 N potassium carbonate (2.5 mL), and palladium(0)-tetrakis-triphenylphosphine (0.070 g, 0.060 mmol, Strem Chemical). The reaction mixture was heated at 1400C for 10 min in a microwave synthesizer, allowed to cool to room temperature and diluted with water (5 mL) and 1 N sodium hydroxide (50 mL). The product was extracted with dichloromethane (2×100 mL), dried over sodium sulfate, and concentrated in vacuum. The crude material was purified by silica gel chromatography (gradient: 1-1.7% 2 N ammonia in methanol/dichloromethane) to obtain the title compound as a white solid. Mp: 67-168° C. MS (ESI, pos. ion.) m/z: 384 (M+1).

ADDITIONAL EXAMPLES

Following the procedure described above for Example 111, or with slight modifications thereof, and following procedures familiar to one of ordinary skill in the art, the following examples were prepared:

| Example | Structure | MS (ESI, pos. ion) m/z | Melting Point ° C. |
|---------|-----------|------------------------|--------------------|
| 112 | 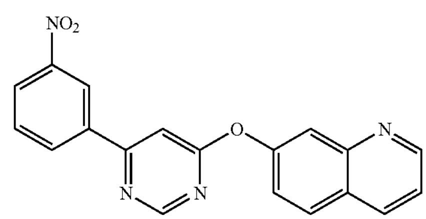 | 345 (M + 1) | 243.9-245.8 |
| 113 | 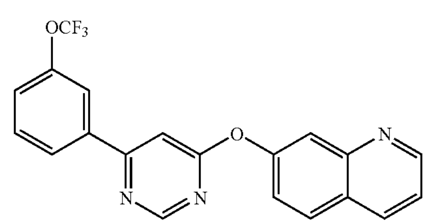 | 384 (M + 1) | 150.2-151.2 |
| 114 | 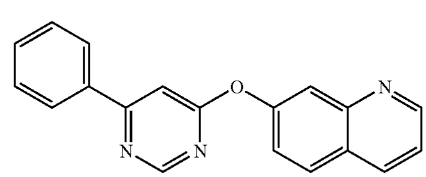 | 300 (M + 1) | 150.0-150.5 |

-continued

| Example | Structure | MS (ESI, pos. ion) m/z | Melting Point ° C. |
|---|---|---|---|
| 115 | 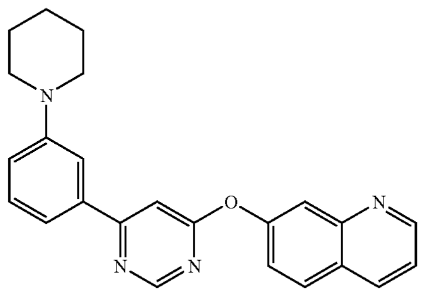 | 383.3 (M + 1) | oil |
| 116 | 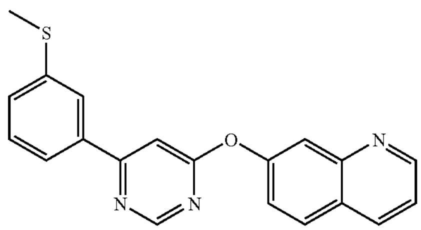 | 346.2 (M + 1) | 137.9-138.3 |
| 117 | 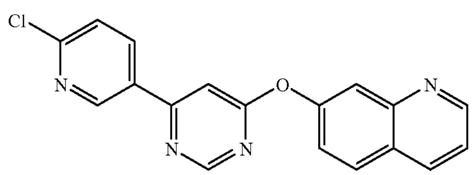 | 335 (M + 1) | 176.4-183.6 |
| 118 | 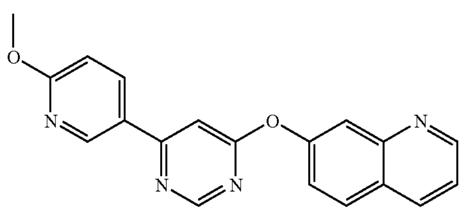 | 330.9 (M + 1) | 172.2-178.0 |
| 119 | 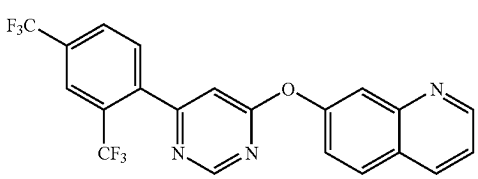 | 435.8 (M + 1) | 146.1-149.8 |
| 120 | 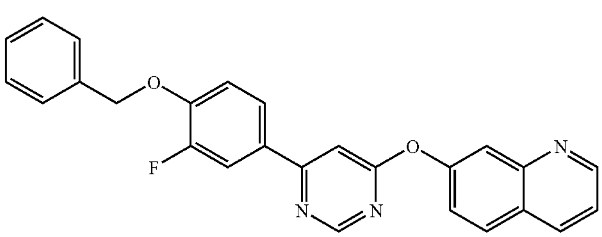 | 424.2 (M + 1) | 170.2-171.6 |
| 121 | 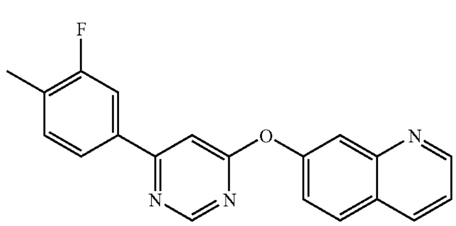 | 332.2 (M + 1) | 165.1-166.5 |

| Example | Structure | MS (ESI, pos. ion) m/z | Melting Point ° C. |
|---|---|---|---|
| 122 | 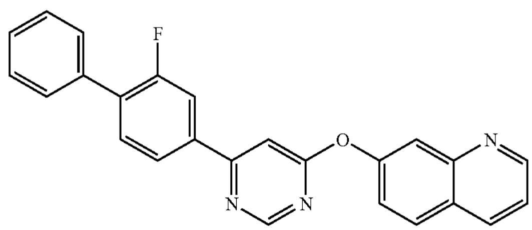 | 394 (M + 1) | 207.7-208.4 |
| 123 | 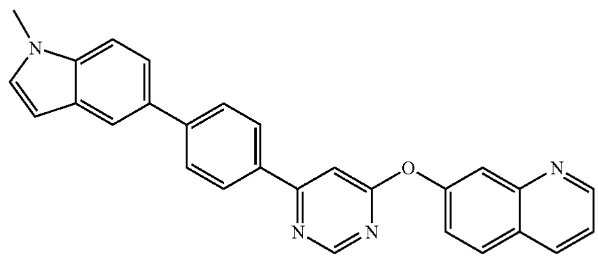 | 353.1 (M + 1) | 164-176 |

EXAMPLE 124

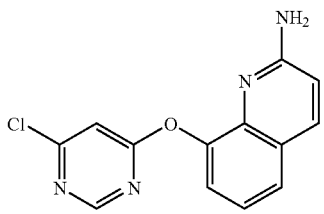

(a) 8-(6-Chloro-pyrimidin-4-yloxy)-quinolin-2-ylamine. To a 100-mL, round-bottomed flask containing 4,6-dichloropyrimidine (1.1 g, 7.5 mmol, Aldrich), 2-amino-8-hydroxyquinoline (0.60 g, 3.8 mmol, Sigma) and DMF (7 mL) at room temperature was added K₂CO₃ (0.52 g, 3.8 mmol, Aldrich). The suspension was stirred for 2 h under a N₂ atmosphere at 60° C. The reaction mixture was treated with H₂O (50 mL) and the mixture was extracted with dichloromethane (2×100 mL). The combined extracts were dried over Na₂SO₄, filtered, concentrated in vacuum and dried under vacuum for 16 h. The crude material was purified by silica gel chromatography (gradient: 1-3.5% 2 N ammonia in methanol/dichloro-methane) to obtain the title compound. Mp: 185-186° C. MS (ESI, pos. ion.) m/z: 273 (M+1).

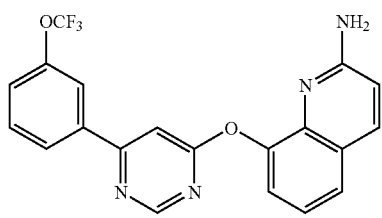

(b) 8-[6-Trifluoromethoxy-phenyl)-pyrimidin-4-yloxy]-quinolin-2-ylamine. To a 5-mL, microwave vial containing 8-(6-chloro-pyrimidin-4-yloxy)-quinolin-2-ylamine (0.20 g, 0.73 mmol) and 1:1 toluene:EtOH (2.5 mL) was added 3-trifluoromethoxyphenylboronic acid (0.23 g, 1.5 mmol, Aldrich), 2 N potassium carbonate (2.5 mL), and palladium (0)-tetrakis-triphenylphosphine (0.040 g, 0.040 mmol, Strem Chemical). The reaction mixture was heated at 140° C. for 10 min in a microwave synthesizer, allowed to cool to room temperature and diluted with water (5 mL) and 1 N sodium hydroxide (50 mL). The mixture was extracted with dichloromethane (2×100 mL), dried over Na₂SO₄, and concentrated in vacuum. The crude material was purified by silica gel chromatography (gradient: 0-1.2% 2 N ammonia in methanol/dichloromethane) to obtain the title compound as a white solid. Mp:148-150° C. MS (ESI, pos. ion.) m/z: 399 (M+1).

EXAMPLE 125

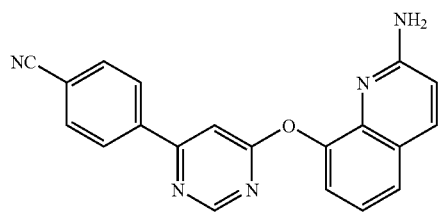

4-[6-(2-Amino-quinolin-8-yloxy)-pyrimidin-4-yl]-benzonitrile. According to the procedure described for Example 124(b), 8-(6-chloro-pyrimidin-4-yloxy)-quinolin-2-ylamine, (Example 124(a)), (0.20 g, 0.73 mmol) and 4-cyanophenylboronic acid (0.16 g, 1.1 mmol, Aldrich) provided the title compound as a white solid. Mp: 234-2360C. MS (ESI, pos. ion.) nzlz:340 (M+1).

EXAMPLE 126

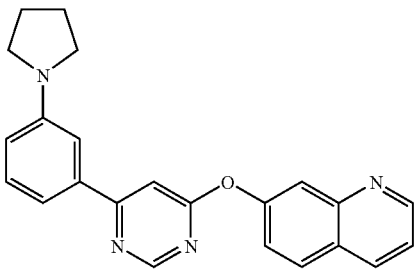

7-[6-(3-Pyrrolidin-1-yl-phenyl)-pyrimidin-4-yloxy]-quinoline. According to the procedure described for Example 124(b), from 7-(6-chloro-pyrimidin-4-yloxy)-quinoline, (Example 102(a)), (0.070 g, 0.25 mmol) and 3-pyrrolidinephenyl-boronic acid (0.070 g, 0.38 mmol, Asymchem) was obtained the title compound as a pale yellow oil. MS (ESI, pos. ion.) m/z:369 (M+1).

EXAMPLE 127

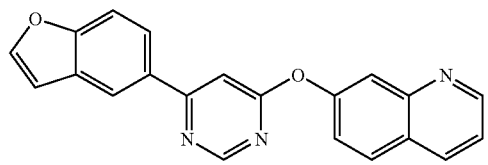

(a) 7-(6-Benzoftiran-5-yl-pyrirnidin-4-yloxy)-quinoline. To a 25-mL, pressure vial containing 7-(6-chloro-pyrimidin-4-yloxy)-quinoline, (Example 102(a)), (0.20 g, 0.78 mmol) and ethylene glycol dimethyl ether (3 mL) was added benzofuran-5-boronic acid (0.14 g, 1.2 mmol, prepared according to Goodby, J. W.; Toyne, K. J.; Hird, M.; Friedman, M. R.; Jones, John C. PCT Int. Appl. WO 0121606, 2001), 1 N sodium carbonate (2.3 mL), palladium acetate (0.010 g, 0.040 mmol, Aldrich), and tri-o-tolyl-phosphine (0.030 g, 0.090 mmol, Aldrich). The reaction mixture was purged with $N_2$ at room temperature for 15 min then the reaction flask was sealed and heated at 800C for 16 h. After cooling, the reaction mixture was diluted with water (5 mL) and 1 N sodium hydroxide (50 mL). The product was extracted with dichloromethane (2×100 mL), dried over $Na_2SO_4$, filtered and concentrated in vacuum. The crude material was purified by silica gel chromatography (gradient: 0-2% 2 N ammonia in methanol/dichloromethane) to obtain the title compound as an off-white solid. Mp: 234-237° C. MS (ESI, pos. ion.) m/z: 340 (M+1).

EXAMPLE 128

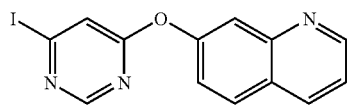

(a) 7-(6-Iodo-pyrimidin-4-yloxy)-quinoline. To a round-bottomed flask containing 7-(6-chloro-pyrimidin-4-yloxy)-quinoline, (Example 102(a)), (0.20 g, 0.80 mmol) and sodium iodide (0.20 g, 1.2 mmol, Aldrich) was added hydriodic acid (2.5 mL, Aldrich). The reaction mixture was stirred at 40° C. for 2 h, treated with 1 N sodium hydroxide and extracted with dichloromethane (2×40 mL). The combined organic layers were dried over $Na_2SO_4$ and concentrated in vacuum. The crude material was purified by silica gel chromatography (gradient: 2-2.5% 2 N ammonia in methanol/dichloromethane) to obtain the title compound as a yellow solid.

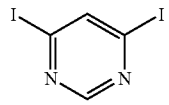

(b) 7-[6-(4-Bromo-phenyl)-pyrimidin-4-yloxy]-quinoline. To a 5 mL, round-bottomed flask containing 7-(6-iodo-pyrimidin-4-yloxy)-quinoline (0.16 g, 0.45 mmol) and ethylene glycol dimethyl ether (2 mL) was added 4-bromophenylboronic acid (0.14 g, 0.68 mmol, Aldrich) and 1 N sodium carbonate (1.4 mL). The reaction mixture was purged with $N_2$ at room temperature for 15 min and palladium(0)-tetrakis-triphenylphosphine (0.030 g, 0.020 mmol, Strem Chemical) was added. The reaction mixture was heated at 100° C. for 1.5 h under a $N_2$ atmosphere, then treated at room temperature with water (50 mL). The mixture was extracted with EtOAc (2 x 100 mL) and the combined organic layers were dried over $Na_2SO_4$ and concentrated in vacuum. The crude material was purified by silica gel chromatography (gradient: 1-2% 2 N ammonia in methanol/dichloromethane) to obtain the title compound as a white solid. Mp: 160-162° C. MS (ESI, pos. ion.) m/z: 378 (M+1).

EXAMPLE 129

(a) 4,6-Diiodo-pyrimidine. A mixture of 4,6-dichloro-pyrimidine (1.0 g, 6.7 mmol, Aldrich), NaI (1.4 g, 9.0 mmol), and hydriodic acid (20 mL, 0.15 mol) was heated at 40° C. for 1 h and stirred at room temperature for additional 20 h. The reaction mixture was basified with 10 N NaOH to pH 10. The resulting precipitate was collected by filtration, washed with water, and dried in vacuum to give the title compound as a light-yellow solid. MS (ESI, pos.ion) m/z: 332 (M+2).

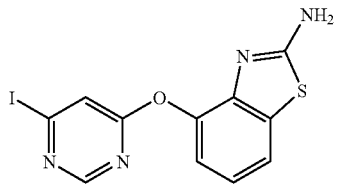

(b) 4-(6-Iodo-pyrimidin-4-yloxy)-benzothiazol-2-ylamine. A mixture of 4,6-diiodo-pyrimidine (720 mg, 2.2 mmol), 2-amino-benzothiazol-4-ol (360 mg, 2.2 mmol, CarboGen), and $K_2CO_3$ (430 mg, 3.1 mmol) in DMSO (3.0 mL) was heated at 80° C. for 1 h. The reaction mixture was allowed to cool to room temperature, treated with water and stirred for 18 h. The resulting precipitate was collected by filtration, washed with water, and dried in vacuum to give the title compound as a light-yellow solid. MS (ESI, pos. ion) m/z: 371 (M+1).

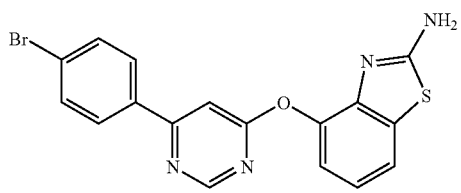

(c) 4-[6-(4-Bromo-phenyl)-pyrimidin-4-yloxy]-benzothiazol-2-ylamine. To a 5-mL, microwave vial containing 4-(6-iodo-pyrimidin-4-yloxy)-benzothiazol-2-ylamine (0.30 g, 0.81 mmol) and 1:1 toluene:EtOH (2 mL) was added 4-bromophenylboronic acid (0.23 g, 1.5 mmol, Aldrich), 2 N potassium carbonate (1.2 mL), and palladium(0)-tetrakis-triphenylphosphine (0.050 g, 0.040 mmol, Strem Chemical). The reaction mixture was heated at 1400C for 10 min in a microwave synthesizer, allowed to cool to room temperature and diluted with water (5 mL) and 1 N sodium hydroxide (50 mL). The mixture was extracted with EtOAc (2×100 mL) and the combined organic layers were dried over $Na_2SO_4$, and concentrated in vacuum. The crude material was purified by silica gel chromatography (gradient: 0-65% EtOAc/Hexanes) to obtain the title compound. Mp: 228-229° C. MS (ESI, pos. ion.) m/z: 401 (M+1).

EXAMPLE 130

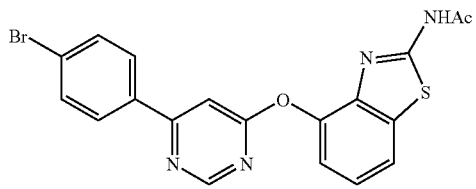

N-{4-[6-(4-Bromo-phenyl)-pyrimidin-4-yloxy]-benzothiazol-2-yl}-acetamide. To a 50 mL, round-bottomed flask containing 4-[6-(4-bromo-phenyl)-pyrimidin-4-yloxy]-benzothiazol-2-ylamine, (Example 129(c)), (0.050 g, 0.13 mmol) was added anhydrous toluene (3 mL) and acetic anhydride (0.010 mL, 0.39 mmol, Aldrich). The mixture was heated at 90° C. and the progress of the reaction was monitored by TLC (developed in 50% EtOAc/hexanes). After reaching completion, the reaction mixture was allowed to cool to room temperature, the white precipitate was collected by filtration, washed with MeOH (5 mL), and dried under vacuum to obtain the title compound as a white solid. Mp: 271-272° C. MS (ESI, pos. ion.) m/z: 441 (M+1).

EXAMPLE 131

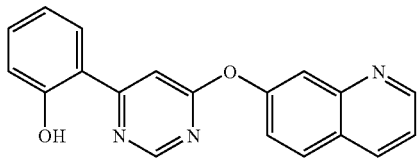

2-[6-(Quinolin-7-yloxy)-pyrimidin-4-yl]-phenol. To a 50-mL, round-bottomed flask containing 7-[6-(2-methoxyphenyl)-pyrimidin-4-yloxy]-quinoline, (Example 109), (0.09 g, 0.27 mmol) was added dichloromethane (3 mL). The solution was cooled to –78° C. and $BBr_3$ (0.82 mL, 0.82 mmol, 1 N in dichloromethane, Aldrich) was added. The reaction mixture was allowed to warm to room temperature over 1 h and then cooled to –78° C. and quenched with satd sodium bicarbonate (10 mL). The reaction mixture was diluted with water (50 mL) and extracted with dichloromethane (2×100 mL). The combined organic layers were dried over $Na_2SO_4$ and concentrated in vacuum. The resulting solid was suspended in methanol (15 mL) and the remaining solid was collected by filtration, and dried under vacuum to obtain the title compound as a white solid. Mp: 188-191° C. MS (ESI, pos. ion.) m/z: 316 (M+1).

EXAMPLE 132

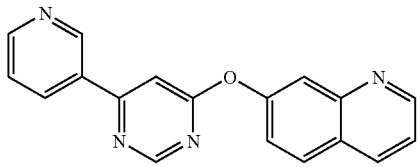

7-(6-Pyridin-3-yl-pyrimidin-4-yloxy)-quinoline. To a 5 mL, microwave vial containing 7-(6-chloro-pyrimidin-4-yloxy)-quinoline, (Example 102(a)), (0.30 g, 1.2 mmol) and ethylene glycol dimethyl ether (2 mL) was added 3-diethyl (3-pyridyl)borane (0.21 g, 1.5 mmol, Aldrich), 1 N sodium carbonate (1.8 mL), and palladium(0)-tetrakis-triphenylphosphine (0.14 g, 0.15 mmol, Strem Chemical). The vial was sealed and heated at 200° C. for 20 min in a microwave synthesizer, allowed to cool to room temperature, and the reaction mixture was diluted with 1 N sodium hydroxide (25 mL) and extracted with dichloromethane (2×50 mL). The organic layers were combined, dried over $Na_2SO_4$, filtered and concentrated onto silica gel. The crude material was purified by silica gel chromatography (gradient: 1-2% 2 N ammonia in methanol/dichloromethane) to obtain the title compound as an off-white solid. Mp: 155-158° C. MS (ESI, pos. ion.) mn/z: 301 (M+1).

EXAMPLE 133

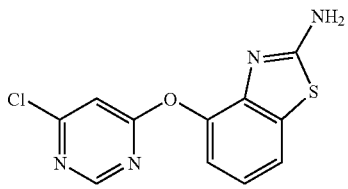

(a) 4-(6-Chloro-pyrimidin-4-yloxy)-benzothiazol-2-ylamine. To a 100-mL, round-bottomed flask containing 4,6-dichloro-pyrimidine (9.0 g, 60 mmol, Aldrich) and 2-amino-benzothiazol-4-ol (5.0 g, 30 mmol, CarboGen) was added potassium carbonate (4.1 g, 30 mmol, Aldrich) and dimethylsulfoxide (10 mL). The reaction mixture was heated at 95° C. with stirring for 4.5 h, and at room temperature for 16 h. The resulting solid was collected by filtration, washed with water (500 mL) and dichloromethane (500 mL), and dried under vacuum to obtain the title compound as a yellow solid.

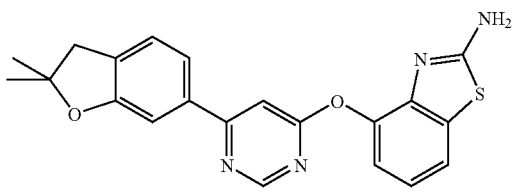

(b) 4-[6-(2,2-Dimethyl-2,3-dihydro-benzofuran-6-yl)-pyrimidin-4-yloxy]-benzothiazol-2-ylamine. A 50-mL, round-bottomed flask containing 2,3-dihydro-2,2-dimethylbenzofuran-6-boronic acid (1.0 g, 5.4 mmol, ChemShop), 4-(6-chloro-pyrimidin-4-yloxy)-benzothiazol-2-ylamine (1.0 g, 3.6 mmol), and ethylene glycol dimethyl ether (6 mL) was degassed with $N_2$ for 15 min. 2 N Potassium carbonate (5.4 mL) and palladium(0)-tetrakis-triphenylphosphine (0.62 g, 0.54 mmol, Strem Chemical) were added and the reaction mixture was heated at 90° C. for 16 h, then allowed to come to room temperature, diluted with water (200 mL), and extracted with dichloromethane (2×200 mL). The dichloromethane layers were dried over $Na_2SO_4$, filtered and concentrated under vacuum. The orange solid was suspended in methanol (50 mL), collected by filtration, and then washed with methanol (50 mL) and dichloromethane (50 mL) to obtain the title compound. Mp: 247-248° C. MS (ESI, pos. ion.) m/z: 391 (M+1).

EXAMPLE 134

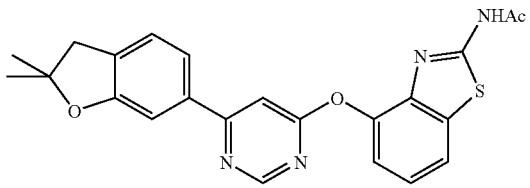

N-{4-[6-(2,2-Dimethyl-2,3-dihydro-benzofuran-6-yl)-pyrimidin-4-yloxy]-benzothiazol-2-yl}-acetamide. To a 100-mL, round-bottomed flask containing 4-[6-(2,2-dimethyl-2,3-dihydro-benzofuran-6-yl)-pyrimidin-4-yloxy]-benzothiazol-2-ylamine, (Example 133(b)), (0.50 g, 1.3 mmol) was added toluene (7 mL) and acetic anhydride (0.40 mL, 3.8 mmol, Aldrich). The reaction mixture was heated at 85° C. for 2 h. The toluene was removed in vacuum and the resulting orange solid was re-dissolved in dichloromethane (125 mL), washed with water (150 mL), dried over $Na_2SO_4$ and concentrated in vacuum. The resulting orange solid was suspended in dichloromethane (100 mL), collected by filtration, and dried under vacuum to obtain the title compound as a white solid. Mp: 224-225° C. MS (ESI, pos. ion.) m/z: 433 (M+1).

EXAMPLE 135

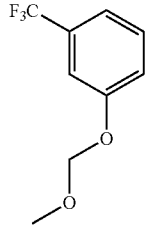

(a) 1-Methoxymethoxy-3-trifluoromethyl-benzene. Chloromethyl methyl ether (1.5 mL, 20 mmol, Aldrich) was added dropwise to a 50-mL, round-bottomed flask containing a solution of α, α, α-trifluoro-m-cresol (2.0 mL, 16 mmol, Aldrich), and N,N-diisopropylethyl-amine (5.7 mL, 33 mmol, Aldrich) in dichloromethane (6 mL) at 0° C. The reaction mixture was allowed to come to room temperature and stirred for 3 h after which the solvents were removed under vacuum. EtOAc (10 mL) was then added to the reaction flask and the resulting white solid was removed by filtration. The filtrate was concentrated onto silica gel and the crude material was purified by silica gel chromatography (gradient: 2.4-10% EtOAc/hexanes) to obtain the title compound as a clear, colorless oil.

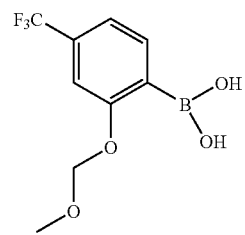

(b) 2-Methoxymethoxy-6-trifluoromethylphenylboronic acid. sec-Butyllithium (220 mL, 290 mmol, 1.35 N in hexanes, Aldrich) was added dropwise to a solution of N,N,N',N'-tetramethylethylenediamine (45 mL, 0.29 mmol, Aldrich) in anhydrous ether (250 mL) with stirring at −40°C under argon. After sirring at −40°C for 15 min, a solution of 1-methoxymethoxy-3-trifluoromethyl-benzene (100 mL, 2.4 N in anhydrous ether) was added dropwise and the reaction mixture was stirred at room temperature for 2 h. Trimethyl borate (82 mL, 0.72 mL, Aldrich) was added slowly at −78°

C. and the reaction mixture was stirred at room temperature for 16 h. Ice water (100 mL) was added to the reaction mixture, which after stirring for 10 min was transferred to a 2-L, Morton flask and stirred vigorously with 1 N sodium hydroxide (1 L) for 1 h. The organic and aqueous layers were separated and the aqueous layer was washed with ether (500 mL). The aqueous layer was cooled in an ice bath and treated with glacial acetic acid until it reached pH 5. The white precipitate was collected by filtration and washed with water (1 L), hexanes (1 L), and dried under vacuum to obtain the title compound as an off-white solid.

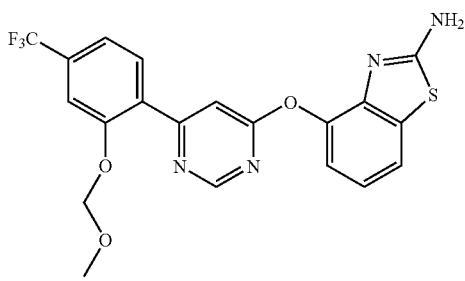

(c) 4-[6-(2-Methoxymethoxy-4-trifluoromethyl-phenyl)-pyrimidin-4-yloxy]-benzothiazol-2-ylamine. 2 N Potassium carbonate (11 mL, 22 mmol) was added to a round-bottomed flask containing 2-methoxymethoxy-4-trifluoromethyl-phenylboronic acid (3.6 g, 14 mmol), 4-(6-chloro-pyrimidin-4-yloxy)-benzo-thiazol-2-ylamine, (Example 133(a), (2.0 g, 7.2 mmol), and ethylene glycol dimethyl ether (13 mL). The mixture was then purged with $N_2$ for 15 min and palladium (0)-tetrakis-triphenylphosphine (0.42 g, 0.36 mmol, Strem Chemical) was added. The reaction mixture was heated at 80° C. for 16 h, allowed to cool to room temperature, diluted with water (300 mL) and extracted with dichloro-methane (2×200 mL). The combined dichloromethane layers were washed with brine (200 mL), dried over $Na_2SO_4$, and concentrated under vacuum. The resulting white solid was suspended in MeOH (50 mL) and collected by filtration to obtain the title compound as a white solid. Mp: 175-176° C. MS (ESI, pos. ion.) m/z: 449 (M+1).

EXAMPLE 136

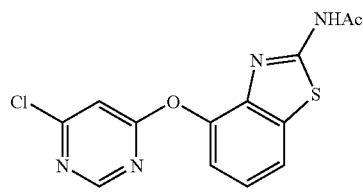

(a) N-[4-(6-Chloro-pyrimidin-4-yloxy)-benzothiazol-2-yl]-acetamide. To a round-bottomed flask containing 4-(6-chloro-pyrimidin-4-yloxy)-benzothiazol-2-ylamine, (Example 133(a)) (4.0 g, 14 mmol) was added toluene (10 mL) and acetic anhydride (4.1 mL, 43 mmol, Aldrich). The reaction mixture was heated at 85° C. for 2 h and then stirred at room temperature for 16 h. The solvent was removed under vacuum and the resulting orange solid was suspended in dichloromethane, collected by filtration and dried under vacuum to obtain the title compound as an off-white solid. Mp: 268-275° C. MS (ESI, pos. ion.) m/z: 321 (M+1)<

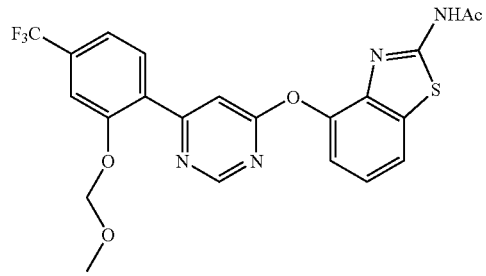

(b) N-{4-[6-(2-Methoxymethoxy-4-trifluoromethyl-phenyl)-pyrimidin-4-yloxy]-benzothiazol-2-yl}-acetamide. 2 N Potassium carbonate (19 mL, 38 mmol) was added to a round-bottomed flask containing 2-methoxymethoxy-4-trifluoro-methylphenylboronic acid, (Example 135(b)), (6.2 g, 25 mmol), N-[4-(6-chloro-pyrimidin-4-yloxy)-benzothiazol-2-yl]-acetamide (4.0 g, 13 mmol), and ethylene glycol dimethyl ether (25 mL). The mixture was then purged with nitrogen for 15 min, and palladium(0)-tetrakis-triphenylphosphine (0.73 g, 0.63 mmol, Strem Chemical) was added. The reaction mixture was heated at 80° C. for 16 h, diluted with water (300 mL) and extracted with dichloromethane (2×200 mL). The combined organic extracts were washed with brine (200 mL), dried over $Na_2SO_4$, and concentrated in vacuum. The resulting white solid was suspended in MeOH (50 mL) and collected by filtration to obtain the title compound as an off-white solid. Mp: 223.0-225.3° C. MS (ESI, pos. ion.) mn/z: 492 (M+1).

EXAMPLE 137

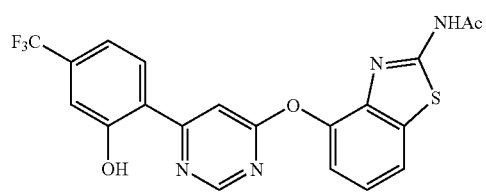

N-{4-[6-(2-Hydroxy-4-trifluoromethyl-phenyl)-pyrimidin-4-yloxy]-benzothiazol-2-yl}-acetamide. Trifluoroacetic acid (0.10 mL, 1.3 mmol, Aldrich) was added dropwise to a solution of N-{4-[6-(2-methoxymethoxy-4-trifluoromethyl-phenyl)-15 pyrimidin-4-yloxy]-benzothiazol-2-yl}-acetamide, (Example 136(b)), (0.50 g, 1.0 mmol) in dichloromethane (10 mL) with stirring and cooling in an ice bath. The reaction mixture was stirred for 16 h at room temperature, diluted with dichloromethane (5 mL) and quenched with satd sodium bicarbonate solution. The reaction mixture was diluted with water (100 mL), extracted with dichloromethane (2×100 mL), and the combined organic extracts were concentrated in vacuum. The resulting white solid was suspended in MeOH (50 mL), collected by filtration, and dried under vacuum to obtain the title compound as a white solid. Mp: 302-304° C. MS (ESI, pos. ion.) m/z: 445 (M+1).

EXAMPLE 138

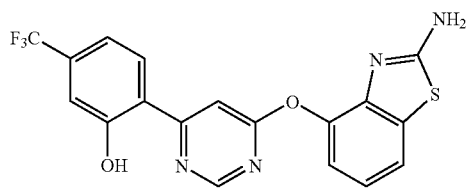

2-[6-(2-Amino-benzothiazol-4-yloxy)-pyrimidin-4-yl]-5-trifluoromethyl-phenol. To a 100-mL, round-bottomed flask containing a solution of 4-[6-(2-methoxy-methoxy-4-trifluoromethyl-phenyl)-pyrimidin-4-yloxy]-benzothiazol-2-ylamine, (Example 135(c)), (1.8 g, 3.9 mmol) in dichloromethane (39 mL) was added boron trifluoride diethyl etherate (1.5 mL, 12 mmol, Aldrich) with stirring at −78° C. The reaction mixture was then stirred at 0° C. for 1 h and at room temperature for 3 h. The mixture was quenched with satd sodium bicarbonate at 0° C. and extracted with dichloromethane (2×100 mL). The combined organic extracts were dried over $Na_2SO_4$, filtered and concentrated in vacuum. The crude material was purified by silica gel chromatography (gradient: 0-3% 2 N ammonia in methanol/dichloromethane) to yield the title compound as an amorphous, white solid. MS (ESI, pos. ion.) m/z: 406 (M+1).

EXAMPLE 19

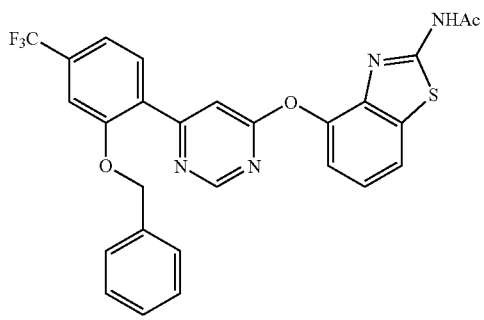

N-{4-[6-(2-Benzyloxy-4-trifluoromethyl-phenyl)-pyrimidin-4-yloxy]-benzothiazol-2-yl}-acetamide. To a mixture of N-{4-[6-(2-hydroxy-4-trifluoromethyl-phenyl)-pyrimidin-4-yloxy]-benzothiazol-2-yl}-acetamide, (Example 137), (0.20 g, 0.50 mmol) and potassium carbonate (0.062 g, 0.45 mmol, Aldrich) in anhydrous acetone (2 mL) was added benzyl bromide (0.053 mL, 0.45 mmol, Aldrich) and the reaction mixture was heated at 70° C. for 2 h. The solvent was removed under vacuum and the residue was diluted with water (50 mL) and extracted with ether (2×100 mL). The combined organic extracts were washed with water (100 mL), dried over $Na_2SO_4$, filtered and concentrated under vacuum. The crude material was purified by silica gel chromatography (gradient: 5-60% EtOAc/hexanes) to obtain the title compound (0.030 g, 13%) as a white solid. Mp: 201-203° C. MS (ESI, pos. ion.) m/z: 537 (M+1).

EXAMPLE 140

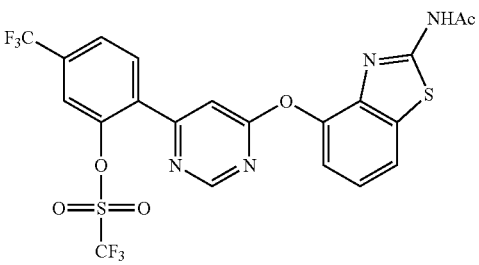

Trifluoro-methanesulfonic acid 2-[6-(2-acetylamino-benzothiazol-4-yloxy)-pyrimidin-4-yl]-5-trifluoromethyl-phenyl ester. To a solution of N-{4-[6-(2-hydroxy-4-trifluoromethyl-phenyl)-pyrimidin-4-yloxy]-benzothiazol-2-yl}-acetamide, (Example 137), (1.5 g, 3.4 mmol) and N-phenyltrifluoromethane sulfonimide (1.5 g, 4.0 mmol, Aldrich) in dichloromethane (10 mL) and DMF (10 mL) was added N,N-diisopropylethylamine (2.4 mL, 14 mmol, Aldrich) and the reaction mixture was stirred at room temperature for 20 h. Water (50 mL) was added and the mixture was extracted with dichloromethane (2×150 mL). The combined organic extracts were washed with water (100 mL), dried over $Na_2SO_4$, filtered and concentrated under vacuum. The white solid was suspended in methanol (50 mL), collected by filtration, and dried under vacuum to obtain the title compound as a white solid. Mp: 209-212° C. MS (ESI, pos. ion.) m/z: 580 (M+1).

EXAMPLE 141

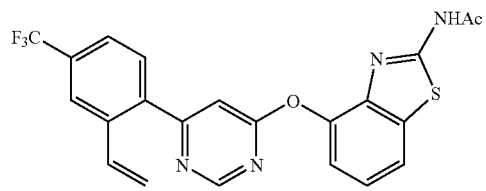

N-{4-[6-(4-Trifluoromethyl-2-vinyl-phenyl)-pyrimidin-4-yloxy]-benzothiazol-2-yl}-acetamide. Trifluoromethanesulfonic acid 2-[6-(2-acetylamino-benzothiazol-4-yloxy)-pyrimidin-4-yl]-5-trifluoromethyl-phenyl ester, (Example 140), (1.0 g, 1.7 mmol) was dissolved in dioxane (7.7 mL) in a 100-mL, round-bottomed flask. Tributylvinylstannane (0.60 mL, 1.9 mmol, Fluka), lithium chloride (0.22 g, 5.1 mmol, Aldrich), palladium(0)-tetrakis-triphenylphosphine (0.040 g, 0.030 mmol, Strem Chemical), and a few crystals 2,6-di-tert-butyl-4-methylphenol (Aldrich) were added to the solution. The reaction was heated at 98° C. for 5 h after which the solvent was removed under vacuum and the crude material was purified by silica gel chromatography (gradient: 0-10% methanol/dichloromethane) to obtain the title compound as a yellow solid. Mp: 234-237 C. MS (ESI, pos. ion.) m/z: 458 (M+1).

EXAMPLE 142

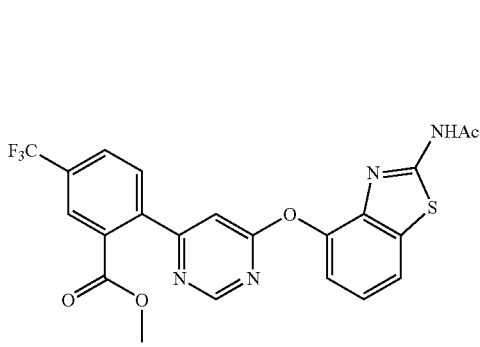

2-[6-(2-Acetylamino-benzothiazol-4-yloxy)-pyrimidin-4-yl]-5-trifluoromethyl-benzoic acid methyl ester. Ozone was passed through a solution of N-{4-[6-(4-trifluoromethyl-2-vinyl-phenyl)-pyrimidin-4-yloxy]-benzothiazol-2-yl}-acetamide, (Example 141), (0.050 g, 0.11 mmol) in dichloromethane (1 mL) and sodium hyroxide (0.22 mL, 2.5 N in methanol) at −78° C. Once the solution showed a noticeable blue color and a yellow precipitate was observed, the reaction mixture was purged with oxygen and diluted with water (50 mL). The product was extracted with ether (2 x 50 mL). The combined ether layers were dried over Na$_2$SO$_4$, filtered and concentrated under vacuum. The crude material was purified by silica gel chromatography (gradient: 0-60% EtOAc/hexanes) yielding the title compound as an amorphous white solid. MS (ESI, pos. ion.) m/z: 489 (M+1).

EXAMPLE 143

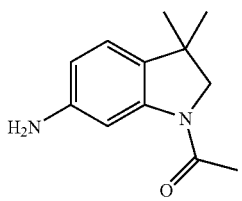

(a) 1-(6-Amino-3,3-dimethyl-2,3-dihydro-indol-1-yl)-ethanone. To a solution of 1-(3,3-dimethyl-6-nitro-2,3-dihydroindol-yl)ethanone (110 mg, 0.47 mmol, prepared according to WO 03/049702 A2) in ethyl ether (3 mL), magnetically stirred in a round-bottomed flask at 0° C., was added tin (II) chloride dihydrate (0.67 g, 2.96 mmol, Aldrich) and cond HCl (0.3 mL). The reaction mixture was stirred at 0° C. for 10 min, allowed to warm to 25° C. then stirred at that temperature for 18 h. The reaction mixture was washed with 10 N NaOH (10 mL), extracted with EtOAc and concentrated in vacuum to give the title compound, which was used in the next step without additional purification.

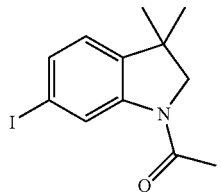

(b) 1-(6-Iodo-3,3-dimethyl-2,3-dihydro-indol-1-yl)-ethanone. To a mixture of 1-(6-amino-3,3-dimethyl-2,3-dihydro-indol-1-yl)-ethanone (2.2 g, 10 mmol), copper iodide (1.9 g, 10 mmol, Aldrich), iodine (1.3 g, 5 mmol, Aldrich) and potassium iodide (1.7 g, 10 mmol, Aldrich) in DME (60 mL) was added isoamyl nitrite (4 mL, 30 mmol, Aldrich). The reaction was heated at 65° C. for 1 h and the insoluble material was filtered through a pad of Celite®, and washed with EtOAc. The filtrate was washed with aqueous ammonium hydroxide, aqueous sodium bisulfite and brine. The organic layer was dried over Na$_2$SO$_4$, filtered, evaporated under vacuum and the residue purified by silica gel chromatography (1:4 of EtOAc/hexanes) to give the title compound as a light-yellow solid. MS (ESI, pos. 15 ion) m/z: 316 (M+1).

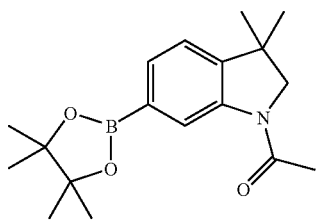

(c) 1-[3,3-Dimethyl-6-(4,4,5,5-tetramethyl-[1,3,2]dioxaborolan-2-yl)-2,3-dihydro-indol-1-yl]-ethanone. To 1-(6-iodo-3,3-dimethyl-2,3-dihydro-indol-1-yl)-ethanone (63 mg, 0.2 mmol) dissolved in DMSO (0.5 mL) was added bis(pinacolato)diboron (56 mg, 0.22 mmol, Aldrich), potassium acetate (59 mg, 0.6 mmol) and [1,1'-bis(diphenylphosphino)ferrocene]dichloropalladium(II), complex with dichloromethane (10 mg, 0.07 mmol %, Aldrich). Nitrogen was bubbled through the reaction for 5 min. The reaction mixture was then heated in a microwave synthesizer at 220° C. for 10 min, allowed to cool to room temperature and partitioned between EtOAc and brine. The aqueous layer was separated, extracted with EtOAc and the combined organic extracts were dried over Na$_2$SO$_4$, filtered and concentrated under vacuum. Purification of the residue by silica gel chromatography (1:2.5 of EtOAc/hexanes) provided the title compound. MS (ESI, pos. ion) m/z: 316 (M+1).

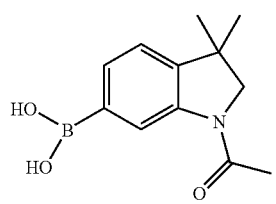

(d) 1-Acetyl-2,3-dihydro-3,3-dimethylindol-6-ylboronic acid. To a solution of 1-[3,3-dimethyl-6-(4,4,5,5-tetramethyl-[1,3,2]dioxaborolan-2-yl)-2,3-dihydro-indol-1-yl]-ethanone (0.14 g, 0.44 mmol) in a mixture of THF (4 mL) and water (1 mL) was added sodium periodate (0.28 g, 1.3 mmol, Aldrich) and the mixture was stirred at 25° C. for 5 min. 2 N HCl was then added dropwise and the reaction mixture was stirred at 25° C. for 16 h. The mixture was partitioned between EtOAc and brine, the aqueous layer was separated and extracted with EtOAc. The combined organic extracts were dried over $Na_2SO_4$, filtered and concentrated under vacuum. Purification of the residue by silica gel chromatography (5:1 of EtOAc/hexanes) provided the title compound as a tan solid. MS (ESI, pos. ion) m/z: 234 (M+1).

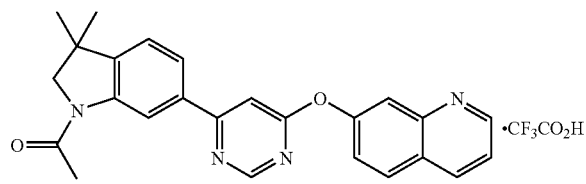

(e) 1-{3,3-Dimethyl-6-[6-(quinolin-7-yloxy)-pyrimidin-4-yl]-2,3-dihydro-indol-1-yl}-ethanone trifluoroacetate. To a solution of 1-acetyl-2,3-dihydro-3,3-dimethylindol-6-ylboronic acid (40 mg, 0.17 mmol) and 7-(6-chloro-pyrimidin-4-yloxy)-quinoline, (Example 102(a)), (50 mg, 0.19 mmol) in DME (0.5 mL) was added $Pd(PPh_3)_4$ (20 mg, 0.017 mmol, Strem Chemical) and aqueous $Na_2CO_3$. The reaction mixture was heated at 80° C. for 16 h, allowed to cool to room temperature and partitioned between EtOAc and brine. The aqueous layer was separated, extracted with EtOAc and the combined organic extracts were dried over $Na_2SO_4$, filtered and concentrated in vacuum. Purification of the residue by silica gel chromatography (5:1 of EtOAc/hexanes), followed by preparative HPLC separation afforded the title compound as a white foam. MS (ESI, pos. ion) m/z: 411 (M+1).

EXAMPLE 144

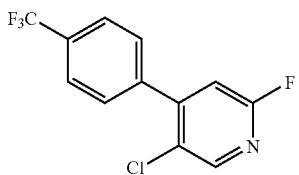

(a) 5-Chloro-2-fluoro-4-(4-trifluoromethyl-phenyl)-pyridine. The title compound was prepared analogous to Example 1 using 5-chloro-2-fluoro-4-iodopyridine (0.64 g, 2.5 mmol, AsymChem), 4-(trifluoromethyl)benzeneboronic acid (0.52 g, 2.8 mmol, Aldrich), tetrakis(triphenylphosphine)palladium(0) (0.29 g, 0.25 mmol, Strem Chemical) and aq sodium carbonate (0.29 g in 10 mL of water) in toluene (10 mL). Purification by silica gel chromatography (1:9 of EtOAc/hexanes) provided the title compound as a white solid. MS m/z: 276 (M+1).

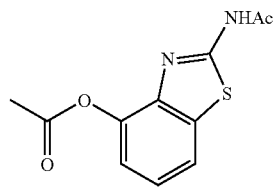

(b) Acetic acid 2-acetylamino-benzothiazol-4-yl ester. To the suspension of 2-amino-4-hydroxybenzothiazole (8.3 g, 50 mmol, Fluorochem Ltd.) in toluene (100 mL) was added acetic anhydride (47 mL, 500 mmol). The reaction mixture was heated at 110° C. for 16 h. The solvents were evaporated to give the title compound as a tan solid. MS m/z: 251 (M+1).

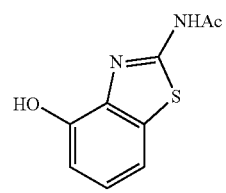

(c) N-(4-Hydroxy-benzothiazol-2-yl)-acetamide. To the suspension of acetic acid 2-acetylamino-benzothiazol-4-yl ester (9.7 g, 39 mmol) in MeOH (200 mL) was added potassium carbonate (11 g, 78 mmol). The reaction mixture was stirred at 25° C. for 6 h, most of the solvent was evaporated uinder vacuum and the residue was acidified with 10% HCl to pH 5. The mixture was then extracted with EtOAc (3 x), the combined EtOAc extracts were washed with brine, dried over $Na_2SO_4$ filtered and concentrated in vacuum to give the title compound as a tan solid. MS m/z: 209 (M+1).

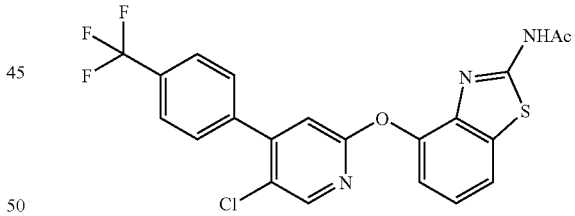

(d) N-{4-[5-Chloro-4-(4-trifluoromethyl-phenyl)-pyridin-2-yloxy]-benzothiazol-2-yl}-acetamide. To N-(4-hydroxy-benzothiazol-2-yl)-acetamide (0.13 g, 0.6 mmol) dissolved in DMSO (2 mL) was added NaH (29 mg, 0.72 mmol). After stirring at 25° C. for 10 min, 5-chloro-2-fluoro-4-(4-trifluoromethyl-phenyl)-pyridine, (Example 144(a)), (0.11 g, 0.4 mmol) and copper iodide (8 mg, 0.04 mmol) were added. The reaction mixture was heated at 90° C. for 20 h, allowed to cool to room temperature and partitioned between EtOAc and brine. The aqueous layer was separated, extracted with EtOAc, and the combined organic extracts were dried over $Na_2SO_4$, filtered and concentrated in vacuum. Purification of the residue by silica gel chromatography (1:2.5 of EtOAc/hexanes) gave the title compound as a white solid. MS (ESI, pos. ion) nzlz: 411 (M+1). Mp: 240.2-240.3° C.

EXAMPLE 145

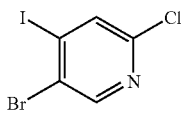

(a) 5-Bromo-2-chloro-4-iodopyridine. n-Butyllithium (16.3 mL, 26 mmol, 1.6 M in hexane, Aldrich) was added dropwise to a solution of diisopropylamine (3.6 mL, 26 mmol, Aldrich) in THF (15 mL) with stirring at −78° C. After the addition was complete, the reaction mixture was stirred at −78° C. for 30 min. Then, 5-bromo-2-chloropyridine (5 g, 26 mmol, Lancaster) dissolved in THF (15 mL) was introduced dropwise and the reaction was stirred at −78° C. for another 5 h. A solution of iodine (8 g, 31.5 mmol) in 15 mL of THF was added slowly and the reaction was stirred at −78° C. for 2 h. THF and water (1:1, 100 mL) was added to quench the reaction. The mixture was allowed to warm to room temperature and 1 M sodium bisulfite (50 mL) was added. The resulting mixture was stirred at room temperature for 1 h, extracted with EtOAc and washed with water. The aqueous layer was extracted with EtOAc and the combined organic extracts were dried over Na₂SO₄, filtered and evaporated under vacuum. Recrystallization of the residue from EtOAc/hexanes provided the title compound as a brown solid.

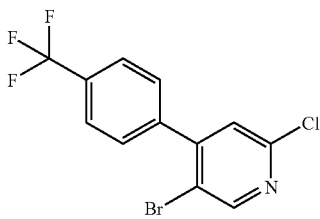

(b) 5-Bromo-2-chloro-4-(4-trifluoromethyl-phenyl)-pyridine. The title compound was prepared analogous to Example 1 using 5-bromo-2-chloro-4-iodopyridine (0.1 g, 0.3 mmol), 4-(trifluoromethyl)benzeneboronic acid (68 mg, 0.36 mmol, Aldrich), tetrakis(triphenylphosphine)palladium (0) (35 mg, 0.03 mmol, Aldrich) and aqueous sodium carbonate (38 mg in 0.3 mL of water) in toluene (1 mL). Purification by silica gel chromatography (1:9 of EtOAc/hexanes) provided the title compound as a white solid. MS (ESI, pos. ion) m/z: 337, 339 (M+1).

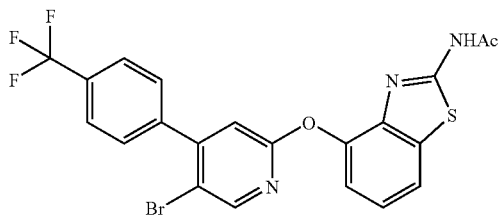

(c) N-{4-[5-Bromo-4-(4-trifluoromethyl-phenyl)-pyridin-2-yloxy]-benzothiazol-2-yl}-acetamide. The title compound was prepared analogous to Example 144(d) using N-(4-hydroxy-benzothiazol-2-yl)-acetamide, (Example 144(c)), (94 mg, 0.45 mmol), 5-bromo-2-chloro-4-(4-trifluoromethyl-phenyl)-pyridine (84 mg, 0.25 mmol), and NaH (16 mg, 0.4 mmol, Aldrich) in DMF (0.5 mL) by heating at 150° C. for 6 h. Purification by silica gel chromatography (1:3 of EtOAc/hexanes) gave the title compound as a white solid. MS (ESI, pos. ion) m/z: 509, 511 (M+1). Mp: 245.7-245.8° C.

EXAMPLE 146

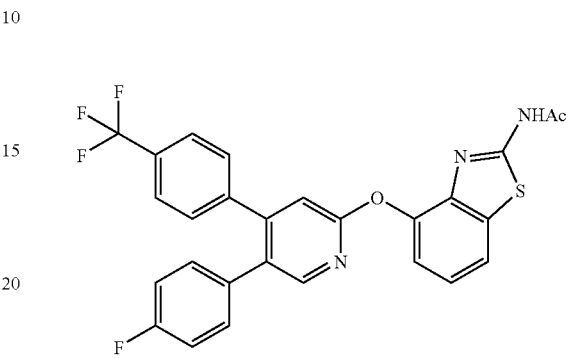

N-{4-[5-(4-Fluoro-phenyl)-4-(4-trifluoromethyl-phenyl)-pyridin-2-yloxy]-benzothiazol-2-yl}-acetamide. To a mixture of N-{4-[5-bromo-4-(4-trifluoromethyl-phenyl)-pyridin-2-yloxy]-benzothiazol-2-yl}-acetamide, (Example 145 (b)), (51 mg, 0.1 mmol) and 4-fluorophenylboronic acid (18 mg, 0.13 mmol, Aldrich) in dioxane (1 mL) was added Pd(PPh₃)₄ (6 mg, 0.005 mmol, Aldrich) and aqueous Na₂CO₃ (16 mg in 0.2 mL of water). The reaction mixture was heated in microwave synthesizer at 1600C for 30 min. Purification by silica gel chromatography (EtOAc/hexanes) gave the title compound as a white solid. MS (ESI, pos. ion) m/z: 524 (M+1). Mp: 112.3-130.1° C.

EXAMPLE 147

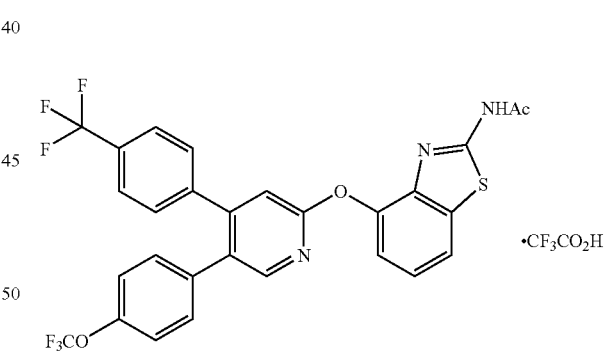

N-{4-[5-(4-Trifluoromethoxy-phenyl)-4-(4-trifluoromethyl-phenyl)-pyridin-2-yloxy]-benzothiazol-2-yl}-acetamide trifluoroacetate. This material was prepared analogous to Example 146 by using N-{4-[5-bromo-4-(4-trifluoromethyl-phenyl)-pyridin-2-yloxy]-benzothiazol-2-yl}-acetamide, (Example 145(b)), (0.1 g, 0.2 mmol), 4-(trifluoromethoxy) phenyl boronic acid (53 mg, 0.26 mmol, Aldrich), Pd(PPh₃)₄ (23 mg, 0.02 mmol, Aldrich) and aq. Na₂CO₃ (32 mg in 0.4 mL of water) in dioxane (2 mL). Purification by silica gel chromatography (1:2 of EtOAc/hexanes), followed by preparative HPLC separation gave the title compound as a white solid. MS (ESI, pos. ion) n7mz: 590 (M+1). Mp: 212.9-222.3° C.

EXAMPLE 148

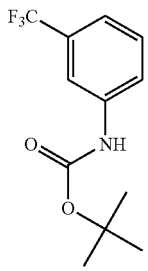

(a) (3-Trifluoromethylphenyl)carbamic acid tert-butyl ester. To a 250-mL, round-bottomed flask was added 3-(trifluoromethyl)aniline (5.0 g, 31 mmol, Aldrich), THF (100 mL), di-tert-butyl dicarbonate (20. g, 93 mmol, Aldrich) and 4-(dimethylamino)pyridine (0.38 g, 3.1 mmol, Aldrich). The mixture was heated at reflux for 3 h. $K_2CO_3$ (13 g, 93 mmol) and MeOH (50 mL) were added, and heating was continued for 18 h. After cooling to room temperature, the mixture was diluted with $CH_2Cl_2$, then filtered and washed with $CH_2Cl_2$ The filtrate was concentrated to afford a brown oil. The oil was dissolved in EtOAc (200 mL) and washed with $H_2O$ (2×100 mL), brine (1×100 mL), dried over $Na_2SO_4$, filtered and concentrated in vacuum onto silica gel. Purification by silica gel chromatography with gradient from 0% to 15% solution of EtOAc in hexanes afforded the title compound as a colorless oil which solidified upon standing to a while solid. MS (ESI, neg. ion.) m/z: 260 (M−1).

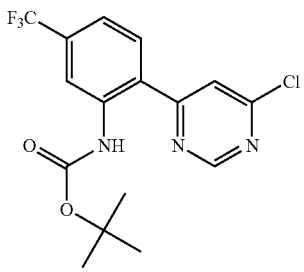

(b) [2-(6-Chloropyrimidin-4-yl)-5-trifluoromethylphenyl] carbamic acid tert-butyl ester. (Analogous to the procedures of Boisnard, S.; Carbonnelle, A. C.; Zhu, J. Org Let. 2001, 3, 2061-2064 and Hewawasam, P.; Meanwell, N. A. Tetrahedron Lett. 1994, 35, 7303). To a 500-mL, round-bottomed flask containing (3-trifluoromethylphenyl)carbamic acid tert-butyl ester (2.5 g, 9.6 mmol) in THF (100 mL) stirred at −40° C. was added sec-BuLi (17 mL, 1.3 M in cyclohexane, Aldrich) over 10 min. The mixture was stirred for 1 h at −40° C. and then cooled to −78° C. Trimethyl borate (4.4 mL, 38 mmol, Aldrich) was added over 10 min. The reaction mixture was allowed to warm to room temperature and stirred for 10 min at that temperature. The mixture was quenched with aq $KH_2PO_4$ and concentrated to remove the THF. The aqueous mixture was then extracted with EtOAc (3×100 mL) and the combined extracts were washed with brine, dried over $Na_2SO_4$, filtered, and concentrated to afford a yellow foam. The foam was dissolved in CH3CN (30 mL) and treated with 4,6-dichloropyrimidine (4.1 g, 28 mmol, Aldrich) followed by a solution of $Na_2CO_3$ (2.9 g, 28 mmol) in $H_2O$ (30 mL). Tetrakis(triphenylphosphine)palladium(0) (0.53 g, 0.46 mmol, Strem) was then added and the mixture was stirred at 75° C. for 15 h. After allowing to cool to room temperature, the mixture was concentrated in vacuum to remove the $CH_3CN$ and then extracted with EtOAc. The combined extracts were washed with $H_2O$ and brine, dried over $Na_2SO_4$ and concentrated in vacuum. Purification of the residue by silica gel chromatography with gradient from 0% to 10% solution of EtOAc in hexanes afforded the title compound as a colorless oil. MS (ESI, pos. ion.) m/z: 374 (M+1).

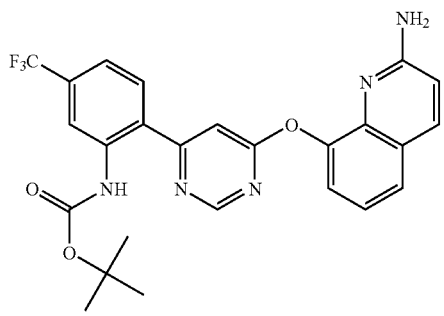

(c) {2-[6-(2-Amino-quinolin-8-yloxy)-pyrimidin-4-yl]-5-trifluoromethyl-phenyl}-carbamic acid tert-butyl ester. To a solution of 2-amino-quinolin-8-ol (1.2 g, 8.0 mmol, Aldrich) in THF (75 mL) at 0° C. was added sodium hydride (0.21 g, 8.8 mmol, 95% dry, Aldrich) in portions. After stirring for 15 min at 0° C., a solution of [2-(6-chloro-pyrimidin-4-yl)-5-trifluoromethyl-phenyl]-carbamic acid tert-butyl ester (3.0 g, 8.0 mmol) in THF (25 mL) was slowly added. The reaction was allowed to warm to room temperature and stirred for 2 h. The reaction was cooled to 0° C., and additional NaH (0.11 g, 4.4 mmol, 95% dry, Aldrich) was added in portions. The reaction was allowed to warm to room temperature and stirred for 2 h and then cooled to 0° C. and $H_2O$ (10 mL) was added carefully. The reaction mixture was concentrated in vacuum and the residue was dissolved in ethyl acetate (50 mL), washed with $H_2O$ (2×25 mL), 1 N NaOH (20 mL), $H_2O$ (2×50 mL), dried over $MgSO_4$, filtered and concentrated in vacuum. Purification by silica gel chromatography (2:1, EtOAc:hexanes) afforded the title compound as a white solid. Mp: 194-195° C. MS (ESI, pos. ion) m/z: 498 (M+1). Anal. Calcd for $C_{25}H_{22}F_3N_5O_3$: C, 60.36; H14.46; F, 11.46; N, 14.08. Found: C, 60.56; H, 4.50; F, 11.57; N, 14.11.

EXAMPLE 149

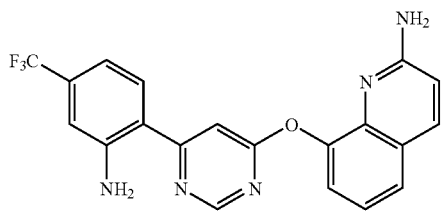

8-[6-(2-Amino-4-tri fluoromethyl-phenyl)-pyrimidin-4-yl oxy]-quinol in-2-ylamine. To {2-[6-(2-amino-quinolin-8-yloxy)-pyrimidin-4-yl]-5-trifluoromethyl-phenyl}-carbamic acid tert-butyl ester, (Example 148), (0.10 g, 0.20 mmol) was added 4 M HCl in dioxane (15 mL). The reaction mixture was stirred for 16 h and then concentrated in vacuum. The residue was dissolved in EtOAc (20 mL) and washed with NaHCO₃ (2×50 mL), dried over Na₂SO₄, filtered and concentrated in vacuum. Purification by silica gel chromatography (2: 1, EtOAc: hexanes) afforded the title compound as thick yellow oil. Mp: 233-234° C. MS (ESI, pos. ion) m/z: 398 (M+1).

EXAMPLE 150

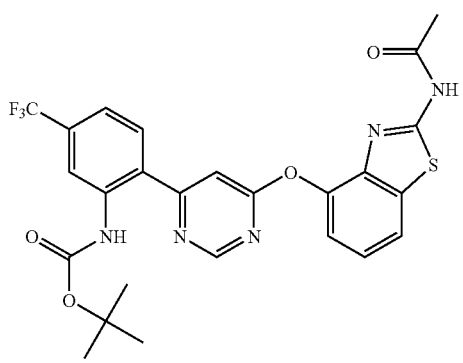

{2-[6-(2-Acetylamino-benzothiazol-4-yloxy)-pyrimidin-4-yl]-5-trifluoromethyl-phenyl}-carbamic acid tert-butyl ester. To a solution of N-(4-hydroxybenzo-thiazol-2-yl)-acetamide, (Example 144(c)), (96 g, 27 mmol) in DMF (200 mL) was added NaH (0.68 g, 28 mmol, 60% dispersion in oil, Aldrich) and the mixture was stirred at 0° C. for 15 min. [2-(6-Chloro-pyrimidin-4-yl)-5-trifluoromethyl-phenyl]-carbamic acid tert-butyl ester, (Example 148(b)), (10 g, 26 mmol) was then added and the reaction mixture was allowed to warm to room temperature, and stirred for 4.5 h. The reaction mixture was quenched with H₂O (200 mL) and poured into a solution containing 30% ethyl acetate/hexanes (500 mL) and 1 N NaOH (800 mL). A white precipitate which formed was filtered and the filtercake was washed with H₂O (100 mL) and 10% EtOAc/hexanes (100 mL). The filtercake was dried in vacuum, redissolved in an acetone/methanol mixture and adsorbed on silica gel. Purification by silica gel chromatography (2:1 EtOAc/hexanes) afforded the product as a white crystalline solid. Mp: 194-195° C. MS (ESI, pos. ion) m/z: 546 (M+1).

EXAMPLE 151

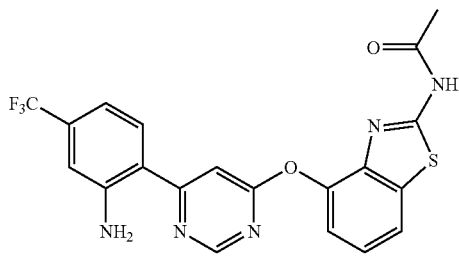

N-{4-[6-(2-Amino-4-trifluoromethyl-phenyl)-pyrimidin-4-yloxy]-benzothiazol-2-yl}-acetamide. To {2-[6-(2-acetylamino-benzothiazol-4-yloxy)-pyrimidin-4-yl]-5-trifluoromethyl-phenyl}-carbamic acid tert-butyl ester, (Example 150) (0.35 g, 0.60 mmol) was added 4 M HCl in dioxane (25 mL). The mixture was stirred for 16 h and then was concentrated in vacuum. The residue was dissolved in ethyl acetate (40 mL) and washed with saturated NaHCO₃ (2×70 mL), dried over Na₂SO₄ and concentrated in vacuum. Purification by silica gel chromatography (2:1, EtOAc:hexanes) afforded the title compound as thick yellow oil. Mp: 160-161° C. MS (ESI, pos. ion) m/z: 446 (M+1). Anal. Calcd for C₂₀H₁₄F₃N₅O₂S₀.₄H₂O: C, 53.07; H, 3.30; F, 15.47; N, 12.59. Found: C, 53.12; H, 3.27; F, 15.19; N, 12.70.

EXAMPLE 152

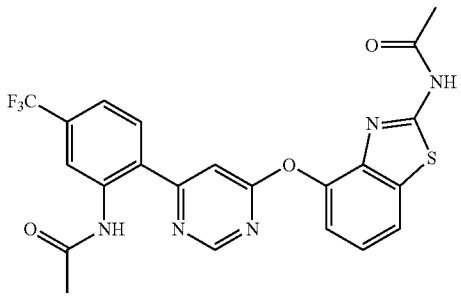

N-{2-[6-(2-Acetylamino-benzothiazol-4-yloxy)-pyrimidin-4-yl]-5-trifluoro-methyl-phenyl}-acetamide. To a suspension of N-{4-[6-(2-amino-4-trifluoro-methyl-phenyl)-pyrimidin-4-yloxy]-benzothiazol-2-yl}-acetamide, (Example 151), (0.20 g, 0.50 mmol) in toluene (10 mL) was added acetic anhydride (0.090 g, 0.80 mmol, Aldrich). The reaction mixture was heated at reflux for 3 h, allowed to cool to room temperature and concentrated in vacuum. The residue was dissolved in EtOAc (20 mL) and washed with satd NaHCO₃ (2×20 mL), dried over Na₂SO₄, filtered and concentrated in vacuum. Purification by silica gel chromatography (1:1:0.5 CH₂Cl₂/hexanes/EtOAc) provided the title compound as an off-white solid. Mp: 259-261° C. MS (ESI, pos. ion) m/z: 488 (M+1).

EXAMPLE 153

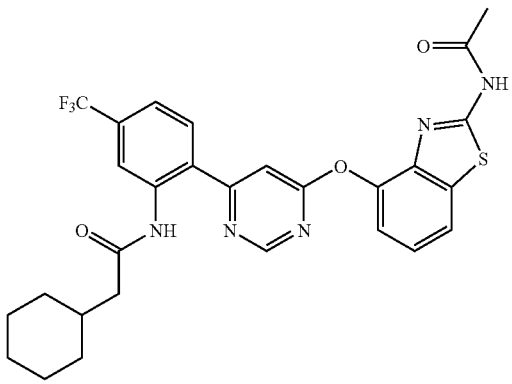

N-{2-[6-(2-Acetylamino-benzothiazol-4-yloxy)-pyrimidin-4-yl]-5-trifluoro-methyl-phenyl}-2-cyclohexyl-acetamide.

To a solution of cyclohexylacetic acid (0.16 g, 1.1 mmol, Aldrich) in $CH_2Cl_2$ (5 mL) and DMF (2 drops) was added oxalyl chloride (0.84 mL, 1.7 mmol, 2 M solution in $CH_2Cl_2$, Aldrich) dropwise. After the addition was complete and gas evolution ceased, the reaction mixture was heated at 40° C. for 30 min. The excess oxalyl chloride and $CH_2Cl_2$ was evaporated in vacuum to provide a yellow oil. The oil was added dropwise to a solution of N-{4-[6-(2-amino-4-trifluoromethyl-phenyl)-pyrimidin-4-yloxy]-benzothiazol-2-yl}-acetamide, (Example 151), (0.25 g, 0.56 mmol) in acetone (15 mL) and triethylamine (0.20 mL, 1.7 mmol, Aldrich) at room temperature. The reaction mixture was stirred for 16 h and then concentrated in vacuum. The residue was dissolved in EtOAc (10 mL) and washed with satd $NaHCO_3$ (2×20 mL), dried over $Na_2SO_4$, filtered and concentrated in vacuum. Purification by silica gel chromatography (1:1:0.5 $CH_2Cl_2$/hexanes/EtOAc) provided the title compound as a white crystalline solid. Mp: 288-289° C. MS (ESI, pos. ion) m/z: 570 (M+1).

ADDITIONAL EXAMPLES

Following the procedure described above in Example 153, or with slight modifications thereof, and following procedures familiar to one of ordinary skill in the art, the following examples were prepared from commercially available reagents:

| Example | Structure | MS (ESI, pos. ion) m/z | Melting Point ° C. |
| --- | --- | --- | --- |
| 154 | 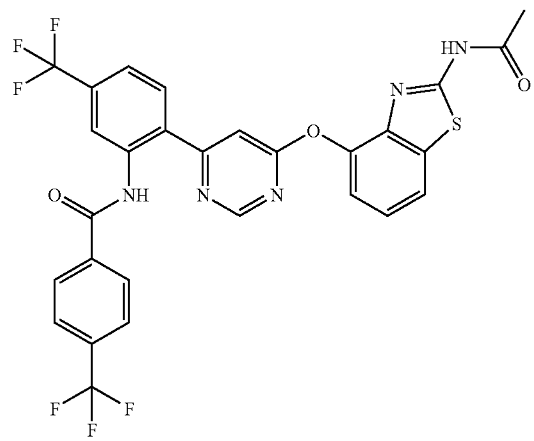 | 618 (M + 1) | 276-277 |
| 155 | 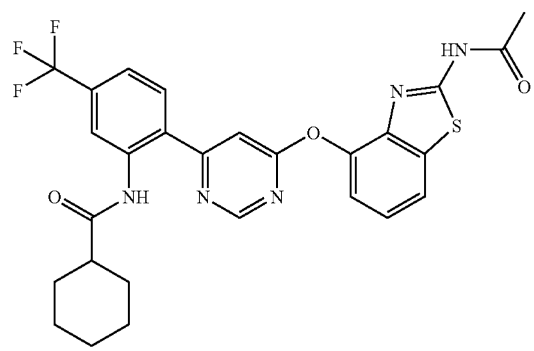 | 556 (M + 1) | 299-302 |
| 156 | 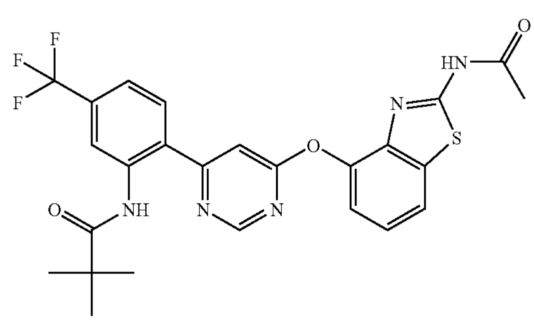 | 530 (M + 1) | 273-275 |

-continued

| Example | Structure | MS (ESI, pos. ion) m/z | Melting Point ° C. |
|---|---|---|---|
| 157 | 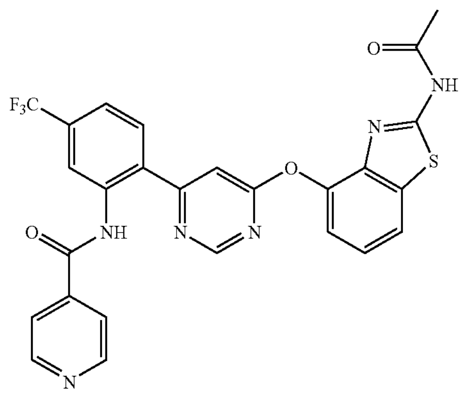 | 551.1 (M + 1) | >295 |
| 158 | 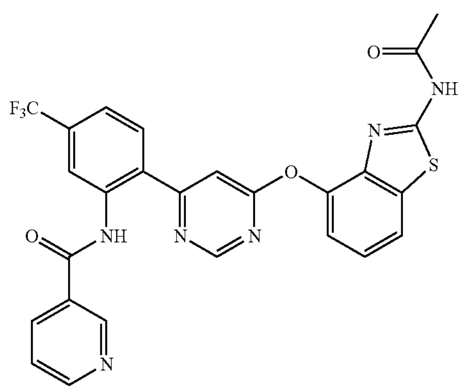 | 551.1 (M + 1) | 294-295 |

EXAMPLE 159

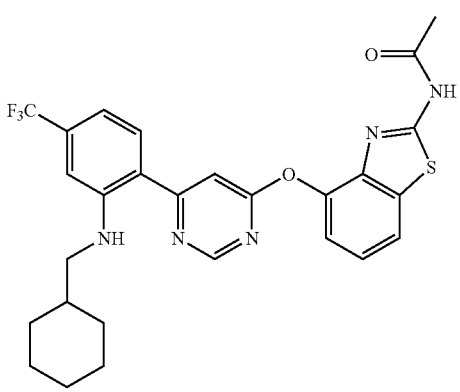

N-(4-{6-[2-(Cyclohexylmethyl-amino)-4-trifluoromethyl-phenyl]-pyrimidin-4-yloxy}-benzothiazol-2-yl)-acetamide.

To a solution of N-{4-[6-(2-amino-4-tri-fluoromethyl-phenyl)-pyrimidin-4-yloxy]-benzothiazol-2-yl}-acetamide, (Example 151), (0.17 g, 0.3 mmol) in 1,2-dichloroethane (10 mL) was added cyclohexanecarboxaldehyde (0.1 g, 0.9 mmol, Aldrich) and the mixture was stirred at 40° C. for 2 h. Sodium triacetoxyborohydride (0.40 g, 1.9 mmol, Aldrich) was added and the reaction mixture was stirred for 18 h at room temperature. After the addition of water (2 mL), the reaction mixture was evaporated in vacuum. The residue was diluted with $H_2O$ (10 mL) and extracted with EtOAc (2×20 mL), dried over $Na_2SO_4$, filtered, and concentrated in vacuum. Purification of the residue by silica gel chromatography (6:1, hexanes: EtOAc) afforded the title compound as an yellow solid. Mp: 232-234° C. MS(ESI, pos. ion) m/z: 542 (M+1).

EXAMPLE 160

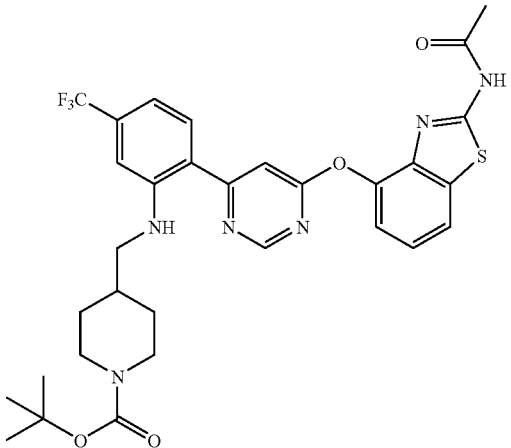

4-({2-[6-(2-Acetylamino-benzothiazol-4-yloxy)-pyrimidin-4-yl]-5-trifluoromethyl-phenylamino}-methyl)-piperidine-1-carboxylic acid tert-butyl ester. The title compound was prepared from N-{4-[6-(2-amino-4-trifluoromethyl-phenyl)-pyrimidin-4-yloxy]-benzothiazol-2-yl}-acetamide (Example 151) and N-Boc-4-piperidinylcarboxaldehyde according the procedure described in Example 159. MS(ESI, pos. ion) m/z: 643 (M+1).

EXAMPLE 161

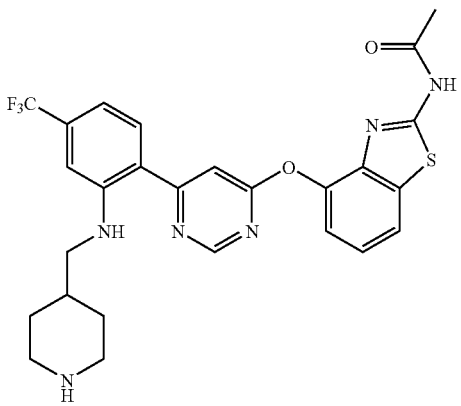

N-[4-(6-{2-[(Piperidin-4-ylmethyl)-amino]-4-trifluoromethyl-phenyl}-pyrimidin-4-yloxy)-benzothiazol-2-yl]-acetamide. To a solution of 4-({2-[6-(2-acetylamino-benzothiazol-4-yloxy)-pyrimidin-4-yl]-5-trifluoromethyl-phenylamino}-methyl)-piperidine-1-carboxylic acid tert-butyl ester, (Example 160), (0.20 g, 0.30 mmol) in $CH_2Cl_2$ (10 mL) was added trifluoroacetic acid (30 mL, Aldrich). The reaction mixture was allowed to stir for 3 h at room temperature and then concentrated in vacuum. The residue was dissolved in EtOAc (30 mL), washed with satd $NaHCO_3$ (2×30 mL), dried over $Na_2SO_4$, filtered and concentrated in vacuum. Purification by silica gel chromatography (2:1, EtOAc:hexanes) afforded the title compound as yellow film. MS (ESI, pos. ion) m/z: 543 (M+1).

EXAMPLE 162

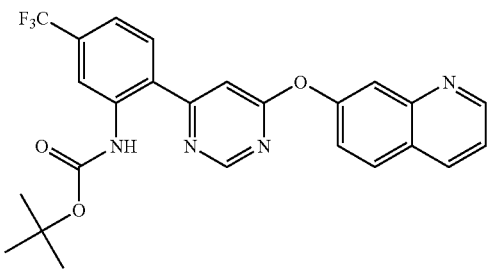

{2-[6-(Quinolin-7-yloxy)-pyrimidin-4-yl]-5-trifluoromethyl-phenyl}-carbamic acid tert-butyl ester. (Analogous to the procedures of Boisnard, S.; Carbonnelle, A. C.; Zhu, *J. Org Let*. 2001, 3, 2061-2064 and Hewawasam, P.; Meanwell, N. A. *Tetrahedron Lett*. 1994, 35, 7303). To a 1-L, three-neck, round-bottom flask containing (3-trifluoromethylphenyl)carbamic acid tert-butyl ester (15 g, 57 mmol) in THF (400 mL) stirred at −40° C. was added sec-BuLi (100 mL, 1.3 M in cyclohexane, Aldrich) over 20 min. The mixture was stirred for 1 h at −40° C. and then cooled to −78° C. Trimethyl borate (26 mL, 230 mmol, Aldrich) was added over 10 min. The reaction mixture was allowed to warm to room temperature and stirred for 0.5 h and then quenched with aq 1 M $NaH_2PO_4$ (200 mL) and $H_2O$ (200 mL). The solution was concentrated to remove the THF and cyclohexane, and the aqueous residue was extracted with EtOAc (2×250 mL). The combined extracts were washed with brine, dried over $Na_2SO_4$, filtered and concentrated in vacuum to afford a yellow foam (16 g). To a 250-mL, round-bottom flask equipped with a reflux condenser was added the yellow foam (6.2 g), 7-(6-chloro-pyrimidin-4-yloxy)-quinoline, (Example 102(a)), (3.0 g, 11.6 mmol), toluene (50 mL), EtOH (12 mL) and aq $K_2CO_3$ (35 mL, 1 M). The flask was carefully evacuated and then backfilled twice with $N_2$. Tetrakis-(triphenylphosphine)palladium(0) (0.67 g, 0.58 mmol, Strem) was then added and the flask was again evacuated and backfilled twice with $N_2$. The mixture was then vigorously stirred at 80° C. for 17 h. After the reaction was allowed to cool to room temperature, 1 N NaOH (100 mL) and $H_2O$ (100 mL) were added. The mixture was extracted with EtOAc (3×100 mL) and the combined extracts were washed with $H_2O$ (2×100 mL), brine (1×100 mL), dried over $Na_2SO_4$, filtered and concentrated in vacuum. The residue was diluted with EtOAc and concentrated onto silica gel. Purification by silica gel chromatography (gradient, 35 to 70% EtOAc/hexanes) afforded the title compound as a pale-yellow solid. Mp: 159-162° C. MS (ESI, pos. ion) m/z: 483.2 (M+1).

EXAMPLE 163

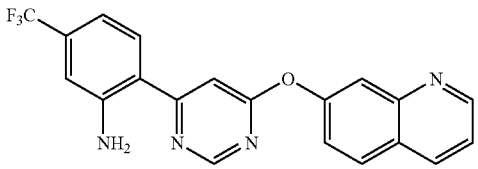

2-[6-(Quinolin-7-yloxy)-pyrimidin-4-yl]-5-trifluoromethyl-phenylamine. To a round-bottom flask was added {2-[6-(quinolin-7-yloxy)-pyrimidin-4-yl]-5-trifluoromethyl-phenyl}-carbamic acid tert-butyl ester, (Example 162), (3.2 g, 6.6 mmol) and $CH_2Cl_2$ (100 mL). The mixture was cooled to 0° C. and trifluoroacetic acid (25 mL) was added. After stirring for 5 min at 0° C., the mixture was allowed to warm to room temperature and stirred for 1.5 h. The reaction mixture was concentrated in vacuum and diluted with CH$_2$Cl$_2$ (200 mL) and satd NaHCO$_3$ (200 mL). The phases were separated and the aqueous phase was extracted with CH$_2$Cl$_2$ (100 mL). The combined extracts were washed with aq NaHCO$_3$ (20% satd NaHCO$_3$/H$_2$O), H$_2$O, brine and then dried over Na$_2$SO$_4$, filtered and concentrated onto silica gel. Purification by silica gel chromatography (gradient, 40 to 75% EtOAc/hexanes) afforded the title compound as a yellow solid. Mp: 193-194° C. MS (ESI, pos. ion) m/z: 383.2 (M+1).

EXAMPLE 164

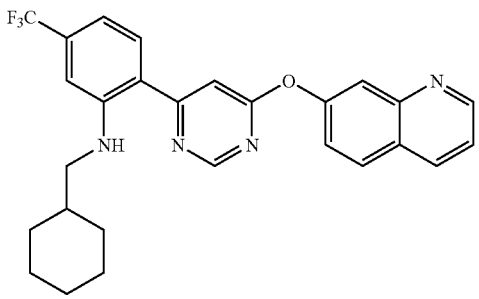

Cyclohexylmethyl-{2-[6-(quinolin-7-yloxy)-pyrimidin-4-yl]-5-trifluoromethyl-phenyl}-amine. To a solution of 2-[6-(quinolin-7-yloxy)-pyrimidin-4-yl]-5-trifluoromethyl-phenylamine, (Example 163), (0.40 g, 1.1 mmol) in 1,2-dichloroethane (11 mL) was added cyclohexanecarboxaldehyde (0.32 mL, 2.6 mmol, Aldrich) and the mixture was stirred at room temperature for 18 h. NaBH(OAc)$_3$ (0.55 g, 2.6 mmol) was added and stirring was continued for 8 h at 40° C. The reaction was diluted with satd NaHCO$_3$ and H$_2$O, and extracted with EtOAc (2×75 mL). The combined extracts were washed with H$_2$O (75 mL) and brine (75 mL), dried over Na$_2$SO$_4$, filtered and concentrated onto silica gel. Purification by silica gel chromatography (gradient, 10 to 40% EtOAc/hexanes) afforded the title compound as a yellow solid. Mp: 137-138° C. MS (ESI, pos. ion) m/z: 479.2 (M+1).

ADDITIONAL EXAMPLES

Following the procedure described in Example 164, or with slight modifications thereof, and following procedures familiar to one of ordinary skill in the art, the following examples were prepared from commercially available reagents:

| Example | Structure | MS (ESI, pos. ion) m/z | Melting Point ° C. |
|---|---|---|---|
| 165 | 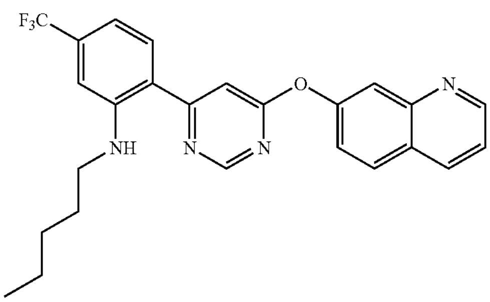 | 453.2 (M + 1) | 98-102 |
| 166 | 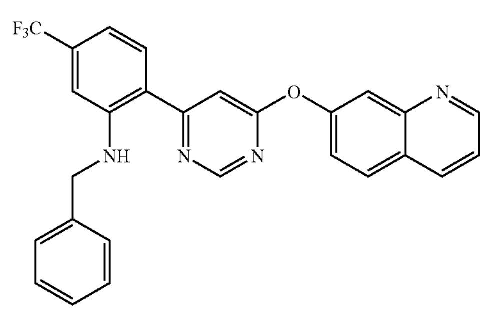 | 473.5 (M + 1) | 108-110 |

-continued

| Example | Structure | MS (ESI, pos. ion) m/z | Melting Point ° C. |
|---------|-----------|------------------------|--------------------|
| 167 | 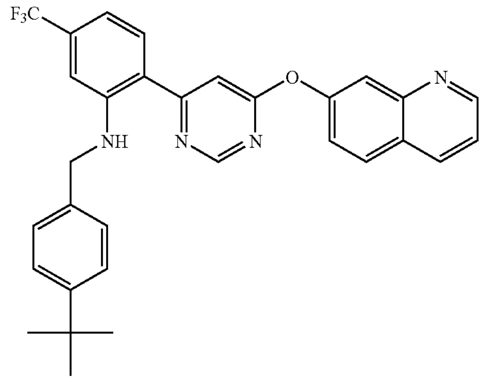 | 529.2 (M + 1) | 62-65 |
| 168 | 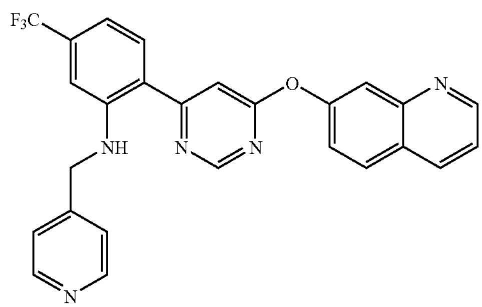 | 474.1 (M + 1) | 132-133 |

EXAMPLE 169

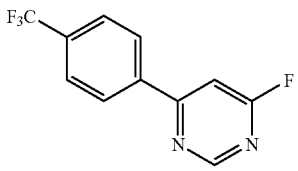

(a) 4-Fluoro-6-[4-(trifluoromethyl)phenyl]pyrimidine. To a 500-mL, round-bottomed flask was added 4-chloro-6-[4-trifluoromethyl)phenyl]pyrimidine, (Example 2(a), Method A), (3.0 g, 11 mmol), potassium fluoride (5.4 g, 93 mmol, Aldrich) and anhydrous DMSO (25 mL). The reaction mixture was stirred at 100° C. for 4 h under a N₂ atmosphere. The mixture was diluted with water (200 mL) and extracted with EtOAc (3×50 mL). The combined extracts were dried over Na₂SO₄, filtered and concentrated in vacuum. Purification by silica gel chromatography with gradient from 5% to 10% ethyl acetate in hexanes afforded the title compound as a white crystalline solid. MS (ESI, pos. ion) m/z: 243 (M+1).

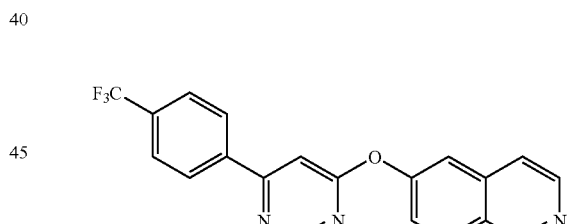

(b) 6-[6-(4-Trifluoromethyl-phenyl)-pyrimidin-4-yloxy]-isoquinoline. To a 15-mL, round-bottom flask was added 4-fluoro-6-(4-trifluoromethyl-phenyl)-pyrimidine (0.18 g, 0.74 mmol), isoquinolin-6-ol (0.060 g, 0.41 mmol, MonomerChem), K₂CO₃ (0.11 g, 0.82 mmol) and DMF (5 mL). The mixture was stirred at room temperature for 48 h and then at 60° C. for 2 h. After the reaction mixture was allowed to cool to room temperature, it was poured into a solution of satd NaHCO₃ (50 mL) and H₂O (50 mL). The mixture was extracted with EtOAc (2×75 mL) and the combined extracts were washed with H₂O (3×50 mL). The organic extracts were washed with brine (50 mL) to give an emulsion, which was filtered through Celite®. The phases of the filtrate were separated and the organic phase was dried over Na₂SO₄, filtered and concentrated onto silica gel. Purification by silica gel chromatography (gradient, 10 to 50% EtOAc/hexanes) afforded the title compound as an off-white solid (0.058 g, 39%). Mp: 195-196° C. MS (ESI, pos. ion) m/z: 368.2 (M+1).

EXAMPLE 170

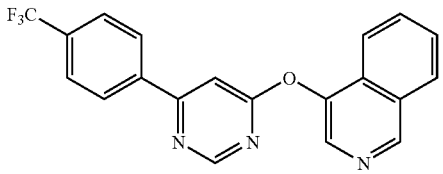

4-[6-(4-Trifluoromethyl-phenyl)-pyrimidin-4-yloxy]-isoquinoline. The title compound was prepared from 4-fluoro-6-(4-trifluoromethyl-phenyl)-pyrimidine (Example 169(a) and isoquinolin-4-ol (MonomerChem) analogous to the conditions described in Example 169(b). Mp: 206-211° C. MS (ESI, pos. ion) m/z: 368.2 (M+1).

EXAMPLE 171

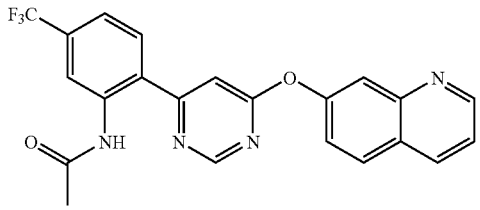

N-{2-[6-(Quinolin-7-yloxy)-pyrimidin-4-yl]-5-trifluoromethyl-phenyl}-acetamide. To a solution of 2-[6-(quinolin-7-yloxy)-pyrimidin-4-yl]-5-trifluoromethyl-phenylamine, (Example 163), (0.25 g, 0.65 mmol) in 1,2-dichloroethane (6.5 mL) was added acetic anhydride (0.15 mL, 1.6 mmol). The mixture was stirred at room temperature for 18 h and then treated with satd NaHCO$_3$ and H$_2$O. The mixture was extracted with EtOAc (2×75 mL) and the combined extracts were washed with H$_2$O (75 mL) and brine (75 mL), dried over Na$_2$SO$_4$, filtered, and concentrated onto silica gel. Purification by silica gel chromatography (gradient, 10 to 40% EtOAc/hexanes) afforded the title compound as a yellow solid. Mp: 137-138° C. MS (ESI, pos. ion) m/z: 479.2 (M+1).

EXAMPLE 172

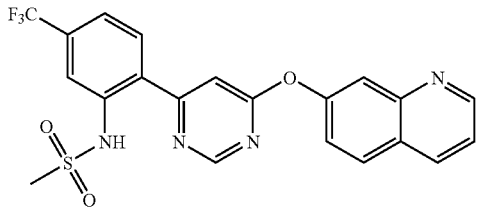

N-{2-[6-(Quinolin-7-yloxy)-pyrimidin-4-yl]-5-trifluoromethyl-phenyl}-methanesulfonamide. To a solution of 2-[6-(quinolin-7-yloxy)-pyrimidin-4-yl]-5-trifluoromethyl-phenylamine, (Example 163), (0.25 g, 0.65 mmol), N,N-diisopropylethylamine (0.57 mL, 3.3 mmol) in 1,2-dichloroethane (6.5 mL) was added methanesulfonyl chloride (0.12 mL, 1.6 mmol, Aldrich). The mixture was stirred at 40° C. for 72 h. After cooling to room temperature, the reaction mixture was treated with satd NaHCO$_3$ and H$_2$O and extracted with EtOAc (2 ×75 mL). The combined extracts were washed with H$_2$O (75 mL) and brine (75 mL), dried over Na$_2$SO$_4$, filtered, and concentrated onto silica gel. Purification by silica gel chromatography (gradient, 30 to 60% EtOAc/hexanes) afforded a pale yellow solid. To the solid was added MeOH (5 mL), CH$_2$Cl$_2$ (5 mL) and K$_2$CO$_3$ (0.050 g). The reaction mixture was stirred at room temperature for 24 h and then diluted with H$_2$O and extracted with EtOAc (2×75 mL). The combined extracts were washed with H$_2$O (75 mL), brine (75 mL), dried over Na$_2$SO$_4$, filtered, and concentrated onto silica gel. Purification by silica gel chromatography (gradient, 30 to 60% EtOAc/hexanes) afforded the title compound as a white solid. Mp: 203-204° C. MS (ESI, pos. ion) m/z: 461.0 (M+1).

EXAMPLE 173

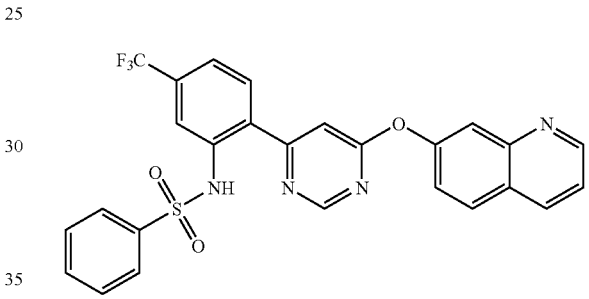

N-{2-[6-(Quinolin-7-yloxy)-pyrimidin-4-yl]-5-trifluoromethyl-phenyl}-benzenesulfonamide. The title compound was prepared from 2-[6-(quinolin-7-yloxy)-pyrimidin-4-yl]-5-trifluoromethyl-phenylamine, (Example 163) and phenylsulfonyl chloride (Aldrich) analogous to the conditions described in Example 172. Mp: 168-170° C. MS (ESI, pos. ion) m/z: 523.1 (M+1).

EXAMPLE 174

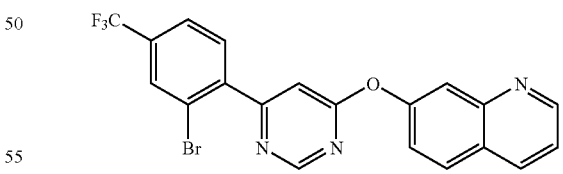

7-[6-(2-Bromo-4-trifluoromethyl-phenyl)-pyrimidin-4-yloxy]-quinoline. To a 15-mL, round-bottomed flask was added CuBr$_2$ (0.14 g, 0.63 mmol, Aldrich) and CH$_3$CN (5 mL). Isoamyl nitrite (0.11 mL, 0.78 mmol, Aldrich) was added and the mixture was stirred for 10 min at room temperature by cooling with a water bath. 2-[6-(Quinolin-7-yloxy)-pyrimidin-4-yl]-5-trifluoromethyl-phenylamine, (Example 163), (0.20 g, 0.52 mmol) was added in portions over 1 h. The reaction was stirred at room temperature for 1.5 h, at 65° C. for 2 h and then at room temperature for 72

EXAMPLE 175

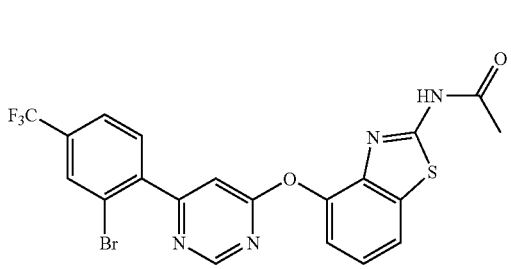

N-{4-[6-(2-Bromo-4-trifluoromethyl-phenyl)-pyrimidin-4-yloxy]-benzothiazol-2-yl}-acetamide. To a solution of CuBr₂ (0.15 g, 0.67 mmol) in CH₃CN (8 ML) was added isoamyl nitrite (0.11 mL, 0.84 mmol). The mixture was stirred for 10 min at room temperature and then N-{4-[6-(2-amino-4-trifluoromethyl-phenyl)-pyrimidin-4-yloxy]-benzothiazol-2-yl}-acetamide (Example 151) was added in portions over 40 min. The reaction mixture was stirred for 1 h at room temperature, 3 h at 65° C. and 16 h at room temperature. The mixture was diluted with MeOH and concentrated. It was then diluted with MeOH (2 M in NH3) and concentrated onto silica gel. Purification by silica gel chromatography (gradient, 0.5 to 1.7% MeOH (2 M in NH₃)/CH₂Cl₂) afforded the title compound as a white solid. Mp: 259.6-259.8° C. MS (ESI, pos. ion) m/z: 510.8 (M+1).

EXAMPLE 176

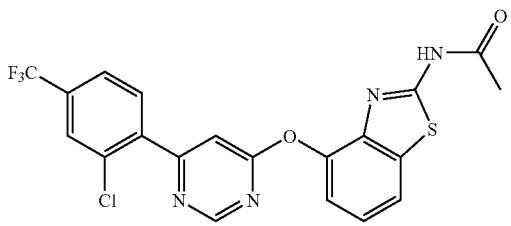

N-{4-[6-(2-Chloro-4-trifluoromethyl-phenyl)-pyrimidin-4-yloxy]-benzothiazol-2-yl}-acetamide. To a solution of CuCl₂ (0.090 g, 0.67 mmol, Aldrich) in CH₃CN (8 mL) was added isoamyl nitrite (0.11 mL, 0.84 mmol, Aldrich) and the mixture was stirred for 10 min by cooling with a 24° C. water bath. N-{4-[6-(2-Amino-4-trifluoromethyl-phenyl)-pyrimidin-4-yloxy]-benzothiazol-2-yl}-acetamide, (Example 151), (0.25 g, 0.56 mmol) was added in portions over 40 min. The reaction mixture was stirred at room temperature for 1 h, at 65° C. for 3 h and then at room temperature for 16 h. The mixture was concentrated and then diluted with MeOH (2 M in NH₃) and concentrated onto silica gel. Purification by silica gel chromatography (gradient, 0.5 to 1.7% MeOH (2 M in NH₃)/CH₂Cl₂) afforded the title compound as a white solid. Mp: 263-264° C. MS (ESI, pos. ion) m/z: 465.1 (M+1).

EXAMPLE 177

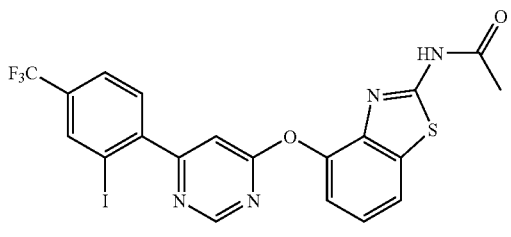

N-{4-[6-(2-Iodo-4-trifluoromethyl-phenyl)-pyrimidin-4-yloxy]-benzothiazol-2-yl}-acetamide. To N-{4-[6-(2-amino-4-trifluoromethyl-phenyl)-pyrimidin-4-yloxy]-benzothiazol-2-yl}-acetamide, (Example 151), (0.25 g, 0.56 mmol) was added CsI (0.15 g, 0.56 mmol, Aldrich), I2 (0.071 g, 0.28 mmol, Aldrich), CuI (0.032 g, 0.17 mmol, Aldrich) and ethylene glycol dimethyl ether (6 mL). To the mixture was added isoamyl nitrite (0.45 mL, 3.4 mmol, Aldrich) and the reaction was stirred for 1 h at room temperature, at 65° C. for 3 h, and then at room temperature for 18 h. The reaction mixture was diluted with MeOH (2 M in NH₃) and concentrated. The residue was taken up in MeOH and concentrated onto silica gel. Purification by silica gel chromatography (gradient, 0.4 to 1.3% MeOH (2 M in NH₃)/CH₂Cl₂) afforded the title compound as a white solid. Mp: 242-243° C. MS (ESI, pos. ion) m/z: 557.0 (M+1).

EXAMPLE 178

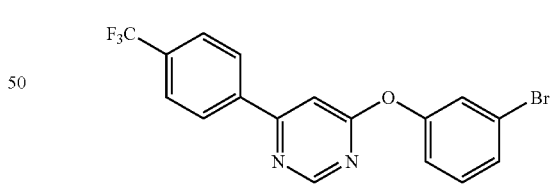

(a) 4-(3-Bromo-phenoxy)-6-(4-trifluoromethyl-phenyl)-pyrimidine. Sodium hydride (0.680 g, 17 mmol, 60% suspension in mineral oil, Aldrich) was added in small portions to a solution of 3-bromophenol (2.595 g, 15 mmol, Aldrich) in DMF (20 mL) and the mixture was stirred at room temperature for 0.5 h. (4-Chloro-6-(4-trifluoromethyl-phenyl)-pyrimidine, (Example 2(a), Method A), (2.586 g, 10 mmol) was then added and the mixture was stirred at room temperature for 18 h. The solvent was evaporated under vacuum, the residue was dissolved in EtOAc, washed with 1 N NaOH and water, dried over MgSO$_4$, and filtered. The filtrate vas evaporated under vacuum and the residue recrystallized from EtOAc/hexanes to give the title compound as white needles. MS (ESI, pos. ion) m/z: 397.0 (M+1).

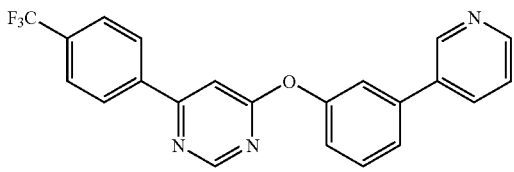

(b) 4-(3-Pyridin-3-yl-phenoxy)-6-(4-trifluoromethyl-phenyl)-pyrimidine. To a slurry of 4-(3-bromo-phenoxy)-6-(4-trifluoromethyl-phenyl)-pyrimidine (0.395 g, 1 mmol), pyridine-3-boronic acid 1,3-propanediol cyclic ester (0.488 g, 1.5 mmol, Lancaster), potassium carbonate (0.106 g, 1 mmol), water (1.2 mL), EtOH (0.8 mL) and dimethoxyethane (2.8 mL) was added (Ph$_3$P)$_2$PdCl$_2$ (0.032 g, 0.075 mmol, Strem) and the mixture was heated in a microwave synthesizer at 120° C. for 15 min with stirring under nitrogen atmosphere. The reaction mixture was allowed to cool to room temperature, diluted with EtOAc (100 mL), washes with 1 N NaOH and water, dried over MgSO$_4$, and filtered. The filtrate was evaporated under vacuum and the residue purified by silica gel chromatography (CHCl$_3$) to give the title compound as an oil. The oil was crystallized from EtOAc/hexanes to give pale yellow needles. Mp: 66° C. MS (ESI, pos. ion) m/z: 394 (M+1).

EXAMPLE 179

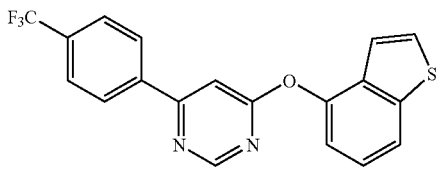

4-(Benzo[b]thiophen-4-yloxy)-6-(4-trifluoromethyl-phenyl)-pyrimidine. Sodium hydride (0.104 g, 2.6 mmol, 60% suspension in mineral oil, Aldrich) was added in small portions to a solution of benzo[b]thiophen-4-ol (0.3 g, 2 mmol, prepared according WO 01/68653) in DMF (4 mL) and the mixture was stirred at room temperature for 0.5 h. (4-Chloro-6-(4-trifluoromethyl-phenyl)-pyrimidine, (Example 2(a), Method A), (0.776 g, 3 mmol) was then added and the mixture was stirred at room temperature for 18 h. The solvent was evaporated under vacuum, the residue was dissolved in EtOAc (50 mL), washed with 1 N NaOH and water, dried over MgSO$_4$, and filtered. The filtrate was evaporated under vacuum and the residue purified by silica gel chromatography (10% EtOAc in hexanes) to give the title compound. Mp: 122.3-122.4° C. MS (ESI, pos. ion) m/z: 373.1 (M+1).

EXAMPLE 180

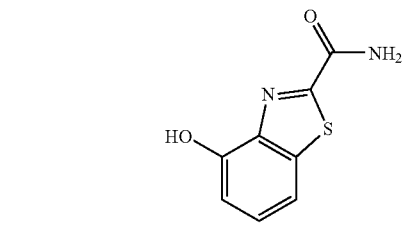

(a) Hydroxy-benzothiazole-2-carboxylic acid amide. To a suspension of 4-methoxy-benzothiazole-2-carboxylic acid amide (0.244 g, 1.175 mmol, prepared according to White, E. H. and Worter, H.; *J. Org Chem*. 1966, 31, 1484-1488) in anhydrous benzene (25 mL) was added AlCl$_3$ (0.939 g, 7 mmol, Aldrich) in small portions with stirring at room temperature. The reaction mixture was heated at reflux for 2 h with stirring under nitrogen atmosphere, quenched with water (2.5 mL) by cooling with an ice bath and neutralized with excess of solid K$_2$CO$_3$. The mixture was filtered and the filter cake was washed with CHCl$_3$ (4×). The combined organic extracts were washed with water, dried over MgSO$_4$, and filtered. The filtrate was evaporated under vacuum to give the title compound as a brown solid. MS (ESI, pos. ion) m/z: 195.2 (M+1).

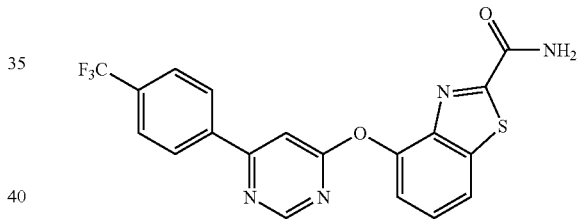

(b) 4-[6-(4-Trifluoromethyl-phenyl)-pyrimidin-4-yloxy]-benzothiazole-2-carboxylic acid amide. The title compound was prepared from hydroxy-benzothiazole-2-carboxylic acid amide and 4-chloro-6-(4-trifluoromethyl-phenyl)-pyrimidine, (Example 2(a), Method A) analogous to the conditions described in Example 179, and isolated as a white amorphous solid. MS (ESI, pos. ion) m/z: 417.3 (M+1).

EXAMPLE 181

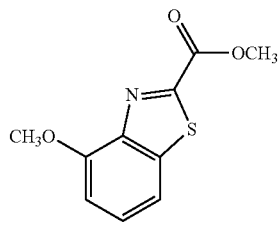

(a) 4-Methoxy-benzothiazole-2-carboxylic acid methyl ester. To a suspension of 4-methoxy-benzothiazole-2-carboxylic acid (16.74 g, 80 mmol, prepared according to White, E. H. and Worter, H.; *J. Org. Chem.* 1966, 31, 1484-1488) in MeOH (160 mL) was added dropwise SOCl₂ (9.6 mL) and the mixture was stirred at room temperature for 18 h. The reaction mixture containing a white precipitate was cooled at −10° C. for 4 h and filtered. The precipitate was washed with cold MeOH (10 mL) and dried under vacuum to give the title compound as a white solid. MS (ESI, pos. ion) m/z: 224 (M+1).

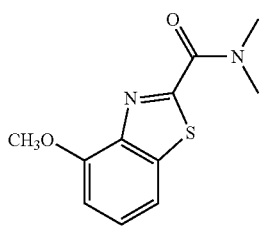

(b) 4-Methoxy-benzothiazole-2-carboxylic acid dimethylamide. To a solution of 4-methoxy-benzothiazole-2-carboxylic acid methyl ester (0.446 g, 2 mmol) in MeOH (10 mL) was added 2M solution of dimethylamine in THF (3 mL, 6 mmol, Aldrich) and the mixture was stirred at room temperature for 3 h. Evaporation of the solvent under vacuum gave the pure title compound as a white solid. MS (ESI, pos. ion) m/z: 237 (M+1).

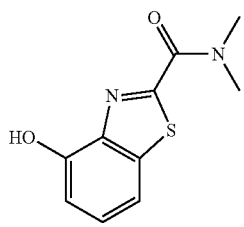

(c) 4-Hydroxy-benzothiazole-2-carboxylic acid dimethylamide. The title compound was prepared by treatment of 4-methoxy-benzothiazole-2-carboxylic acid dimethylamide with AlCl₃ under the conditions of Example 180(a) and isolated as brown crystals after recrystallization from EtOAc. MS (ESI, pos. ion) m/z: 223.3 (M+1).

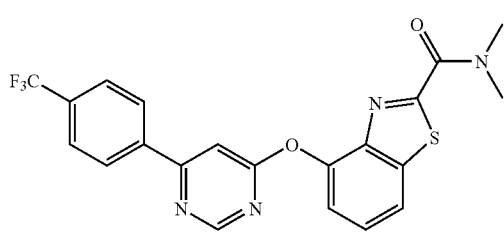

(d) 4-[6-(4-Trifluoromethyl-phenyl)-pyrimidin-4-yloxy]-benzothiazole-2-carboxylic acid dimethylamide. The title compound was prepared from 4-hydroxy-benzothiazole-2-carboxylic acid dimethylamide and (4-chloro-6-(4-trifluoromethyl-phenyl)-pyrimidine, (Example 2(a), Method A) analogous to the conditions described in Example 179 and isolated as white crystals after recrystallization from EtOAc. Mp: 152.5-152.6° C. MS (ESI, pos. ion) m/z: 445.4 (M+1).

EXAMPLE 182

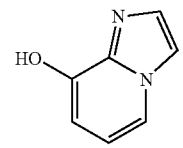

(a) Imidazo[1,2-a]pyridin-8-ol. To a solution of 2-amino-3-hydroxypyridine (1.65 g, 15 mmol, Aldrich) in 30 mL EtOH was added chloroacetaldehyde (2.0 mL, 15.7 mmol, 50 wt. % solution in water, Aldrich) and the mixture was heated at reflux for 18 h. The reaction mixture was cooled with an ice bath and the precipitated white solid was filtered, rinsed with cold EtOH and dried under vacuum to give the title compound. MS (ESI, pos. ion.) m/z: 135 (M+1)

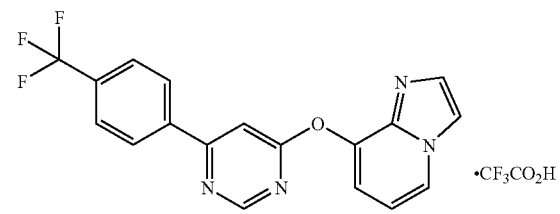

(b) 8-[6-(4-Trifluoromethyl-phenyl)-pyrimidin-4-yloxy]-imidazo[1,2-a]pyridine trifluoroacetate. A solution of 4-chloro-6-(4-trifluoromethyl-phenyl)-pyrimidine, (Example 2(a), Method A), (46.2 m g, 0.18 mmol), 1,8-diazabicyclo[5.4.0]undec-7-ene (40 µl, 0.26 mmol, Aldrich) and imidazo[1,2-a]pyridin-8-ol (24 mg, 0.18 mmol) in CH₃CN (0.5 mL) was heated in a microwave synthesizer at 180° C. for 15 min. The reaction mixture was allowed to cool to room temperature, evaporated under vacuum and the residue purified by prep. LC (10-90% CH₃CN/H₂O modified with 0.1% TFA) to give the title compound as a white solid. MS (ESI, pos. ion.) m/z: 357 (M+1).

EXAMPLE 183

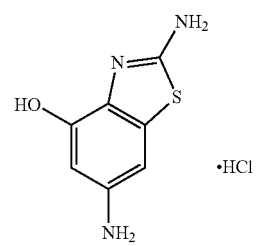

(a) 2,6-Diamino-benzothiazol-4-ol hydrochloride. A solution of N-(6-amino-4-methoxy-benzothiazol-2-yl)-acetamide (350 mg, 1.8 mmol, Asinex) in hydrobromic acid (2 mL, 48 wt. % in water, Aldrich) was heated in a microwave synthesizer at 170° C. for 10 min. The reaction mixture was allowed to cool to room temperature and the volatiles were removed under reduced pressure. The residue was treated with EtOAc (10 mL) and 1 N NaOH (5 mL). The aqueous layer was separated and treated with 2 N HCl (5 mL), and extracted with EtOAc (2×20 mL). The combined organic extracts were dried over Na₂SO₄, filtered and evaporated in vacuum to afford the title compound as a brown solid. MS (ESI, pos. ion.) m/z: 182 (M+1).

EtOAc and washed with 1 N NaOH and water. The EtOAc layer was separated, dried over Na₂SO₄, filtered and evaporated in vacuum to give the crude title compound, which was used in the next step without additional purification. MS (ESI, pos. ion.) m/z: 266 (M+1).

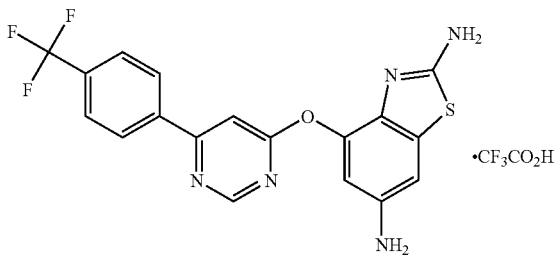

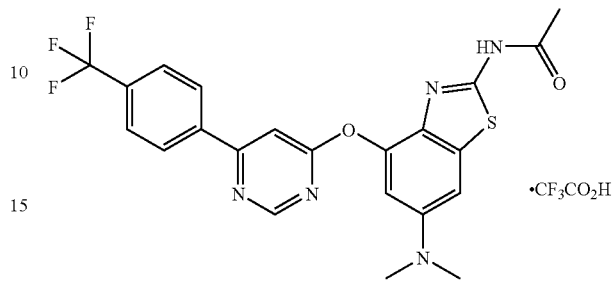

(b) 4-[6-(4-Trifluoromethyl-phenyl)-pyrimidin-4-yloxy]-benzothiazole-2,6-diamine trifluoroacetate. To a solution of 2,6-diamino-benzothiazol-4-ol hydrochloride (144 mg, 0.55 mmol) in MeOH (1 mL) and THF (1 mL) was added N,N-diisopropylethylamine (0.29 mL, 1.65 mmol, Aldrich) and di-tert-butyl dicarbonate (130 mg, 0.61 mmol, Aldrich) with stirring at 0° C. The reaction mixture was stirred at room temperature for 18 h, diluted with EtOAc and washed with satd NaHCO₃. The organic layer was separated, dried over Na₂SO₄, filtered and evaporated in vacuum. The solid residue was dissolved in DMF (2 mL) and treated with K₂CO₃ (138 mg, 1 mmol) and 4-chloro-6-(4-trifluoromethyl-phenyl)-pyrimidine, (Example 2(a), Method A), (142 m g, 0.55 mmol). The resulting mixture was heated at 80° C. with stirring for 1 h, allowed to cool to room temperature, filtered and rinsed with MeOH. The filtrate was evaporated under vacuum and the resulting brown solid was dissolved in dichloromethane (5 mL) and trifluoroacetic acid (2.5 mL). The mixture was stirred at room temperature for min, the solvents were evaporated under vacuum, and the residue was purified by prep. LC (10-90% CH₃CN/H₂O modified with 0.1% TFA) to give the title compound as a white solid. Mp: 220-221° C. MS (ESI, pos. ion.) m/z: 404 (M+1).

(b) N-{6-Dimethylamino-4-[6-(4-trifluoromethyl-phenyl)-pyrimidin-4-yloxy]-benzothiazol-2-yl}-acetamide trifluoroacetate. To a solution of ethanethiol (0.2 mL, 2.70 mmol, Aldrich) in DMF (3 mL) was added NaH (87 mg, 3.45 mmol, Aldrich) and the mixture was stirred at 0° C. for 10 min. A solution of the crude N-(6-dimethylamino-4-methoxy-benzothiazol-2-yl)-acetamide from step (a) above in DMF (3 mL) was then added and the mixture was heated at 130° C. for 3 h. The reaction mixture was allowed to cool to room temperature, concentrated to dryness under reduced pressure, and the residue was treated with EtOAc and satd NH₄Cl. The EtOAc layer was separated, dried over Na₂SO₄, filtered, and evaporated in vacuum. The residue was dissolved in DMF (3 mL) and mixed with potassium carbonate (284 mg, 2.07 mmol) and 4-chloro-6-(4-trifluoromethyl-phenyl)-pyrimidine, (Example 2(a), Method A), (266 mg, 1.03 mmol). The mixture was heated at 80° C. for 3 h, allowed to cool to room temperature and filtered. The filtrate was evaporated under vacuum and the residue purified by prep. LC (10-90% CH₃CN/H₂O modified with 0.1% TFA) to give the title compound as a yellow solid. Mp: 243-245° C. MS (ESI, pos. ion.) m/z: 474 (M+1).

EXAMPLE 184

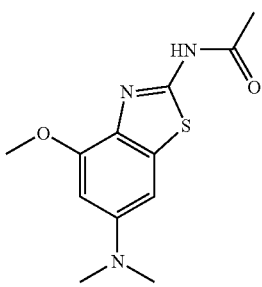

(a) N-(6-Dimethylamino-4-methoxy-benzothiazol-2-yl)-acetamide. To a solution of N-(6-amino-4-methoxy-benzothiazol-2-yl)-acetamide (156 mg, 0.66 mmol, Asinex) and formaldehyde (0.5 mL, 37 wt. % solution in water, Aldrich) in MeOH (2 mL) was added glacial acetic acid (2 drops), and sodium triacetoxyborohydride (557 mg, 2.64 mmol, Aldrich), and the resulting mixture was stirred at room temperature for 5 h. The reaction mixture was diluted with

EXAMPLE 185

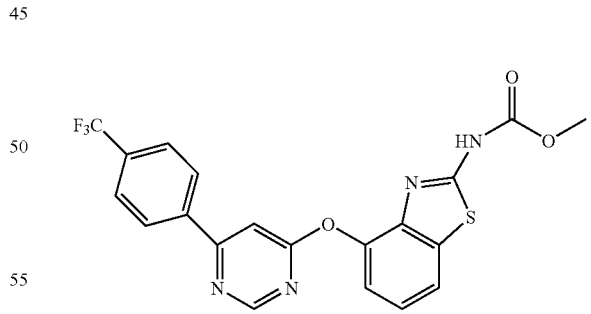

{4-[6-(4-Trifluoromethyl-phenyl)-pyrimidin-4-yloxy]-benzothiazol-2-yl}-carbamic acid methyl ester. To a solution of 4-[6-(4-trifluoromethyl-phenyl)-pyrimidin-4-yloxy]-benzothiazol-2-ylamine, (Example 65) (100 mg, 0.26 mmol) in pyridine (2 mL) was added methyl chloroformate (28 mg, 0.29 mmol, Aldrich) at 0° C. The reaction mixture was stirred at room temperature for 2 h, diluted with EtOAc and washed with 1 N NaOH and water. The EtOAc layer was separated, dried over Na₂SO₄, filtered and evaporated in vacuum. Purification of the residue by silica gel chromatography with gradient: 40 to 80% EtOAc in hexanes gave the title compound as an off white solid. MS (ESI, pos. ion.) m/z: 447 (M+1).

EXAMPLE 186

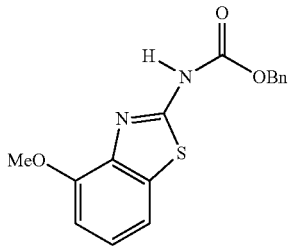

(a) (4-Methoxy-benzothiazol-2-yl)-carbamic acid benzyl ester. To a stirred solution of 4-methoxy-benzothiazol-2-ylamine (4.2 g, 23.4 mmol, Aldrich) in pyridine (20 mL) at 90° C. was added benzyl chloroformate (10 mL, 71.2 mmol, Aldrich) in three portions over 6 h. The reaction mixture was then evaporated to dryness, the residue was treated with brine (100 mL) and extracted with dichloromethane (3×100 mL). The combined organic extracts were dried over Na₂SO₄, filtered and evaporated in vacuum. Purification of the residue by silica gel chromatography (3:1 dichloromethane/EtOAc) gave the title compound as an off-white solid. MS (ESI, pos. ion.) m/z: 315 (M+1).

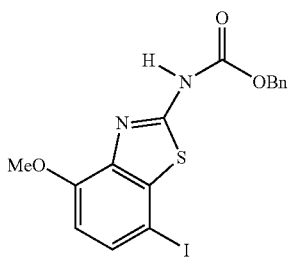

(b) (7-Iodo-4-methoxy-benzothiazol-2-yl)-carbamic acid benzyl ester. To a mixture of (4-methoxy-benzothiazol-2-yl)-carbamic acid benzyl ester (628 mg, 2 mmol) and sodium acetate (498 mg, 6 mmol) in glacial acetic acid (10 mL) was added iodine monochloride (648 mg, 4 mmol, Aldrich) with stirring at 0° C. The reaction mixture was stirred at room temperature for 15 h and diluted with water (200 mL). The precipitate was filtered, washed with water, dissolved in EtOAc, and washed with satd aq. Na₂S₂O₃. The organic layer was separated, dried over Na₂SO₄, filtered and evaporated in vacuum to give the title compound as a dark brown solid, which was used in the next step without additional purification. MS (ESI, pos. ion.) m/z: 441 (M+1).

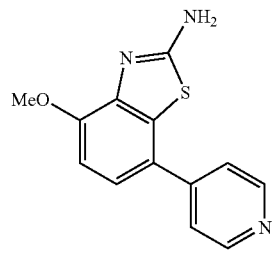

(c) 4-Methoxy-7-pyridin-4-yl-benzothiazol-2-ylamine. A mixture of (7-iodo-4-methoxy-benzothiazol-2-yl)-carbamic acid benzyl ester (197 mg, 0.45 mmol), pyridine-4-boronic acid (61 mg, 0.49 mmol, Aldrich), and Pd (PPh₃)₄ (51 mg, 0.04 mmol, Aldrich) in 1,4-dioxane (3 mL) and 2 M Na₂CO₃ (1 mL) was heated in a microwave synthesizer at 170° C. for 15 min. The mixture was allowed to cool to room temperature, diluted with EtOAc, and washed with satd aq. NaHCO₃. The EtOAc layer was separated, dried over Na₂SO₄, filtered, and evaporated in vacuum to give the title compound as a brown solid (100 mg), which was used in next step without additional purification. MS (ESI, pos. ion.) m/z: 258 (M+1).

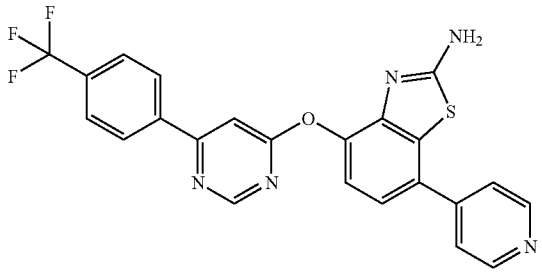

(d) 7-Pyridin-4-yl-4-[6-(4-trifluoromethyl-phenyl)-pyrimidin-4-yloxy]-benzothiazol-2-ylamine. A mixture of 4-methoxy-7-pyridin-4-yl-benzothiazol-2-ylamine (100 mg, 0.38 mmol) in cond HBr (0.5 mL) was heated in a microwave synthesizer at 165° C. for 12 min. The reaction mixture was allowed to cool to room temperature and the solvents were evaporated under vacuum. To the residue was added toluene (5 mL) and the mixture was evaporated again to afford a brown solid. The solid was dissolved in DMF (2 mL) and to the solution were added 4-chloro-6-(4-trifluoromethyl-phenyl)-pyrimidine, (Example 2(a), Method A), (98 mg, 0.38 mmol) and K₂CO₃ (267 mg, 1.93 mmol). The resulting mixture was heated at 80° C. for 2 h, the solvents were removed under reduced pressure and to the residue was added EtOAc (50 mL) and 1 N NaOH (10 mL). The organic phase was separated, dried over Na₂SO₄, filtered and concentrated. Purification of the residue by silica gel chromatography with gradient: 40 to 90% EtOAc in hexanes gave the title compound as an off white solid. MS (ESI, pos. ion.) m/z: 466 (M+1).

EXAMPLE 187

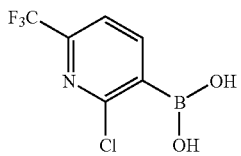

(a) 2-Chloro-6-trifluoromethylpyrid-3-ylboronic acid. A solution of N,N'-diisopropylamine (990 µL, 7.0 mmol, Aldrich) in dry THF (7.0 mL) was stirred at −78° C. and treated with n-butyllithium (1.6 M in hexanes, 3.8 mL, 6.0 mmol, Aldrich). After stirring at −78° C. for 15 min, a solution of 2-chloro-6-(trifluoromethyl)pyridine (910 mg, 5.0 mmol, Matrix Scientific) in dry THF (2.0 mL) was introduced and the reaction mixture was stirred for 1.5 h at −78° C. The resulting mixture was then treated with trimethyl boratel (1.7 mL, 15 mmol, Aldrich) at −78° C. and then stirred at room temperature for 20 h. The reaction mixture was cooled to 0° C. and treated with 2 N aq HCl to reach pH 6. The organic phase was separated, and the aqueous phase was extracted with EtOAc. The combined extracts were washed with water and brine, dried over $Na_2SO_4$, filtered and concentrated in vacuum to provide the title compound as a light-brown foam. MS (ESI, pos. ion) m/z: 224 (M−1).

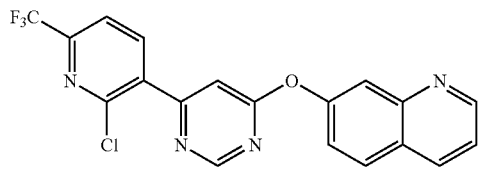

(b) 7-[6-(2-Chloro-6-trifluoromethyl-pyridin-3-yl)-pyrimidin-4-yloxy]-quinoline. To a suspension of 2-chloro-6-trifluoromethylpyrid-3-ylboronic acid (340 mg, 1.5 mmol) and 7-(6-chloro-pyrimidin-4-yloxy)-quinoline, (Example 102), (260 mg, 1.0 mmol) in toluene/EtOH (1:1, 3.0 mL) was added 2 M $K_2CO_3$ (2.0 mL, 4.0 mmol) and $Pd(PPh_3)_4$ (58 mg, 0.050 mmol, Strem). The reaction mixture was stirred and heated in a microwave synthesizer at 140° C. for 10 min. The mixture was partitioned between $CH_2Cl_2$ and 1 N NaOH. The organic phase was separated, and the aqueous phase was extracted with $CH_2Cl_2$. The combined extracts were dried over $Na_2SO_4$, filtered and concentrated in vacuum. Purification by silica gel chromatography (MeOH/ $CH_2Cl_2$ 1:120) afforded a yellow-orange solid. The title compound was obtained as a white solid after recrystallization from MeOH. MP: 209° C. MS (ESI, pos. ion) m/z: 403 (M+1). Anal. Calcd for $C_{19}H_{10}ClF_3N_4O$: C, 56.66; H, 2.50; N, 13.91. Found: C, 56.47; H, 2.53; N, 13.83.

EXAMPLE 188

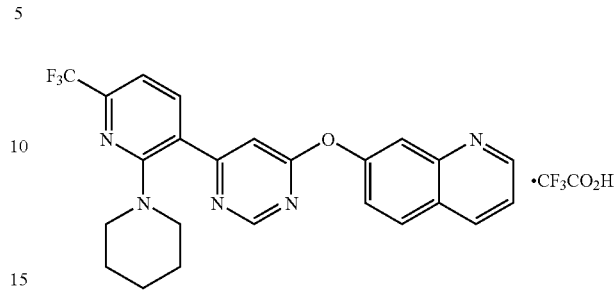

3'-[6-(Quinolin-7-yloxy)-pyrimidin-4-yl]-6'-trifluoromethyl-3,4,5,6-tetrahydro-2H-[1,2']bipyridinyl trifluoroacetate. To a solution of 7-[6-(2-chloro-6-trifluoromethyl-pyridin-3-yl)-pyrimidin-4-yloxy]-quinoline, (Example 187), (190 mg, 0.47 mmol) in DMF (4.6 mL) stirred at 60° C. was added piperidine (140 µL, 1.43 mmol, Aldrich). After the starting material was completely consumed, the reaction mixture was concentrated in vacuum to remove the DMF. The crude product was purified by silica gel chromatography (gradient, 0 to 4% MeOH/ $CH_2Cl_2$) and then by HPLC to afford the title compound as a yellow foam. MS (ESI, pos. ion) m/z: 452 (M+1). $C_{24}H_{20}F_3N_5O$: C, 63.85; H, 4.47; N, 15.51. Found: C, 63.84; H, 4.49; N, 15.39.

EXAMPLE 189

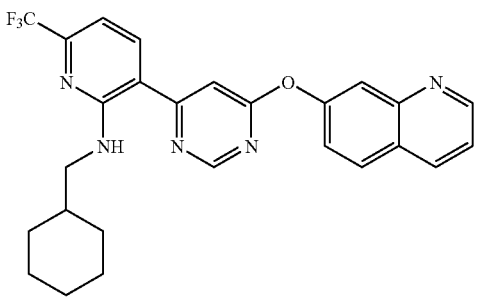

Cyclohexylmethyl-{3-[6-(quinolin-7-yloxy)-pyrimidin-4-yl]-6-trifluoromethyl-pyridin-2-yl}-amine. According to the procedure described in Example 188, 7-[6-(2-chloro-6-trifluoromethyl-pyridin-3-yl)-pyrimidin-4-yloxy]-quinoline (Example 187) (110 mg, 0.27 mmol) and cyclohexanemethylamine (43 pL, 0.33 mmol, Aldrich), after purification by silica gel chromatography (gradient, 0 to 3% MeOH/ $CH_2Cl_2$) and then preparative TLC (4% MeOH/$CH_2Cl_2$), provided the title compound as a yellow solid. MP: 151-152° C. MS (ESI, pos. ion) m/z: 480 (M+1).

EXAMPLE 190

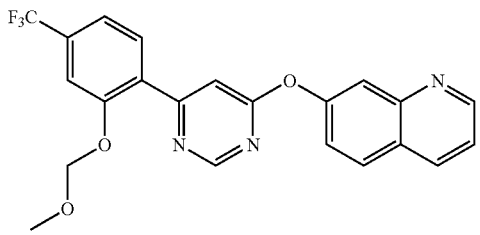

7-[6-(2-Methoxymethoxy-4-trifluoromethyl-phenyl)-pyrimidin-4-yloxy]-quinoline. To a suspension of 2-methoxymethoxy-4-trifluoromethylphenyl-boronic acid, (Example 135(b)), (220 mg, 0.87 mmol) and 7-(6-chloropyrimidin-4-yloxy)-quinoline, (Example 102(a)), (150 mg, 0.58 mmol) in toluene/EtOH (1:4, 3.8 mL) was added 2 M $K_2CO_3$ (1.2 mL, 2.3 mmol) and $Pd(PPh_3)_4$ (34 mg, 0.030 mmol, Strem). The reaction mixture was stirred and heated by microwave synthesizer at 140° C. for 10 min. The mixture was partitioned between $CH_2Cl_2$ and 1 N NaOH. The organic phase was separated, and the aqueous phase was extracted with $CH_2Cl_2$. The combined extracts were dried over $Na_2SO_4$, filtered and concentrated in vacuum. Purification by silica gel chromatography (MeOH/$CH_2Cl_2$ 1:125 and then 1:100) afforded a light-yellow gum. The title compound was obtained as a white solid after recrystallization from MeOH. MP: 98.8-99.4° C. MS (ESI, pos. ion) m/z: 428 (M+1). Anal. Calcd for $C_{22}H_{16}F_3N_3O_3$: C, 61.83; H, 3.77; N, 9.83. Found: C, 62.13; H, 3.87; N, 9.52.

EXAMPLE 191

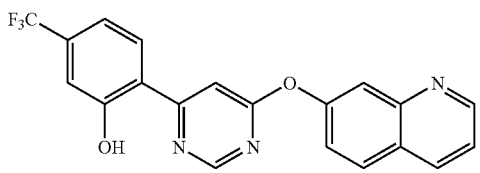

2-[6-(Quinolin-7-yloxy)-pyrimidin-4-yl]-5-trifluoromethyl-phenol. To a stirred solution of 7-[6-(2-methoxymethoxy-4-trifluoromethyl-phenyl)-pyrimidin-4-yloxy]-quinoline, (Example 190), (1.1 g, 2.5 mmol) in $CH_2Cl_2$ (25 mL) at −78° C. was added borontrifluoride diethyl etherate (0.95 mL, 7.6 mmol, Aldrich). The reaction mixture was allowed to warm to 0° C. over 1 h and then left to stir at room temperature for 16 h. The reaction mixture was quenched with satd $NaHCO_3$ at 0° C. The organic phase was separated, and the aqueous phase was extracted with $CH_2Cl_2$. The combined extracts were washed with brine, dried over $Na_2SO_4$, filtered, and concentrated in vacuum. The crude yellow solid was suspended in MeOH, collected by filtration, washed with MeOH, and dried under high vacuum to give the title compound as a light-yellow solid. MP: 210.5-212.3° C. MS (ESI, pos. ion) m/z: 384 (M+1), 382 (M−1). Anal. Calcd for $C_{20}H_{12}F_3N_3O_2$: C, 62.67; H, 3.16; N, 10.96; F, 14.87. Found: C, 62.85; H, 3.18; N, 11.02; F, 14.57.

EXAMPLE 192

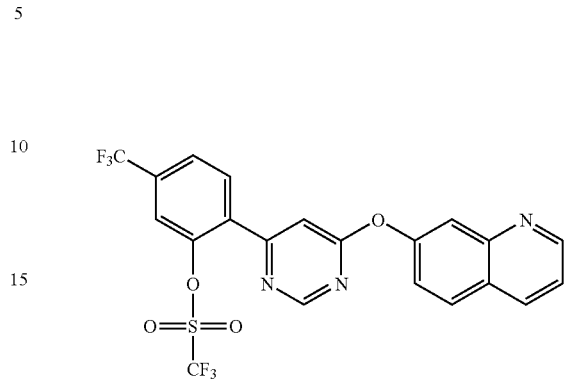

(a) Trifluoro-methanesulfonic acid 2-[6-(quinolin-7-yloxy)-pyrimidin-4-yl]-5-trifluoromethyl-phenyl ester. To a mixture of 2-[6-(quinolin-7-yloxy)-pyrimidin-4-yl]-5-trifluoromethyl-phenol, (Example 191), (1.6 g, 4.3 mmol) and N-phenyltrifluoromethanesulfonimide (1.8 g, 5.1 mmol, Aldrich) in $CH_2Cl_2$/DMF (1:1, 20 mL) was added N,N'-diisopropylethylamine (3.0 mL, 17 mmol, Aldrich) at room temperature with stirring. The reaction mixture was stirred at room temperature for 20 h, then diluted with water (20 mL). The organic phase was separated, and the aqueous phase was extracted with $CH_2Cl_2$. The combined extracts were washed with water, dried over $Na_2SO_4$, filtered and concentrated in vacuum. The crude yellow solid was purified by silica gel chromatography (MeOH/$CH_2Cl_2$ 1: 110) to give the title compound as a light-yellow solid. MS (ESI, pos. ion) m/z: 516 (M+1).

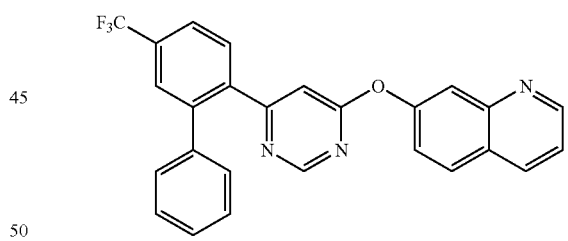

(b) 7-[6-(5-Trifluoromethyl-biphenyl-2-yl)-pyrimidin-4-yloxy]-quinoline. A mixture of trifluoromethanesulfonic acid 2-[6-(quinolin-7-yloxy)-pyrimidin-4-yl]-5-trifluoromethylphenyl ester (100 mg, 0.19 mmol), phenylboronic acid (36 mg, 0.29 mmol, Aldrich), $K_3PO_4$ (82 mg, 0.39 mmol), KBr (35 mg, 0.29 mmol) and $Pd(PPh_3)_4$ (11 mg, 0.010 mmol, Strem) in dioxane (2.0 mL) was stirred and heated at 85° C. for 20 h. The mixture was partitioned between $CH_2Cl_2$ and 1 N NaOH. The organic phase was separated, and the aqueous phase was extracted with $CH_2Cl_2$. The combined extracts were dried over $Na_2SO_4$, filtered and concentrated in vacuum. Purification by silica gel chromatography (gradient 0.5 to 3.0% MeOH/$CH_2Cl_2$) afforded the title compound as a white amorphous solid. MS (ESI, pos. ion) m/z: 444 (M+1).

EXAMPLE 193

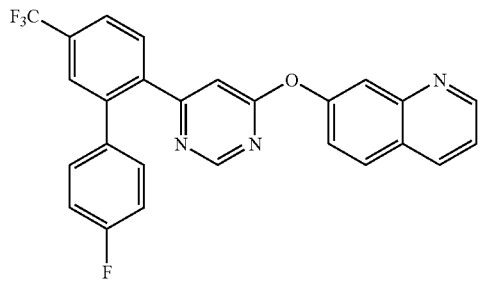

7-[6-(4'-Fluoro-5-trifluoromethyl-biphenyl-2-yl)-pyrimidin-4-yloxy]-quinoline. A mixture of trifluoromethanesulfonic acid 2-[6-(quinolin-7-yloxy)-pyrimidin-4-yl]-5-trifluoromethylphenyl ester, (Example 192(a)), (100 mg, 0.19 mmol), 4-fluorophenyl boronic acid (41 mg, 0.29 mmol, Aldrich), $K_3PO_4$ (82 mg, 0.39 mmol), KBr (35 mg, 0.29 mmol) and $Pd(PPh_3)_4$ (11 mg, 0.010 mmol, Strem) in dioxane (2.0 mL) was stirred and heated by microwave synthesizer at 140° C. for 10 min. The mixture was partitioned between $CH_2Cl_2$ and 1 N NaOH. The organic phase was separated, and the aqueous phase was extracted with $CH_2Cl_2$. The combined extracts were dried over $Na_2SO_4$, filtered and concentrated in vacuum. Purification by silica gel chromatography (gradient 0.5 to 3.0% MeOH/$CH_2Cl_2$) afforded the title compound as a white amorphous solid. MS (ESI, pos. ion) m/z: 462 (M+1).

EXAMPLE 194

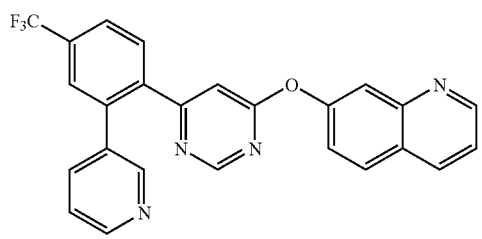

7-[6-(2-Pyridin-3-yl-4-trifluoromethyl-phenyl)-pyrimidin-4-yloxy]-quinoline. A mixture of trifluoromethanesulfonic acid 2-[6-(quinolin-7-yloxy)-pyrimidin-4-yl]-5-trifluoromethylphenyl ester, (Example 192(a)), (200 mg, 0.39 mmol), diethyl (3-pyridyl)borane (230 mg, 1.6 mmol, Aldrich), $K_3PO_4$ (170 mg, 0.78 mmol), KBr (69 mg, 0.58 mmol) and $Pd(PPh_3)_4$ (23 mg, 0.020 mmol, Strem) in dioxane (2.0 mL) was stirred and heated by microwave synthesizer at 150° C. for 20 min. The mixture was filtered and washed with $CH_2Cl_2$. The filtrate was concentrated in vacuum to dryness. Purification by silica gel chromatography (gradient 0.5 to 4.0% MeOHI $CH_2Cl_2$) afforded the title compound as a white amorphous solid. MS (ESI, pos. ion) m/z: 445 (M+1).

EXAMPLE 195

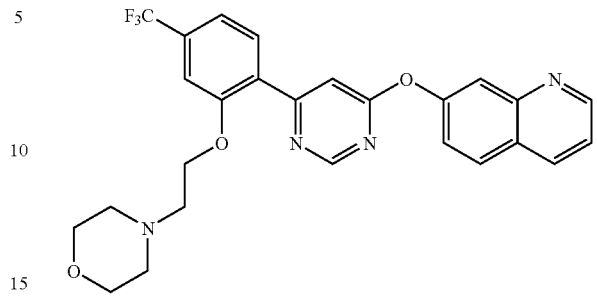

7-{6-[2-(2-Morpholin-4-yl-ethoxy)-4-trifluoromethyl-phenyl]-pyrimidin-4-yloxy}-quinoline. A solution of 4-(2-chloroethyl)morpholine hydrochloride (58 mg, 0.31 mmol, Aldrich) in DMF (1.0 mL) was stirred at room temperature and treated with $K_2CO_3$ (86 mg, 0.62 mmol). After stirring for 5 min, the resulting solution was added to a mixture of 2-[6-(quinolin-7-yloxy)-pyrimidin-4-yl]-5-trifluoromethylphenol, (Example 191), (100 mg, 0.26 mmol) and NaH (13 mg, 0.52 mmol, 95%, Aldrich) in DMF (2.0 mL) at room temperature. The reaction mixture was stirred at room temperature for 1 h and then heated at 70° C. for 20 h. The resulting mixture was allowed to cool to room temperature and diluted with water. The organic phase was separated, and the aqueous phase was extracted with $CH_2Cl_2$. The combined extracts were washed with water and brine, dried over $Na_2SO_4$, filtered and concentrated in vacuum. Purification by silica gel chromatography (gradient 0% to 4.0% MeOHW $CH_2Cl_2$) afforded the title compound as a white solid. MP: 132-133° C. MS (ESI, pos. ion) m/z: 497 (M+1).

EXAMPLE 196

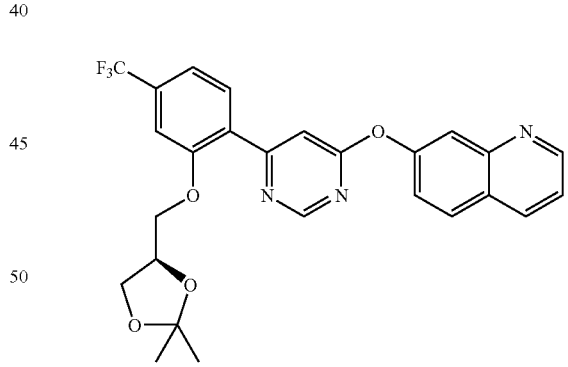

(a) 7-{6-[2-(2,2-Dimethyl-[1,3]dioxolan-4-ylmethoxy)-4-trifluoromethyl-phenyl]-pyrimidin-4-yloxy}-quinoline. A mixture of 2-[6-(quinolin-7-yloxy)-pyrimidin-4-yl]-5-trifluoromethyl-phenol, (Example 191), (100 mg, 0.26 mmol), D-α,β-isopropylidene-glycerol-γ-tosylate (150 mg, 0.52 mmol, Fluka) and $K_2CO_3$ (110 mg, 0.73 mmol) was stirred and heated at 80° C. for 20 h. The resulting mixture was allowed to cool to room temperature and diluted with water. The organic phase was separated, and the aqueous phase was extracted with $CH_2Cl_2$. The combined extracts were washed with water and brine, dried over $Na_2SO_4$, filtered and concentrated in vacuum. Purification by silica gel chromatography (gradient 0% to 4.0% MeOH/CH₂Cl₂) provided the title compound as a colorless oil. MS (ESI, pos. ion) m/z: 498 (M+1).

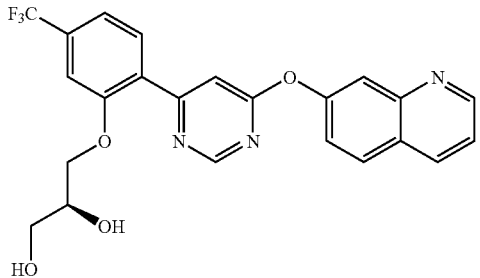

(b) 3-{2-[6-(Quinolin-7-yloxy)-pyrimidin-4-yl]-5-trifluoromethyl-phenoxy}-propane-1,2-diol. To a solution of 7-{6-[2-(2,2-dimethyl-[1,3]dioxolan-4-ylmethoxy)-4-trifluoromethyl-phenyl]-pyrimidin-4-yloxy}-quinoline (130 mg, 0.26 mmol) in MeOH (1.3 mL) stirred at room temperature was added water (0.4 mL) and p-toluenesulfonic acid monohydrate (25 mg, 0.35 mmol, Aldrich). The reaction mixture was stirred at 60° C. for 3 h, then at 80° C. for 1 h. The resulting mixture was allowed to cool to room temperature and treated with satd NaHCO₃. The reaction mixture was extracted with CH₂Cl₂. The combined extracts were washed with water and brine, dried over Na₂SO₄, filtered, and concentrated in vacuum. Purification by preparative TLC (MeOH/CH₂Cl₂ 40:1) provided the title compound as a light-yellow amorphous solid. MS (ESI, pos. ion) m/z: 458 (M+1).

EXAMPLE 197

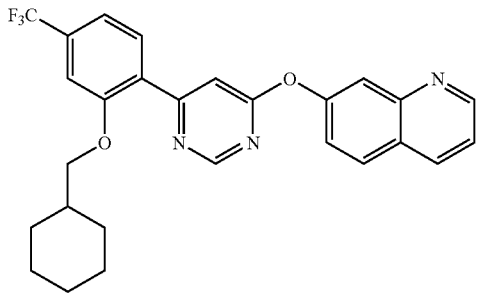

7-[6-(2-Cyclohexylmethoxy-4-trifluoromethyl-phenyl)-pyrimidin-4-yloxy]-quinoline. To a mixture of 2-[6-(quinolin-7-yloxy)-pyrimidin-4-yl]-5-trifluoromethyl-phenol, (Example 191), (50 mg, 0.13 mmol) and K₂CO₃ (54 mg, 0.39 mmol) in DMF (2.0 mL) was added (bromomethyl)cyclohexane (20 μL, 0.14 mmol, Aldrich). The reaction mixture was stirred at 60° C. for 23 h. The resulting mixture was allowed to cool to room temperature and filtered. The filtrate was concentrated in vacuum and purified by silica gel chromatography (gradient: 0% to 3.0% MeOH/CH₂Cl₂) to provide the title compound as a white amorphous solid. MS (ESI, pos. ion) nt/z: 480 (M+1).

EXAMPLE 198

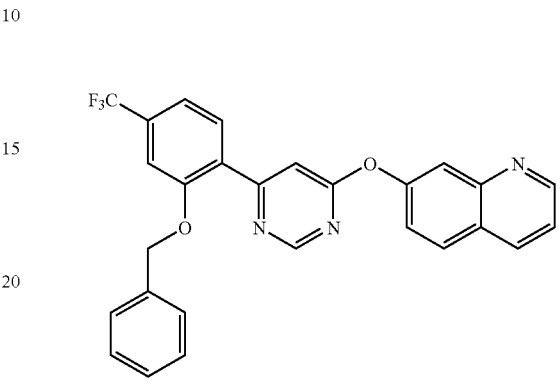

7-[6-(2-Benzyloxy-4-trifluoromethyl-phenyl)-pyrimidin-4-yloxy]-quinoline. To a mixture of 2-[6-(quinolin-7-yloxy)-pyrimidin-4-yl]-5-trifluoromethyl-phenol, (Example 191), (50 mg, 0.13 mmol) and K₂CO₃ (54 mg, 0.39 mmol) in DMF (2.0 mL) was added benzyl bromide (17 μL, 0.14 mmol, Aldrich) and the reaction mixture was stirred at room temperature for 4 h. The resulting mixture was diluted with water and extracted with CH₂Cl₂. The combined extracts were washed with water and brine, dried over Na₂SO₄, filtered and concentrated in vacuum. Purification by silica gel chromatography (gradient: 0% to 3.0% MeOH/CH₂Cl₂) provided the title compound as a light-yellow amorphous solid. MS (ESI, pos. ion) m/z: 474 (M+1).

EXAMPLE 199

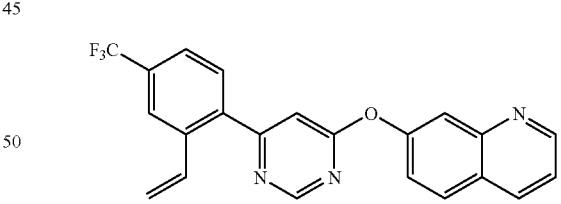

7-[6-(4-Trifluoromethyl-2-vinyl-phenyl)-pyrimidin-4-yloxy]-quinoline. To a solution of trifluoromethanesulfonic acid 2-[6-(quinolin-7-yloxy)-pyrimidin-4-yl]-5-trifluoromethyl-phenyl ester, (Example 192(a)), (600 mg, 1.2 mmol) in dioxane (6.0 mL) was added vinyltributylstannate (370 μL, 1.6 mmol, Fluka), LiCl (150 mg, 3.5 mmol, Aldrich), Pd(PPh₃)₄ (27 mg, 0.02 mmol, Strem) and a few crystals of 2,6-di-tert-butyl-4-methylphenol (Aldrich). The reaction mixture was stirred at reflux for 21 h. The resulting mixture was allowed to cool to room temperature and concentrated in vacuum. Purification by silica gel chromatography (1% MeOH/CH₂Cl₂) provided the title compound as a white amorphous solid. MS (ESI, pos. ion) m/z: 394 (M+1).

EXAMPLE 200

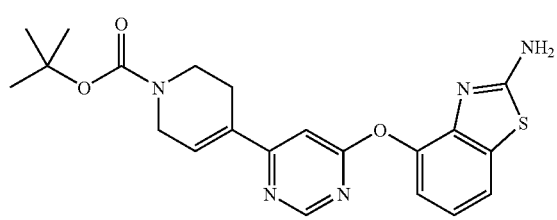

4-[6-(2-Amino-benzothiazol-4-yloxy)-pyrimidin-4-yl]-3,6-dihydro-2H-pyridine-1-carboxylic acid tert-butyl ester. A mixture of 4-(6-iodo-pyrimidin-4-yloxy)-benzothiazol-2-ylamine, (Example 129(b)), (200 mg, 0.54 mmol), 1,1-dimethylethyl 4-(4,4,5,5-tetramethyl-1,3,2-dioxaborolan-2-yl)-3,6-dihydro-[(2H)-pyridinecarboxylate (200 mg, 0.65 mmol, prepared according Eastwood, P. R. *Tetrahedron Lett.* 2000, 41, 3705-3708), PdCl$_2$(PPh$_3$)$_2$ (38 mg, 0.050 mmol, Aldrich), and Na$_2$CO$_3$ (86 mg, 0.81 mmol) in DME/EtOH/H$_2$O (2:1:2, 2.0 mL) was stirred and heated by microwave synthesizer at 120° C. for 15 min. The reaction mixture was concentrated in vacuum to dryness. Purification by silica gel chromatography (gradient: 0% to 5.0% MeOH/CH$_2$Cl$_2$) provided the title compound as a light-yellow solid. Mp: 188° C. (decomp.). MS (ESI, pos. ion) m/z: 426 (M+1).

EXAMPLE 201

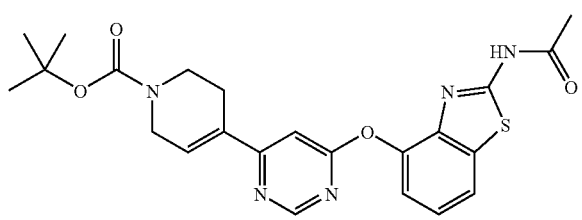

4-[6-(2-Acetylamino-benzothiazol-4-yloxy)-pyrimidin-4-yl]-3,6-dihydro-2H-pyridine-1-carboxylic acid tert-butyl ester. 4-[6-(2-Amino-benzothiazol-4-yloxy)-pyrimidin-4-yl]-3,6-dihydro-2H-pyridine-1-carboxylic acid tert-butyl ester, (Example 200), (110 mg, 0.26 mmol) was dissolved in toluene (1.0 mL) and treated with acetic anhydride (100 μL, 1.0 mmol, Aldrich) at room temperature. The reaction mixture was stirred at 90° C. for 30 min. The resulting mixture was allowed to cool to room temperature and the solvents were removed in vacuum. The residue was purified by silica gel chromatography (gradient: 0% to 4.0% MeOH/CH$_2$Cl$_2$) to provide the title compound as a light-yellow foam. MS (ESI, pos. ion) m/z: 468 (M+1), 466 (M−1).

EXAMPLE 202

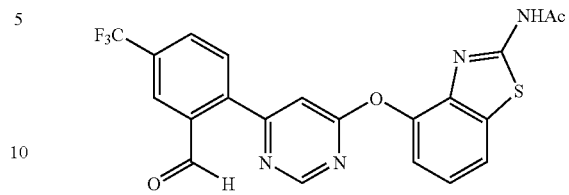

(a) N-{4-[6-(2-Formyl-4-trifluoromethyl-phenyl)-pyrimidin-4-yloxy]-benzothiazol-2-yl}-acetamide. To a suspension of N-{4-[6-(4-trifluoromethyl-2-vinyl-phenyl)-pyrimidin-4-yloxy]-benzothiazol-2-yl}-acetamide, (Example 141), (120 mg, 0.25 mmol) in acetone (5.0 mL) was added water (0.5 mL), N-methylmorpholine (44 mg, 0.38 mmol, Aldrich), and OSO$_4$ (160 μL, 0.02 mmol, 4 wt. % in water, Aldrich). The mixture was stirred at room temperature for 20 h then treated with a solution of NaIO$_4$ (160 mg, 0.75 mmol, Aldrich) in water (1.5 mL). The reaction mixture was stirred for 3 h and extracted with CH$_2$Cl$_2$ and EtOAc. The combined extracts were washed with 0.5 M Na$_2$S$_2$O$_3$ and brine, dried over Na$_2$SO$_4$, filtered and concentrated in vacuum. Purification by silica gel chromatography (gradient 0% to 4.0% MeOH/CH$_2$Cl$_2$) provided the title compound as a yellow foam. MS (ESI, pos. ion) m/z: 459 (M+1), 457 (M−1).

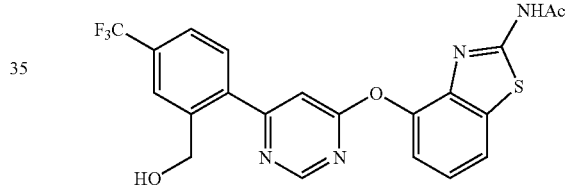

(b) N-{4-[6-(2-Hydroxymethyl-4-trifluoromethyl-phenyl)-pyrimidin-4-yloxy]-benzothiazol-2-yl}-acetamide. To a solution of N-{4-[6-(2-formyl-4-trifluoromethyl-phenyl)-pyrimidin-4-yloxy]-benzothiazol-2-yl}-acetamide (83 mg, 0.18 mmol) in MeOH (2.0 mL) at 0° C. was added NaBH4 (10 mg, 0.27 mmol, Aldrich) and the reaction mixture was stirred for 1 h. The reaction mixture was treated with water and extracted with CH$_2$Cl$_2$ and EtOAc. The combined extracts were washed with brine, dried over Na$_2$SO$_4$, filtered and concentrated in vacuum. Purification by silica gel chromatography twice (gradient 0% to 4.0% MeOH/CH$_2$Cl$_2$ and then 1:1 hexanes/EtOAc) provided the title compound as a white amorphous solid. MS (ESI, pos. ion) m/z: 461 (M+1), 459 (M−1).

EXAMPLE 203

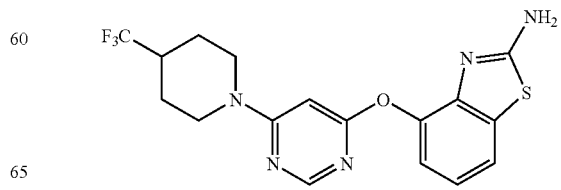

4-[6-(4-Trifluoromethyl-piperidin-1-yl)-pyrimidin-4-yloxy]-benzothiazol-2-ylamine. To a solution of 4-(6-chloro-pyrimidin-4-yloxy)-benzothiazol-2-ylamine, (Example 133(a)), (300 mg, 1.1 mmol) in dry DMF (3.0 mL) stirred at room temperature was added $K_2CO_3$ (590 mg, 4.3 mmol) and 4-(trifluoromethyl)piperidine hydrochloride (410 mg, 2.1 mmol, Matrix Scientific). The reaction mixture was stirred at 80° C. for 4 h. The resulting mixture was allowed to cool to room temperature and treated with water (20 mL). The resulting precipitate was collected by filtration, washed with water (2×), MeOH (1×), and EtOAc (3×), then dried in vacuum. The title compound was obtained as a white amorphous solid. MS (ESI, pos. ion) m/z: 396 (M+1). Anal. Calcd for $C_{17}H_{16}F_3N_5OS$: C, 51.64; H, 4.08; N, 17.71; F, 14.41. Found: C, 51.62; H, 4.09; N, 17.61; F, 14.33.

ADDITIONAL EXAMPLES

Following the procedure described above for Example 203, or with slight modifications thereof, the following examples were prepared:

| Example | Structure | MS (ESI, pos. ion) m/z | Melting Point ° C. |
|---|---|---|---|
| 204 | 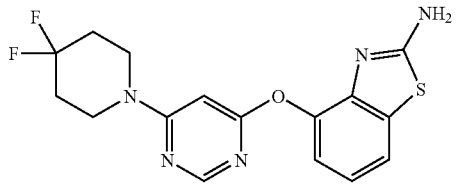 | 332 (M + 1) | Amorphous solid |
| 205 | 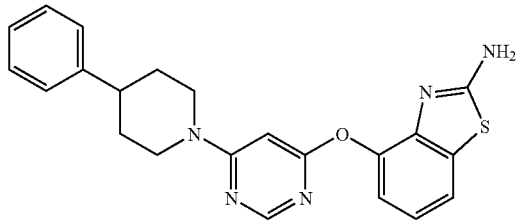 | 404 (M + 1) | 256-257 |
| 206 | 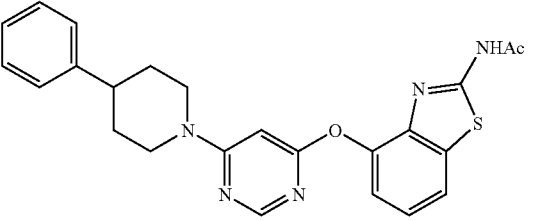 | 446 (M + 1) | 208 (decomp.) |
| 207 | 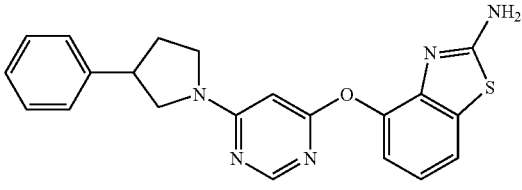 | 390 (M + 1) | 230-232 |
| 208 | 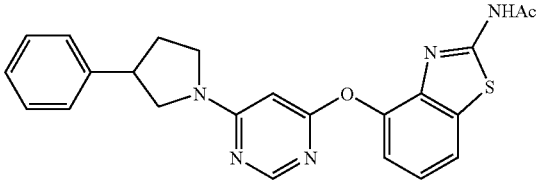 | 432 (M + 1) | 236-238 |

-continued

| Example | Structure | MS (ESI, pos. ion) m/z | Melting Point ° C. |
|---|---|---|---|
| 209 | 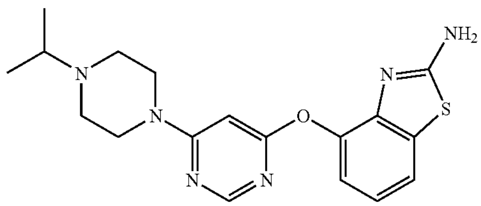 | 371 (M + 1) | 214 |
| 210 | 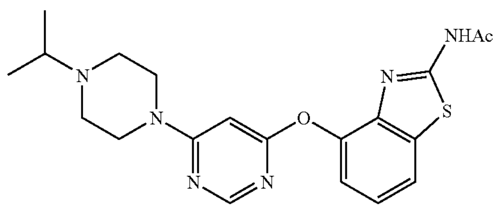 | 413 (M + 1) | 264-265 |
| 211 | 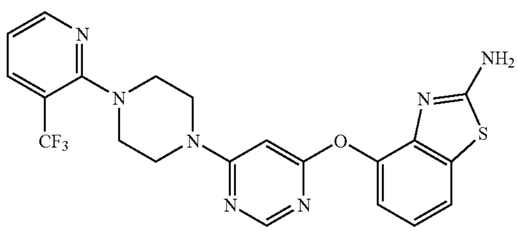 | 474 (M + 1) | 247 |
| 212 | 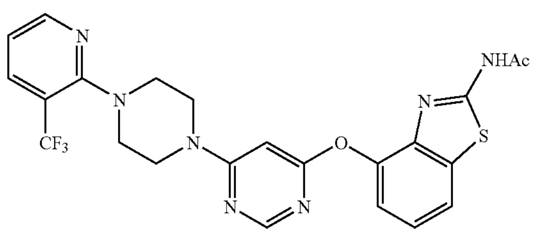 | 516 (M + 1) | 208-209 |
| 213 | 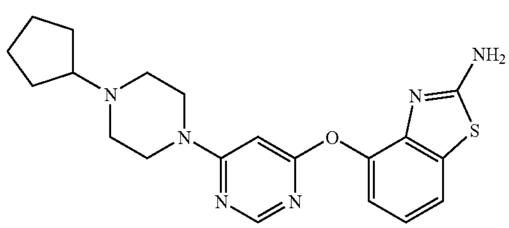 | 397.2 (M + 1) | 101.9-102.0 |
| 214 | 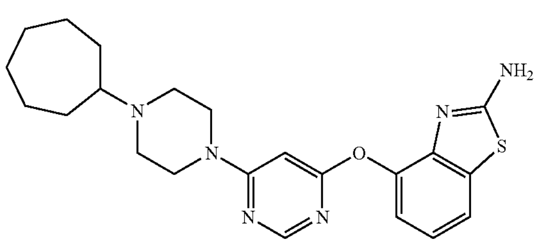 | 425.4 (M + 1) | 245.5-252.7 |

-continued

| Example | Structure | MS (ESI, pos. ion) m/z | Melting Point ° C. |
|---|---|---|---|
| 215 | 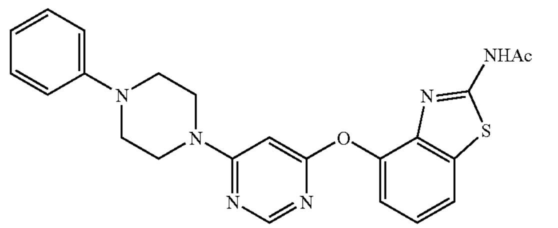 | 447.1 (M + 1) | 292.0-292.3 |
| 216 | 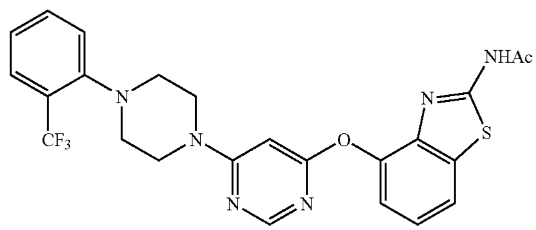 | 515 (M + 1) | 236.1-238.0 |
| 217 | 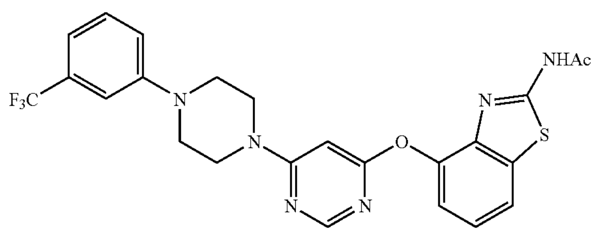 | 515 (M + 1) | 254.7-255.0 |
| 218 | 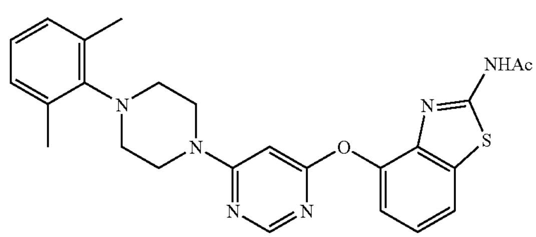 | 476 (M + 1) | 270.5-271.0 |
| 219 | 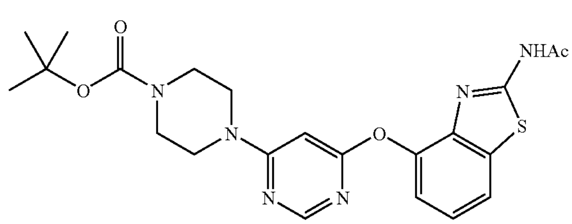 | 471.2 (M + 1) | 230.8-233.4 |
| 220 | 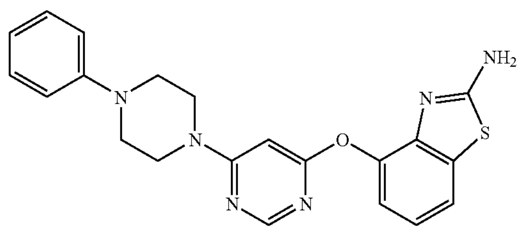 | 405.2 (M + 1) | 256.6-258.9 |

-continued

| Example | Structure | MS (ESI, pos. ion) m/z | Melting Point ° C. |
|---|---|---|---|
| 221 | 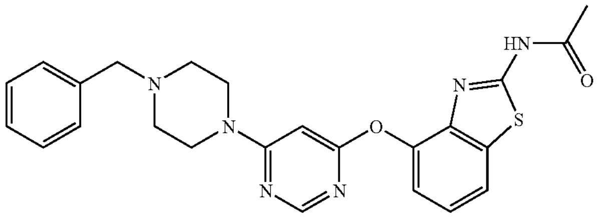 | 461 (M + 1) | 217-218 |
| 222 | 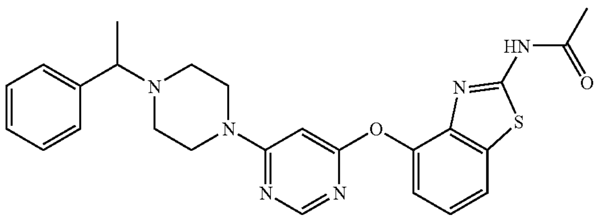 | 475 (M + 1) | 132-135 |

EXAMPLE 223

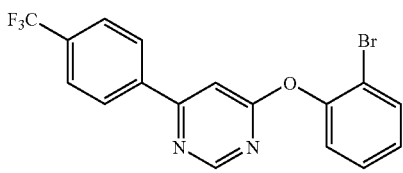

4-(2-Bromo-phenoxy)-6-(4-trifluoromethyl-phenyl)-pyrimidine. To a solution of 2-bromophenol (2.595 g, 15 mmol, Aldrich) in anhydrous DMF (20 mL) was added NaH (0.68 g, 17 mmol, 60% suspension in mineral oil, Aldrich) in small portions with stirring at room temperature. The reaction mixture was stirred for 0.5 h at room temperature and 4-chloro-6-(4-trifluoromethyl-phenyl)-pyrimidine, (Example 2(a), Method A), (2.586 g, 10 mmol) was added in one portion. The reaction mixture was stirred for 18 h at room temperature and most of the solvent was removed in vacuo. The residue was dissolved in EtOAc, washed with 1N NaOH (2×) and H$_2$O, dried over Na$_2$SO$_4$, filtered and concentrated in vacuum. The residue was recrystallized from EtOAc/hexane to give 3.21 g (81%) of the title compound. MS (ESI, pos. ion) m/z: 397 (M+1).

ADDITIONAL EXAMPLES

Following the procedures described above for Example 223, or with slight modifications thereof, the following examples were prepared:

| Example | Structure | MS (ESI, pos. ion) m/z | Melting Point ° C. |
|---|---|---|---|
| 224 | 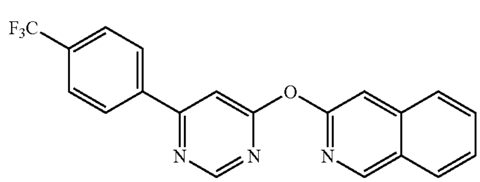 | 368 (M + 1) | 156.8-159.6 |
| 225 | 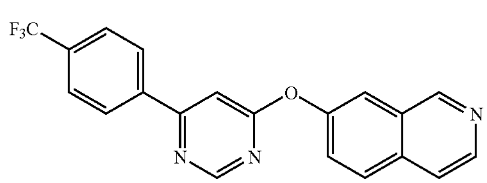 | 368.4 (M + 1) | 166.5-167.9 |

-continued
| Example | Structure | MS (ESI, pos. ion) m/z | Melting Point ° C. |
|---|---|---|---|
| 226 | 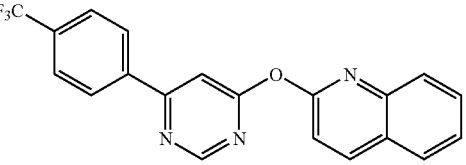 | 368.3 (M + 1) | 144.8-148.9 |
| 227 | 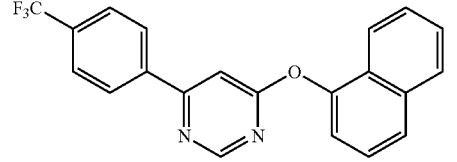 | 367.2 (M + 1) | 152.1-153.4 |
| 228 | 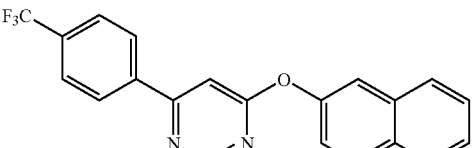 | 367.2 (M + 1) | 181-182.5 |
| 229 | 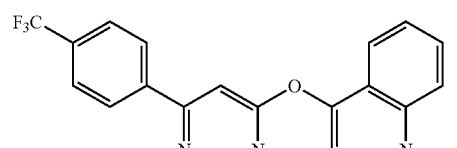 | 368.4 (M + 1) | 209-210 |
| 230 | 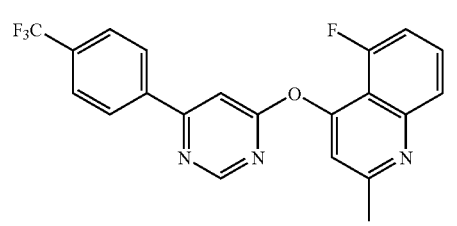 | 400.3 (M + 1) | 171.1-172.5 |
| 231 | 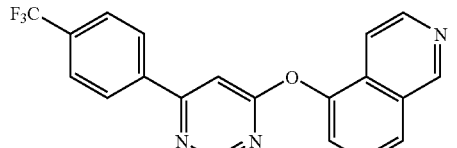 | 368.4 (M + 1) | 183-185 |
| 232 | 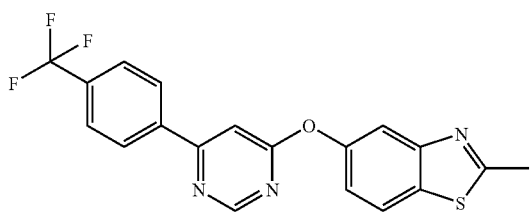 | 388 (M + 1) | 158-159 |
| 233 | 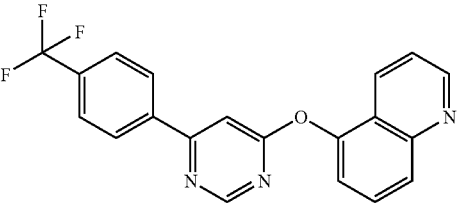 | 368 (M + 1) | 159-161 |

-continued

| Example | Structure | MS (ESI, pos. ion) m/z | Melting Point ° C. |
|---|---|---|---|
| 234 | 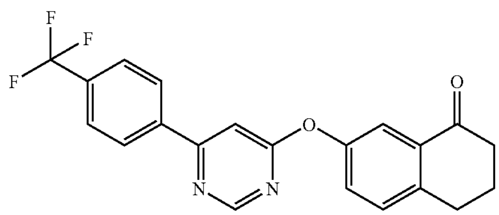 | 385 (M + 1) | Amorphous solid |
| 235 | 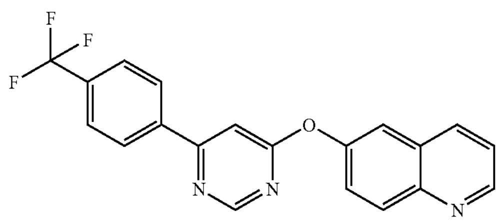 | 368 (M + 1) | 165-166 |
| 236 | 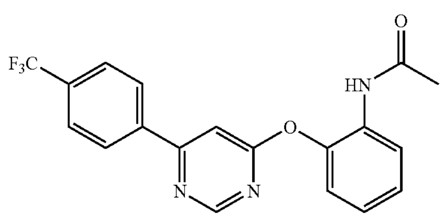 | 374 (M + 1) | 166-169 |
| 237 | 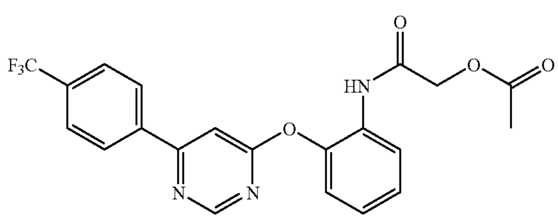 | 432 (M + 1) | 132-134 |
| 238 | 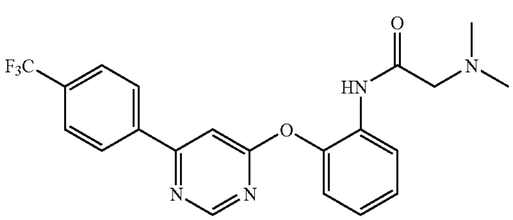 | 417 (M + 1) | 140-143 |
| 239 | 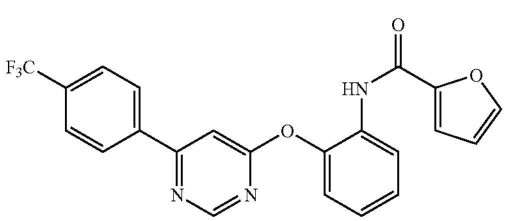 | 426 (M + 1) | 145-147 |

-continued

| Example | Structure | MS (ESI, pos. ion) m/z | Melting Point ° C. |
|---|---|---|---|
| 240 | 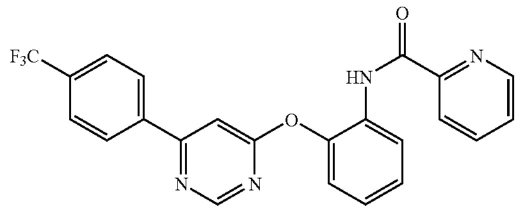 | 437 (M + 1) | 194-197 |
| 241 | 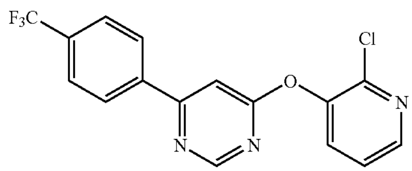 | 352 (M + 1) | Amorphous solid |
| 242 | 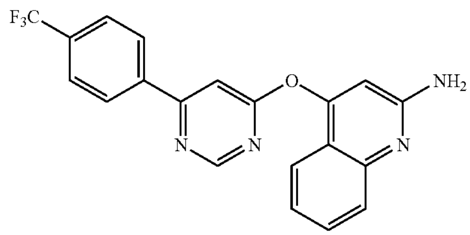 | 383 (M + 1) | Amorphous solid |
| 243 | 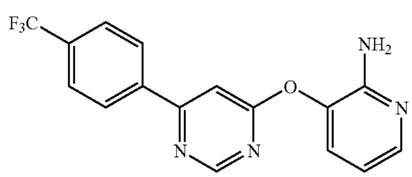 | 333 (M + 1) | Amorphous solid |

EXAMPLE 244

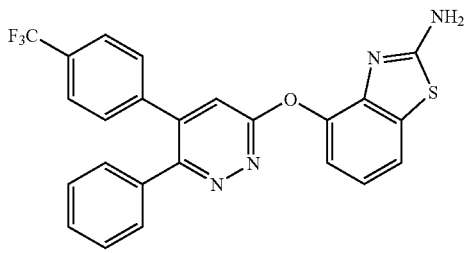

(a) 4-[6-Phenyl-5-(4-trifluoromethyl-phenyl)-pyridazin-3-yloxy]-benzothiazol-2-ylamine. A mixture of 6-chloro-3,4-bis-(4-trifluoromethyl-phenyl)-pyridazine, (Example 13(e)), (399, 1.2 mmol), 2-amino-4-hydroxybenzothiazole (200 mg, 1.2 mmol, Astatech) and $K_2CO_3$ (225 mg, 1.6 mmol) in DMF (5 mL) was heated at 80° C. for 24 h. The reaction mixture was allowed to cool to room temperature, diluted with $H_2O$ and extracted with EtOAc (3×). The combined organic layers were dried over $Na_2SO_4$, filtered and concentrated in vacuum. The residue was dissolved in MeOH, evaporated onto $SiO_2$ and purified by flash silica gel chromatography with EtOAc/hexane (0:1→2:3) as eluant to give of the title compound as a white amorphous solid. MS (ESI, pos ion.) m/z: 465 (M+1).

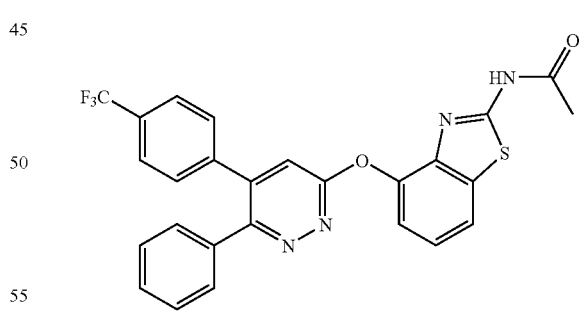

(b) N-{4-[6-Phenyl-5-(4-trifluoromethyl-phenyl)-pyridazin-3-yloxy]-benzothiazol-2-yl}-acetamide. A mixture of 4-[6-phenyl-5-(4-trifluoromethyl-phenyl)-pyridazin-3-yloxy]-benzothiazol-2-ylamine (142 mg, 0.3 mmol) and acetic anhydride (0.6 mL, 6.3 mmol, Aldrich) in 3 mL toluene was heated at 75° C. for 4 h. The reaction was allowed to cool to room temperature and the precipitate was filtered, washed with toluene and dried in vacuum to give the title compound as a white amorphous solid. Mp:>250° C. MS (ESI, pos ion.) m/z: 507 (M+1).

Capsaicin-Induced Ca2+ Influx in Primary Dorsal Root Ganglion Neurons

Embryonic 19 day old (E19) dorsal root ganglia (DRG) were dissected from timed-pregnant, terminally anesthetized Sprague-Dawley rats (Charles River, Wilmington, Mass.) and collected in ice-cold L-15 media (Life Technologies, Grand Island, N.Y.) containing 5% heat inactivated horse serum (Life Technologies). The DRG were then dissociated into single cell suspension using a papain dissociation system (Worthington Biochemical Corp., Freehold, N.J.). The dissociated cells were pelleted at 200×g for 5 min and re-suspended in EBSS containing 1 mg/ml ovomucoid inhibitor, 1 mg/ml ovalbumin and 0.005% DNase. Cell suspension was centrifuged through a gradient solution containing 10 mg/ml ovomucoid inhibitor, 10 mg/ml ovalbumin at 200×g for 6 min to remove cell debris; and filtered through a 88-µm nylon mesh (Fisher Scientific, Pittsburgh, Pa.) to remove any clumps. Cell number was determined with a hemocytometer and cells were seeded into poly-ornithine 100 µg/ml (Sigma) and mouse laminin 1 µg/ml (Life Technologies)-coated 96-well plates at $10 \times 10^3$ cells/well in complete medium. The complete medium consists of minimal essential medium (MEM) and Ham's F12, 1:1, penicillin (100 U/ml), and streptomycin (100 µg/ml), and nerve growth factor (10 ng/ml), 10% heat inactivated horse serum (Life Technologies). The cultures were kept at 37° C., 5% $CO_2$ and 100% humidity. For controlling the growth of non-neuronal cells, 5-fluoro-2'-deoxyuridine (75 µM) and uridine (180 µM) were included in the medium. Activation of VR1 is achieved in these cellular assays using either a capsaicin stimulus (ranging from 0.01-101M) or by an acid stimulus (addition of 30 mM Hepes/Mes buffered at pH 4.1). Compounds are also tested in an assay format to evaluate their agonist properties at VR1.

Capsaicin Antagonist Assay: E-19 DRG cells at 5 days in culture are incubated with serial concentrations of VR1 antagonists, in HBSS (Hanks buffered saline solution supplemented with BSA 0.1 mg/ml and 1 mM Hepes at pH 7.4) for 15 min, 37° C. Cells are then challenged with a VR1 agonist, capsaicin 200 nM, in activation buffer containing 0.1 mg/ml BSA, 15 mM Hepes, pH 7.4, and 10 µCi/ml $^{45}Ca^{2+}$ (Amersham) in Ham's F12 for 2 min at 37° C.

Acid Antagonist Assay: Compounds are pre-incubated with E-19 DRG cells for 2 minutes prior to addition of Calcium-45 in 30 mM Hepes/Mes buffer (Final Assay pH 5) and then left for an additional 2 minutes prior to compound washout. Final 45Ca (Amersham CES3-2 mCi) at 10 µCi/mL.

Agonist Assay: Compounds are incubated with E-19 DRG cells for 2 minutes in the presence of Calcium-45 prior to compound washout. Final $^{45}Ca^{2+}$ (Amersham CES3-2mCi) at 10 µCi/mL.

Compound Washout and Analysis: Assay plates are washed using an ELX405 plate washer (Bio-Tek Instruments Inc.) immediately after functional assay. Wash 3× with PBS Mg2+/Ca2+ free, 0.1 mg/mL BSA. Aspirate between washes. Read plates using a MicroBeta Jet (Wallac Inc.). Compound activity is then calculated using appropriate computational algorithms.

$^{45}Calcium^{2+}$ Assay Protocol

Compounds may be assayed using Chinese Hamster Ovary cell lines stably expressing either human VR1 or rat VR1 under a CMV promoter. Cells can be cultured in Growth Medium, routinely passaged at 70% confluency using trypsin and plated in the assay plate 24 hours prior to compound evaluation.

Possible Growth Medium:
  DMEM, high glucose (Gibco 11965-084).
  10% Dialyzed serum (Hyclone SH30079.03).
  1× Non-Essential Amino Acids (Gibco 11140-050).
  1× Glutamine-Pen-Strep (Gibco 10378-016).
  Geneticin, 450 µg/mL (Gibco 10131-035).

Compounds can be diluted in 100% DMSO and tested for activity over several log units of concentration [40 µM-2 µM]. Compounds may be further diluted in HBSS buffer (pH 7.4) 0.1 mg/mL BSA, prior to evaluation. Final DMSO concentration in assay would be 0.5%. Each assay plate can be controlled with a buffer only and a known antagonist compound (either capsazepine or one of the described VR1 antagonists).

Activation of VR1 can be achieved in these cellular assays using either a capsaicin stimulus (ranging from 0.1-1 µM) or by an acid stimulus (addition of 30 mM Hepes/Mes buffered at pH 4.1). Compounds may also tested in an assay format to evaluate their agonist properties at VR1.

Capsaicin Antagonist Assay: Compounds may be pre-incubated with cells (expressing either human or rat VR1) for 2 minutes prior to addition of Calcium-45 and Capsaicin and then left for an additional 2 minutes prior to compound 20 washout. Capsaicin (0.5 nM) can be added in HAM's F12, 0.1 mg/mL BSA, 15 mM Hepes at pH 7.4. Final $^{45}Ca$ (Amersham CES3-2 mCi) at 10 µCi/mL.

Acid Antagonist Assay: Compounds can be pre-incubated with cells (expressing either human or rat VR1) for 2 minutes prior to addition of Calcium-45 in 30 mM Hepes/Mes buffer (Final Assay pH 5) and then left for an additional 2 minutes prior to compound washout. Final $^{45}Ca$ (Amersham CES3-2mCi) at 10 µCi/mL. Agonist Assay: Compounds can be incubated with cells (expressing either human or rat VR1) for 2 minutes in the presence of Calcium-45 prior to compound washout. Final $^{45}Ca$ (Amersham CES3-2mCi) at 10 µCi/mL.

Compound Washout and Analysis: Assay plates can be washed using an ELX405 plate washer (Bio-Tek Instruments Inc.) immediately after functional assay. One can wash 3× with PBS Mg2+/$Ca^{2+}$ free, 0.1 mg/mL BSA, aspirating between washes. Plates may be read using a MicroBeta Jet (Wallac Inc.). Compound activity may then be calculated using appropriate computational algorithms.

Useful nucleic acid sequences and proteins may be found in U.S. Pat. Nos. 6,335,180, 6,406,908 and 6,239,267, herein incorporated by reference in their entirety.

For the treatment of vanilloid-receptor-diseases, such as acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, the compounds of the present invention may be administered orally, parentally, by inhalation spray, rectally, or topically in dosage unit formulations containing conventional pharmaceutically acceptable carriers, adjuvants, and vehicles. The term parenteral as used herein includes, subcutaneous, intravenous, intramuscular, intrastemal, infusion techniques or intraperitoneally.

Treatment of diseases and disorders herein is intended to also include the prophylactic administration of a compound of the invention, a pharmaceutical salt thereof, or a pharmaceutical composition of either to a subject (i.e., an animal, preferably a mammal, most preferably a human) believed to be in need of preventative treatment, such as, for example, pain, inflammation and the like.

The dosage regimen for treating vanilloid-receptor-mediated diseases, cancer, and/or hyperglycemia with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aqueous or oleaginous suspensions, may be formulated according to the known are using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulfuric acids, acacia, gelatin, sodium alginate, polyvinyl-pyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

Compounds of the present invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt.

Likewise, the compounds of this invention may exist as isomers, that is compounds of the same molecular formula but in which the atoms, relative to one another, are arranged differently. In particular, the alkylene substituents of the compounds of this invention, are normally and preferably arranged and inserted into the molecules as indicated in the definitions for each of these groups, being read from left to right. However, in certain cases, one skilled in the art will appreciate that it is possible to prepare compounds of this invention in which these substituents are reversed in orientation relative to the other atoms in the molecule. That is, the substituent to be inserted may be the same as that noted above except that it is inserted into the molecule in the reverse orientation. One skilled in the art will appreciate that these isomeric forms of the compounds of this invention are to be construed as encompassed within the scope of the present invention.

The compounds of the present invention can be used in the form of salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methansulfonate, nicotinate, 2-naphthalenesulfonate, oxalate, palmoate, pectinate, persulfate, 2-phenylpropionate, picrate, pivalate, propionate, succinate, tartrate, thiocyanate, tosylate, mesylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to from pharmaceutically acceptable acid addition salts include such inorganic acids as hydrochloric acid, sulfuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Also encompassed in the scope of the present invention are pharmaceutically acceptable esters of a carboxylic acid or hydroxyl containing group, including a metabolically labile ester or a prodrug form of a compound of this invention. A metabolically labile ester is one which may produce, for example, an increase in blood levels and prolong the efficacy of the corresponding non-esterified form of the compound. A prodrug form is one which is not in an active form of the molecule as administered but which becomes therapeutically active after some in vivo activity or biotransformation, such as metabolism, for example, enzymatic or hydrolytic cleavage. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use. Esters of a compound of this invention, may include, for example, the methyl, ethyl, propyl, and butyl esters, as well as other suitable esters formed between an acidic moiety and a hydroxyl containing moiety. Metabolically labile esters, may include, for example, methoxymethyl, ethoxymethyl, iso-propoxymethyl, α-methoxyethyl, groups such as α-(($C_1$-$C_4$)alkyloxy)ethyl, for example, methoxyethyl, ethoxyethyl, propoxyethyl, iso-propoxyethyl, etc.; 2-oxo-1,3-dioxolen-4-ylmethyl groups, such as 5-methyl-2-oxo-1,3,dioxolen-4-ylmethyl, etc.; $C_1$-$C_3$ alkylthiomethyl groups, for example, methylthiomethyl, ethylthiomethyl, isopropylthiomethyl, etc.; acyloxymethyl groups, for example, pivaloyloxymethyl, α-acetoxymethyl, etc.; ethoxycarbonyl-1-methyl; or α-acyloxy-α-substituted methyl groups, for example α-acetoxyethyl.

Further, the compounds of the invention may exist as crystalline solids which can be crystallized from common solvents such as ethanol, N,N-dimethyl-formamide, water, or the like. Thus, crystalline forms of the compounds of the invention may exist as polymorphs, solvates and/or hydrates of the parent compounds or their pharmaceutically acceptable salts. All of such forms likewise are to be construed as falling within the scope of the invention.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

We claim:
1. A compound having the structure:

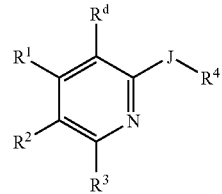

or any pharmaceutically-acceptable salt thereof, wherein:
J is O or S;
n is independently, at each instance, 0, 1 or 2.
R$^1$ is

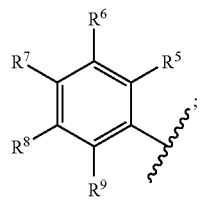

or R$^1$ is R$^b$ substituted by 1, 2 or 3 substituents independently selected from R$^f$, R$^g$, halo, nitro, cyano, —OR$^e$, —OR$^g$, —OC$_{2-6}$alkylNR$^a$R$^f$, —OC$_{2-6}$alkylOR$^f$, —NR$^a$R$^f$, —NR$^a$R$^g$, —NR$^f$C$_{2-6}$alkylNR$^a$R$^f$, —NR$^f$C$_{2-6}$ alkylOR$^f$, naphthyl, —CO$_2$R$^e$, —C(=O)R$^e$, —C(=O)NR$^a$R$^f$, —C(=O)NR$^a$R$^g$, —NR$^f$C(=O)R$^e$, —NR$^f$C(=O)R$^g$, —NR$^f$C(=O)NR$^a$R$^f$, —NR$^f$CO$_2$R$^e$, —C$_{1-8}$alkylOR$^f$, —C$_{1-6}$ alkylNR$^a$R$^f$, —S(=O)$_n$R$^e$, —S(=O)$_2$NR$^a$R$^f$, —NR$^f$S(=O)$_2$R$^e$ and —OC(=O)NR$^a$R$^f$, and R$^b$ is additionally substituted by 0, 1 or 2 groups independently selected from R$^c$; or R$^1$ is phenyl that is vicinally fused with a saturated or unsaturated 3-, 4- or 5-atom bridge containing 0, 1, 2 or 3 atoms selected from O, N and S with the remaining atoms being carbon, so long as the combination of O and S atoms is not greater than 2, wherein the heterocycle and bridge are substituted by 0, 1, 2 or 3 substituents independently selected from R$^5$;
R$^2$ is, independently, in each instance, R$^{14}$, halo, C$_{1-8}$alkyl substituted by 0, 1 or 2 substituents selected from R$^{14}$, halo, —(CH$_2$)$_n$phenyl substituted by 0, 1, 2 or 3 substituents independently selected from R$^{14}$ and halo, or a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the heterocycle or fused phenyl ring is substituted by 0, 1, 2 or 3 substituents independently selected from R$^{14}$ and halo; or R$^2$ is —OR$^4$ or —N(R$^a$)R$^4$;
R$^3$ is, independently, in each instance, H, halo, —NH$_2$, —NHC$_{1-3}$alkyl, —N(C$_{1-3}$alkyl)C$_{1-3}$alkyl, or C$_{1-3}$alkyl;

R$^4$ is independently at each instance

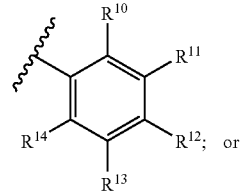

R$^4$ is independently at each instance a saturated or unsaturated 5- or 6-membered ring heterocycle containing 1, 2 or 3 atoms selected from O, N and S that is optionally vicinally fused with a saturated or unsaturated 3-, 4- or 5-atom bridge containing 0, 1, 2 or 3 atoms selected from O, N and S with the remaining atoms being carbon, so long as the combination of O and S atoms is not greater than 2, wherein the heterocycle and bridge are substituted by 0, 1, 2 or 3 substituents independently selected from R$^e$, C$_{1-4}$haloalkyl, halo, cyano, oxo, thioxo, —OR$^f$, —S(=O)$_n$R$^e$, —OC$_{1-4}$haloalkyl, —OC$_{2-6}$alkylNR$^a$R$^f$, —OC$_{2-6}$alkylOR$^f$, —OC$_{1-6}$alkylC(=O)OR$^e$, —NR$^a$R$^f$, —NR$^a$C$_{1-4}$haloalkyl, —NR$^a$C$_{2-6}$alkylNR$^a$R$^f$, —NR$^a$C$_{2-6}$alkylOR$^f$, —C(=O)R$^e$, —C(=O)OR$^f$, —OC(=O)R$^e$, —C(=O)NR$^a$R$^f$ and —NR$^a$C(=O)R$^e$; or R$^4$ is independently at each instance naphthyl substituted by 1, 2 or 3 substituents independently selected from C$_{1-4}$haloalkyl, halo, nitro, cyano, —S(=O)$_n$R$^e$, —OC$_{1-4}$haloalkyl, —OC$_{2-6}$alkylNR$^a$R$^f$, —OC$_{2-6}$alkylOR$^f$, —OC$_{1-6}$alkIC(=O)OR$^e$, —NR$^a$C$_{1-4}$haloalkyl, —NR$^a$C$_{2-6}$alkylNR$^a$R$^f$, —NR$^a$C$_{2-6}$alkylOR$^f$, —C(=O)R$^e$, —C(=O)OR$^f$, —OC(=O)R$^e$ and —C(=O)NR$^a$R$^f$; but in no instance is R$^4$-phenyl-(C$_{1-8}$alkyl), -phenyl-O—(C$_{1-6}$alkyl), -phenyl-NR$^a$R$^a$ or -phenyl-N(R$^a$)C(=O)(C$_{1-8}$alkyl);
R$^5$ is independently, at each instance, R$^f$, R$^h$, halo, nitro, cyano, —OR$^f$, —OR$^h$, —OC$_{2-6}$alkylNR$^a$R$^f$, —OC$_{2-6}$alkylOR$^f$, —NR$^a$R$^f$, —NR$^a$R$^h$, —NR$^f$C$_{2-6}$alkylNR$^a$R$^f$, —NR$^f$C$_{2-6}$alkylOR$^f$, naphthyl, —CO$_2$R$^e$, —C(=O)R$^e$, —OC(=O)R$^e$, —C(=O)NR$^a$R$^f$, —C(=O)NR$^a$R$^h$, —NR$^f$C(=O)R$^e$, —NR$^f$C(=O)R$^h$, —NR$^f$C(=O)NR$^a$R$^f$, —NR$^f$CO$_2$R$^e$, —C$_{1-8}$alkylOR$^f$, —C$_{1-6}$alkylNR$^a$R$^f$, —S(=O)$_n$R$^e$, —S(=O)$_2$NR$^a$R$^f$, —NR$^a$S(=O)$_2$R$^e$, —OS(=O)$_2$R$^e$, —OC(=O)NR$^a$R$^f$, —OR$^h$, —OC$_{2-6}$alkylNR$^a$R$^h$, —OC$_{2-6}$alkylOR$^h$, —NR$^a$R$^h$, —NR$^f$C$_{2-6}$alkylNR$^a$R$^h$, —NR$^h$C$_{2-6}$alkylNR$^a$R$^f$, —NR$^h$C$_{2-6}$alkylOR$^f$, —NR$^f$C$_{2-6}$alkylOR$^h$, —CO$_2$R$^h$, —OC(=O)R$^h$, —C(=O)R$^h$, —C(=O)NR$^a$R$^h$, —NR$^f$C(=O)R$^h$, —NR$^h$C(=O)R$^f$, —NR$^h$C(=O)NR$^a$R$^f$, —NR$^f$C(=O)NR$^a$R$^h$, —NR$^h$CO$_2$R$^e$, —NR$^f$CO$_2$R$^h$, —C$_{1-8}$alkylOR$^h$, —C$_{1-6}$alkylNR$^a$R$^h$, —S(=O)$_n$R$^h$, —S(=O)$_2$NR$^a$R$^h$, —NR$^a$S(=O)$_2$R$^h$, —NR$^h$S(=O)$_2$R$^e$, —OS(=O)$_2$R$^h$ or —OC(=O)NR$^a$R$^h$;
R$^6$ is independently, at each instance, H, C$_{1-5}$alkyl, C$_{1-4}$haloalkyl, halo, nitro —OR$^e$, —OC$_{2-6}$alkylNR$^a$R$^a$, —OC$_{2-6}$alkylOR$^a$, —NR$^a$R$^a$, —NR$^a$C$_{1-4}$haloalkyl, —NR$^a$C$_{2-6}$alkylNR$^a$R$^a$ or —NR$^a$C$_{2-6}$alkylOR$^a$, —C$_{1-8}$alkylOR$^a$, —C$_{1-6}$alkylNR$^a$R$^a$, —S(C$_{1-6}$alkyl), a phenyl ring substituted with 1, 2, or 3 substituents independently selected from R$^{14}$ and halo; or R$^6$ is a saturated or unsaturated 5- or 6-membered ring heterocycle containing 1, 2 or 3 atoms selected from O, N and S substituted with 0, 1, 2, or 3 substituents independently selected from R$^{14}$ and halo;

R$^7$ is independently, at each instance, H, C$_{1-8}$alkyl, C$_{1-4}$haloalkyl, halo, cyano, —OC$_{1-6}$alkyl, —OC$_{1-4}$haloalkyl, —OC$_{2-6}$alkylNR$^a$R$^a$, —OC$_{2-6}$alkylOR$^a$, —NR$^a$R$^a$, —NR$^a$C$_{1-4}$haloalkyl, —NR$^a$C$_{2-6}$alkylNR$^a$R$^a$, —NR$^a$C$_{2-6}$alkylOR$^a$, —C$_{1-8}$alkylOR$^a$, —C$_{1-6}$alkylNR$^a$R$^a$ or —S(C$_{1-6}$alkyl); or R$^7$ is a saturated or unsaturated 4- or 5-membered ring heterocycle containing a single nitrogen atom, wherein the ring is substituted with 0, 1 or 2 substituents independently selected from halo, C$_{1-2}$haloalkyl and C$_{1-3}$alkyl;

R$^8$ is independently, at each instance, H, C$_{1-5}$alkyl, C$_{1-4}$haloalkyl, halo, nitro, —OC$_{1-6}$alkyl, —OC$_{1-4}$haloalkyl, —OC$_{2-6}$alkylNR$^a$R$^a$, —OC$_{2-6}$alkylOR$^a$, —NR$^a$R$^a$, —NR$^a$C$_{1-4}$haloalkyl, —NR$^a$C$_{2-6}$alkylNR$^a$R$^a$, —NR$^a$C$_{2-6}$alkylOR$^a$, —C$_{1-8}$alkylOR$^a$, —C$_{1-6}$alkylNR$^a$R$^a$, —S(C$_{1-6}$alkyl), a phenyl ring substituted with 1, 2, or 3 substituents independently selected from R$^{14}$ and halo, or R$^8$ is a saturated or unsaturated 5- or 6-membered ring heterocycle containing 1, 2 or 3 atoms selected from O, N and S substituted with 0, 1, 2, or 3 substituents independently selected from R$^{14}$ and halo;

R$^9$ is independently, at each instance, R$^f$, R$^h$, halo, nitro, cyano, —OR$^f$, —OR$^h$, —OC$_{2-6}$alkylNR$^a$R$^f$, —OC$_{2-6}$alkylOR$^f$, —NR$^a$R$^f$, —NR$^a$R$^h$, —NR$^f$C$_{2-6}$alkylNR$^a$R$^f$, —NR$^f$C$_{2-6}$alkylOR$^f$, naphthyl, —CO$_2$R$^e$, —OC(=O)R$^e$, —C(=O)R$^e$, —C(=O)NR$^a$R$^f$, —C(=O)NR$^a$R$^h$, —NR$^f$C(=O)R$^e$, —NR$^f$C(=O)R$^h$, —NR$^f$C(=O)NR$^a$R$^f$, —NR$^f$CO$_2$R$^e$, —C$_{1-8}$alkylOR$^f$, —C$_{1-6}$alkylNR$^a$R$^f$, —S(=O)$_n$R$^e$, —S(=O)$_2$NR$^a$R$^f$, —NR$^a$S(=O)$_2$R$^e$, —OS(=O)$_2$R$^e$, —OC(=O)NR$^a$R$^f$, —OR$^h$, —OC$_{2-6}$alkylNR$^a$R$^h$, —OC$_{2-6}$alkylOR$^h$, —NR$^a$R$^h$, —NR$^f$C$_{2-6}$alkylNR$^a$R$^h$, —NR$^h$C$_{2-6}$alkylNR$^a$R$^f$, —NR$^h$C$_{2-6}$alkylOR$^f$, —NR$^f$C$_{2-6}$alkylOR$^h$, —CO$_2$R$^h$, —OC(=O)R$^h$, —C(=O)R$^h$, —C(=O)NR$^a$R$^h$, —NR$^f$C(=O)R$^h$, —NR$^h$C(=O)R$^f$, —NR$^h$C(=O)NR$^a$R$^f$, —NR$^f$C(=O)NR$^a$R$^h$, —NR$^h$CO$_2$R$^e$, —NR$^f$CO$_2$R$^h$, —C$_{1-8}$alkylOR$^h$, —C$_{1-6}$alkylNR$^a$R$^h$, —S(=O)$_n$R$^h$, —S(=O)$_2$NR$^a$R$^h$, —NR$^a$S(=O)$_2$R$^h$, —NR$^h$S(=O)$_2$R$^e$, —OS(=O)$_2$R$^h$ or —OC(=O)NR$^a$R$^h$; or R$^9$ is a saturated or unsaturated 4- or 5-membered ring heterocycle containing a single nitrogen atom, wherein the ring is substituted with 0, 1 or 2 substituents independently selected from halo, C$_{1-2}$haloalkyl and C$_{1-3}$alkyl;

wherein at least one of R$^5$, R$^6$, R$^7$, R$^8$ and R$^9$ is R$^e$, R$^h$, halo, nitro, cyano, —OR$^h$, —NR$^a$R$^f$, —NR$^a$R$^h$, —NR$^f$C$_{2-6}$alkylNR$^a$R$^f$, —NR$^f$C$_{2-6}$alkylOR$^f$, naphthyl, —CO$_2$R$^e$, —C(=O)R$^e$, —OC(=O)R$^e$, —C(=O)NR$^a$R$^f$, —C(=O)NR$^a$R$^h$, —NR$^f$C(=O)R$^e$, —NR$^f$C(=O)R$^h$, —NR$^f$C(=O)NR$^a$R$^f$, —NR$^f$CO$_2$R$^e$, —C$_{1-8}$alkylOR$^f$, —C$_{1-6}$alkylNR$^a$R$^f$, —S(=O)$_n$R$^e$, —S(=O)$_2$NR$^a$R$^f$, —NR$^a$S(=O)$_2$R$^e$, —OS(=O)$_2$R$^e$, —OC(=O)NR$^a$R$^f$, —OR$^h$, —OC$_{2-6}$alkylNR$^a$R$^h$, —OC$_{2-6}$alkylOR$^h$, —NR$^a$R$^h$, —NR$^f$C$_{2-6}$alkylNR$^a$R$^h$, —NR$^h$C$_{2-6}$alkylNR$^a$R$^f$, —NR$^h$C$_{2-6}$alkylOR$^f$, —NR$^f$C$_{2-6}$alkylOR$^h$, —CO$_2$R$^h$, —OC(=O)R$^h$, —C(=O)R$^h$, —C(=O)NR$^a$R$^h$, —NR$^f$C(=O)R$^h$, —NR$^h$C(=O)R$^f$, —NR$^h$C(=O)NR$^a$R$^f$, —NR$^f$C(=O)NR$^a$R$^h$, —NR$^h$CO$_2$R$^e$, —NR$^f$CO$_2$R$^h$, —C$_{1-8}$alkylOR$^h$, —C$_{1-6}$alkylNR$^a$R$^h$, —S(=O)$_n$R$^h$, —S(=O)$_2$NR$^a$R$^h$, —NR$^a$S(=O)$_2$R$^h$, —NR$^h$S(=O)$_2$R$^e$, —OS(=O)$_2$R$^h$, —OC(=O)NR$^a$R$^h$, or —OC$_{1-8}$alkyl substituted by 1, 2 or 3 substituents independently selected from R$^f$, R$^h$, halo, nitro, cyano, —OR$^f$, —OR$^h$, —OC$_{2-6}$alkylNR$^a$R$^f$, —OC$_{2-6}$alkylOR$^f$, —NR$^a$R$^f$, —NR$^a$R$^h$, —NR$^f$C$_{2-6}$alkylNR$^a$R$^f$, —NR$^f$C$_{2-6}$alkylOR$^f$, naphthyl, —CO$_2$R$^e$, —OC(=O)R$^e$, —C(=O)R$^e$, —C(=O) NR$^a$R$^f$, —C(=O)NR$^a$R$^h$, —NR$^f$C(O)R$^e$, —NR$^f$C(=O)R$^h$, —NR$^f$C(=O)NR$^a$R$^f$, —NR$^f$CO$_2$R$^e$, —C$_{1-8}$alkylOR$^f$, —C$_{1-6}$alkylNR$^a$R$^f$, —S(=O)$_n$R$^e$, —S(=O)$_2$NR$^a$R$^f$, —NR$^a$S(=O)$_2$R$^e$, —OS(=O)$_2$R$^e$, —OC(=O)NR$^a$R$^f$, —OR$^h$, —OC$_{2-6}$alkylNR$^a$R$^h$, —OC$_{2-6}$alkylOR$^h$, —NR$^a$R$^h$, —NR$^f$C$_{2-6}$alkylNR$^a$R$^h$, —NR$^h$C$_{2-6}$alkylNR$^a$R$^f$, —NR$^h$C$_{2-6}$alkylOR$^f$, —NR$^f$C$_{2-6}$alkylOR$^h$, —CO$_2$R$^h$, —OC(=O)R$^h$, —C(=O)R$^h$, —C(=O)NR$^a$R$^h$, —NR$^f$C(=O)R$^h$, —NR$^h$C(=O)R$^f$, —NR$^h$C(=O)NR$^a$R$^f$, —NR$^f$C(=O)NR$^a$R$^h$, —NR$^h$CO$_2$R$^e$, —NR$^f$CO$_2$R$^h$, —C$_{1-8}$alkylOR$^h$, —C$_{1-6}$alkylNR$^a$R$^h$, —S(=O)$_n$R$^h$, —S(=O)$_2$NR$^a$R$^h$, —NR$^a$S(=O)$_2$R$^h$, —NR$^h$S(=O)$_2$R$^e$, —OS(=O)$_2$R$^h$ and —OC(=O)NR$^a$R$^h$;

R$^{10}$ is independently, at each instance, selected from H, C$_{1-5}$alkyl, C$_{1-4}$haloalkyl, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^h$C$_{2-6}$alkylOR$^f$ and —NR$^a$C$_{2-6}$alkylOR$^h$; or R$^{10}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein there are no more than 2 N atoms, wherein the ring is substituted by 0, 1 or 2 oxo or thioxo groups, wherein the ring is substituted by 0, 1, 2 or 3 groups selected from R$^e$, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C (=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; or R$^{10}$ is C$_{1-4}$alkyl substituted by 0, 1, 2 or 3 groups selected from C$_{1-4}$haloalkyl, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$ NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$;

R$^{11}$ is independently, at each instance, selected from H, C$_{1-8}$alkyl, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; or R$^{11}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is substituted by 0, 1 or 2 oxo or thioxo groups, wherein the ring is substituted by 0, 1, 2 or 3 groups selected from R$^e$, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$ NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; or R$^{11}$ is C$_{1-4}$alkyl substituted by 0, 1, 2 or 3 groups selected from C$_{1-4}$haloalkyl, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$ NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; or R$^{10}$ and R$^{11}$ together are a saturated or unsaturated 3-, 4- or 5-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from oxo, thioxo, R$^C$, R$^e$, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)₂N(Rᵃ)C(=O)Rᵉ, —S(=O)₂N(Rᵃ)C(=O)ORᶠ, —S(=O)₂N(Rᵃ)C(=O)NRᵃRᶠ, —NRᵃRᶠ, —N(Rᵃ)C(=O)Rᵉ, —N(Rᵃ)C(=O)ORᵉ, —N(Rᵃ)C(=O)NRᵃRᶠ, —N(Rᵃ)C(=NRᵃ)NRᵃRᶠ, —N(Rᵃ)S(=O)₂Rᵉ, —N(Rᵃ)S(=O)₂NRᵃRᶠ, —NRᵃC₂₋₆alkylNRᵃRᶠ, —NRᵃC₂₋₆alkylORᶠ, —C(=O)Rʰ, —C(=O)ORʰ, —C(=O)NRᵃRʰ, —C(=NRᵃ)NRᵃRʰ, —ORʰ, —OC(=O)Rʰ, —OC(=O)NRᵃRʰ, —OC(=O)N(Rᵃ)S(=O)₂Rʰ, —OC(=O)N(Rʰ)S(=O)₂Rᵉ, —OC₂₋₆alkylNRᵃRʰ, —OC₂₋₆alkylORʰ, —SRʰ, —S(=O)Rʰ, —S(=O)₂Rʰ, —S(=O)₂NRᵃRʰ, —S(=O)₂N(Rʰ)C(=O)Rᵉ, —S(=O)₂N(Rᵃ)C(=O)Rʰ, —S(=O)₂N(Rʰ)C(=O)ORᶠ, —S(=O)₂N(Rᵃ)C(=O)ORʰ, —S(=O)₂N(Rʰ)C(=O)NRᵃRᶠ, —S(=O)₂N(Rᵃ)C(=O)NRᵃRʰ, —NRᵃRʰ, —N(Rʰ)C(=O)Rᵉ, —N(Rᵃ)C(=O)Rʰ, —N(Rʰ)C(=O)ORᶠ, —N(Rᵃ)C(=O)ORʰ, —N(Rʰ)C(=O)NRᵃRᶠ, —N(Rᵃ)C(=O)NRᵃRʰ, —N(Rʰ)C(=NRᵃ)NRᵃRᶠ, —N(Rᵃ)C(=NRᵃ)NRᵃRʰ, —N(Rʰ)S(=O)₂Rᵉ, —N(Rᵃ)S(=O)₂Rʰ, —N(Rʰ)S(=O)₂NRᵃRᶠ, —N(Rᵃ)S(=O)₂NRᵃRʰ, —NRʰC₂₋₆alkylNRᵃRᶠ, —NRᵃC₂₋₆alkylNRᵃRʰ, —NRʰC₂₋₆alkylORᶠ and —NRᵃC₂₋₆alkylORʰ; or R¹⁰ and R¹¹ together are a saturated or partially unsaturated 3-, 4- or 5-carbon bridge, wherein the bridge is substituted by 0, 1 or 2 substituents selected from oxo, thioxo, Rᶜ, Rᵉ, halo, cyano, nitro, —C(=O)Rᵉ, —C(=O)ORᵉ, —C(=O)NRᵃRᶠ, —C(=NRᵃ)NRᵃRᶠ, —ORᶠ, —OC(=O)Rᵉ, —OC(=O)NRᵃRᶠ, —OC(=O)N(Rᵃ)S(=O)₂Rᵉ, —OC₂₋₆alkylNRᵃRᶠ, —OC₂₋₆alkylORᶠ, —SRᵉ, —S(=O)Rᵉ, —S(=O)₂Rᵉ, —S(=O)₂NRᵃRᶠ, —S(=O)₂N(Rᵃ)C(=O)Rᵉ, —S(=O)₂N(Rᵃ)C(=O)ORᶠ, —S(=O)₂N(Rᵃ)C(=O)NRᵃRᶠ, —NRᵃRᶠ, —N(Rᵃ)C(=O)Rᵉ, —N(Rᵃ)C(=O)ORᶠ, —N(Rᵃ)C(=O)NRᵃRᶠ, —N(Rᵃ)C(=NRᵃ)NRᵃRᶠ, —N(Rᵃ)S(=O)₂Rᵉ, —N(Rᵃ)S(=O)₂NRᵃRᶠ, —NRᵃC₂₋₆alkylNRᵃRᶠ, —NRᵃC₂₋₆alkylORᶠ, —C(=O)Rʰ, —C(=O)ORʰ, —C(=O)NRᵃRʰ, —C(=NRᵃ)NRᵃRʰ, —ORʰ, —OC(=O)Rʰ, —OC(=O)NRᵃRʰ, —OC(=O)N(Rᵃ)S(=O)₂Rʰ, —OC(=O)N(Rʰ)S(=O)₂Rᵉ, —OC₂₋₆alkylNRᵃRʰ, —OC₂₋₆alkylORʰ, —SRʰ, —S(=O)Rʰ, —S(=O)₂Rʰ, —S(=O)₂NRᵃRʰ, —S(=O)₂N(Rʰ)C(=O)Rᵉ, —S(=O)₂N(Rᵃ)C(=O)Rʰ, —S(=O)₂N(Rʰ)C(=O)ORᶠ, —S(=O)₂N(Rᵃ)C(=O)ORʰ, —S(=O)₂N(Rʰ)C(=O)NRᵃRᶠ, —S(=O)₂N(Rᵃ)C(=O)NRᵃRʰ, —NRᵃRʰ, —N(Rʰ)C(=O)Rᵉ, —N(Rᵃ)C(=O)Rʰ, —N(Rʰ)C(=O)ORᶠ, —N(Rᵃ)C(=O)ORʰ, —N(Rʰ)C(=O)NRᵃRᶠ, —N(Rᵃ)C(=O)NRᵃRʰ, —N(Rʰ)C(=NRᵃ)NRᵃRᶠ, —N(Rᵃ)C(=NRᵃ)NRᵃRʰ, —N(Rʰ)S(=O)₂Rᵉ, —N(Rᵃ)S(=O)₂Rʰ, —N(Rʰ)S(=O)₂NRᵃRᶠ, —N(Rᵃ)S(=O)₂NRᵃRʰ, —NRʰC₂₋₆alkylNRᵃRᶠ, —NRᵃC₂₋₆alkylNRᵃRʰ, —NRʰC₂₋₆alkylORᶠ and —NRᵃC₂₋₆alkylORʰ; and when R¹⁰ and R¹¹ together form a bridge, R¹² may additionally be halo or —CF₃, R¹³ may additionally be halo or —ORᵃ or cyano or nitro, and R¹⁴ may additionally be halo;

R¹² is independently, at each instance, selected from H, C₁₋₈alkyl, cyano, nitro, —C(=O)Rᵉ, —C(=O)ORᶠ, —C(=O)NRᵃRᶠ, —C(=NRᵃ)NRᵃRᶠ, —ORᶠ, —OC(=O)Rᵉ, —OC(=O)NRᵃRᶠ, —OC(=O)N(Rᵃ)S(=O)₂Rᵉ, —OC₂₋₆alkylNRᵃRᶠ, —OC₂₋₆alkylORᶠ, —S(=O)₂NRᵃRᶠ, —S(=O)₂N(Rᵃ)C(=O)Rᵉ, —S(=O)₂N(Rᵃ)C(=O)ORᶠ, —S(=O)₂N(Rᵃ)C(=O)NRᵃRᶠ, —NRᵃRᶠ, —N(Rᵃ)C(=O)Rᵉ, —N(Rᵃ)C(=NRᵃ)NRᵃRᶠ, —N(Rᵃ)C(=O)ORᶠ, —N(Rᵃ)C(=O)NRᵃRᶠ, —N(Rᵃ)C(=NRᵃ)NRᵃRᶠ, —N(Rᵃ)S(=O)₂Rᵉ, —N(Rᵃ)S(=O)₂NRᵃRᶠ, —NRᵃC₂₋₆alkylNRᵃRᶠ, —NRᵃC₂₋₆alkylORᶠ, —C(=O)Rʰ, —C(=O)ORʰ, —C(=O)NRᵃRʰ, —C(=NRᵃ)NRᵃRʰ, —ORʰ, —OC(=O)Rʰ, —OC(=O)NRᵃRʰ, —OC(=O)N(Rᵃ)S(=O)₂Rʰ, —OC(=O)N(Rʰ)S(=O)₂Rᵉ, —OC₂₋₆alkylNRᵃRʰ, —OC₂₋₆alkylORʰ, —SRʰ, —S(=O)Rʰ, —S(=O)₂Rʰ, —S(=O)₂NRᵃRʰ, —S(=O)₂N(Rʰ)C(=O)Rᵉ, —S(=O)₂N(Rᵃ)C(=O)Rʰ, —S(=O)₂N(Rʰ)C(=O)ORᶠ, —S(=O)₂N(Rᵃ)C(=O)ORʰ, —S(=O)₂N(Rʰ)C(=O)NRᵃRᶠ, —S(=O)₂N(Rᵃ)C(=O)NRᵃRʰ, —NRᵃRʰ, —N(Rʰ)C(=O)Rᵉ, —N(Rᵃ)C(=O)Rʰ, —N(Rʰ)C(=O)ORᶠ, —N(Rᵃ)C(=O)ORʰ, —N(Rʰ)C(=O)NRᵃRᶠ, —N(Rᵃ)C(=O)NRᵃRʰ, —N(Rʰ)C(=NRᵃ)NRᵃRᶠ, —N(Rᵃ)C(=NRᵃ)NRᵃRʰ, —N(Rʰ)S(=O)₂Rᵉ, —N(Rᵃ)S(=O)₂Rʰ, —N(Rʰ)S(=O)₂NRᵃRᶠ, —N(Rᵃ)S(=O)₂NRᵃRʰ, —NRʰC₂₋₆alkylNRᵃRᶠ, —NRᵃC₂₋₆alkylNRᵃRʰ, —NRʰC₂₋₆alkylORᶠ and —NRᵃC₂₋₆alkylORʰ; or R¹² is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is substituted by 0, 1 or 2 oxo or thioxo groups, wherein the ring is substituted by 0, 1, 2 or 3 groups selected from Rᵉ, halo, cyano, nitro, —C(=O)Rᵉ, —C(=O)ORᵉ, —C(=O)NRᵃRᶠ, —C(=NRᵃ)NRᵃRᶠ, —ORᶠ, —OC(=O)Rᵉ, —OC(=O)NRᵃRᶠ, —OC(=O)N(Rᵃ)S(=O)₂Rᵉ, —OC₂₋₆alkylNRᵃRᶠ, —OC₂₋₆alkylORᶠ, —SRᵉ, —S(=O)Rᵉ, —S(=O)₂Rᵉ, —S(=O)₂NRᵃRᶠ, —S(=O)₂N(Rᵃ)C(=O)Rᵉ, —S(=O)₂N(Rᵃ)C(=O)ORᶠ, —S(=O)₂N(Rᵃ)C(=O)NRᵃRᶠ, —NRᵃRᶠ, —N(Rᵃ)C(=O)Rᵉ, —N(Rᵃ)C(=O)ORᶠ, —N(Rᵃ)C(=O)NRᵃRᶠ, —N(Rᵃ)C(=NRᵃ)NRᵃRᶠ, —N(Rᵃ)S(=O)₂Rᵉ, —N(Rᵃ)S(=O)₂NRᵃRᶠ, —NRᵃC₂₋₆alkylNRᵃRᶠ, —NRᵃC₂₋₆alkylORᶠ, —C(=O)Rʰ, —C(=O)ORʰ, —C(=O)NRᵃRʰ, —C(=NRᵃ)NRᵃRʰ, —ORʰ, —OC(=O)Rʰ, —OC(=O)NRᵃRʰ, —OC(=O)N(Rᵃ)S(=O)₂Rʰ, —OC(=O)N(Rʰ)S(=O)₂Rᵉ, —OC₂₋₆alkylNRᵃRʰ, —OC₂₋₆alkylORʰ, —SRʰ, —S(=O)Rʰ, —S(=O)₂Rʰ, —S(=O)₂NRᵃRʰ, —S(=O)₂N(Rʰ)C(=O)Rᵉ, —S(=O)₂N(Rᵃ)C(=O)Rʰ, —S(=O)₂N(Rʰ)C(=O)ORᶠ, —S(=O)₂N(Rᵃ)C(=O)ORʰ, —S(=O)₂N(Rʰ)C(=O)NRᵃRᶠ, —S(=O)₂N(Rᵃ)C(=O)NRᵃRʰ, —NRᵃRʰ, —N(Rʰ)C(=O)Rᵉ, —N(Rᵃ)C(=O)Rʰ, —N(Rʰ)C(=O)ORᶠ, —N(Rᵃ)C(=O)ORʰ, —N(Rʰ)C(=O)NRᵃRᶠ, —N(Rᵃ)C(=O)NRᵃRʰ, —N(Rʰ)C(=NRᵃ)NRᵃRᶠ, —N(Rᵃ)C(=NRᵃ)NRᵃRʰ, —N(Rʰ)S(=O)₂Rᵉ, —N(Rᵃ)S(=O)₂Rʰ, —N(Rʰ)S(=O)₂NRᵃRᶠ, —N(Rᵃ)S(=O)₂NRᵃRʰ, —NRʰC₂₋₆alkylNRᵃRᶠ, —NRᵃC₂₋₆alkylNRᵃRʰ, —NRʰC₂₋₆alkylORᶠ and —NRᵃC₂₋₆alkylORʰ; or R¹² is C₁₋₄alkyl substituted by 0, 1, 2 or 3 groups selected from C₁₋₄haloalkyl, cyano, nitro, —C(=O)Rᵉ, —C(=O)ORᶠ, —C(=O)NRᵃRᶠ, —C(=NRᵃ)NRᵃRᶠ, —ORᶠ, —OC(=O)Rᵉ, —OC(=O)NRᵃRᶠ, —OC(=O)N(Rᵃ)S(=O)₂Rᵉ, —OC₂₋₆alkylNRᵃRᶠ, —OC₂₋₆alkylORᶠ, —SRᵉ, —S(=O)Rᵉ, —S(=O)₂Rᵉ, —S(=O)₂NRᵃRᶠ, —S(=O)₂N(Rᵃ)C(=O)Rᵉ, —S(=O)₂N(Rᵃ)C(=O)ORᶠ, —S(=O)₂N(Rᵃ)C(=O)NRᵃRᶠ, —NRᵃRᶠ, —N(Rᵃ)C(=O)Rᵉ, —N(Rᵃ)C(=O)ORᶠ, —N(Rᵃ)C(=O)NRᵃRᶠ, —N(Rᵃ)C(=NRᵃ)NRᵃRᶠ, —N(Rᵃ)S(=O)₂Rᵉ, —N(Rᵃ)S(=O)₂NRᵃRᶠ, —NRᵃC₂₋₆alkylNRᵃRᶠ, —NRᵃC₂₋₆alkylORᶠ, —C(=O)Rʰ, —C(=O)ORʰ, —C(=O)NRᵃRʰ, —C(=NRᵃ)NRᵃRʰ, —ORʰ, —OC(=O)Rʰ, —OC(=O)NRᵃRʰ, —OC(=O)N(Rᵃ)S(=O)₂Rʰ, —OC(=O)N(Rʰ)S(=O)₂Rᵉ, —OC₂₋₆alkylNRᵃRʰ, —OC₂₋₆alkylORʰ, —SRʰ, —S(=O)Rʰ, S(=O)₂Rʰ, —S(=O)₂NRᵃRʰ, —S(=O)₂N(Rʰ)C(=O)Rᵉ, —S(=O)₂N(Rᵃ)C(=O)Rʰ, —S(=O)₂N(Rʰ)C(=O)ORᶠ, —S(=O)₂N(Rᵃ)C(=O)ORʰ, —S(=O)₂N(Rʰ)C (=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$, and additionally substituted by 0, 1 or 2 halo groups; or R$^{11}$ and R$^{12}$ together are a saturated or unsaturated 3-, 4- or 5-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from oxo, thioxo, R$^c$, R$^e$, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; wherein when R$^3$ is NH$_2$, then —R$^{11}$—R$^{12}$— is not —C=C—C=N— or any substituted version thereof; or R$^{11}$ and R$^{12}$ together are a saturated or partially unsaturated 3-, 4- or 5-carbon bridge, wherein the bridge is substituted by 0, 1 or 2 substituents selected from oxo, thioxo, R$^c$, R$^e$, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; and when R$^{11}$ and R$^{12}$ together form a bridge, R$^{10}$ may additionally be halo, R$^{13}$ may additionally be halo or —OR$^a$ or cyano or nitro, and R$^{14}$ may additionally be halo;

R$^{13}$ is independently, at each instance, selected from H, C$_{1-8}$alkyl, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; or R$^{13}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is substituted by 0, 1 or 2 oxo or thioxo groups, wherein the ring is substituted by 0, 1, 2 or 3 groups selected from R$^e$, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C

269

(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; or R$^{13}$ is C$_{1-4}$alkyl substituted by 0, 1, 2 or 3 groups selected from C$_{1-4}$haloalkyl, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$;

R$^{14}$ is independently, at each instance, selected from H, C$_{1-5}$alkyl, C$_{1-4}$haloalkyl, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; or R$^{14}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein there are no more than 2 N atoms, wherein the ring is substituted by 0, 1 or 2 oxo or thioxo groups, wherein the ring is substituted by 0, 1, 2 or 3 groups

270 selected from R$^e$, halo, cyano, nitro, —C(=O)R$^e$, —C(=O)OR$^f$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$R$^h$, —N(R$^h$)C(=NR$^a$)NR$^a$R$^f$, —N(R$^a$)C(=NR$^a$)NR$^a$R$^h$, —N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; or R$^{14}$ is C$_{1-4}$alkyl substituted by 0, 1, 2 or 3 groups selected from C$_{1-4}$haloalkyl, halo, cyano, nitro, —C(=O)R$^e$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^e$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^f$, —S(=O)$_2$N(R$^a$)C(=O)NR$^a$R$^f$, —NR$^a$R$^f$, —N(R$^a$)C(=O)R$^e$, —N(R$^a$)C(=O)OR$^f$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$R$^f$, —NR$^a$C$_{2-6}$alkylOR$^f$, —C(=O)R$^h$, —C(=O)OR$^h$, —C(=O)NR$^a$R$^h$, —C(=NR$^a$)NR$^a$R$^h$, —OR$^h$, —OC(=O)R$^h$, —OC(=O)NR$^a$R$^h$, —OC(=O)N(R$^a$)S(=O)$_2$R$^h$, —OC(=O)N(R$^h$)S(=O)$_2$R$^e$, —OC$_{2-6}$alkylNR$^a$R$^h$, —OC$_{2-6}$alkylOR$^h$, —SR$^h$, —S(=O)R$^h$, —S(=O)$_2$R$^h$, —S(=O)$_2$NR$^a$R$^h$, —S(=O)$_2$N(R$^h$)C(=O)R$^e$, —S(=O)$_2$N(R$^a$)C(=O)R$^h$, —S(=O)$_2$N(R$^h$)C(=O)OR$^f$, —S(=O)$_2$N(R$^a$)C(=O)OR$^h$, —S(=O)$_2$N(R$^h$)C(=O)NR$^a$R$^f$, —S(=O)$_2$N(R$^a$)C(=O)NR$^a$R$^h$, —NR$^a$R$^h$, —N(R$^h$)C(=O)R$^e$, —N(R$^a$)C(=O)R$^h$, —N(R$^h$)C(=O)OR$^f$, —N(R$^a$)C(=O)OR$^h$, —N(R$^h$)C(=O)NR$^a$R$^f$, —N(R$^a$)C(=O)NR$^a$ R$^h$, —N(R$^h$)C(=NR$^a$)NR$^a$R$^f$, —N(R$^a$)C(=NR$^a$)NR$^a$R$^h$, 13 N(R$^h$)S(=O)$_2$R$^e$, —N(R$^a$)S(=O)$_2$R$^h$, —N(R$^h$)S(=O)$_2$NR$^a$R$^f$, —N(R$^a$)S(=O)$_2$NR$^a$R$^h$, —NR$^h$C$_{2-6}$alkylNR$^a$R$^f$, —NR$^a$C$_{2-6}$alkylNR$^a$R$^h$, —NR$^h$C$_{2-6}$alkylOR$^f$ and —NR$^a$C$_{2-6}$alkylOR$^h$; wherein at least one of R$^{10}$, R$^{11}$, R$^{12}$, R$^{13}$ and R$^{14}$ is other than H;

R$^a$ is independently, at each instance, H, phenyl, benzyl or C$_{1-6}$alkyl, the phenyl, benzyl and C$_{1-6}$alkyl being substituted by 0, 1, 2 or 3 substituents selected from halo, C$_{1-4}$alkyl, C$_{1-3}$haloalkyl, —OC$_{1-4}$alkyl, —NH$_2$, —NHC$_{1-4}$alkyl, —N(C$_{1-4}$alkyl)C$_{1-4}$alkyl;

R$^b$ is a heterocycle selected from the group of thiophene, pyrrole, 1,3-oxazole, 1,3-thiazol-4-yl, 1,3,4-oxadiazole, 1,3,4-thiadiazole, 1,2,3-oxadiazole, 1,2,3-thiadiazole, 1H-1,2,3-triazole, isothiazole, 1,2,4-oxadiazole, 1,2,4-thiadiazole, 1,2,3,4-oxatriazole, 1,2,3,4-thiatriazole, 1H-1,2,3,4-tetraazole, 1,2,3,5-oxatriazole, 1,2,3,5- thiatriazole, furan, imidazol-2-yl, benzimidazole, 1,2,4-triazole, isoxazole, pyrazol-3-yl, pyrazol-4-yl, pyrazol-5-yl, thiolane, pyrrolidine, tetrahydrofuran, 4,5-dihydrothiophene, 2-pyrroline, 4,5-dihydrofuran, pyridazine, pyrimidine, pyrazine, 1,2,3-triazine, 1,2,4-triazine, 1,3,5-triazine, pyridine, 2H-3,4,5,6-tetrahydropyran, thiane, 1,2-diazaperhydroine, 1,3-diazaperhydroine, piperazine, 1,3-oxazaperhydroine, morpholine, 1,3-thiazaperhydroine, 1,4-thiazaperhydroine, piperidine, 2H-3,4-dihydropyran, 2,3-dihydro-4H-thiin, 1,4,5,6-tetrahydropyridine, 2H-5,6-dihydropyran, 2,3-dihydro-6H-thiin, 1,2,5,6-tetrahydropyridine, 3,4,5,6-tetrahydropyridine, 4H-pyran, 4H-thiin, 1,4-dihydropyridine, 1,4-dithiane, 1,4-dioxane, 1,4-oxathiane, 1,2-oxazolidine, 1,2-thiazolidine, pyrazolidine, 1,3-oxazolidine, 1,3-thiazolidine, imidazolidine, 1,2,4-oxadiazolidine, 1,3,4-oxadiazolidine, 1,2,4-thiadiazolidine, 1,3,4-thiadiazolidine, 1,2,4-triazolidine, 2-imidazolin-1-yl, 2-imidazolin-2-yl, 3-imidazoline, 2-pyrazoline, 4-imidazoline, 2,3-dihydroisothiazole, 4,5-dihydroisoxazole, 4,5-dihydroisothiazole, 2,5-dihydroisoxazole, 2,5-dihydroisothiazole, 2,3-dihydroisoxazole, 4,5-dihydrooxazole, 2,3-dihydrooxazole, 2,5-dihydrooxazole, 4,5-dihydrothiazole, 2,3-dihydrothiazole, 2,5-dihydrothiazole, 1,3,4-oxathiazolidine, 1,4,2-oxathiazolidine, 2,3-dihydro-1H-[1,2,3]triazole, 2,5-dihydro-1H-[1,2,3]triazole, 4,5-dihydro-1H-[1,2,3]triazol-1-yl, 4,5-dihydro-1H-[1,2,3]triazol-3-yl, 4,5-dihydro-1H-[1,2,3]triazol-5-yl, 2,3-dihydro-1H-[1,2,4]triazole, 4,5-dihydro-1H-[1,2,4]triazole, 2,3-dihydro-[1,2,4]oxadiazole, 2,5-dihydro-[1,2,4]oxadiazole, 4,5-dihydro-[1,2,4]thiadiazole, 2,3-dihydro-[1,2,4]thiadiazole, 2,5-dihydro-[1,2,4]thiadiazole, 4,5-dihydro-[1,2,4]thiadiazole, 2,5-dihydro-[1,2,4]oxadiazole, 2,3-dihydro-[1,2,4]oxadiazole, 4,5-dihydro-[1,2,4]oxadiazole, 2,5-dihydro-[1,2,4]thiadiazole, 2,3-dihydro-[1,2,4]thiadiazole, 4,5-dihydro-[1,2,4]thiadiazole, 2,3-dihydro-[1,3,4]oxadiazole, 2,3-dihydro-[1,3,4]thiadiazole, [1,4,2]oxathiazole, [1,3,4]oxathiazole, 1,3,5-triazaperhydroine, 1,2,4-triazaperhydroine, 1,4,2-dithiazaperhydroine, 1,4,2-dioxazaperhydroine, 1,3,5-oxadiazaperhydroine, 1,2,5-oxadiazaperhydroine, 1,3,4-thiadiazaperhydroine, 1,3,5-thiadiazaperhydroine, 1,2,5-thiadiazaperhydroine, 1,3,4-oxadiazaperhydroine, 1,4,3-oxathiazaperhydroine, 1,4,2-oxathiazaperhydroine, 1,4,5,6-tetrahydropyridazine, 1,2,3,4-tetrahydropyridazine, 1,2,3,6-tetrahydropyridazine, 1,2,5,6-tetrahydropyrimidine, 1,2,3,4-tetrahydropyrimidine, 1,4,5,6-tetrahydropyrimidine, 1,2,3,6-tetrahydropyrazine, 1,2,3,4-tetrahydropyrazine, 5,6-dihydro-4H-[1,2]oxazine, 5,6-dihydro-2H-[1,2]oxazine, 3,6-dihydro-2H-[1,2]oxazine, 3,4-dihydro-2H-[1,2]oxazine, 5,6-dihydro-4H-[1,2]thiazine, 5,6-dihydro-2H-[1,2]thiazine, 3,6-dihydro-2H-[1,2]thiazine, 3,4-dihydro-2H-[1,2]thiazine, 5,6-dihydro-2H-[1,3]oxazine, 5,6-dihydro-4H-[1,3]oxazine, 3,6-dihydro-2H-[1,3]oxazine, 3,4-dihydro-2H-[1,3]oxazine, 3,6-dihydro-2H-[1,4]oxazine, 3,4-dihydro-2H-[1,4]oxazine, 5,6-dihydro-2H-[1,3]thiazine, 5,6-dihydro-4H-[1,3]thiazine, 3,6-dihydro-2H-[1,3]thiazine, 3,4-dihydro-2H-[1,3]thiazine, 3,6-dihydro-2H-[1,4]thiazine, 3,4-dihydro-2H-[1,4]thiazine, 1,2,3,6-tetrahydro-[1,2,4]triazine, 1,2,3,4-tetrahydro-[1,2,4]triazine, 1,2,3,4-tetrahydro-[1,3,5]triazine, 2,3,4,5-tetrahydro-[1,2,4]triazine, 1,4,5,6-tetrahydro-[1,2,4]triazine, 5,6-dihydro-[1,4,2]dioxazine, 5,6-dihydro-[1,4,2]dithiazine, 2,3-dihydro-[1,4,2]dioxazine, 3,4-dihydro-2H-[1,3,4]oxadiazine, 3,6-dihydro-2H-[1,3,4]oxadiazine, 3,4-dihydro-2H-[1,3,5]oxadiazine, 3,6-dihydro-2H-[1,3,5]oxadiazine, 5,6-dihydro-2H-[1,2,5]oxadiazine, 5,6-dihydro-4H-[1,2,5]oxadiazine, 3,4-dihydro-2H-[1,3,4]thiadiazine, 3,6-dihydro-2H-[1,3,4]thiadiazine, 3,4-dihydro-2H-[1,3,5]thiadiazine, 3,6-dihydro-2H-[1,3,5]thiadiazine, 5,6-dihydro-2H-[1,2,5]thiadiazine, 5,6-dihydro-4H-[1,2,5]thiadiazine, 5,6-dihydro-2H-[1,2,3]oxadiazine, 3,6-dihydro-2H-[1,2,5]oxadiazine, 5,6-dihydro-4H-[1,3,4]oxadiazine, 3,4-dihydro-2H-[1,2,5]oxadiazine, 5,6-dihydro-2H-[1,2,3]thiadiazine, 3,6-dihydro-2H-[1,2,5]thiadiazine, 5,6-dihydro-4H-[1,3,4]thiadiazine, 3,4-dihydro-2H-[1,2,5]thiadiazine, 5,6-dihydro-[1,4,3]oxathiazine, 5,6-dihydro-[1,4,2]oxathiazine, 2,3-dihydro-[1,4,3]oxathiazine, 2,3-dihydro-[1,4,2]oxathiazine, 3,4-dihydropyridine, 1,2-dihydropyridine, 5,6-dihydropyridine, 2H-pyran, 2H-thiin, 3,6-dihydropyridine, 2,3-dihydropyridazine, 2,5-dihydropyridazine, 4,5-dihydropyridazine, 1,2-dihydropyridazine, 1,4-dihydropyrimidin-1-yl, 1,4-dihydropyrimidin-4-yl, 1,4-dihydropyrimidin-5-yl, 1,4-dihydropyrimidin-6-yl, 2,3-dihydropyrimidine, 2,5-dihydropyrimidine, 5,6-dihydropyrimidine, 3,6-dihydropyrimidine, 5,6-dihydropyrazine, 3,6-dihydropyrazine, 4,5-dihydropyrazine, 1,4-dihydropyrazine, 1,4-dithiin, 1,4-dioxin, 2H-1,2-oxazine, 6H-1,2-oxazine, 4H-1,2-oxazine, 2H-1,3-oxazine, 4H-1,3-oxazine, 6H-1,3-oxazine, 2H-1,4-oxazine, 4H-1,4-oxazine, 2H-1,3-thiazine, 2H-1,4-thiazine, 4H-1,2-thiazine, 6H-1,3-thiazine, 4H-1,4-thiazine, 2H-1,2-thiazine, 6H-1,2-thiazine, 1,4-oxathiin, 2H,5H-1,2,3-triazine, 1H,4H-1,2,3-triazine, 4,5-dihydro-1,2,3-triazine, 1H,6H-1,2,3-triazine, 1,2-dihydro-1,2,3-triazine, 2,3-dihydro-1,2,4-triazine, 3H,6H-1,2,4-triazine, 1H,6H-1,2,4-triazine, 3,4-dihydro-1,2,4-triazine, 1H,4H-1,2,4-triazine, 5,6-dihydro-1,2,4-triazine, 4,5-dihydro-1,2,4-triazine, 2H,5H-1,2,4-triazine, 1,2-dihydro-1,2,4-triazine, 1H,4H-1,3,5-triazine, 1,2-dihydro-1,3,5-triazine, 1,4,2-dithiazine, 1,4,2-dioxazine, 2H-1,3,4-oxadiazine, 2H-1,3,5-oxadiazine, 6H-1,2,5-oxadiazine, 4H-1,3,4-oxadiazine, 4H-1,3,5-oxadiazine, 4H-1,2,5-oxadiazine, 2H-1,3,5-thiadiazine, 6H-1,2,5-thiadiazine, 4H-1,3,4-thiadiazine, 4H-1,3,5-thiadiazine, 4H-1,2,5-thiadiazine, 2H-1,3,4-thiadiazine, 6H-1,3,4-thiadiazine, 6H-1,3,4-oxadiazine, and 1,4,2-oxathiazine, wherein the heterocycle is optionally vicinally fused with a saturated or unsaturated 5-, 6- or 7-membered ring containing 0, 1 or 2 atoms independently selected from N, O and S;

$R^c$ is independently, in each instance, phenyl substituted by 0, 1 or 2 groups selected from halo, $C_{1-4}$alkyl, $C_{1-3}$haloalkyl, —$OR^a$ and —$NR^aR^a$; or $R^c$ is a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the carbon atoms of the heterocycle are substituted by 0, 1 or 2 oxo or thioxo groups, wherein the heterocycle or fused phenyl ring is substituted by 0, 1, 2 or 3 substituents selected from halo, $C_{1-4}$alkyl, $C_{1-3}$haloalkyl, —$OR^a$ and —$NR^aR^a$;

$R^d$ is independently in each instance hydrogen or —$CH_3$;

$R^e$ is, independently, in each instance, $C_{1-9}$alkyl or $C_{1-4}$alkyl(phenyl) wherein either is substituted by 0, 1, 2, 3 or 4 substituents selected from halo, $C_{1-4}$haloalkyl, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —O$C_{2-6}$alkylN$R^aR^a$, —O$C_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$ —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkylN$R^aR^a$ and —N$R^aC_{2-6}$alkylO$R^a$; and wherein the $C_{1-9}$alkyl is additionally substituted by 0 or 1 groups independently selected from $R^h$;

$R^f$ is, independently, in each instance, $R^e$ or H;

$R^g$ is, independently, in each instance, a saturated or unsaturated 5- or 6-membered monocyclic ring containing 1, 2 or 3 atoms selected from N, O and S, so long as the combination of O and S atoms is not greater than 2, wherein the ring is substituted by 0 or 1 oxo or thioxo groups; and $R^h$ is, independently, in each instance, phenyl or a saturated or unsaturated 5- or 6-membered monocyclic ring containing 1, 2 or 3 atoms selected from N, O and S, so long as the combination of O and S atoms is not greater than 2, wherein the ring is substituted by 0 or 1 oxo or thioxo groups, wherein the phenyl or monocycle are substituted by 0, 1, 2 or 3 substituents selected from halo, cyano, nitro, —C(=O)$R^e$, —C(=O)O$R^e$, —C(=O)N$R^aR^f$, —C(=N$R^a$)N$R^aR^f$, —O$R^f$, —OC(=O)$R^e$, —OC(=O)N$R^aR^f$, —OC(=O)N($R^a$)S(=O)$_2$ $R^e$, —O$C_{2-6}$alkylN$R^aR^f$, —O$C_{2-6}$alkylO$R^f$, —S$R^f$, —S(=O)$R^e$, —S(=O)$_2R^e$, —S(=O)$_2$N$R^aR^f$, —S(=O)$_2$N($R^a$)C(=O)$R^e$, —S(=O)$_2$N($R^a$)C(=O)O$R^e$, —S(=O)$_2$N($R^a$)C(=O)N$R^aR^f$, —N$R^aR^f$, —N($R^a$)C(=O)$R^e$, —N($R^a$)C(=O)O$R^e$, —N($R^a$)C(=O)N$R^aR^f$, —N($R^a$)C(=N$R^a$)N$R^aR^f$, —N($R^a$)S(=O)$_2R^e$, —N($R^a$)S(=O)$_2$N$R^aR^f$, —N$R^aC_{2-6}$alkylN$R^aR^f$ and —N$R^aC_{2-6}$alkylO$R^f$.

2. A compound selected from the group of:

N-[4-({5-(4-fluorophenyl)-4-[4-(trifluoromethyl)phenyl]pyridin-2-yl}oxy)-1,3-benzothiazol-2-yl]acetamide;

N-[4-({5-[4-(trifluoromethoxy)phenyl]-4-[4-(trifluoromethyl)phenyl]pyridin-2-yl}oxy)-1,3-benzothiazol-2-yl]acetamide;

N-[4-({5-bromo-4-[4-(trifluoromethyl)phenyl]pyridin-2-yl}oxy)-1,3-benzothiazol-2-yl]acetamide;

N-[4-({5-chloro-4-[4-(trifluoromethyl)phenyl]pyridin-2-yl}oxy)-1,3-benzothiazol-2-yl]acetamide;

or any pharmaceutically-acceptable salts thereof.

3. A compound according to claim 1, $R^1$ is piperidine or pyrimidine, either one substituted by 1, 2 or 3 substituents independently selected from $R^f$, $R^g$ halo, nitro, cyano, —O$R^e$, —O$R^g$, —O$C_{2-6}$alkylN$R^aR^f$, —O$C_{2-6}$alkylO$R^f$, —N$R^aR^f$, —N$R^aR^g$, —N$R^fC_{2-6}$alkylN$R^aR^f$, —N$R^fC_{2-6}$alkylO$R^f$, naphthyl, —CO$_2R^e$, —C(=O)$R^e$, —C(=O)N$R^aR^f$, —C(=O)N$R^aR^g$, —N$R^fC$(=O)$R^e$, —N$R^fC$(=O)$R^g$, —N$R^fC$(=O)N$R^aR^f$, —N$R^f$CO$_2R^e$, —$C_{1-8}$alkylO$R^f$, —$C_{1-6}$alkylN$R^aR^f$, —S(=O)$_nR^e$, —S(=O)$_2$N$R^aR^f$, —N$R^a$S(=O)$_2R^e$ and —OC(=O)N$R^aR^f$, and $R^b$ is additionally substituted by 0, 1 or 2 groups independently selected from $R^c$.

4. A compound according to claim 3, wherein $R^7$ is —CF$_3$.

5. A compound according to claim 3, wherein $R^7$ is —C(CH$_3$)$_3$.

6. A compound according to claim 1, $R^1$ is $R^b$, wherein $R^b$ substituted by 1, 2 or 3 substituents independently selected from $R^f$, $R^g$, halo, nitro, cyano, —O$R^e$, —O$R^g$, —O$C_{2-6}$alkylN$R^aR^f$, —O$C_{2-6}$alkylO$R^f$, —N$R^aR^f$, —N$R^aR^g$, —N$R^fC_{2-6}$alkylN$R^aR^f$, —N$R^fC_{2-6}$alkylO$R^f$, naphthyl, —CO$_2R^e$, —C(=O)$R^e$, —C(=O)N$R^aR^f$, —C(=O)N$R^aR^g$, —N$R^fC$(=O)$R^e$, —N$R^fC$(=O)$R^g$, —N$R^fC$(=O)N$R^aR^f$, —N$R^f$CO$_2R^e$, —$C_{1-8}$alkylO$R^f$, —$C_{1-6}$alkylN$R^aR^f$, —S(=O)$_nR^e$, —S(=O)$_2$N$R^aR^f$, —N$R^a$S(=O)$_2R^e$ and —OC(=O)N$R^aR^f$, and $R^b$ is additionally substituted by 0, 1 or 2 groups independently selected from $R^c$.

7. A compound according to claim 1, $R^1$ is pyridine substituted by 1, 2 or 3 substituents independently selected from $R^f$, $R^g$, halo, nitro, cyano, —O$R^e$, —O$R^g$, —O$C_{2-6}$alkylN$R^aR^f$, —O$C_{2-6}$alkylO$R^f$, —N$R^aR^f$, —N$R^aR^g$, —N$R^fC_{2-6}$alkylN$R^aR^f$, —N$R^fC_{2-6}$alkylO$R^f$, naphthyl, —CO$_2R^e$, —C(=O)$R^e$, —C(=O)N$R^aR^f$, —C(=O)N$R^aR^g$, —N$R^fC$(=O)$R^e$, —N$R^fC$(=O)$R^g$, —N$R^fC$(=O)N$R^aR^f$, —N$R^f$CO$_2R^e$, —$C_{1-8}$alkylO$R^f$, —$C_{1-6}$alkylN$R^aR^f$, —S(=O)$_nR^e$, —S(=O)$_2$N$R^aR^f$, —N$R^a$S(=O)$_2R^e$ and —OC(=O)N$R^aR^f$, and $R^b$ is additionally substituted by 0, 1 or 2 groups independently selected from $R^c$.

8. A compound according to claim 1, wherein $R^1$ is phenyl that is vicinally fused with a saturated or unsaturated 3-, 4- or 5-atom bridge containing 0, 1, 2 or 3 atoms selected from O, N and S with the remaining atoms being carbon, so long as the combination of O and S atoms is not greater than 2, wherein the heterocycle and bridge are substituted by 0, 1, 2 or 3 substituents independently selected from $R^5$.

9. A compound according to claim 1, wherein $R^2$ is, independently, in each instance, $R^{14}$, halo, $C_{1-8}$alkyl substituted by 0, 1 or 2 substituents selected from $R^{14}$, halo, —(CH$_2$)$_n$phenyl substituted by 0, 1, 2 or 3 substituents independently selected from $R^{14}$ and halo, or a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the heterocycle or fused phenyl ring is substituted by 0, 1, 2 or 3 substituents independently selected from $R^{14}$ and halo; or $R^2$ is —O$R^4$ or —N($R^a$)$R^4$; and $R^3$ is H, wherein at least one of $R^2$ and $R^3$ is other than H.

10. A compound according to claim 1, wherein $R^2$ is H; and $R^3$ is halo, —NH$_2$, —NHC$_{1-3}$alkyl, —N(C$_{1-3}$alkyl)C$_{1-3}$alkyl, or C$_{1-3}$alkyl.

11. A compound according to claim 1, wherein $R^4$ is independently at each instance

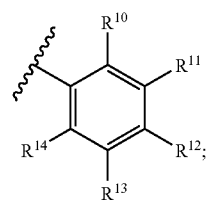

but in no instance is $R^4$-phenyl-O—(C$_{1-6}$alkyl), -phenyl-N$R^aR^a$ or -phenyl-N($R^a$)C(=O)(C$_{1-8}$alkyl).

12. A compound according to claim 1, wherein $R^5$ is H.

13. A compound according to claim 12, wherein $R^{10}$ and $R^{11}$ together are a saturated or unsaturated 3-, 4- or 5-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from oxo, thioxo, $R^c$, $R^e$, halo, cyano, nitro, —C(=O)$R^e$, —C(=O)O$R^f$, —C(=O)N$R^aR^f$, —C(=N$R^a$)N$R^aR^f$, —O$R^f$, —OC(=O)$R^e$, —OC(=O)N$R^aR^f$, —OC(=O)N($R^a$)S(=O)$_2R^e$, —OC$_{2-6}$alkylN$R^aR^f$, —OC$_{2-6}$alkylO$R^f$, —S$R^e$, —S(=O)$R^e$, —S(=O)$_2R^e$, —S(=O)$_2$N$R^aR^f$, —S(=O)$_2$N($R^a$)C(=O)$R^e$, —S(=O)$_2$N($R^a$)C(=O)O$R^f$, —S(=O)$_2$N($R^a$)C(=O)N$R^aR^f$, —N$R^aR^f$, —N($R^a$)C(=O)$R^e$, —N($R^a$)C(=O)O$R^f$, —N($R^a$)C(=O)N$R^aR^f$, —N($R^a$)C(=N$R^a$)N$R^aR^f$, —N($R^a$)S(=O)$_2R^e$, —N($R^a$)S(=O)$_2$N$R^aR^f$, —N$R^aC_{2-6}$alkylN$R^aR^f$, —N$R^aC_{2-6}$alkylO$R^f$, —C(=O)$R^h$, —C(=O)O$R^h$, —C(=O)N$R^aR^h$, —C(=N$R^a$)N$R^aR^h$, —O$R^h$, —OC(=O)$R^h$, —OC(=O)N$R^aR^h$, —OC(=O)N($R^a$)S(=O)$_2R^h$, —OC(=O)N($R^h$)S(=O)$_2R^e$, —OC$_{2-6}$alkylN$R^aR^h$, —OC$_{2-6}$alkylO$R^h$, —S$R^h$, —S(=O)$R^h$, —S(=O)$_2R^h$, —S(=O)$_2$N$R^aR^h$, —S(=O)$_2$N($R^h$)C(=O)$R^e$, —S(=O)$_2$N($R^a$)C(=O)$R^h$, —S(=O)$_2$N($R^h$)C(=O)O$R^f$, —S(=O)$_2$N($R^a$)C(=O)O$R^h$, —S(=O)$_2$N($R^h$)C(=O)N$R^aR^f$, —S(=O)$_2$N($R^a$)C(=O)N$R^aR^h$, —N$R^aR^h$, —N($R^h$)C(=O)$R^e$, —N($R^a$)C(=O)$R^h$, —N($R^h$)C(=O)O$R^f$, —N($R^a$)C(=O)O$R^h$, —N($R^h$)C(=O)N$R^aR^f$, —N($R^a$)C(=O)N$R^aR^h$, —N($R^h$)C(=N$R^a$)N$R^aR^f$, —N($R^a$)C(=N$R^a$)N$R^aR^h$, —N($R^h$)S(=O)$_2R^e$, —N($R^a$)S(=O)$_2R^h$, —N($R^h$)S(=O)$_2$N$R^aR^f$, —N($R^a$)S(=O)$_2$N$R^aR^h$, —N$R^hC_{2-6}$alkylN$R^aR^f$, —N$R^aC_{2-6}$alkylN$R^aR^h$, —N$R^hC_{2-6}$alkylO$R^f$ and —N$R^aC_{2-6}$alkylO$R^h$; and when $R^{10}$ and $R^{11}$ together form a bridge, $R^{12}$ may additionally be halo or —CF$_3$, $R^{13}$ may additionally be halo or —O$R^a$ or cyano or nitro, and $R^{14}$ may additionally be halo.

14. A compound according to claim 12, wherein $R^{11}$ and $R^{12}$ together are a saturated or unsaturated 3-, 4- or 5-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from oxo, thioxo, $R^c$, $R^e$, halo, cyano, nitro, —C(=O)$R^e$, —C(=O)O$R^f$, —C(=O)N$R^aR^f$, —C(=N$R^a$)N$R^aR^f$, —O$R^f$, —OC(=O)$R^e$, —OC(=O)N$R^aR^f$, —OC(=O)N($R^a$)S(=O)$_2R^e$, —OC$_{2-6}$alkylN$R^aR^f$, —OC$_{2-6}$alkylO$R^f$, —S$R^e$, —S(=O)$R^e$, —S(=O)$_2R^e$, —S(=O)$_2$N$R^aR^f$, —S(=O)$_2$N($R^a$)C(=O)$R^e$, —S(=O)$_2$N($R^a$)C(=O)O$R^f$, —S(=O)$_2$N($R^a$)C(=O)N$R^aR^f$, —N$R^aR^f$, —N($R^a$)C(=O)$R^e$, —N($R^a$)C(=O)O$R^f$, —N($R^a$)C(=O)N$R^aR^f$, —N($R^a$)C(=N$R^a$)N$R^aR^f$, —N($R^a$)S(=O)$_2R^e$, —N($R^a$)S(=O)$_2$N$R^aR^f$, —N$R^aC_{2-6}$alkylN$R^aR^f$, —N$R^aC_{2-6}$alkylO$R^f$, —C(=O)$R^h$, —C(=O)O$R^h$, —C(=O)N$R^aR^h$, —C(=N$R^a$)N$R^aR^h$, —O$R^h$, —OC(=O)$R^h$, —OC(=O)N$R^aR^h$, —OC(=O)N($R^a$)S(=O)$_2R^h$, —OC(=O)N($R^h$)S(=O)$_2R^e$, —OC$_{2-6}$alkylN$R^aR^h$, —OC$_{2-6}$alkylO$R^h$, —S$R^h$, —S(=O)$R^h$, —S(=O)$_2R^h$, —S(=O)$_2$N$R^aR^h$, —S(=O)$_2$N($R^h$)C(=O)$R^e$, —S(=O)$_2$N($R^a$)C(=O)$R^h$, —S(=O)$_2$N($R^h$)C(=O)O$R^f$, —S(=O)$_2$N($R^a$)C(=O)O$R^h$, —S(=O)$_2$N($R^h$)C(=O)N$R^aR^f$, —S(=O)$_2$N($R^a$)C(=O)N$R^aR^h$, —N$R^aR^h$, —N($R^h$)C(=O)$R^e$, —N($R^a$)C(=O)$R^h$, —N($R^h$)C(=O)O$R^f$, —N($R^a$)C(=O)O$R^h$, —N($R^h$)C(=O)N$R^aR^f$, —N($R^a$)C(=O)N$R^aR^h$, —N($R^h$)C(=N$R^a$)N$R^aR^f$, —N($R^a$)C(=N$R^a$)N$R^aR^h$, —N($R^h$)S(=O)$_2R^e$, —N($R^a$)S(=O)$_2R^h$, —N($R^h$)S(=O)$_2$N$R^aR^f$, —N($R^a$)S(=O)$_2$N$R^aR^h$, —N$R^hC_{2-6}$alkylN$R^aR^f$, —N$R^aC_{2-6}$alkylN$R^aR^h$, —N$R^hC_{2-6}$alkylO$R^f$ and —N$R^aC_{2-6}$alkylO$R^h$; wherein —$R^{11}$—$R^{12}$— is not —C(NH$_2$)=C—C=N— or any substituted version thereof; or $R^{11}$ and $R^{12}$ together are a saturated or partially unsaturated 3-, 4- or 5-carbon bridge, wherein the bridge is substituted by 0, 1 or 2 substituents selected from oxo, thioxo, $R^c$, $R^e$, halo, cyano, nitro, —C(=O)$R^e$, —C(=O)O$R^f$, —C(=O)N$R^aR^f$, —C(=N$R^a$)N$R^aR^f$, —O$R^f$, —OC(=O)$R^e$, —OC(=O)N$R^aR^f$, —OC(=O)N($R^a$)S(=O)$_2R^e$, —OC$_{2-6}$alkylN$R^aR^f$, —OC$_{2-6}$alkylO$R^f$, —S$R^e$, —S(=O)$R^e$, —S(=O)$_2R^e$, —S(=O)$_2$N$R^aR^f$, —S(=O)$_2$N($R^a$)C(=O)$R^e$, —S(=O)$_2$N($R^a$)C(=O)O$R^f$, —S(=O)$_2$N($R^a$)C(=O)N$R^aR^f$, —N$R^aR^f$, —N($R^a$)C(=O)$R^e$, —N($R^a$)C(=O)O$R^f$, —N($R^a$)C(=O)N$R^aR^f$, —N($R^a$)C(=N$R^a$)N$R^aR^f$, —N($R^a$)S(=O)$_2R^e$, —N($R^a$)S(=O)$_2$N$R^aR^f$, —N$R^aC_{2-6}$alkylN$R^aR^f$, —N$R^aC_{2-6}$alkylO$R^f$, —C(=O)$R^h$, —C(O)O$R^h$, —C(=O)N$R^aR^h$ C(=N$R^a$)N$R^aR^h$, O$R^h$, —OC(=O)$R^h$, —OC(=O)N$R^aR^h$, —OC(=O)N($R^a$)S(=O)$_2R^h$, —OC(=O)N($R^h$)S(=O)$_2R^e$, —OC$_{2-6}$alkylN$R^aR^h$, —OC$_{2-6}$alkylO$R^h$, —S$R^h$, —S(=O)$R^h$, —S(=O)$_2R^h$, —S(=O)$_2$N$R^aR^h$, —S(=O)$_2$N($R^h$)C(=O)$R^e$, —S(=O)$_2$N($R^a$)C(=O)$R^h$, —S(=O)$_2$N($R^h$)C(=O)O$R^f$, —S(=O)$_2$N($R^a$)C(=O)O$R^h$, —S(=O)$_2$N($R^h$)C(=O)N$R^aR^f$, —S(=O)$_2$N($R^a$)C(=O)N$R^aR^h$, —N$R^aR^h$, —N($R^h$)C(=O)$R^e$, —N($R^a$)C(=O)$R^h$, —N($R^h$)C(=O)O$R^f$, —N($R^a$)C(=O)O$R^h$, —N($R^h$)C(=O)N$R^aR^f$, —N($R^a$)C(=O)N$R^aR^h$, —N($R^h$)C(=N$R^a$)N$R^aR^f$, —N($R^a$)C(=N$R^a$)N$R^aR^h$, —N($R^h$)S(=O)$_2R^e$, —N($R^a$)S(=O)$_2R^h$, —N($R^h$)S(=O)$_2$N$R^aR^f$, —N($R^a$)S(=O)$_2$N$R^aR^h$, —N$R^hC_{2-6}$alkylN$R^aR^f$, —N$R^aC_{2-6}$alkylN$R^aR^h$, —N$R^hC_{2-6}$alkylO$R^f$ and —N$R^aC_{2-6}$alkylO$R^h$; and when $R^{11}$ and $R^{12}$ together form a bridge, $R^{10}$ may additionally be halo, $R^{13}$ may additionally be halo or —O$R^a$ or cyano or nitro, and R]$^4$ may additionally be halo.

15. A compound according to claim 1, wherein $R^4$ is independently at each instance a saturated or unsaturated 5- or 6-membered ring heterocycle containing 1, 2 or 3 atoms selected from O, N and S that is optionally vicinally fused with a saturated or unsaturated 3-, 4- or 5-atom bridge containing 0, 1, 2 or 3 atoms selected from O, N and S with the remaining atoms being carbon, so long as the combination of 0 and S atoms is not greater than 2, wherein the heterocycle and bridge are substituted by 0, 1, 2 or 3 substituents independently selected from $R^e$, $C_{1-4}$haloalkyl, halo, cyano, oxo, thioxo, —O$R^f$, —S(=O)$_nR^e$, —OC$_{1-4}$haloalkyl, —OC$_{2-6}$alkylN$R^aR^f$, —OC$_{2-6}$alkylO$R^f$, —OC$_{1-6}$alkylO$R^f$, —C(=O)O$R^e$, —N$R^aR^f$, —N$R^aC_{1-4}$haloalkyl, —N$R^aC_{2-6}$alkylN$R^aR^f$, —N$R^aC_{2-6}$alkylO$R^f$, —C(=O)$R^e$, —C(=O)O$R^f$, —OC(=O)$R^e$, —C(=O)N$R^aR^f$ and —N$R^aC$(=O)$R^e$.

16. A compound according to claim 3, wherein $R^5$ is $R^f$, $R^h$, halo, nitro, cyano, —O$R^f$, —O$R^f$, —OC$_{2-6}$alkylN$R^aR^f$, —OC$_{2-6}$alkylO$R^f$, —N$R^aR^f$, —N$R^aR^h$, —N$R^fC_{2-6}$alkylN$R^aR^f$, —N$R^fC_{2-6}$alkylO$R^f$, naphthyl, —CO$_2R^e$, —OC(=O)$R^e$, —C(=O)$R^e$, —C(=O)N$R^aR^f$, —C(=O)N$R^aR^h$, —N$R^fC$(=O)$R^e$, —N$R^fC$(=O)$R^h$, —N$R^fC$(=O)N$R^aR^f$, —N$R^fCO_2R^e$, —C$_{1-8}$alkylO$R^f$, —C$_{1-6}$alkylN$R^aR^f$, —S(=O)$_n$R$^e$, —S(=O)$_2$NR$^a$R$^f$, —NR$^a$S(=O)$_2$R$^e$, —OS(=O)$_2$R$^e$, —OC(=O)NR$^a$R$^f$, —OR$^h$, —OC$_{2-6}$alkylNR$^a$R$^h$, —OC$_{2-6}$alkylOR$^h$, —NR$^a$R$^h$, —NR$^f$C$_{2-6}$alkylNR$^a$R$^h$, —NR$^h$C$_{2-6}$alkylNR$^a$R$^f$, —NR$^h$C$_{2-6}$alkylOR$^f$, —NR$^f$C$_{2-6}$alkylOR$^h$, —CO$_2$R$^h$, —OC(=O)R$^h$, —C(=O)R$^h$, —C(=O)NR$^a$R$^h$, —NR$^f$C(=O)R$^h$, —NR$^h$C(=O)R$^f$, —NR$^h$C(=O)NR$^a$R$^f$, —NR$^f$C(=O)NR$^a$R$^h$, —NR$^h$CO$_2$R$^e$, —NR$^f$CO$_2$R$^h$, —C$_{1-8}$alkylOR$^h$, —C$_{1-8}$alkylNR$^a$R$^h$, —S(=O)$_n$R$^h$, —S(=O)$_2$NR$^a$R$^h$, —NR$^a$S(=O)$_2$R$^h$, —NR$^h$S(=O)$_2$R$^h$, —OS(=O)$_2$R$^h$ or —OC(=O)NR$^a$R$^h$.

17. A compound according to claim 1, wherein R$^5$ is R$^f$ or R$^h$.

18. A pharmaceutical composition comprising a compound according to claim 1 and a pharmaceutically-acceptable diluent or carrier.

19. A compound according to claim 1, wherein R$^1$ is

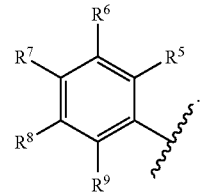

* * * * *